United States Patent
Becker et al.

(10) Patent No.: US 11,771,543 B2
(45) Date of Patent: Oct. 3, 2023

(54) POLY(ESTER UREA) ADHESION BARRIERS FOR USE IN THE TREATMENT OF HERNIA-MESH REPAIR

(71) Applicants: THE UNIVERSITY OF AKRON, Akron, OH (US); COOK MEDICAL TECHNOLOGIES LLC, Bloomington, IN (US)

(72) Inventors: Matthew Becker, Chapel Hill, NC (US); Nathan Z. Dreger, Copley, OH (US); Zachary K. Zander, Sheffield Village, OH (US); Trenton Parsell, Lafayette, IN (US); Michael Hiles, Lafayette, IN (US)

(73) Assignees: The University of Akron, Akron, OH (US); Cook Medical Technologies LLC, Bloomington, IN (US)

( * ) Notice: Subject to any disclaimer, the term of this patent is extended or adjusted under 35 U.S.C. 154(b) by 272 days.

(21) Appl. No.: 17/052,982

(22) PCT Filed: May 7, 2019

(86) PCT No.: PCT/US2019/031025
§ 371 (c)(1),
(2) Date: Nov. 4, 2020

(87) PCT Pub. No.: WO2020/226622
PCT Pub. Date: Nov. 12, 2020

(65) Prior Publication Data
US 2021/0212807 A1  Jul. 15, 2021

(51) Int. Cl.
*A61F 2/00* (2006.01)
*A61F 2/02* (2006.01)
*C08G 63/685* (2006.01)

(52) U.S. Cl.
CPC .......... *A61F 2/0077* (2013.01); *A61F 2/0063* (2013.01); *A61F 2/02* (2013.01); *C08G 63/685* (2013.01); *A61F 2002/0091* (2015.04)

(58) Field of Classification Search
CPC ........ A61F 2/0077; A61F 2/0063; A61F 2/02; A61F 2002/0091; C08G 63/685
See application file for complete search history.

(56) References Cited

U.S. PATENT DOCUMENTS

| 7,713,541 | B1 | 5/2010 | Pacetti et al. |
| 2007/0299155 | A1 | 12/2007 | Carpenter et al. |
| 2016/0237212 | A1* | 8/2016 | Becker .................. C07C 229/34 |

FOREIGN PATENT DOCUMENTS

WO  WO-2016014471 A1 *  1/2016  ............. A61K 47/34

OTHER PUBLICATIONS

Dreger et al., "Zwitterionic amino acid-based poly(ester urea)s suppress adhesion formation in a rat intra-abdominal cecal abrasion model," in Biomaterials (available on line on Aug. 7, 2019) (Year: 2019).*

(Continued)

*Primary Examiner* — Blessing M Fubara
(74) *Attorney, Agent, or Firm* — Renner, Kenner, Greive, Bobak, Taylor & Weber

(57) ABSTRACT

In various embodiments, the present invention is directed to a degradable poly(ester urea) (PEU)-based adhesion barrier, particularly suitable for use in connection with surgical mesh repair in the treatment of hernias and other soft tissue injuries comprising an amino acid based poly(ester urea) backbone and one or more zwitterionic side chains connected to the amino acid based poly(ester urea) backbone through a sulfide bond. In some other embodiments, the present invention is directed to method of making the PEU-based adhesion barriers comprising: preparing an amino acid based PEU polymer or terpolymer having one or (Continued)

1-VAL-8 Monomer more allyl functional groups; preparing a thiol functionalized zwitterionic compound; and reacting the allyl functionalized PEU polymer or terpolymer with the thiol functionalized zwitterionic compound to form a degradable PEU-based adhesion barrier having an amino acid based PEU backbone having zwitterionic side chains.

34 Claims, 27 Drawing Sheets

(56) References Cited

OTHER PUBLICATIONS

Dreger et al., "Amino acid-based Poly(ester urea) copolymer films for hernia repair applications" in Biomaterials, available online on Aug. 3, 2018) (Year: 2018).*

Jiayu YU et al., "Branched Amino Acid Based Poly(ester urea)s with Tunable Thermal and Water Uptake Properties" in Macromolecules, Apr. 30, 2015 (Year: 2015).*

Dreger, et al. Amino acid-based poly (ester urea) copolymer films for hernia-repair applications, Biomaterials, vol. 182,, Nov. 2018, pp. 44-57; https://doi.org/10.1016/j.biomaterials.2018.08.003; Abstract; p. 47, Scheme 1; p. 56, col. 1, para 3 to col. 2, para 1.

* cited by examiner

1-VAL-8 Monomer
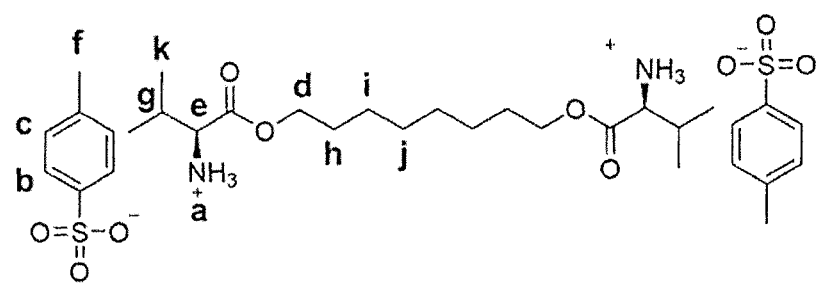
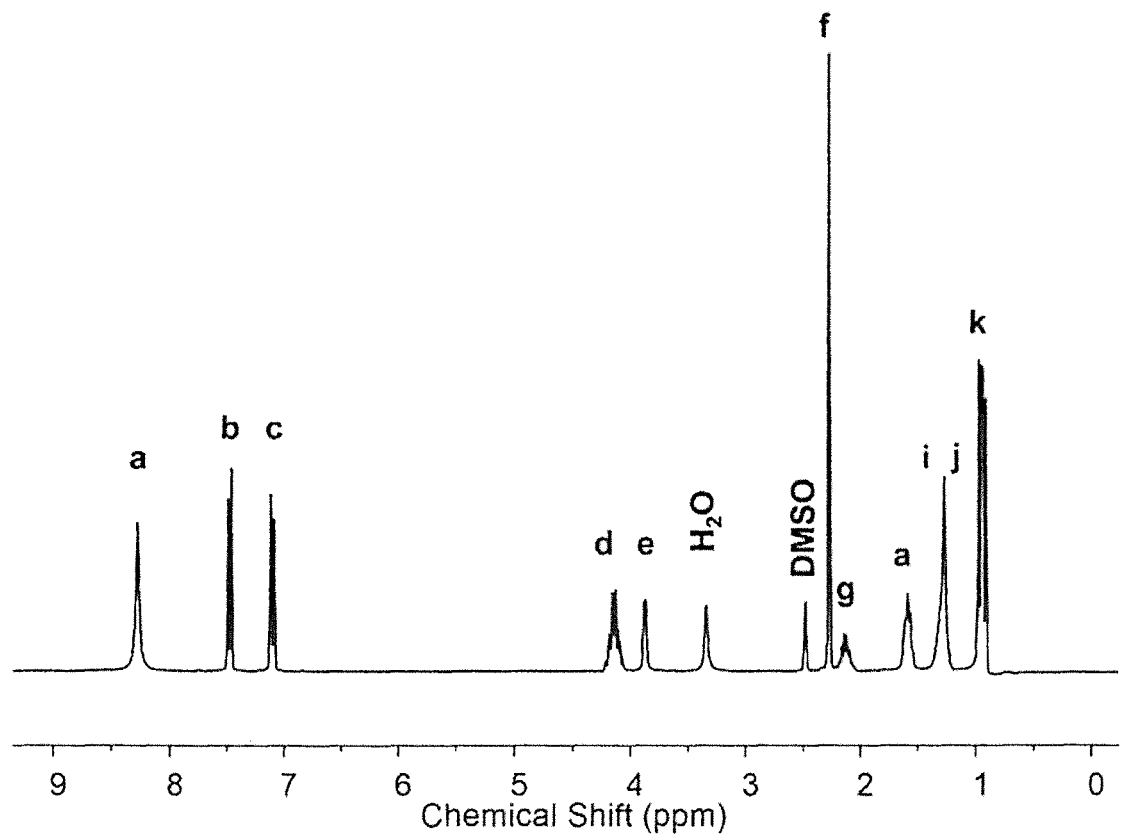
FIG. 2

Blank at 10 min

Clicked at 10 min

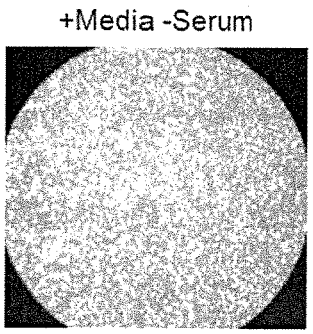
FIG. 26E
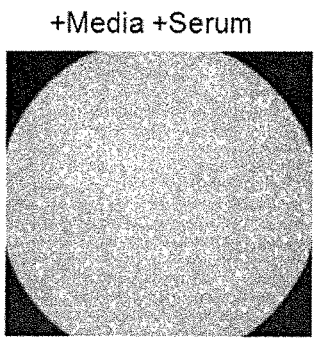
FIG. 26F
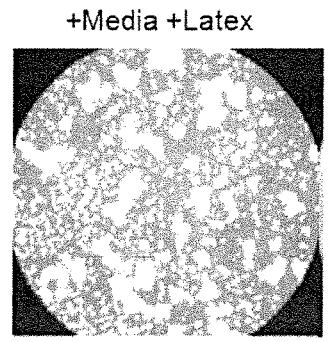
FIG. 26G
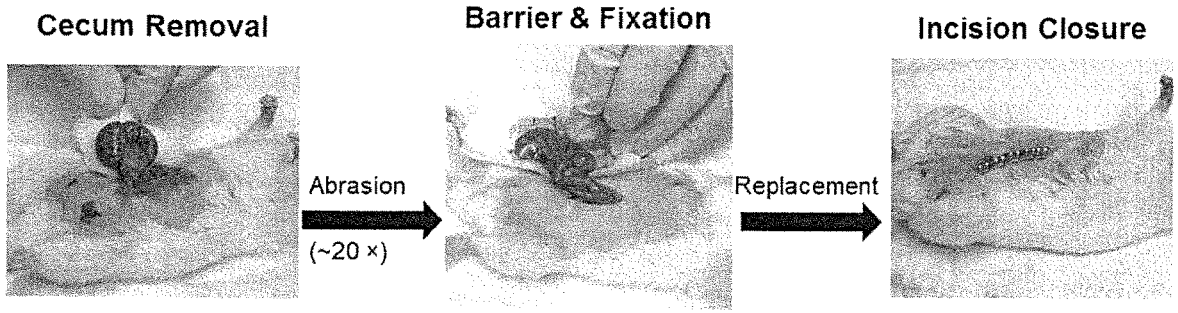
FIG. 27
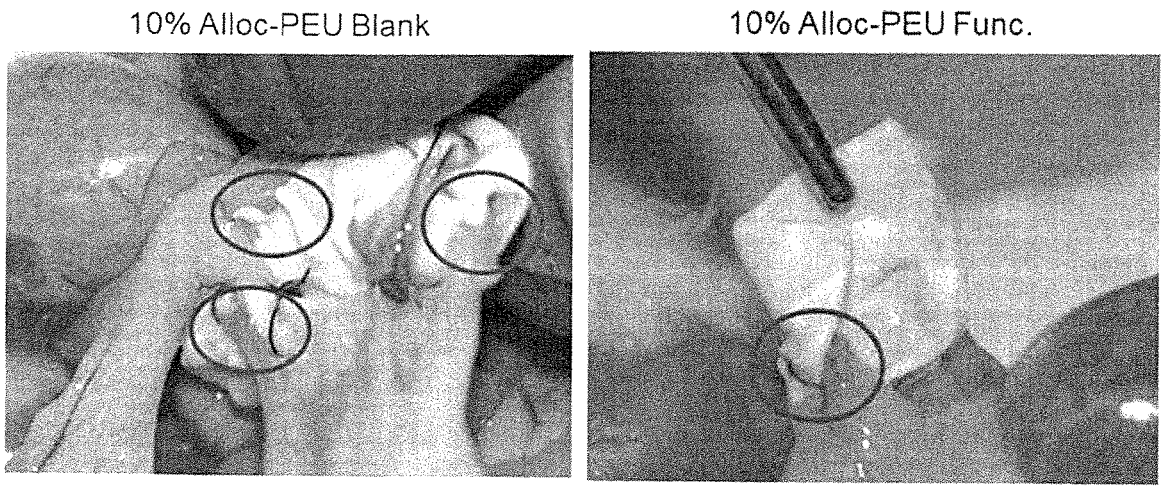
FIG. 28A      FIG. 28B

Extent to Tissue and Device

Tenacity to Tissue and Device

POLY(ESTER UREA) ADHESION BARRIERS FOR USE IN THE TREATMENT OF HERNIA-MESH REPAIR

CROSS REFERENCE TO RELATED APPLICATIONS

This application claims the benefit of International application serial number PCT/US2019/031025 entitled "Poly (Ester Urea) Adhesion Barriers for Use in the Treatment of Hernia-Mesh Repair," filed May 7, 2019, which is incorporated herein by reference in its entirety.

NAMES OF THE PARTIES TO A JOINT RESEARCH AGREEMENT

The present application stems from work done pursuant to a Joint Research Agreement between The University of Akron of Akron, Ohio and Cook Biotech Incorporated of West Layfette, Ind.

FIELD OF THE INVENTION

One or more embodiments of the present invention relates to surgical adhesion barriers. In certain embodiments, the present invention relates to poly(ester urea) polymers for use as surgical adhesion barriers.

BACKGROUND OF THE INVENTION

Treatments in ventral hernia mesh repair have been greatly improved over the past several decades. The use of polymer materials to augment a defect in open or laparoscopic ventral hernias has resulted in recurrence rates lower than 20%. While significant strides have been made, there still exists the chance of mesh adhesion. Ideally, the implant would simply cover the defect in the abdominal wall and augment the required mechanical properties. Unfortunately, there is a chance that the mesh can become adhered to other layers inside the peritoneum space. As will be appreciated by those of skill in the art, when a material is implanted in to the body, there is an immediate deposition of proteins, albumin, cell signaling receptors, and ultimately extracellular matrix polysaccharides. Cells can begin to lay down on the surface with immune cells attempting to identify toxicity, biocompatibility, and wall off the implant from the rest of the body with a dense fibrous capsule. This is part of the natural immune response to any implanted material and is part of the healing process. The outcomes and chance of problematic adhesion can vary depending on the mesh selected.

Standard mesh selection criteria is largely based on surgeon preference and material availability. The types of mesh available through a surgical unit can be broken down in to two main categories: resorbable (temporary) or nonresorbable (permanent). Nonresorbable materials will not be fully engulfed and broken down by the body which leads to a chronic inflammatory response. While this response could be tolerated if the material prevents recurrence, permanent implants are often prone to forming adhesions with various organs as the inflammatory response promotes a fibrous capsule which has the ability to adhere to other sites. Alterations in surgical technique (i.e. inlay versus onlay) can play a role in adhesion rates, however there is no guarantee as the implant will be in for the lifetime of the patient and there can be complications years after a successful hernia surgery. Attempts to reduce adhesions to surrounding tissue have been attempted by altering the surface chemistry of the implant. Examples of coating nonresorbable meshes in silicone to reduce surface tension have been employed with moderate success. In other fields, antiadhesion using polyethylene glycol (PEG) and derivatives thereof have been used to prevent adhesions however, their degradative products are less than ideal. More exotic chemistry techniques have been employed in the attempt to create anti-fouling and anti-adhesive surfaces with success in vitro however, these surface chemistries are often challenging to scale and limited to the benchtop. While the optics of these design strategies appear to be steps in the right direction, they only act as a stopgap; emblematic of a larger material problem.

Resorbable materials currently used in hernia-mesh repair are at an advantage from a tissue remodeling standpoint. When implanted in the body, resorbable materials degrade over time under physiological conditions until the material is complete cleared by the body, whereas nonresorbable materials are considered permanent as they lack the readily cleavable moieties and remain in the patient the lifetime of the device. As the implant degrades, cellular integration and remodeling can occur leaving behind native tissue. One of the most widely used resorbable materials are decellularized extracellular matrix (ECM). This material has suitable mechanical properties while also being porous allowing for cellular integration and tissue remodeling. The increase in tissue remodeling does not, however, prevent this mesh type from adhesion. But, depending on the location and time frame of adhesion formation, a resorbable material has the potential to overcome an adhesion without failure. While adhesions can still occur during the lifetime of a resorbable implant, the material will ultimately degrade, and the adhesion has the chance to resolve without fusing the abdominal wall to an organ in the peritoneal space. Unfortunately, if the adhesion occurs to an organ, the implant may need to be removed prior to resolution. This is also not desired and could lead to complications including herniation, strangulation, and repeat surgery.

It would be advantageous to combine the antiadhesion properties present on select nonresorbable meshes with the degradability of resorbable materials. A class of resorbable materials of interest are poly(ester urea)s (PEUs). Amino acid-based PEUs are finding use in a number of regenerative medicine applications due to their inherent synthetic flexibility, which results in tunable mechanical and degradation properties. The resulting polymers are semi-crystalline depending on the amino acid precursors, and the hydrogen bonding in the urea groups imparts the polymers with strong mechanical properties. The ester and urea bonds allow for both hydrolytic and enzymatic degradation. The final degradation byproducts are amino acids, small diol segments and $CO_2$, which can be readily metabolized and/or removed by the body. Moreover, unlike the acidic degradation byproducts of polyesters, the carboxyl group in PEU is buffered by the urea linkages at each repeat unit. It is believed, therefore, that the lack of inflammation found in vivo with PEU polymers is due, at least in part, to the absence of localized acidification during and after PEU degradation. Further, histological analysis of PEUs has shown that they are nontoxic and are therefore excellent candidates for tissue engineering constructs. Significantly, PEUs are synthetically flexible in that there are 20 kinds of naturally occurring amino acids and a number of non-natural amino acids derivatives have been successfully used in a number of applications. These amino acids, along with the various diols commercially available, permit the synthesis of PEUs having vastly different properties. These materials also lend themselves to facile roll-to-roll fabrication methods.

Accordingly, what is needed in the art is a PEU material to serve as an antiadhesive layer between a resorbable or nonresorbable hernia mesh and surrounding tissues or as a stand-alone hernia mesh, for use in connection with the surgical repair of ventral hernias and other similar soft tissue injuries.

SUMMARY OF THE INVENTION

In various embodiments, the present invention is directed to degradable anti-adhesion poly(ester urea)s (PEUs) that are surface functionalized with a scalable zwitterion thiol and methods for their making and use. Burst testing mechanical properties indicate that these PEUs are similar to soft tissue while preventing adhesion (force at break: 54-118 N). These degradable materials were shown to elicit a limited inflammatory response in vivo in a rat model (2.5-6.5 on ISO 10993-6 Annex E for implanted biomaterials, the disclosure of which is incorporated herein by reference in its entirety). It is believed that these functionalized anti-adhesion PEUs have the potential to be translatable materials for use as an aid in ventral hernia treatment.

In a first aspect, the present invention is directed to a poly(ester urea) (PEU)-based adhesion barrier comprising an amino acid based poly(ester urea) backbone and one or more zwitterionic side chains connected to the amino acid based poly(ester urea) backbone through a sulfide bond. In one or more of these embodiments, the amino acid based poly(ester urea) backbone comprises one or more amino acid-based diester monomer residues and one or more amino acid-based allyloxy diester monomer residues. In one or more embodiments, the PEU-based adhesion barrier of the present invention includes any one or more of the above referenced embodiments of the first aspect of the present invention wherein each one of the one or more amino acid-based diester monomer residues comprises two valine, phenylalanine, leucine, isoleucine, tyrosine, alanine, methionine, glycine, or cysteine with residues separated by from 2 to 20 carbon atoms. In one or more embodiments, the one or more amino acid-based allyloxy diester monomer residues are residues of an amine protected L-tyrosine-1,3-allyloxy-diester monomer. In one or more embodiments, the amino acid based poly(ester urea) backbone will contain the residues of one or more first amino acid-based diester monomers residues, one or more second amino acid-based diester monomers, and one or more amino acid-based allyloxy diester monomers connected by urea linkages. In these embodiments, the zwitterionic side chains are attached to the amino acid based poly(ester urea) backbone through the one or more amino acid-based allyloxy diester monomer residues.

In one or more of these embodiments, the PEU-based adhesion barrier of the present invention includes any one or more of the above referenced embodiments of the first aspect of the present invention wherein the one or more first amino acid-based diester monomer comprises two valine, phenylalanine, leucine, isoleucine, tyrosine, alanine, methionine, glycine, or cysteine with residues separated by from 2 to 20 carbon atoms and one or more second amino acid-based diester monomer comprises two lysine, phenylalanine, or valine, phenylalanine, leucine, isoleucine, tyrosine, alanine, methionine, glycine, or cysteine with residues separated by from 2 to 20 carbon atoms. In one or more of these embodiments, the one or more first amino acid-based diester monomers comprise two lysine residues separated by from 2 to 20 carbon atoms. In one or more embodiments, the one or more second amino acid-based diester monomers comprise two phenylalanine residues separated by from 2 to 20 carbon atoms. In one or more embodiments, the amino acid residues forming the first and second amino acid-based diester monomers are different.

In one or more of these embodiments, the PEU-based adhesion barrier of the present invention includes any one or more of the above referenced embodiments of the first aspect of the present invention wherein the amino acid-based allyloxy diester monomer residue is the residue of a monomer having the formula:

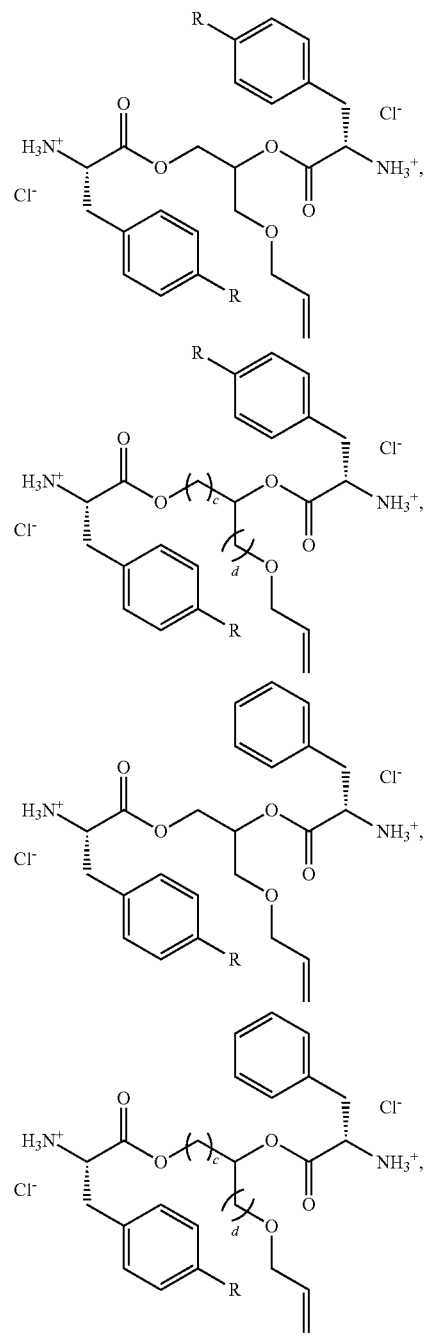

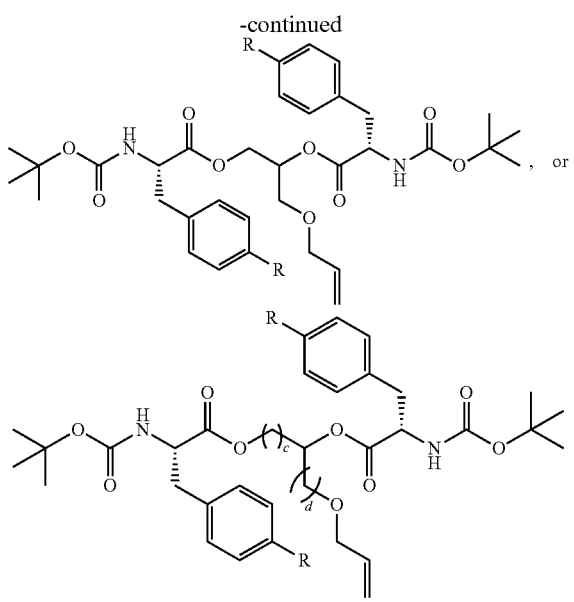

where R is OCH$_2$Ph, H, OCH$_2$C≡CH, OCH$_2$CH$_2$CH$_2$N$_3$, OCH$_2$CH$_2$CH$_2$CH═CH$_2$, OCH$_2$Ph, OCOCH$_2$CH$_2$COCH$_3$ or OH; and c and d are each an integer from about 1 to about 20. In one or more of these embodiments, the amino acid-based allyloxy diester monomer is an Boc protected L-tyrosine-1,3-allyloxy-diester monomer.

In one or more embodiments, the PEU-based adhesion barrier of the present invention includes any one or more of the above referenced embodiments of the first aspect of the present invention wherein the one or more zwitterionic side chains comprise the residue of a zwitterionic thiol. In one or more of these embodiments, the zwitterionic thiol has the formula:

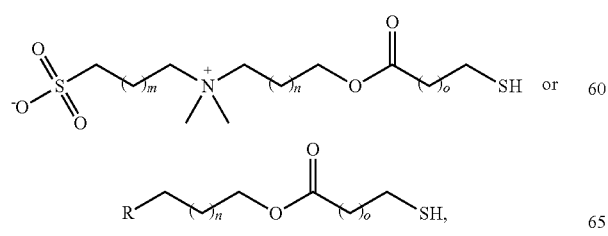

where R comprises a quaternary ammonium compound and a ring opened sultone; and m, n, and o are each an integer from 1 to 20. In some of these embodiments, the zwitterionic thiol will have the formula:

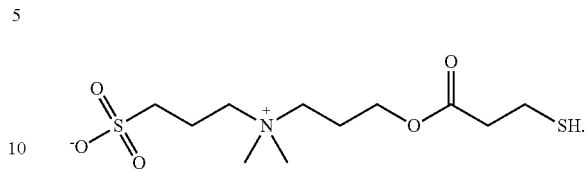

In one or more of these embodiments, the one or more zwitterionic side chains will comprise a zwitterionic moiety containing a quaternary ammonium compound and a ring opened sultone.

In one or more embodiments, the PEU-based adhesion barrier of the present invention includes any one or more of the above referenced embodiments of the first aspect of the present invention comprising from about 0.5 to about 50 mole percent L-tyrosine-based allyloxy diester monomer residues. In one or more embodiments, the PEU-based adhesion barrier of the present invention includes any one or more of the above referenced embodiments of the first aspect of the present invention having a relative stiffness of from about 20 N/cm to about 40 N/cm as measured by burst force testing.

In one or more embodiments, the PEU-based adhesion barrier of the present invention will comprise a zwitterionic copolymer having the formula:

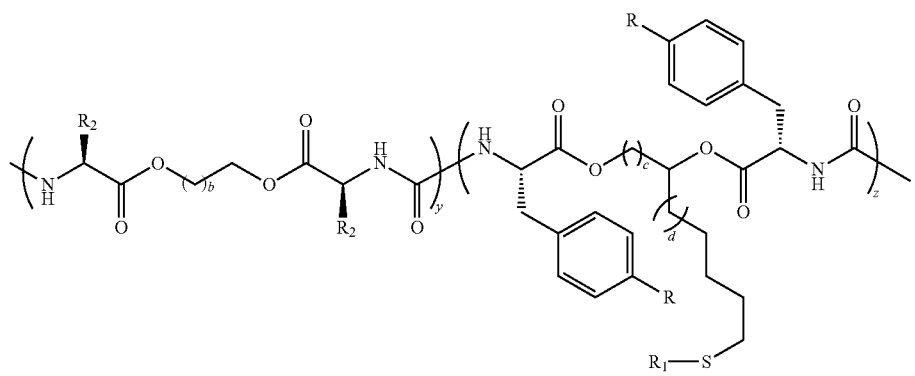

where R is OCH$_2$Ph, H, OCH$_2$C≡CH, OCH$_2$CH$_2$CH$_2$N$_3$, OCH$_2$CH$_2$CH$_2$CH═CH$_2$, OCH$_2$Ph, OCOCH$_2$CH$_2$COCH$_3$ or OH; R$_1$ is an alkyl or aryl group comprising a zwitterionic moiety; R$_2$ is an amino acid side chain; b is an integer from 1 to 20; c and d are each an integer from about 1 to about 20; y is a mole fraction from about 0.500 to about 0.995; and z is a mole fraction from about 0.005 to about 0.500.

In some other embodiments, the PEU-based adhesion barrier of the present invention will comprise a zwitterionic terpolymer having the formula:

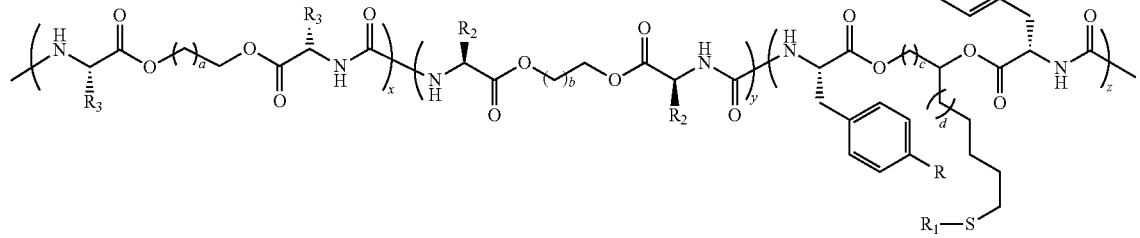

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; $R_1$ is an alkyl or aryl group comprising a zwitterionic moiety; $R_2$ is a first amino acid side chain; $R_3$ is a second amino acid side chain; a is an integer from 1 to 20; b is an integer from 1 to 20; each c and d are each an integer from about 1 to about 20; x is a mole fraction from about 0 to about 0.995; y is a mole fraction from about 0 to about 0.995; and z is a mole fraction from about 0.005 to about 0.500.

In one or more of these embodiments, the PEU-based adhesion barrier of the present invention comprises a zwitterionic terpolymer having the formula:

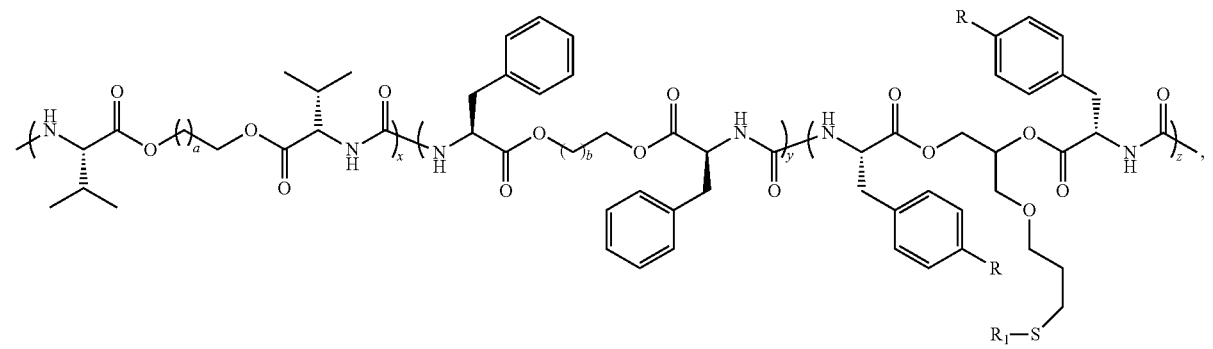

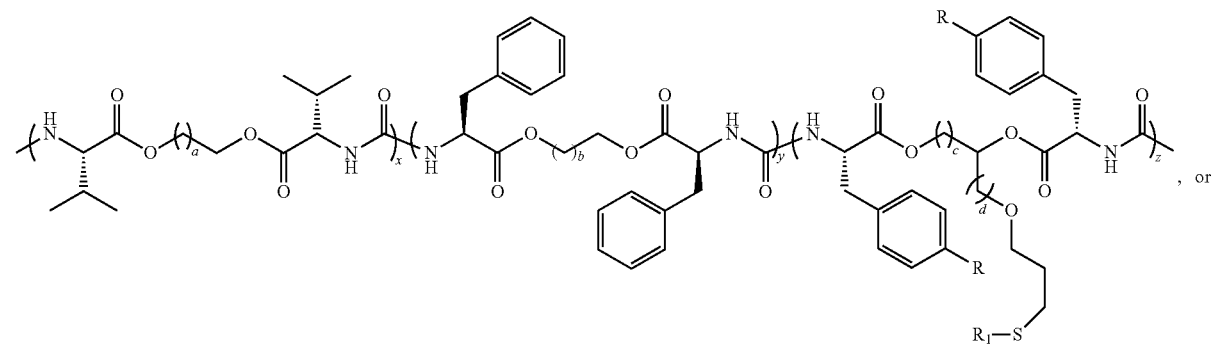

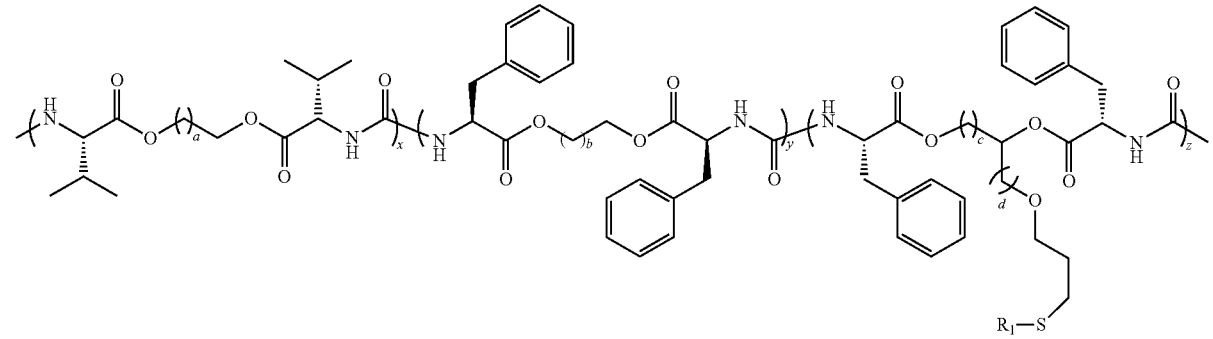

where R is OCH$_2$Ph, H, OCH$_2$C≡CH, OCH$_2$CH$_2$CH$_2$N$_3$, OCH$_2$CH$_2$CH$_2$CH=CH$_2$, OCH$_2$Ph, OCOCH$_2$CH$_2$COCH$_3$ or OH; R$_1$ is an alkyl or aryl group comprising a zwitterionic moiety; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500.

In one or more embodiments, the PEU-based adhesion barrier of the present invention will comprise a zwitterionic terpolymer having the formula:

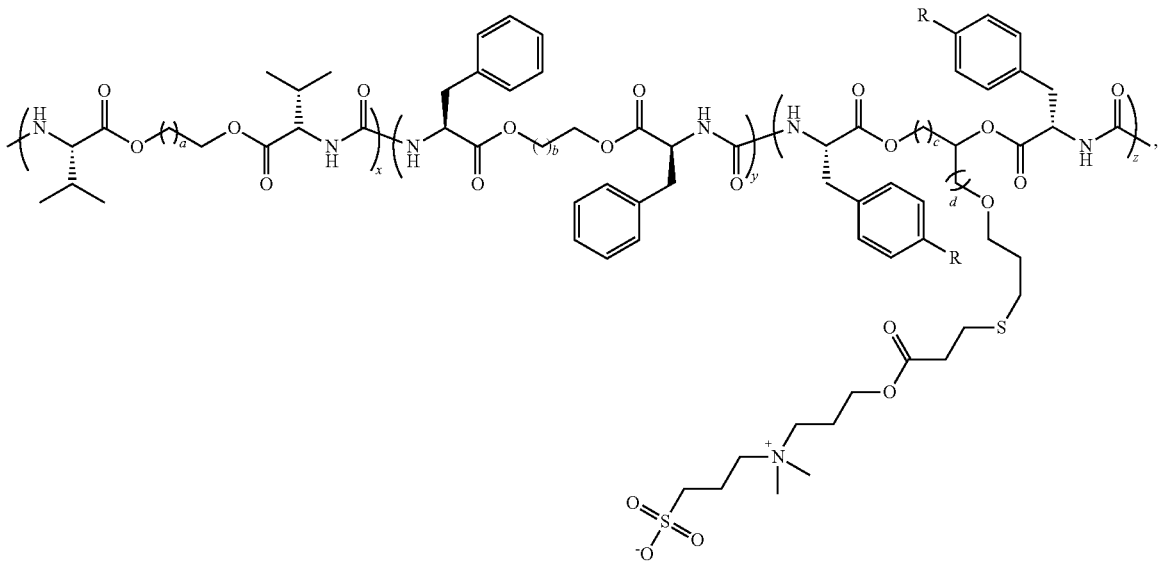

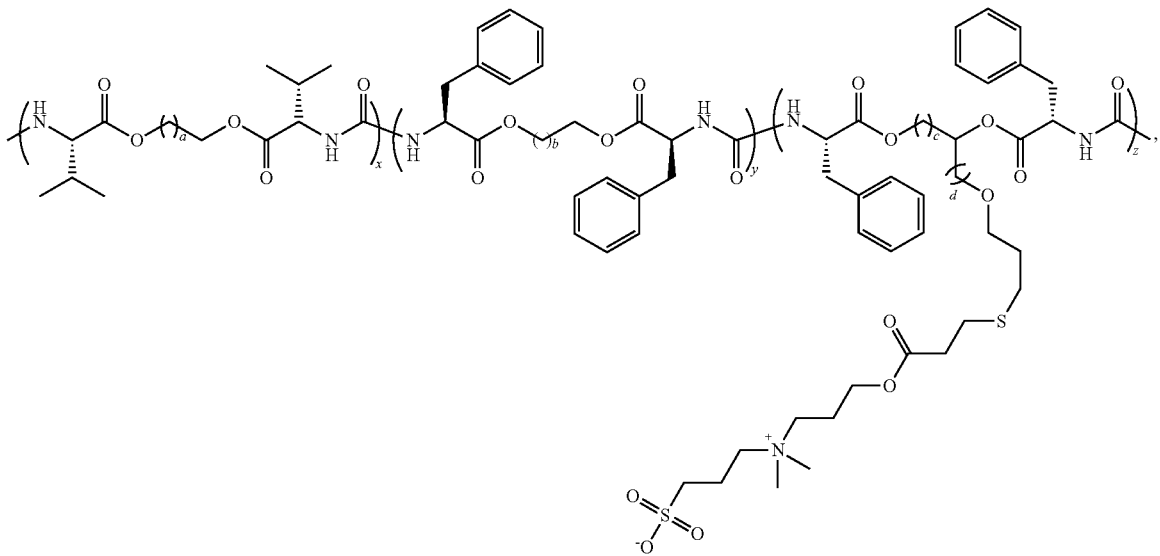

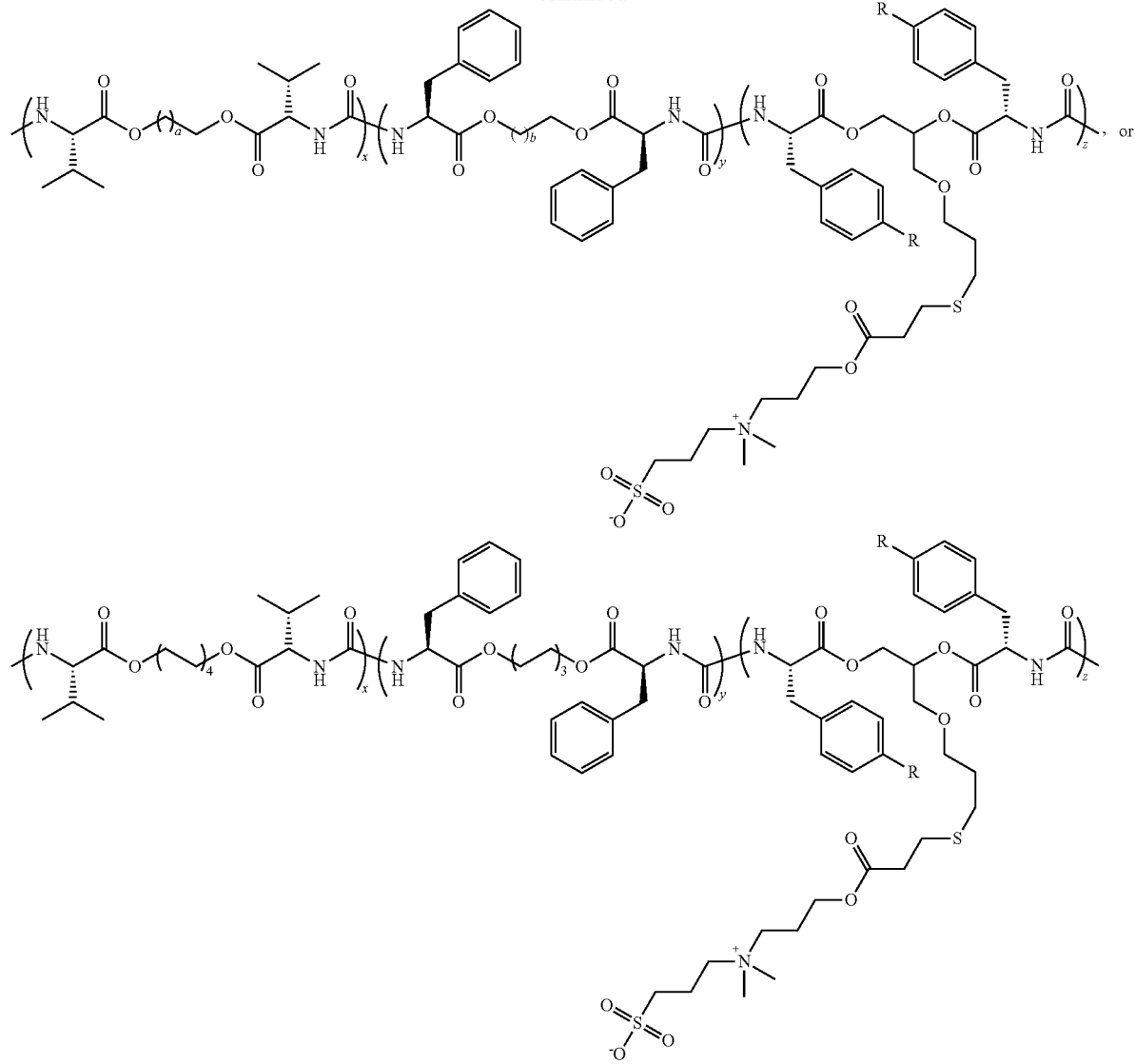

where R is OCH$_2$Ph, H, OCH$_2$C≡CH, OCH$_2$CH$_2$CH$_2$N$_3$, OCH$_2$CH$_2$CH$_2$CH=CH$_2$, OCH$_2$Ph, OCOCH$_2$CH$_2$COCH$_3$ or OH; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500.

In a second aspect, the present invention is directed to PEU polymers for use as an adhesion barrier comprising the reaction product of one or more amine protected amino acid-based diester monomers, one or more amine protected amino acid based-based allyloxy diester monomers, a urea bond forming compound, and one or more thiol functionalized zwitterionic compounds. In one or more of these embodiments, the PEU polymer will comprise: (1) an amino acid based poly(ester urea) backbone (as described above) comprising the residues of the one or more amino acid-based diester monomers, the one or more amino acid based-based allyloxy diester monomers, and the urea bond forming compound; and (2) one or more zwitterionic side chains comprising the residues of the one or more thiol functionalized zwitterionic compounds connected to the amino acid based poly(ester urea) backbone through a sulfide bond.

In these embodiments, the one or more amino acid-based diester monomers will comprise the residues of two valine, phenylalanine, lysine, phenylalanine, leucine, isoleucine, tyrosine, alanine, methionine, glycine, or cysteine residues separated by from 2 to 20 carbon atoms, as set forth above. In one or more embodiments, the amino acid-based allyloxy diester monomer may be as set forth above, but is preferably an Boc protected L-tyrosine-1,3-allyloxy-diester monomer. In these embodiments, the one or more thiol functionalized zwitterionic compounds may be any of those described above in connection with the first aspected of the invention.

In a third aspect, the present invention is directed to PEU terpolymer for use as an adhesion barrier comprising the reaction product of amine protected one or more first amine protected amino acid-based diester monomers, one or more second amine protected amino acid-based diester monomers, an amine protected L-tyrosine-based allyloxy diester monomer, a urea bond forming compound and one or more thiol functionalized zwitterionic compounds. In these embodiments, the PEU terpolymer will comprise: (1) an amino acid based poly(ester urea) backbone comprising the residue of the one or more first amino acid-based diester monomer, the one or more second amino acid-based diester monomer, the one or more L-tyrosine-based allyloxy diester monomers, and the urea bond forming compound; and (2) one or more zwitterionic side chains connected to the amino acid based poly(ester urea) backbone through a sulfide bond. In these embodiments, the one or more first amino acid-based diester monomer, the one or more second amino acid-based diester monomer, and the one or more L-tyrosine-based allyloxy diester monomers may be as set forth in the first, fourth, fifth and sixth aspects of the present invention. Likewise, the PEU terpolymer of the present invention includes any terpolymers having a terpolymer formula as identified above with respect to the first aspect of the present invention.

In one or more embodiments, the PEU terpolymer of the present invention includes any one or more of the above referenced embodiments of the third aspect of the present invention comprising from about 0.5 to about 50 mole percent amino acid-based allyloxy diester monomer residues. In one or more embodiments, the PEU terpolymer of the present invention includes any one or more of the above referenced embodiments of the third aspect of the present invention having a relative stiffness of from about 20 N/cm to about 40 N/cm as measured by burst force testing.

In a fourth aspect, the present invention is directed to method of making the PEU-based adhesion barrier described above comprising the steps of: preparing an amino acid based PEU polymer having one or more allyl functional groups; preparing a thiol functionalized zwitterionic compound; and reacting the allyl functionalized PEU polymer with the thiol functionalized zwitterionic compound to form a PEU-based adhesion barrier comprising an amino acid based PEU backbone having zwitterionic side chains. In one or more of these embodiments, the step of preparing an amino acid based PEU terpolymer having an allyl functional group comprises: preparing one or more amine protected amino acid-based diester monomers; preparing an amine protected allyl functionalized amino acid-based polyester monomer; dissolving the amino acid-based diester monomer and the allyl functionalized amino acid-based diester monomers is a suitable solvent with a suitable water soluble organic base; and adding a urea bond forming compound to the solution to form an amino acid based PEU polymer having one or more allyl functional groups.

In one or more of these embodiments, the one or more amino acid-based diester monomers comprises two lysine, phenylalanine, or valine, phenylalanine, lysine, phenylalanine, leucine, isoleucine, tyrosine, alanine, methionine, glycine, or cysteine with residues separated by from 2 to 20 carbon atoms. In one or more embodiments, the method of making the PEU-based adhesion barrier of the present invention includes any one or more of the above referenced embodiments of the fourth aspect of the present invention wherein the one or more allyl functionalized amino acid-based polyester monomer has a formula as identified above with respect to the first aspect of the present invention.

In one or more of these embodiments, the suitable solvent for the amino acid-based diester monomers and allyl functionalized amino acid-based diester monomers may be water, chloroform, and combinations thereof. In one or more embodiments, the suitable water soluble organic base may be sodium carbonate, potassium carbonate, sodium bicarbonate, potassium bicarbonate, or a combinations thereof. In one or more embodiments, the urea bond forming compound is triphosgene, diphosgene, phosgene or a combination thereof. In some of these embodiments, the step of adding a urea bond forming compound comprises dissolving triphosgene in chloroform to form a triphosgene solution and then adding the triphosgene solution to the monomer solution.

In one or more embodiments, the step of preparing a thiol functionalized zwitterionic compound comprises: reacting 3,3'-dithiodipropionic acid with thionyl chloride under an inert atmosphere to form a 3,3'-dithiodiproionyl chloride intermediate; dissolving 3-dimethyamino-1-propanol in anhydrous dichloromethane under an inert atmosphere and adding the 3,3'-dithiodipropionyl chloride intermediate, wherein the 3-dimethyamino-1-propanol and the 3,3'-dithiodipropionyl chloride intermediate react to form a bis((3-dimethylamino)propyl) 3,3'-disulfanediyldipropionate intermediate; dissolving 1,3-propane sultone in a suitable solvent; dissolving the bis((3-dimethylamino)propyl) 3,3'-disulfanediyldipropionate intermediate in a suitable solvent and adding it to the solution to form a zwitterion disulfide intermediate; and cleaving the zwitterion disulfide intermediate using 1,4-dithiothreitol (DTT) to produce two thiol functionalized zwitterionic compounds. In one or more embodiments, the method of making the PEU-based adhesion barrier of the present invention includes any one or more of the above referenced embodiments of the fourth aspect of the present invention wherein the step of reacting comprises: combining the allyl functionalized PEU terpolymer and the thiol functionalized zwitterionic compounds and adding a suitable photoinitiator; and irradiating the combination to form the PEU-based adhesion barrier comprising an amino acid based PEU backbone having zwitterionic side chains.

In a fifth aspect, the present invention is directed to method of making the PEU-based adhesion barrier described above comprising: preparing an amino acid based PEU terpolymer having one or more allyl functional groups; preparing a thiol functionalized zwitterionic compound; and reacting the allyl functionalized PEU terpolymer with the thiol functionalized zwitterionic compound to form a PEU-based adhesion barrier comprising an amino acid based PEU backbone having zwitterionic side chains. In one or more of these embodiments, the step of preparing an amino acid based PEU terpolymer having an allyl functional groups comprises: preparing a first amine protected amino acid-based diester monomer; preparing a second amine protected amino acid-based diester monomer; preparing an amine protected allyl functionalized amino acid-based polyester monomer; dissolving the first amino acid-based diester monomer, the second amino acid-based diester monomer; and the allyl functionalized amino acid-based polyester monomer is a suitable solvent with a suitable water soluble organic base; and adding a urea bond forming compound to the solution to form an amino acid based PEU terpolymer having one or more allyl functional groups.

In one or more embodiments, the method of making the PEU-based adhesion barrier of the present invention includes any one or more of the above referenced embodiments of the fifth aspect of the present invention wherein the one or more first amino acid-based diester monomers comprises two lysine, phenylalanine, or valine, phenylalanine, lysine, phenylalanine, leucine, isoleucine, tyrosine, alanine, methionine, glycine, or cysteine with residues separated by from 2 to 20 carbon atoms. In one or more embodiments, the one or more first amino acid-based diester monomers comprises two lysine residues separated by from 2 to about 20 carbon atoms. In one or more embodiments, the first amine protected amino acid-based diester monomer has the formula:

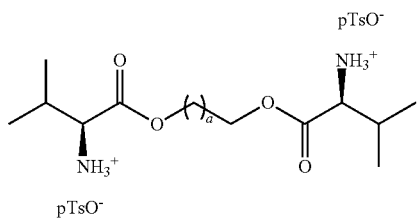

where a is an integer from about 1 to about 20.

In one or more of these embodiments, the one or more second amino acid-based diester monomers comprises two lysine, phenylalanine, or valine, phenylalanine, lysine, phenylalanine, leucine, isoleucine, tyrosine, alanine, methionine, glycine, or cysteine with residues separated by from 2 to 20 carbon atoms. In some of these embodiments, the one or more second amino acid-based diester monomers comprises two phenylalanine residues separated by from 2 to about 20 carbon atoms. In some embodiments, the second amine protected amino acid-based diester monomer has the formula:

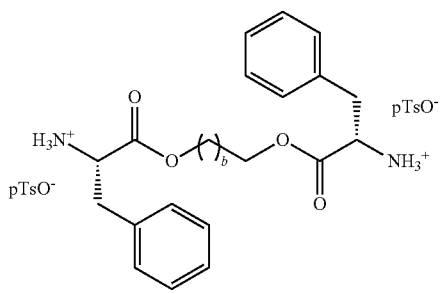

where b is an integer from about 1 to about 20. In of these embodiments the amino acid residues forming the one or more first amino acid-based diester monomers and the amino acid residues forming the one or more second amino acid-based diester monomers are different.

In one or more of these embodiments, the allyl functionalized amino acid-based polyester monomer is bis-O-benzyl-L-tyrosine-1,3-alkoxy-diester monomer or In some embodiments, the allyl functionalized amino acid-based polyester monomer comprises valine, phenylalanine, lysine, phenylalanine, leucine, isoleucine, tyrosine, alanine, methionine, glycine, or cysteine with residues separated by from 2 to 20 carbon atoms. In one or more embodiments, the amine protected allyl functionalized amino acid-based polyester monomer may have one of the amine protected allyl functionalized amino acid-based polyester monomer formulas identified above with respect to the first aspect of the present invention.

In these embodiments, solvent for the monomers, soluble organic base, urea bond forming compound, step of adding a urea bond forming compound, step of preparing a thiol functionalized zwitterionic compound, and the step of reacting comprises the allyl functionalized PEU terpolymer and the thiol functionalized zwitterionic compounds may all be as set forth above with respect to the fourth aspect of the present invention.

In a sixth aspect, the present invention is directed to method of making the PEU terpolymer described above comprising: preparing an acid salt of a first amino acid-based diester monomer having the formula:

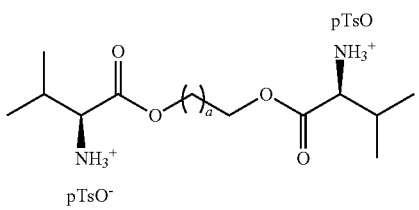

where a is an integer from about 1 to about 20; preparing an acid salt of a second amino acid-based diester monomer having the formula:

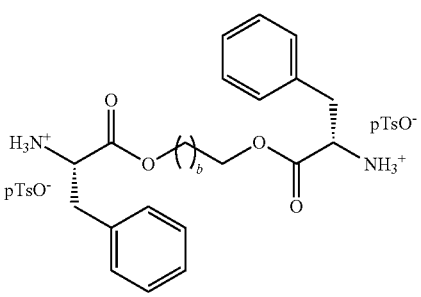

where b is an integer from about 1 to about 20; preparing an acid salt of an allyl functionalized amino acid-based polyester monomer having a formula identified above with respect to the first aspect of the present invention; dissolving the first amino acid-based diester monomer, the second amino acid-based diester monomer; and the allyl functionalized amino acid-based polyester monomer is a suitable solvent with a suitable water soluble organic base; adding a urea bond forming compound to the solution to form an allyl functionalized amino acid based PEU terpolymer intermediate having a formula selected from:

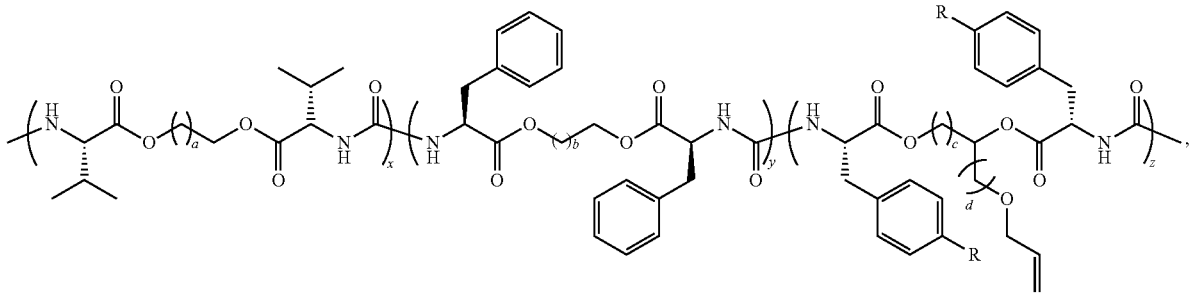

-continued

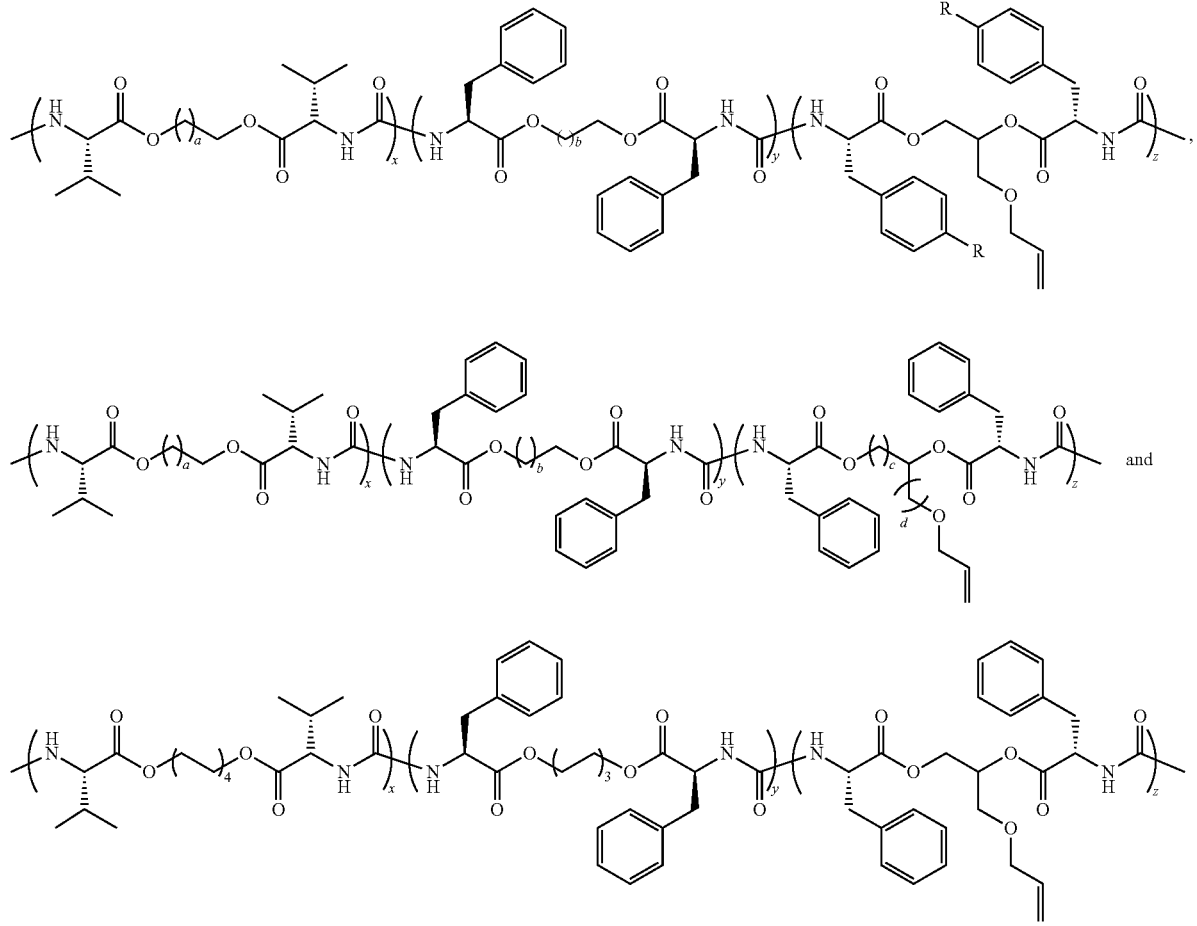

where R is OCH$_2$Ph, H, OCH$_2$C≡CH, OCH$_2$CH$_2$CH$_2$N$_3$, OCH$_2$CH$_2$CH$_2$CH=CH$_2$, OCH$_2$Ph, OCOCH$_2$CH$_2$COCH$_3$ or OH; a is an integer from 1 to 20; b is an integer from 1 to 20; c and d are each is an integer from about 1 to about 20; x is a mole fraction from about 0 to about 0.995; y is a mole fraction from about 0 to about 0.995; and z is a mole fraction from about 0.005 to about 0.500; reacting 3,3'-dithiodipropionic acid with thionyl chloride under an inert atmosphere to form a 3,3'-dithiodiproionyl chloride intermediate; dissolving 3-dimethyamino-1-propanol in anhydrous dichloromethane under an inert atmosphere and adding the 3,3'-dithiodipropionyl chloride intermediate, wherein the 3-dimethyamino-1-propanol and the 3,3'-dithiodipropionyl chloride intermediate react to form a bis((3-dimethylamino)propyl) 3,3'-disulfanediyldipropionate intermediate; dissolving 1,3-propane sultone in a suitable solvent; dissolving the bis((3-dimethylamino)propyl) 3,3'-disulfanediyldipropionate intermediate in a suitable solvent and adding it to the solution to form a zwitterion disulfide intermediate having the formula:

where m, n, and o are each an integer from about 1 to about 20; cleaving the zwitterion disulfide intermediate using 1,4-dithiothreitol (DTT) to produce two thiol functionalized zwitterionic compounds each having the formula:

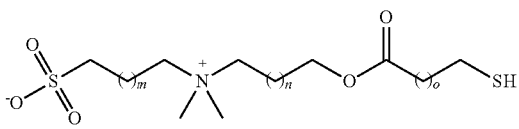

where m, n, and o are each an integer from about 1 to about 20; combining the allyl functionalized amino acid based PEU terpolymer intermediate and the thiol functionalized zwitterionic compounds and adding a suitable photoinitiator; and irradiating the combination to form the PEU-based adhesion barrier having a formula as identified above with respect to the first aspect of the present invention.

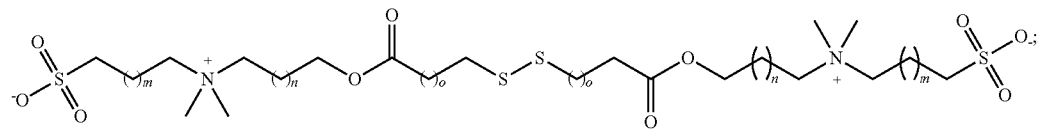

BRIEF DESCRIPTION OF THE DRAWINGS

For a more complete understanding of the features and advantages of the present invention, reference is now made to the detailed description of the invention along with the accompanying figures in which:

FIG. 2 is a $^1$H-NMR overlay for the 1-VAL-8 monomer. The 1-VAL-8 monomer shows successful synthesis based on the characteristic l-valine methyl resonance denoted 'k' and p-toluenesulfonic acid aromatic resonances. Integration confirms that this monomer is a bifunctional monomer with two protonated amine moieties.

Figure 23A:
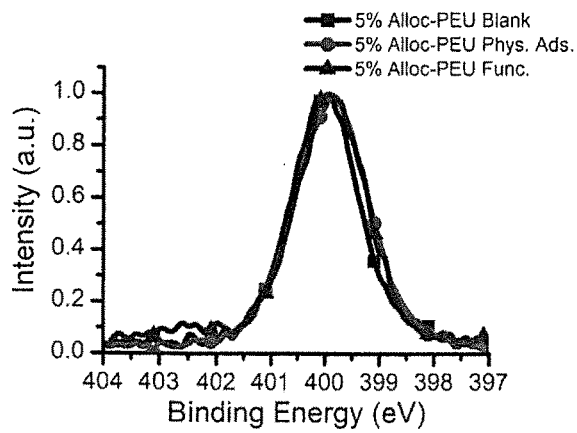
FIGS. 23A-F are graphs showing the results of high resolution XPS scans of the N is and S 2p orbitals for 5% alloc-PEU functionalized, physically adsorbed, and blank materials (FIGS. 23A-C) and 10% alloc-PEU functionalized, physically adsorbed, and blank materials (FIGS. 23D-F). High resolution XPS of the N is orbital for the 5% alloc-PEU functionalized, physically adsorbed, and blank materials were plotted (FIG. 23A). A slight broadening is observed with curve fitting indicating that there are two distinct peaks for the urea nitrogen (~399.9 eV) and quaternary ammonium nitrogen (~401.5 eV) for the 5% alloc-PEU functionalized material (integration 95.2:4.8) (FIG. 23B). High resolution XPS of the S 2p orbital was also taken and two distinct sulfur peaks correlating to the zwitterion-S—C sulfur (~162 eV) and ring opened sultone sulfur (~168 eV) are observed (integration 48:52) (FIG. 23C) were observed. High resolution XPS of the N is orbital for the 10% alloc-PEU functionalized, physically adsorbed, and blank materials were plotted (FIG. 23D). A broadening is observed with curve fitting for the urea nitrogen (~399.9 eV)
Figure 23D:
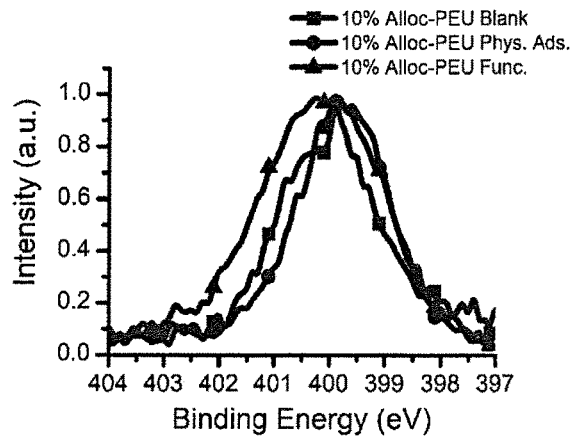
Figure 23B:
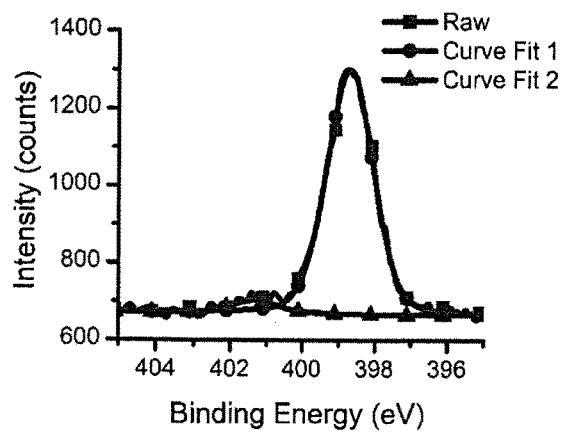
Figure 23E:
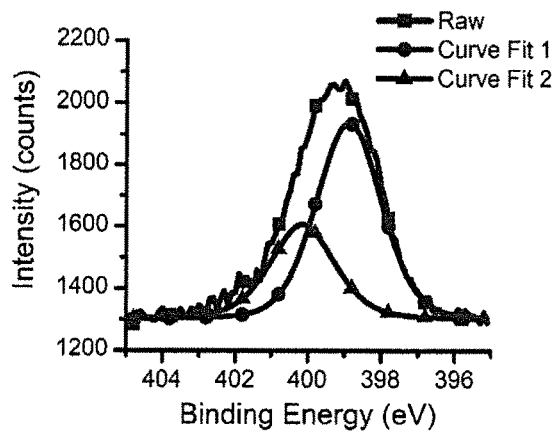
Figure 23C:
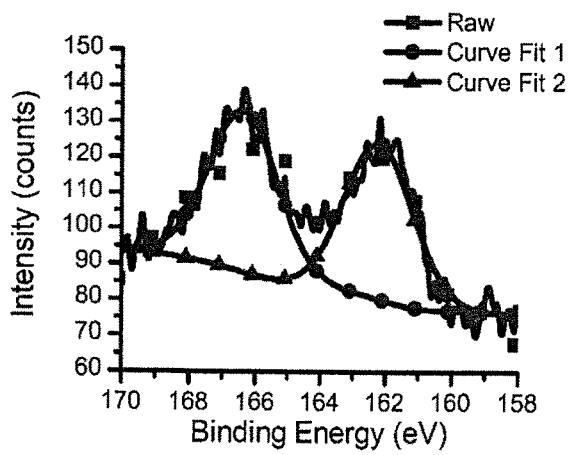
Figure 23F:
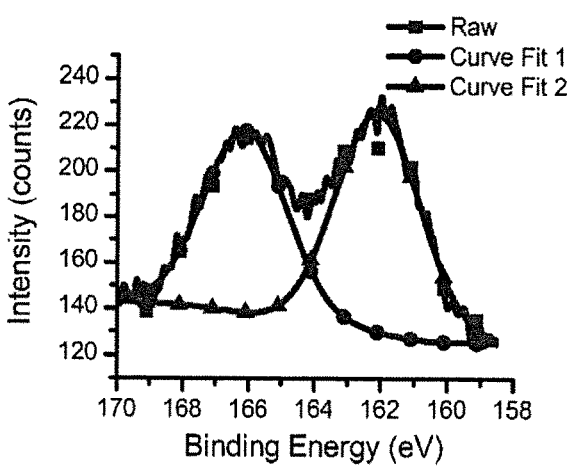

and quaternary ammonium nitrogen (~401.5 eV) showing integration values of 65.5:35.5 (FIG. 23E). High resolution XPS of the S 2p orbital of the 10% alloc-PEU functionalized material showed two distinct sulfur peaks correlating to the zwitterion-S—C sulfur and ring opened sultone sulfur are again observed (integration 55:45) (FIG. 23F).

Figure 24A:
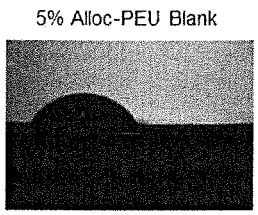
Figure 24B:
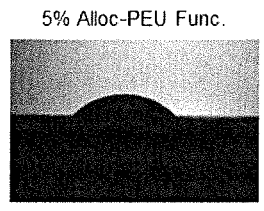
Figure 24C:
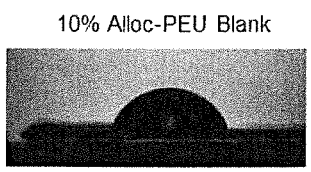
Figure 24D:
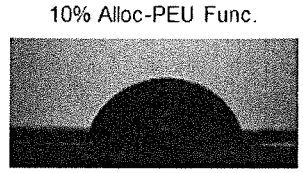
Figure 24E:
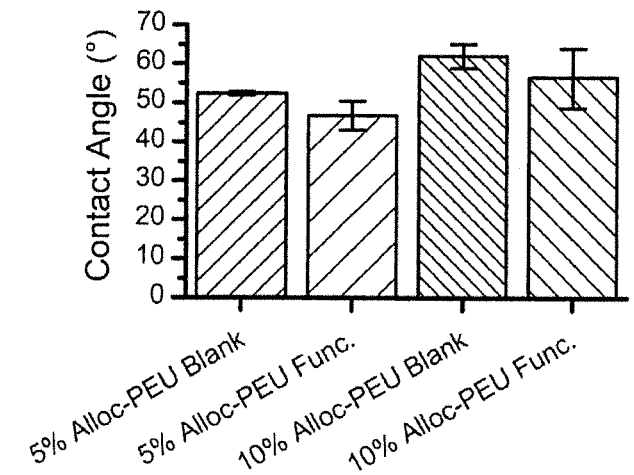

FIGS. 24A-E show the results of contact angle studies for functionalized and blank 5% and 10% alloc-PEU analogues. In these studies, the alloc-PEUs were coated with deionized water (5 µL), allowed to equilibrate for 10 minutes, and finally imaged with a goniometer (FIGS. 24A-D). The contact angles were measured using ImageJ software to afford the contact angle for each material (FIG. 24E). The contact angle of the 5% alloc-PEU blank material and the 5% alloc-PEU functionalized material is 52.3±0.5 and 46.6±3.6 respectively (n=4-6). The contact angle of the 10% alloc-PEU blank and 10% alloc-PEU functionalized materials were 61.8±3.1 and 56.3±7.6 respectively (n=4-6).

Figure 25A:
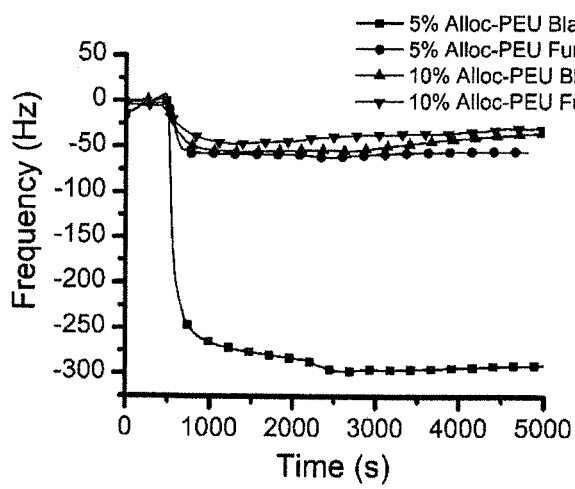
Figure 25B:
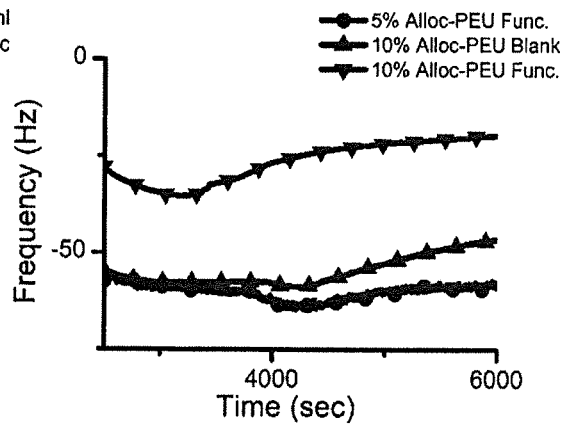
Figure 25C:
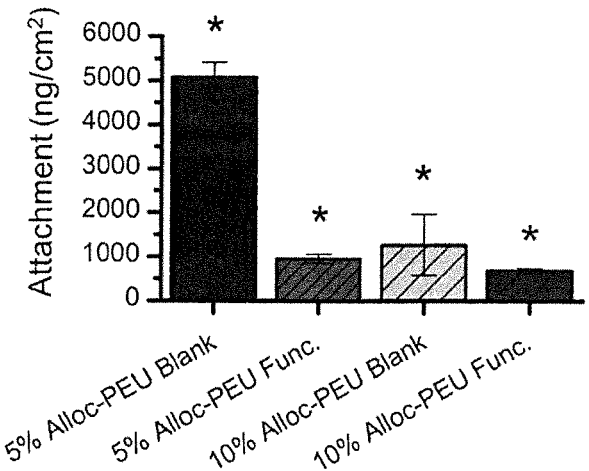
Figure 25D:
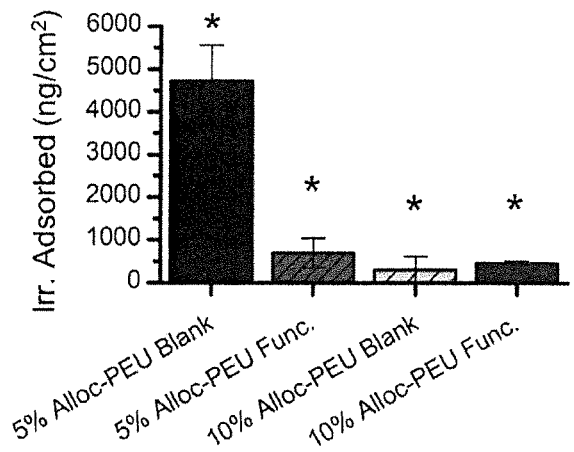

FIGS. 25A-D are graphs showing the results of QCM studies for 5% and 10% alloc-PEU analogues with fibrinogen. QCM representative curves for fibrinogen (1.5 mg/mL) on alloc-PEU analogues from the $5^{th}$ overtone are reported (FIGS. 25A-B). The amount of initially attached fibrinogen to the surface is reported (FIG. 25C) for 5% alloc-PEU blank (5072±339 ng/cm$^2$), 5% alloc-PEU functionalized (953±97 ng/cm$^2$), 10% alloc-PEU blank (1271±691 ng/cm$^2$), and 10% alloc-PEU functionalized (686±50 ng/cm$^2$) materials (n=3-4) (an * indicates a statistical difference between 5% alloc-PEU blank materials and any material that shares this symbol, $p<0.05$). The amount of fibrinogen irreversibly attached to the surface is reported for 5% alloc-PEU blank (4720±841 ng/cm$^2$), 5% alloc-PEU functionalized (701±344 ng/cm$^2$), 10% alloc-PEU blank (307±318 ng/cm$^2$), and 10% alloc-PEU functionalized 468±51 ng/cm$^2$) materials (n=3-4) (an * indicates a statistical difference between 5% alloc-PEU blank materials and any material that shares this symbol, $p<0.05$) (FIG. 25D).

Figure 26A:
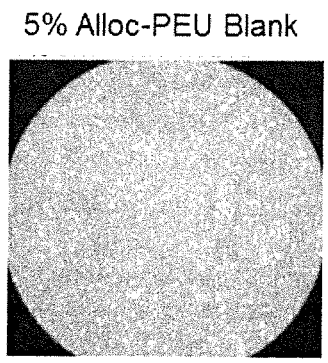
Figure 26B:
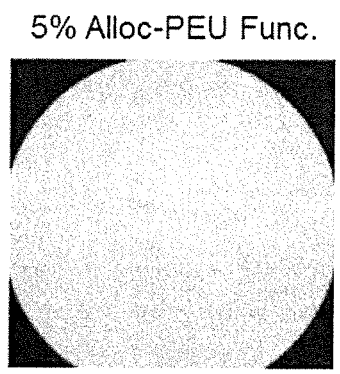
Figure 26C:
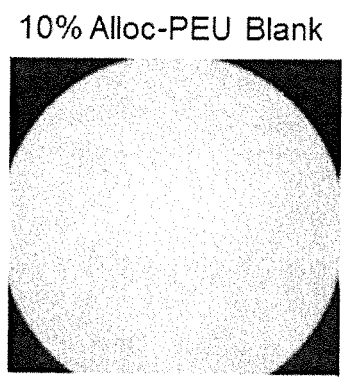
Figure 26D:
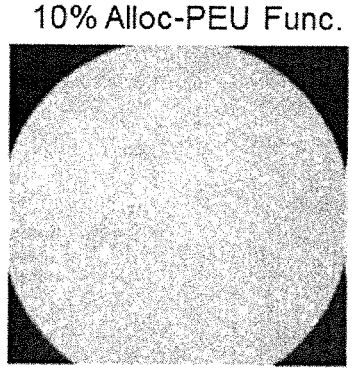

FIGS. 26A-G are images showing the results of in vitro cytotoxicity assessments of alloc-PEUs. 5% alloc-PEU blank (FIG. 26A), 5% alloc-PEU functionalized (FIG. 26B), 10% alloc-PEU blank (FIG. 26C), and 10% alloc-PEU functionalized (FIG. 26D) materials' extracted media was cultured with NIH-3T3 cells for 48 hours. Cell culture plates were then imaged and cell death and distress were scored from 0-4 (0=limited cell death and equivalent to negative control, 1=<25% cell death and distress, 2=<50% cell death and distress, 3=<75% cell death and distress, and 4=>75% cell death and distress)(See Tables 4, 5, below). Three controls were used where cells cultured without serum acted as a positive control (FIG. 26E), cells cultured with serum acted as a negative control (FIG. 26F), and cells cultured with media from Latex cots acted as a positive material control (FIG. 26G). All groups were scored with all alloc-PEU materials scoring equivalent to the negative control (score=0) (n=3 for alloc-PEUs, n=2 for negative control). Both positive controls elicited a cytotoxic score (score=4) (n=2 for positive controls).

FIG. 27 is a schematic drawing containing images showing the surgical procedures used for the antiadhesion rat hernia modeling discussed herein below. In these experiments, a paramedium laparotomy was first performed to expose the cecum (left image). The surgical sham control group of animals was closed without further procedures. All other groups had the cecum abraded to ensure adhesion development (center image). The adhesion control group was replaced without further modification. 10% alloc-PEU blank and functionalized films (2×8 cm) were sutured around the abraded cecum acting as a physical barrier between the underlying tissue (right image) and subsequently replaced in to the abdominal cavity (n=8 for all surgical groups).

FIGS. 28A-B are images showing the extent of adhesion images for implanted 10% alloc-PEU materials after three weeks of implantation. The highlighted areas in FIG. 28A show adhesions that circumvented the device and adhesions that formed to the sutures used to retain the 10% alloc-PEU blank device. The highlighted area in FIG. 28B shows adhesions circumventing the device to form on the abraded cecum underneath for the 10% alloc-PEU functionalized device.

Figure 29A:
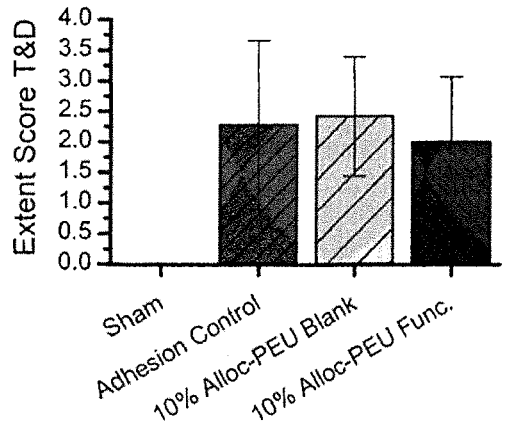
Figure 29B:
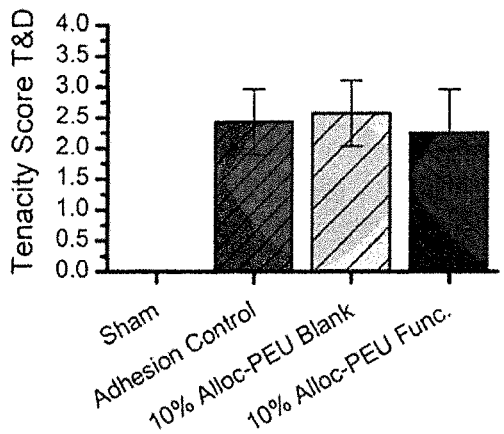
Figure 29C:
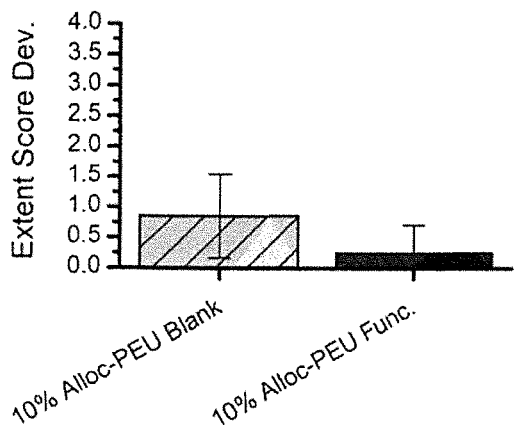
Figure 29D:
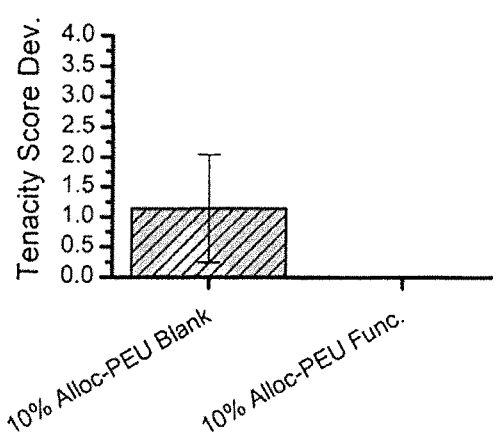

FIGS. 29A-D are graphs showing the adhesion extent and tenacity of explanted materials in the rat hernia modeling experiments shown in FIG. 27. The overall extent of adhesion (includes adhesions between tissue and abraded cecum and adhesion of abraded cecum to the device) with the sham, adhesion positive control, 10% alloc-PEU blank, and 10% alloc-PEU functionalized material having scores of 0±0, 2.3±1.4, 2.4±1.0, and 2.0±1.1 respectively (FIG. 29A). The tenacity of adhesions to the device and underlying tissue were scored with the sham, adhesion positive control, 10% alloc-PEU blank, and 10% alloc-PEU functionalized material having scores of 0.0±0.0, 2.4±0.5, 2.6±0.5, and 2.3±0.7 respectively (FIG. 29B). The extent of adhesions exclusively attached to the implanted device and abraded cecum were scored with minimally observed adhesions for the 10% alloc-PEU functionalized material (0.3±0.5) and the 10% alloc-PEU blank material (0.9±0.7) (FIG. 29C). No tenacity of adhesion was observed for the 10% alloc-PEU functionalized material with slight tenacity being shown for the 10% alloc-PEU blank material (1.1±0.9) (FIG. 29D). No difference was observed for extent of adhesion however there was statistically significant difference in tenacity between the 10% alloc-PEU blank material and the 10% alloc-PEU functionalized material ($p<0.004$). All values reported are mean standard deviation.

Figure 30A:
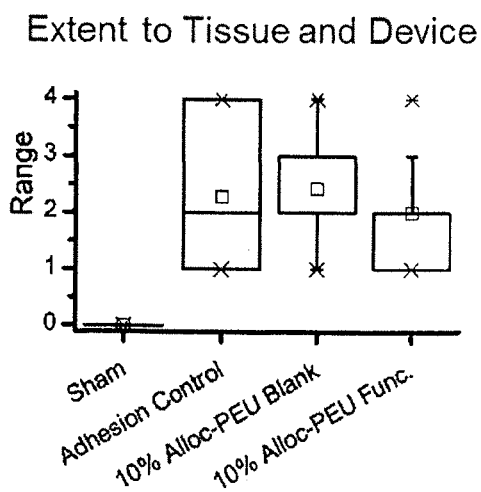
Figure 30B:
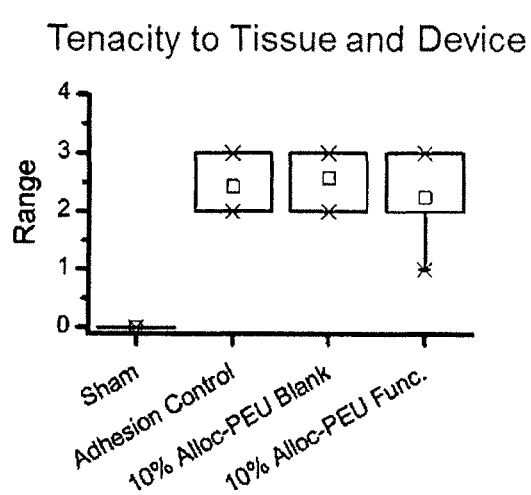
Figure 30C:
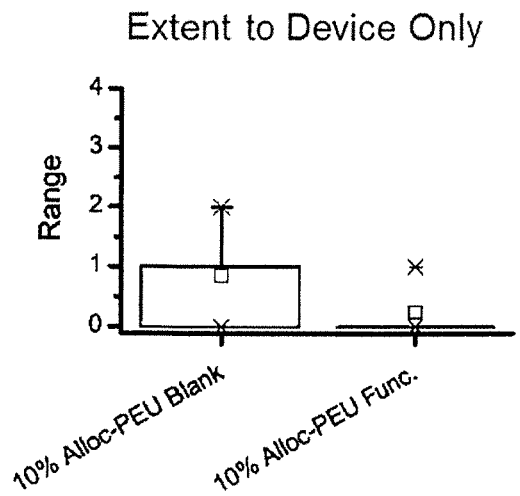
Figure 30D:
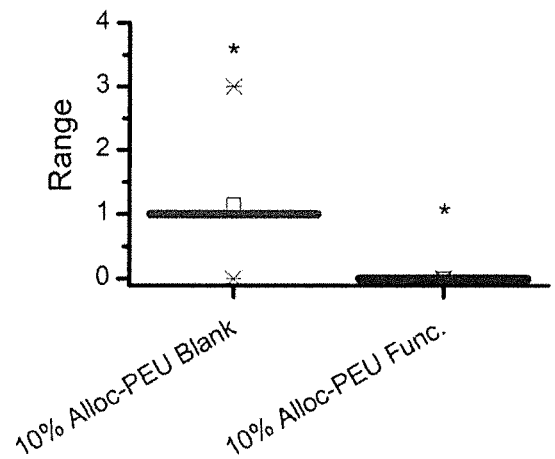
Figure 31A:
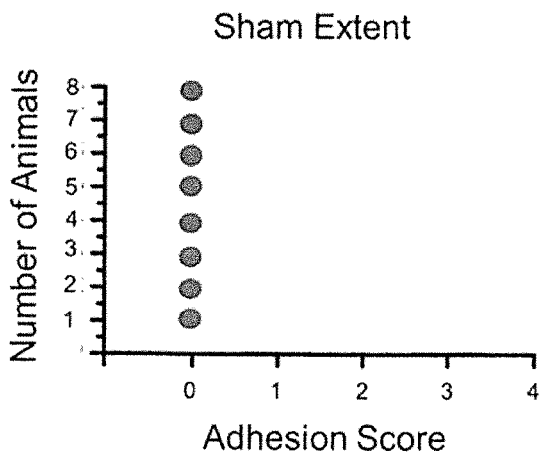
Figure 31B:
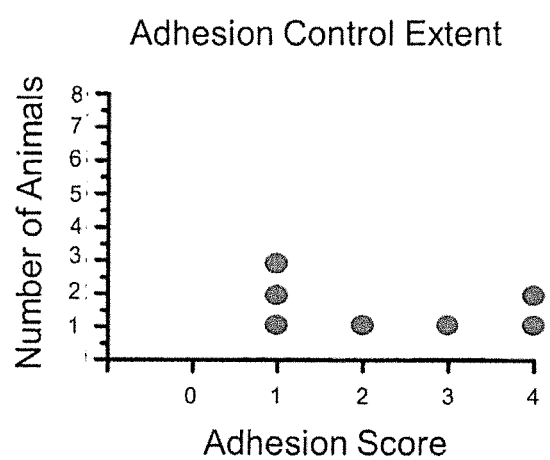
Figure 31C:
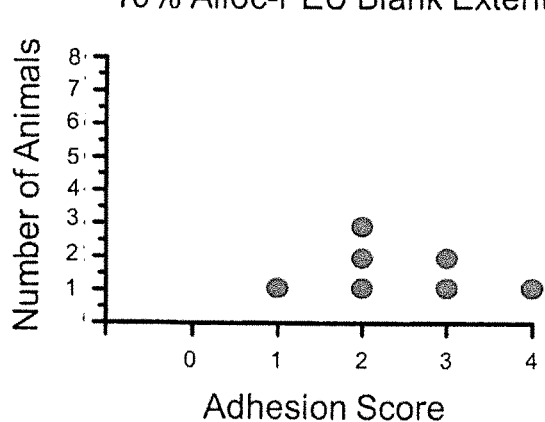
Figure 31D:
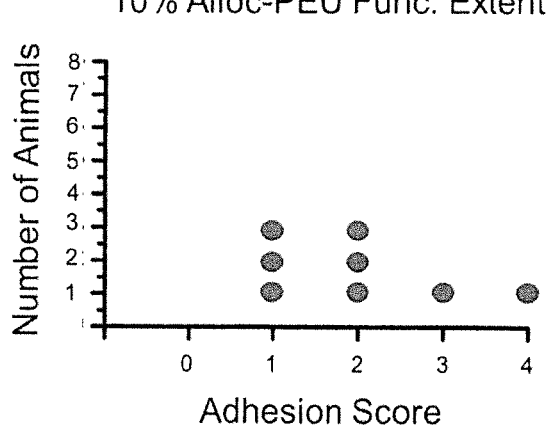
Figure 31E:
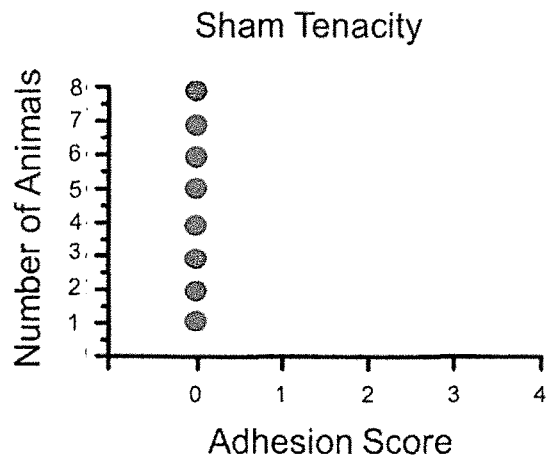
Figure 31F:
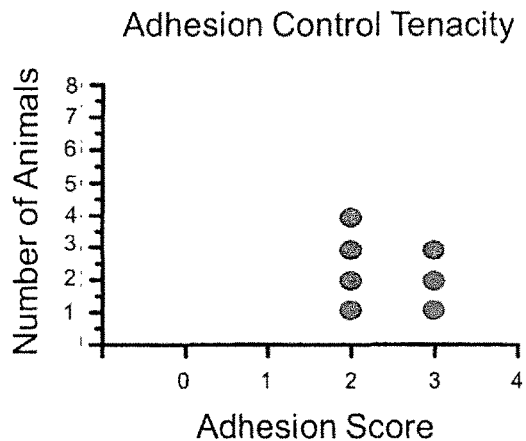
Figure 31G:
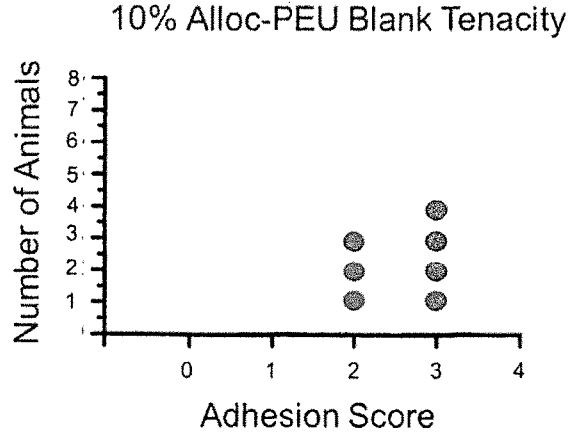
Figure 31H:
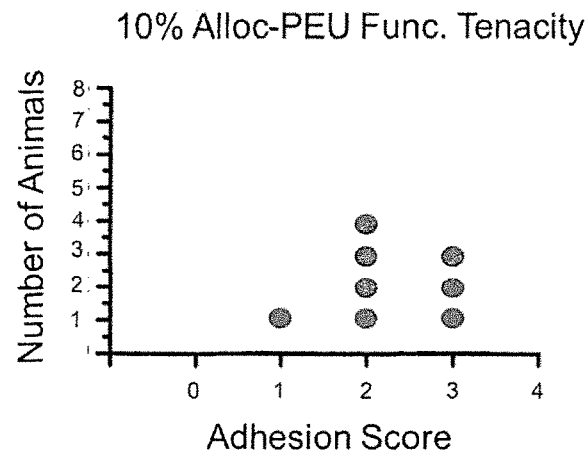

FIGS. 30A-D are adhesion extent and tenacity box plots of explanted materials. The overall extent of adhesion (includes adhesions between tissue and abraded cecum and adhesion of abraded cecum to the device) with the sham, adhesion positive control, 10% alloc-PEU blank, and 10% alloc-PEU functionalized material having average scores of 0±0, 2.3±1.4, 2.4±1.0, and 2.0±1.1 respectively (FIG. 30A). Tenacity of adhesions to the device and underlying tissue were scored with the sham, adhesion positive control, 10% alloc-PEU blank, and 10% alloc-PEU functionalized material having scores of 0.0±0.0, 2.4±0.5, 2.6±0.5, and 2.3±0.7 respectively (FIG. 30B). No significant difference was observed between the adhesion control, 10% alloc-PEU blank, and 10% alloc-PEU functionalized material using a Kruskall-Wallis test with exact option and a post-hoc Mann-Whitney U test with a Bonferroni adjusted alpha of 0.0083. The extent of adhesions exclusively attached to the implanted device and abraded cecum were scored with minimally observed adhesions for the 10% alloc-PEU functionalized material (0.3±0.5) and the 10% alloc-PEU blank material (0.9±0.7) (FIG. 30C). No tenacity of adhesion was observed for the 10% alloc-PEU functionalized material with slight tenacity being shown for the 10% alloc-PEU blank material (1.1±0.9) (FIG. 30D). Statistical analysis was shown using a Mann-Whitney U test and statistical difference was observed between the 10% alloc-PEU blank, and 10% alloc-PEU functionalized material indicated by an * with a p value<0.004.

FIGS. 31A-H are graphs showing adhesion extent and tenacity of explanted materials. The overall extent of adhesion (includes adhesions between tissue and abraded cecum and adhesion of abraded cecum to the device) with the sham, adhesion positive control, 10% alloc-PEU blank, and 10% alloc-PEU functionalized material having average scores of 0±0, 2.3±1.4, 2.4±1.0, and 2.0±1.1, respectively (FIGS. 31A-D). No significant difference was observed between the adhesion control, 10% alloc-PEU blank, and 10% alloc-PEU functionalized material using a Kruskall-Wallis test with exact option and a post-hoc Mann-Whitney U test with a Bonferroni adjusted alpha of 0.0083. Tenacity of adhesions to the device and underlying tissue were scored with the sham, adhesion positive control, 10% alloc-PEU blank, and 10% alloc-PEU functionalized material having scores of 0.0±0.0, 2.4±0.5, 2.6±0.5, and 2.3±0.7, respectively (FIGS. 31E-H). Statistical analysis was again done using a Kruskall-Wallis test with exact option and a post-hoc Mann-Whitney U test with a Bonferroni adjusted alpha of 0.0083. No statistical difference was observed between the adhesion control, 10% alloc-PEU blank, and 10% alloc-PEU functionalized material. All values reported are mean±standard deviation.

Figure 32A:
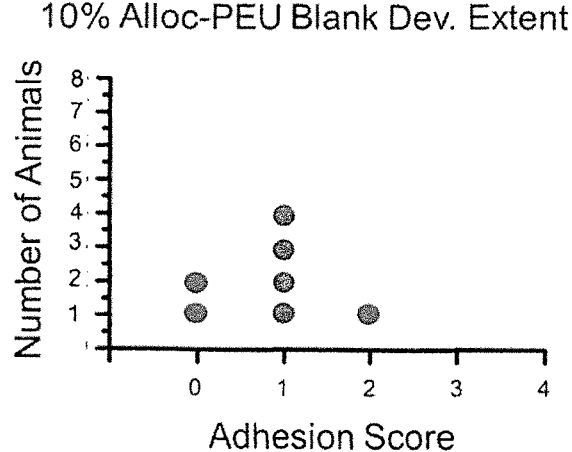
Figure 32B:
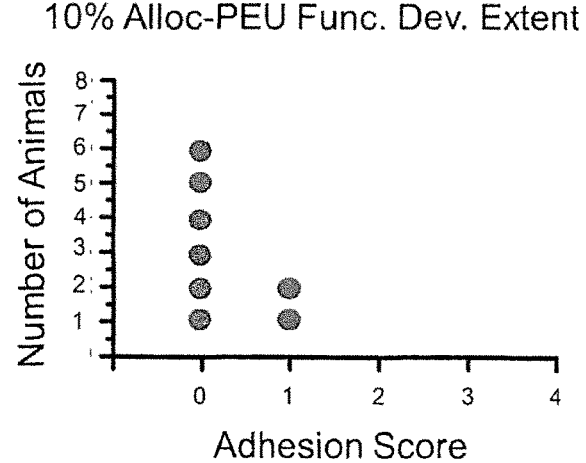
Figure 32C:
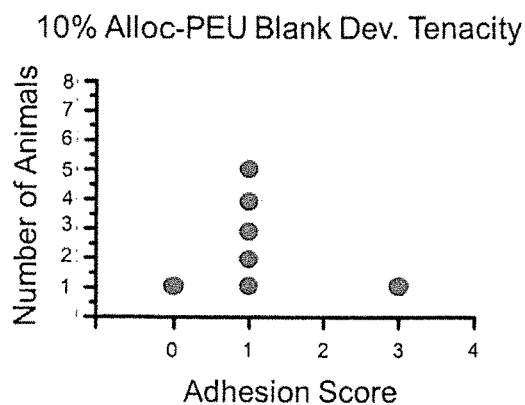

FIGS. 32A-D are graphs showing the extent of adhesions exclusively attached to the implanted device and abraded cecum were scored with minimally observed adhesions for the 10% alloc-PEU functionalized material (0.3±0.5) and the 10% alloc-PEU blank material (0.9±0.7) (FIGS. 32A-B). No tenacity of adhesion was observed for the 10% alloc-PEU functionalized material (FIG. 32D) with slight tenacity being shown for the 10% alloc-PEU blank material (1.1±0.9) (FIG. 32C). Extent and tenacity to device for each material were compared using a Mann-Whitney U test with exact option. No difference was observed for extent of adhesion however there was statistically significant difference in tenacity between the 10% alloc-PEU blank material and the 10% alloc-PEU functionalized material (p<0.004). All values reported are mean standard deviation.

Figure 33A:
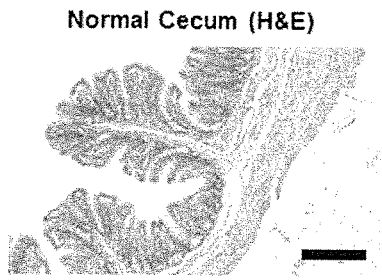
Figure 33B:
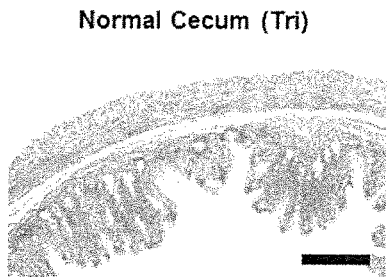
Figure 33C:
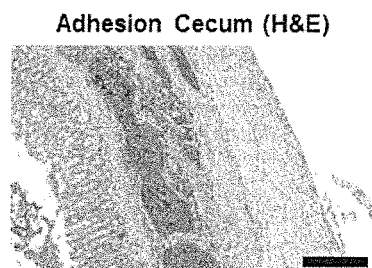
Figure 33D:
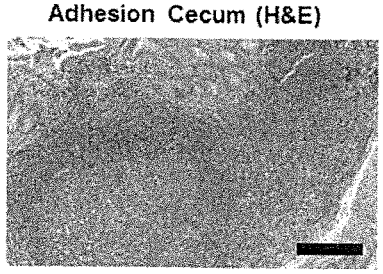
Figure 33E:
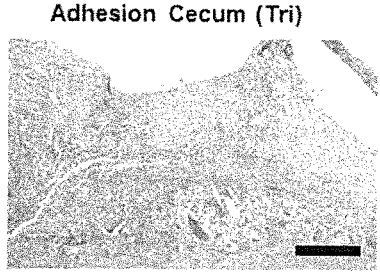
Figure 33F:
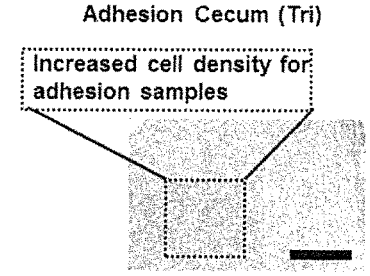

FIGS. 33A-F are micrographs showing the results of adhesion histological assessment of tissue samples collected post-mortem and subjected to histological staining to identify cell type and inflammation present at the location of observed adhesions. The tissue samples were stained with hematoxylin and eosin (H&E) or Masson's trichrome (tri) to identify collagen deposition and cell types present surrounding the adhesion areas. Representative images are shown for the groups under study. Sham control groups displayed a normal cecum without abnormal cellular densities (FIGS. 33A-B). All other groups displayed hyperplastic lymphoid tissue (FIGS. 33C-D) and dark-stained bundles of collagen fibers containing numerous fibroblasts and several giant cells (FIGS. 33E-F).

Figure 34A:
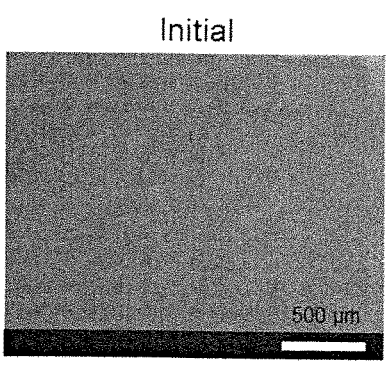
Figure 34B:
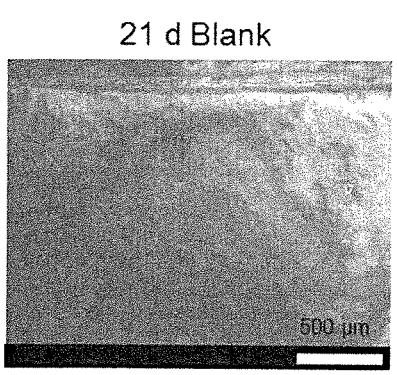
Figure 34C:
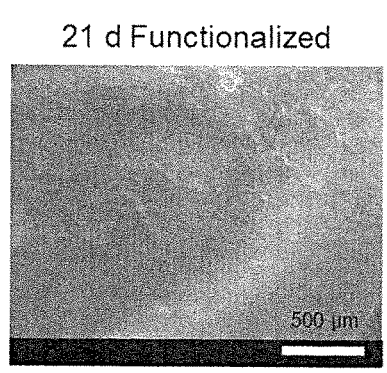

FIGS. 34A-C are scanning electron microscopy (SEM) images of solvent cast films post-EtO sterilization (FIG. 34A), and of 10% alloc-PEU blank (FIG. 34B) and 10% alloc-PEU functionalized (FIG. 34C) films after 21 days of implantation.

Figure 35:
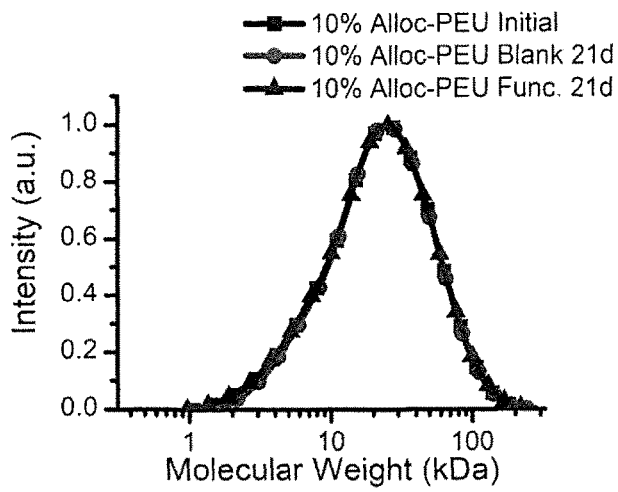

FIG. 35 is a graph showing molecular mass degradation of 10% alloc-PEU derivatives using size-exclusion chromatography-gel permeation chromatography (SEC-GPC) in THF. As can be seen, there was little, if any, degradation of the polymer chains for these 10% alloc-PEU derivatives when implanted over a 21 day period.

Figure 36A:
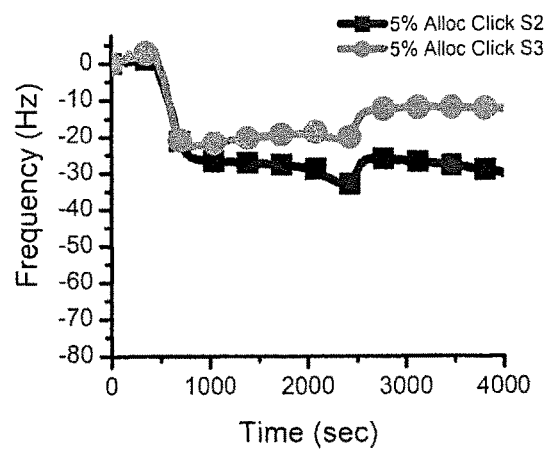
Figure 36B:
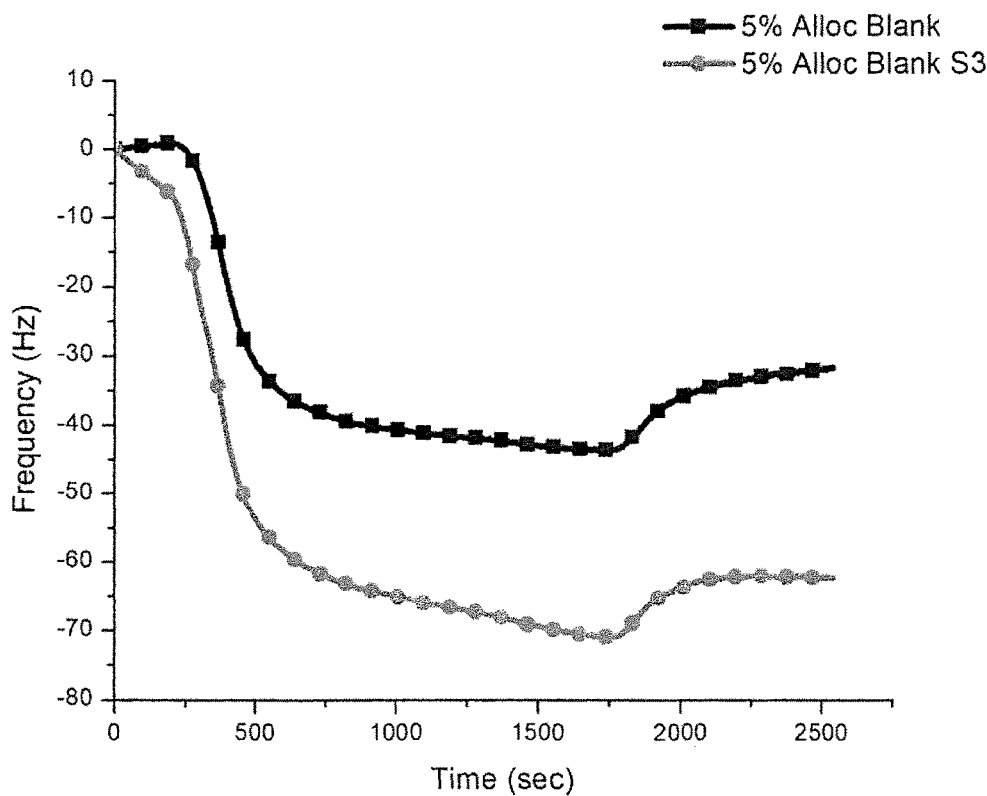

FIGS. 36A-B are graphs showing quartz crystal microbalance (QCM) results for protein adhesion for a zwitterionic amino acid based PEU polymer according to the present invention (FIG. 36A) and an amino acid based PEU polymer without the zwitterionic side chain (FIG. 36B).

DETAILED DESCRIPTION OF THE ILLUSTRATIVE EMBODIMENTS

In various embodiments, the present invention is directed to a the present invention is directed to anti-adhesion poly (ester urea)s (PEUs) that are surface functionalized with a scalable zwitterion thiol. As set forth above, burst testing mechanical properties indicate that these PEUs are similar to soft tissue while preventing adhesion (Force at break 54-118 N). These materials elicit a limited inflammatory response in vivo in a rat model (2.5-6.5 on ISO 10993-6 Annex E for implanted biomaterials). It is believed that these functionalized anti-adhesion PEUs have the potential to be translatable materials to aid in ventral hernia treatment.

As used herein, the terms "comprising" "to comprise" and the like do not exclude the presence of further elements or steps in addition to those listed in a claim. Similarly, the terms "a," "an" or "the" before an element or feature does not exclude the presence of a plurality of these elements or features, unless the context clearly dictates otherwise. Unless specifically stated or obvious from context, as used herein, the term "about" is understood as within a range of normal tolerance in the art, for example within 2 standard deviations of the mean. Unless otherwise clear from context, all numerical values provided herein in the specification and the claim can be modified by the term "about." It should be also understood that the ranges provided herein are a shorthand for all of the values within the range and, further, that the individual range values presented herein can be combined to form additional non-disclosed ranges.

In a first aspect, the present invention is directed to a poly(ester urea) (PEU)-based adhesion barrier comprising an amino acid based poly(ester urea) backbone and one or more zwitterionic side chains connected to said amino acid based poly(ester urea) backbone through a sulfide bond. In these embodiments, the amino acid based poly(ester urea) backbone comprises the residues of one or more amino acid-based diester monomers and the residues of one or more amino acid-based allyloxy diester monomers.

In various embodiments, the amino acid-based diester monomers residues in the amino acid based poly(ester urea) backbone of the PEU-based adhesion barrier of the present invention may comprise, without limitation, two valine, phenylalanine, leucine, isoleucine, tyrosine, alanine, methionine, glycine, or cysteine residues separated by from 2 to 20 carbon atoms. In some embodiments, the amino acid-based diester segments are linear and the amino acid residues of the amino-acid-based diester segments are separated by from about 2 to about 20 carbon atoms. In some embodiments, all of the amino acids in the amino acid based diester monomers are residues of the same amino acid, but this need not be the case and one or more embodiments in which the amino acid based diester monomers are comprise residues of the different amino acids. In some of these embodiments, the amino acid residues are separated by from about 2 to about 15 carbon atoms. In some of these embodiments, the amino acid residues are separated by from about 2 to about 20 carbon atoms. In some of these embodiments, the amino acid residues are separated by from about 4 to about 12 carbon atoms. In some of these embodiments, the amino acid residues are separated by from about 6 to about 12 carbon atoms. In some of these embodiments, the amino acid residues are separated by from about 6 to about 15 carbon atoms. In some of these embodiments, the amino acid residues are separated by from about 8 to about 12 carbon atoms.

In some embodiments, the amino acids residues may be separated from each other by the residue of a linear diol. Suitable linear diols may include, without limitation, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol, 1,17-heptadecanediol, 1,18-octadecanediol, 1,19-nonadecanediol, 1,20-icosanediol, and combinations thereof. In some embodiments, the polyol may be 1,8-octanediol and is commercially available from Sigma Aldrich Company LLC (St. Louis, Mo.) or Alfa Aesar (Ward Hill, Mass.).

In some embodiments, the amino acid-based diester monomer residues may form segments in the amino acid based poly(ester urea) backbone having the formula:

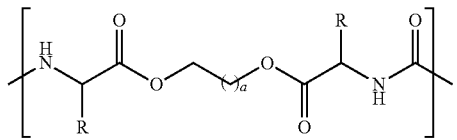

wherein R is —CH$_3$, —(CH$_2$)$_3$NHC(NH$_2$)C=NH, —CH$_2$CONH$_2$, —CH$_2$COOH, —CH$_2$SH, —(CH$_2$)$_2$COOH, —(CH$_2$)$_2$CONH$_2$, —NH$_2$, —CH$_2$C=CH—N=CH—NH, —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH$_2$OH, —CH(OH)CH$_3$, —CH$_2$—C=CH—NH-Ph, —CH$_2$-Ph-OH, —CH(CH$_3$)$_2$, or —CH$_2$C$_6$H$_4$OCH$_2$C$_6$H$_5$ and a is an integer from 1 to 20. In some of these embodiments, a may be an integer from about 1 to about 18. In some embodiments, a may be an integer from 1 to 18, in other embodiments, from 1 to 15, in other embodiments, from 1 to 12, in other embodiments, from 1 to 8, in other embodiments, from 1 to 4, in other embodiments, from 2 to 20, in other embodiments, from 6 to 20, in other embodiments, from 10 to 20, in other embodiments, from 15 to 20, and in other embodiments, from 4 to 12. Here, as well as elsewhere in the specification and claims, individual range values can be combined to form additional non-disclosed ranges. Here, as well as elsewhere in the specification and claims, individual range values can be combined to form additional non-disclosed ranges.

In one or more embodiments, the amino acid based poly(ester urea) backbone may be branched. In these embodiments, the amino acid based poly(ester urea) backbone may comprise the residues of one or more amino acid-based multiester monomers or one or more amino acid-based allyloxy multiester monomers. In some of these embodiments, the one or more amino acid-based multiester monomers will comprise the residues of three or more amino acids separated by from 2 to about 60 carbon atoms. In some embodiments, the one or more amino acid-based multiester monomers will comprise the residues of three or more amino acids joined to the residue of a polyol having from about 2 to about 60 carbon atoms. In some embodiments, the one or more amino acid-based multiester monomers will comprise the residues of three or more amino acids each separated from the other amino acid residues by from 2 to about 20 carbon atoms. In some embodiments, the one or more amino acid-based multiester monomers will comprise the residues of three or more amino acids joined to the residue of a allyloxy polyol having a pendent allyloxy group and from about 2 to about 60 carbon atoms.

In one or more embodiments, the amino acid-based diester monomers residues in the amino acid based poly (ester urea) backbone of the PEU-based adhesion barrier of the present invention may comprise one or more of those disclosed in U.S. Pat. Nos. 9,745,414 and 9,988,492; U.S. Published Patent Application Nos. U.S. 2016/0250382, US 2017/0081476, and US2017/0210852; and International Application Nos. WO 2017/189534 and WO 2019/032541, the disclosures of which are incorporated herein by reference in their entireties.

In one or more embodiments, the amino acid-based diester monomers residues in the amino acid based PEU backbone of the PEU-based adhesion barrier of the present invention may comprise the residues of one or more amino acid-based diester monomers having the formula:

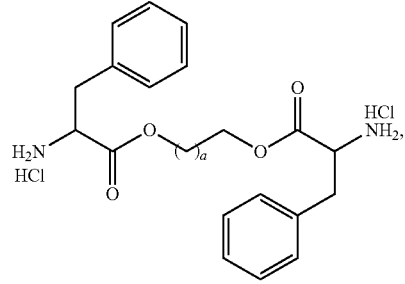

(XIII)

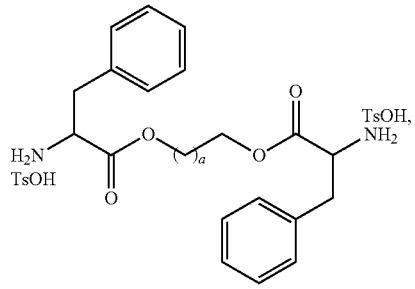

(VII)

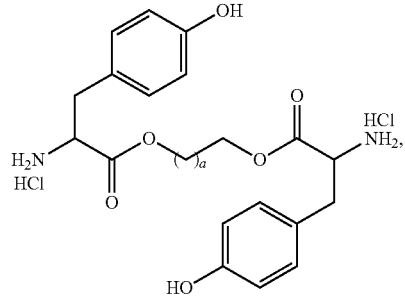

(XIV)

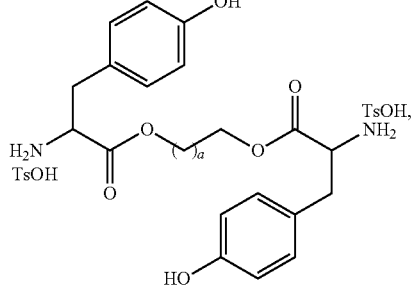

(XV)

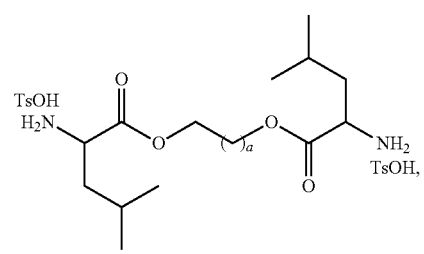 (IX)
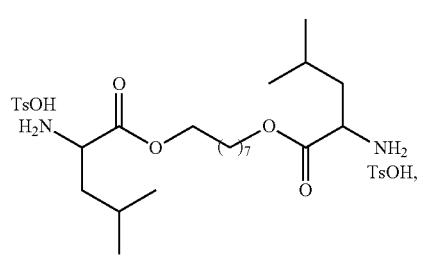 (XVI)
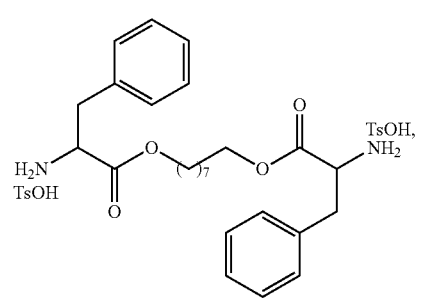 (XVII)
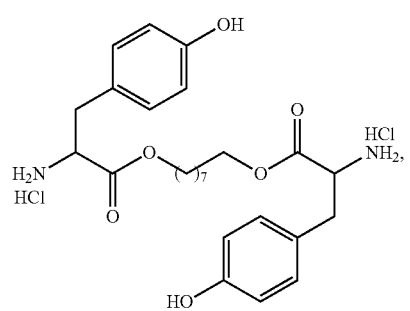 (XVIII)
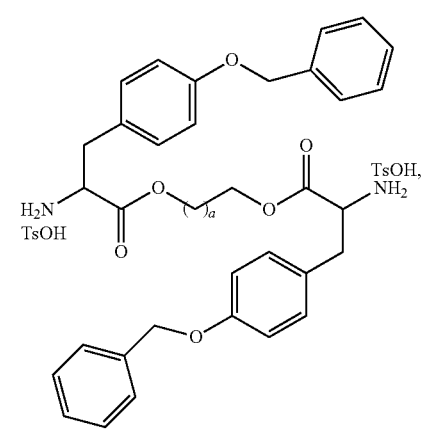 (XI)
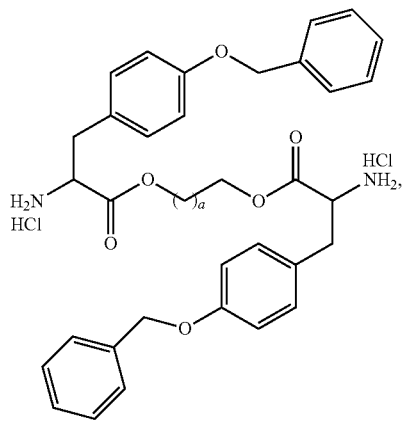 (XII)
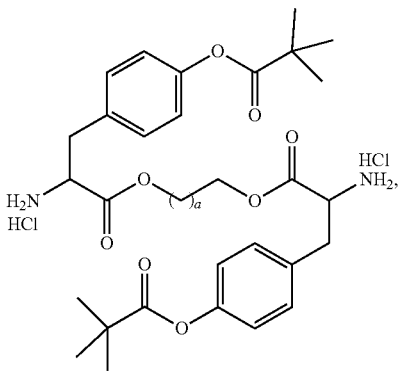 (XIX)
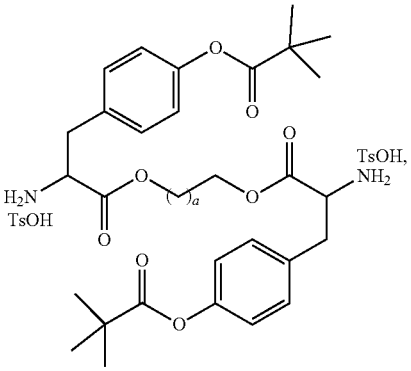 (XX)
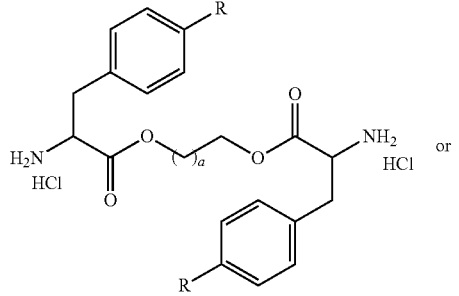 (XXI)

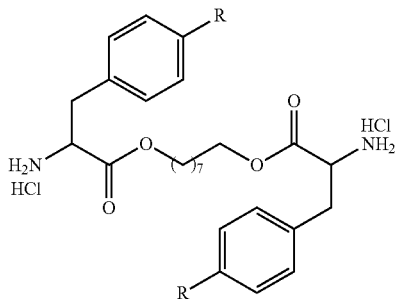

where a is an integer from about 1 to about 20 and R is H, OH, or —OCOO(CH$_2$)$_2$C$_6$H$_3$(OH)$_2$. In one or more embodiments, a may be any value or range of values for a set forth above.

In some embodiments, the amino acid-based diester monomers residues in the amino acid based PEU backbone of the PEU-based adhesion barrier of the present invention may be residues of amino acid-based diester monomers having the formula:

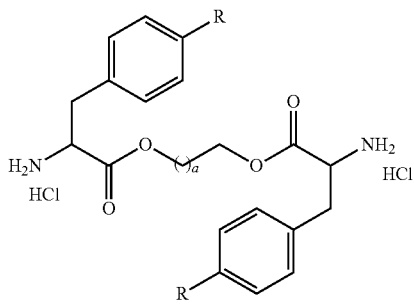

where R is I, OH, OCH$_2$C≡CH, OCH$_2$CH$_2$CH$_2$N$_3$, OCH$_2$CH$_2$CH$_2$CH=CH$_2$, OCH$_2$Ph, or OCOCH$_2$CH$_2$COCH$_3$; and a in an integer from 1 to 20. In one or more embodiments, a may be any value or range of values for a set forth above.

In one or more embodiments, the amino acid-based diester monomers residues in the amino acid based PEU backbone of the PEU-based adhesion barrier of the present invention may include residues of amino acid-based diester monomers having the formula:

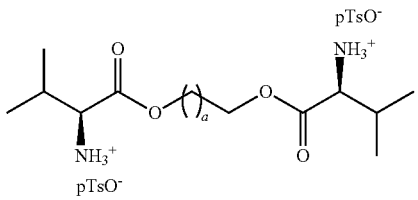

where a is an integer from 1 to 20. In one or more embodiments, a may be any value or range of values for a set forth above.

In one or more embodiments, the amino acid-based diester monomers residues in the amino acid based PEU backbone of the PEU-based adhesion barrier of the present invention may include residues of amino acid-based diester monomers having the formula:

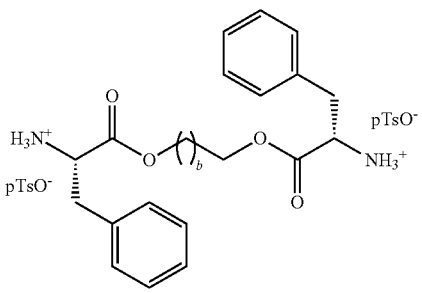

where b is an integer from 1 to 20. In some embodiments, b may be an integer from 1 to 18, in other embodiments, from 1 to 15, in other embodiments, from 1 to 12, in other embodiments, from 1 to 8, in other embodiments, from 1 to 4, in other embodiments, from 2 to 20, in other embodiments, from 6 to 20, in other embodiments, from 10 to 20, in other embodiments, from 15 to 20, and in other embodiments, from 4 to 12. Here, as well as elsewhere in the specification and claims, individual range values can be combined to form additional non-disclosed ranges.

In one or more embodiments, the amino acid-based PEU adhesion barrier may be comprised of two or more different types of amino acid-based diester residues, each type of diester segment being the residue of a different monomer used to form the PEU. As used herein, reference to a particular "type" of amino acid-based diester residue is intended to refer to one or more amino acid-based diester residues formed from the same amino acid-based diester monomer (or an amine protected analog thereof) and having identical structure and function. In some embodiments, the amino acid-based PEU adhesion barriers of the present invention will comprise one type of amino acid-based diester monomers residue. In other embodiments, the amino acid-based PEU adhesion barriers of the present invention will comprise two or more different types of amino acid-based diester monomer residues.

In some embodiments, the amino acid-based PEU adhesion barriers of the present invention will comprise a PEU terpolymer comprising the residues of two different types of amino acid-based diester monomers, and the residue of an amino acid-based allyloxy diester monomer. As used herein, the term "terpolymer" refers generally to a polymer formed of three different types of monomers and the term "PEU terpolymer" refers to a poly(ester urea) polymer formed from and comprising the residues of three different types of diester or multi-ester monomers, joined together by urea bonds. As follows, the term "amino acid based PEU terpolymer" refers to an amino acid based poly(ester urea) polymer formed from and comprising the residues of three different types of amino acid based diester or multi-ester monomers, joined together by urea bonds. In one or more embodiments, the amino acid based poly(ester urea) backbone of the PEU-based adhesion barrier of the present invention will be an amino acid based PEU terpolymer comprising one or more first amino acid-based diester monomers residues, one or more second amino acid-based diester monomers, and one or more amino acid-based allyloxy diester monomer residues, as described above. In these embodiments, the first and second amino acid-based diester monomers residues may be any of the amino acid-based diester monomers described above, but are different from each other.

As set forth above, the amino acid based poly(ester urea) backbone of the PEU-based adhesion barrier of the present invention also comprises the residue of one or more amino acid-based allyloxy diester monomer. The amino acid-based allyloxy diester monomer residues are not particularly limited and may include the residue of any suitable diester monomer having a pendent allyl group, preferably a pendent allyloxy functional group. In one or more embodiments, the amino acid-based allyloxy diester monomer residue is the residue of an amine protected L-tyrosine-1,3-allyloxy-diester monomer.

In one or more embodiments, the amino acid-based allyloxy diester monomer residue is the residue of a compound having the formula:

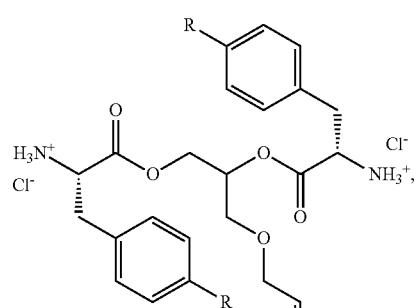

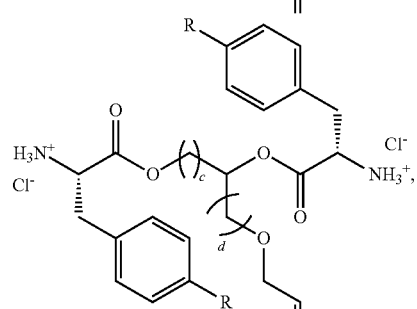

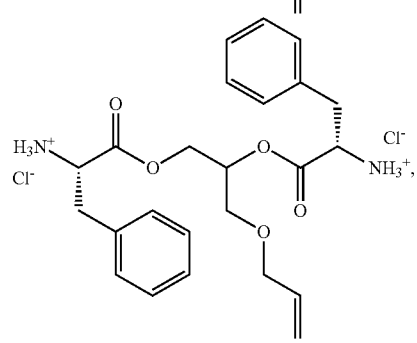

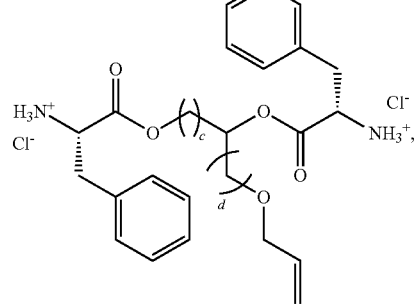

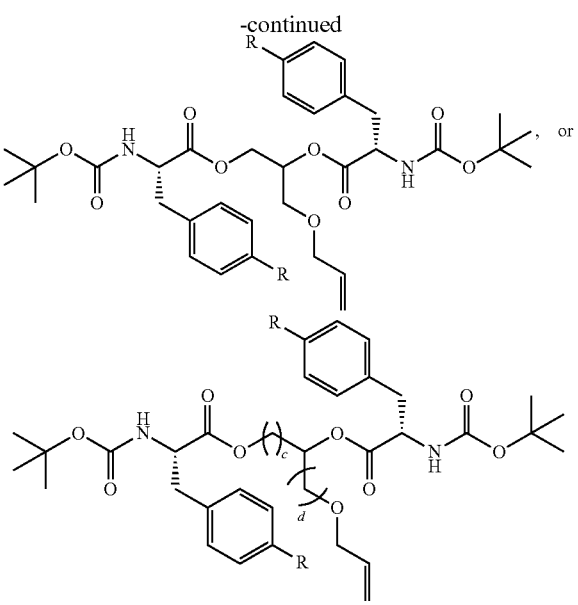

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; and c and d are each an integer from about 1 to about 20. In one or more embodiments, c and d may have any of the values or range of values for a and b set forth above.

Finally, the amino acid based PEU backbone of the PEU-based adhesion barriers of the present invention will also include the residue of one or more PEU forming materials. As used herein, the terms "PEU forming compound(s)," "PEU forming material(s)" "urea bond forming compound(s)," and "urea bond forming material(s)," are used interchangeably to refer to a material capable of placing a carboxyl group between two amine groups, thereby forming a urea bond. Suitable PEU forming material may include, without limitation, triphosgene, diphosgene, or phosgene.

In one or more embodiments, the amino acid based PEU backbone of the PEU-based adhesion barrier of the present invention will comprise from about 0.5 to about 50 mole percent amino acid-based allyloxy diester monomer residues. In some embodiments, the amino acid based PEU backbone of the PEU-based adhesion barrier of the present invention will comprise from about 1 mol % to about 50 mol %, in other embodiments, from about 5 mol % to about 50 mol %, in other embodiments, from about 10 mol % to about 50 mol %, in other embodiments, from about 15 mol % to about 50 mol %, in other embodiments, from about 20 mol % to about 50 mol %, in other embodiments, from about 30 mol % to about 50 mol %, in other embodiments, from about 0.5 mol % to about 40 mol %, in other embodiments, from about 0.5 mol % to about 30 mol %, and in other embodiments, from about 0.5 mol % to about 20 mol % amino acid-based allyloxy diester monomer residues.

As set forth above, the PEU-based adhesion barrier of the present invention further comprises one or more zwitterionic side chains connected to the amino acid based poly(ester urea) backbone through a sulfide bond. In one or more embodiments, the zwitterionic side chains connected to the amino acid based poly(ester urea) backbone comprise the residue of a zwitterionic thiol. As will be apparent, in these embodiments, the residues of these zwitterionic thiols are connected to the amino acid-based allyloxy diester monomer residues on the amino acid based PEU backbone through a sulfide bond formed as a result of a thiol-ene type "click" reaction between the thiol group on the zwitterionic thiol and the pendent allyl group on the amino acid-based allyloxy diester monomer. As used herein, the terms "click reaction," "click chemistry," "click chemistry methods," "click chemistry reactions," are used interchangeably to refer to a group of orthogonal conjugation reactions, generally referred to in the art as "click" reactions, that fulfill the following prerequisites: (i) high yield, nearly quantitative conversion; (ii) biologically benign conditions (aqueous solution, ambient temperature, and near physiologic pH); (iii) limited or no residual byproduct. These reactions are typically simple to perform, high yielding, stereospecific, wide in scope, create only byproducts that can be removed without chromatography, and can be conducted in easily removable or benign solvents. Similarly, the term "clickable" refers to a molecule or functional group capable of bonding via a click reaction.

In various embodiments, the zwitterionic side chains will comprise a zwitterionic moiety. In one or more embodiments, the zwitterionic moiety may be a quaternary ammonium compound or a ring opened sultone. In one or more embodiments, the zwitterionic side chains will comprise the residue of a thiol functionalized ring-opened sultone. In some of these embodiments, the zwitterionic side chains comprise the residue of a zwitterionic thiol having the formula:

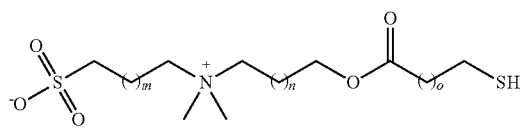

where m is an integer from about 1 to about 20; n is an integer from about 1 to about 20, and o is an integer from about 1 to about 20. In some embodiments, m may be an integer from 1 to 18, in other embodiments, from 1 to 15, in other embodiments, from 1 to 12, in other embodiments, from 1 to 8, in other embodiments, from 1 to 4, in other embodiments, from 2 to 20, in other embodiments, from 6 to 20, in other embodiments, from 10 to 20, in other embodiments, from 15 to 20, and in other embodiments, from 4 to 12. In some embodiments, n may be an integer from 1 to 18, in other embodiments, from 1 to 15, in other embodiments, from 1 to 12, in other embodiments, from 1 to 8, in other embodiments, from 1 to 4, in other embodiments, from 2 to 20, in other embodiments, from 6 to 20, in other embodiments, from 10 to 20, in other embodiments, from 15 to 20, and in other embodiments, from 4 to 12. In some embodiments, o may be an integer from 1 to 18, in other embodiments, from 1 to 15, in other embodiments, from 1 to 12, in other embodiments, from 1 to 8, in other embodiments, from 1 to 4, in other embodiments, from 2 to 20, in other embodiments, from 6 to 20, in other embodiments, from 10 to 20, in other embodiments, from 15 to 20, and in other embodiments, from 4 to 12. Here, as well as elsewhere in the specification and claims, individual range values can be combined to form additional non-disclosed ranges.

In some embodiments, the zwitterionic side chains comprise the residue of a thiol functionalized zwitterionic compound having the formula:

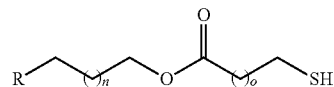

where R comprises a quaternary ammonium compound or a ring opened sultone; and n is an integer from 1 to 20; and o is an integer from 1 to 20. In one more embodiments, n and o may be any of the values or range of values for n and o set forth above.

In one or more embodiments, the PEU-based adhesion barrier of the present invention will comprise a zwitterionic copolymer having the formula:

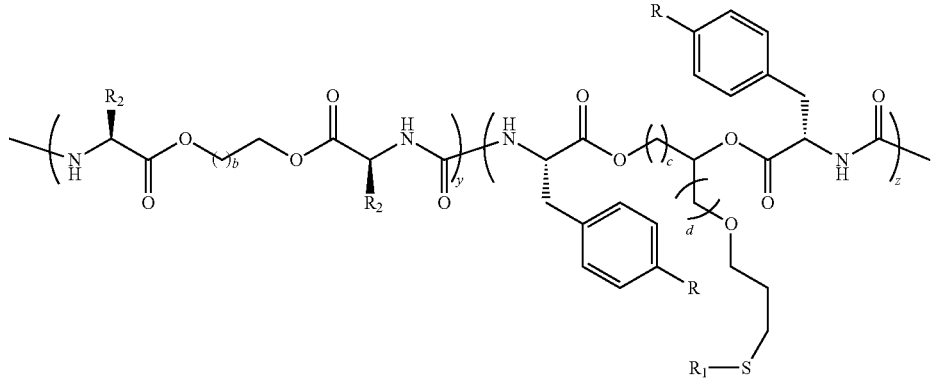

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; $R_1$ is an alkyl or aryl group comprising a zwitterionic moiety; $R_2$ is an amino acid side chain; b is an integer from 1 to 20; c and d are each an integer from about 1 to about 20; y is a mole fraction from about 0.500 to about 0.995; and z is a mole fraction from about 0.005 to about 0.500. In various embodiments, $R_2$ may be any one or more of —$CH_3$, —$(CH_2)_3NHC(NH_2)C=NH$, —$CH_2CONH_2$, —$CH_2COOH$, —$CH_2SH$, —$(CH_2)_2COOH$, —$(CH_2)_2CONH_2$, —$NH_2$, —$CH_2C=CH-N=CH-NH$, —$CH(CH_3)CH_2CH_3$, —$CH_2CH(CH_3)_2$, —$(CH_2)_4NH_2$, —(CH$_2$)$_2$SCH$_3$, —CH$_2$Ph, —CH$_2$OH, —CH(OH)CH$_3$, —CH$_2$—C≡CH—NH-Ph, —CH$_2$-Ph-OH, —CH(CH$_3$)$_2$. or —CH$_2$C$_6$H$_4$OCH$_2$C$_6$H$_5$. In some embodiments, both R$_2$ side chains are the same, but this need not be the case. In one more embodiments, b may be any of the values or range of values for b set forth above. In some embodiments, c may be an integer from 1 to 18, in other embodiments, from 1 to 15, in other embodiments, from 1 to 12, in other embodiments, from 1 to 8, in other embodiments, from 1 to 4, in other embodiments, from 2 to 20, in other embodiments, from 6 to 20, in other embodiments, from 10 to 20, in other embodiments, from 15 to 20, and in other embodiments, from 4 to 12. In some embodiments, d may be an integer from 1 to 18, in other embodiments, from 1 to 15, in other embodiments, from 1 to 12, in other embodiments, from 1 to 8, in other embodiments, from 1 to 4, in other embodiments, from 2 to 20, in other embodiments, from 6 to 20, in other embodiments, from 10 to 20, in other embodiments, from 15 to 20, and in other embodiments, from 4 to 12. Here, as well as elsewhere in the specification and claims, individual range values can be combined to form additional non-disclosed ranges.

In some of these embodiments, z is a mole fraction from about 0.05 to about 0.500, in other embodiments, from about 0.100 to about 0.500, in other embodiments, from about 0.200 to about 0.500, in other embodiments, from about 0.300 to about 0.500, in other embodiments, from about 0.005 to about 0.500, in other embodiments, from about 0.005 to about 0.400, in other embodiments, from about 0.005 to about 0.300, in other embodiments, from about 0.005 to about 0.200. In some embodiments, y is a mole fraction from about 0.1 to about 0.995, in other embodiments, from about 0.2 to about 0.995, in other embodiments, from about 0.4 to about 0.995, in other embodiments, from about 0.6 to about 0.995, in other embodiments, from about 0.1 to about 0.900, in other embodiments, from about 0.1 to about 0.800, in other embodiments, from about 0.1 to about 0.600, and in other embodiments, from about 0.1 to about 0.400. Here, as well as elsewhere in the specification and claims, individual range values can be combined to form additional non-disclosed ranges.

In one or more embodiments, the PEU-based adhesion barrier of the present invention will comprise a zwitterionic terpolymer having the formula:

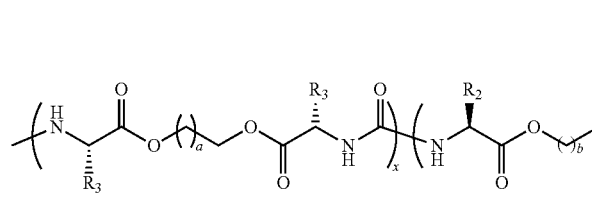

where R is OCH$_2$Ph, H, OCH$_2$C≡CH, OCH$_2$CH$_2$CH$_2$N$_3$, OCH$_2$CH$_2$CH$_2$CH═CH$_2$, OCH$_2$Ph, OCOCH$_2$CH$_2$COCH$_3$ or OH; R$_1$ is an alkyl or aryl group comprising a zwitterionic moiety; R$_2$ is a first amino acid side chain; R$_3$ is a second amino acid side chain; a is an integer from 1 to 20; b is an integer from 1 to 20; each c and d are each an integer from about 1 to about 20; x is a mole fraction from about 0 to about 0.995; y is a mole fraction from about 0 to about 0.995; and z is a mole fraction from about 0.005 to about 0.500. In various embodiments, R$_2$ and R$_3$ may be any one or more of —CH$_3$, —(CH$_2$)$_3$NHC(NH$_2$)C═NH, —CH$_2$CONH$_2$, —CH$_2$COOH, —CH$_2$SH, —(CH$_2$)$_2$COOH, —(CH$_2$)$_2$CONH$_2$, —NH$_2$, —CH$_2$C═CH—N═CH—NH, —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH$_2$OH, —CH(OH)CH$_3$, —CH$_2$—C═CH—NH-Ph, —CH$_2$-Ph-OH, —CH(CH$_3$)$_2$. or —CH$_2$C$_6$H$_4$OCH$_2$C$_6$H$_5$, but are different from each other. In some embodiments, both R$_2$ side chains are the same, but this need not be the case. In some embodiments, both R$_3$ side chains are the same, but this need not be the case. In various embodiments, a, b, c, and d may each have any value or range of values set forth above for that variable.

In some of these embodiments, z is a mole fraction from about 0.05 to about 0.500, in other embodiments, from about 0.100 to about 0.500, in other embodiments, from about 0.200 to about 0.500, in other embodiments, from about 0.300 to about 0.500, in other embodiments, from about 0.005 to about 0.500, in other embodiments, from about 0.005 to about 0.400, in other embodiments, from about 0.005 to about 0.300, in other embodiments, from about 0.005 to about 0.200. Here, as well as elsewhere in the specification and claims, individual range values can be combined to form additional non-disclosed ranges.

In some of these embodiments, z is a mole fraction from about 0.05 to about 0.500, in other embodiments, from about 0.100 to about 0.500, in other embodiments, from about 0.200 to about 0.500, in other embodiments, from about 0.300 to about 0.500, in other embodiments, from about 0.005 to about 0.500, in other embodiments, from about 0.005 to about 0.400, in other embodiments, from about 0.005 to about 0.300, in other embodiments, from about 0.005 to about 0.200. In some embodiments, y is a mole fraction from about 0.1 to about 0.995, in other embodiments, from about 0.2 to about 0.995, in other embodiments, from about 0.4 to about 0.995, in other embodiments, from about 0.6 to about 0.995, in other embodiments, from about 0.1 to about 0.900, in other embodiments, from about 0.1 to about 0.800, in other embodiments, from about 0.1 to about 0.600, and in other embodiments, from about 0.1 to about

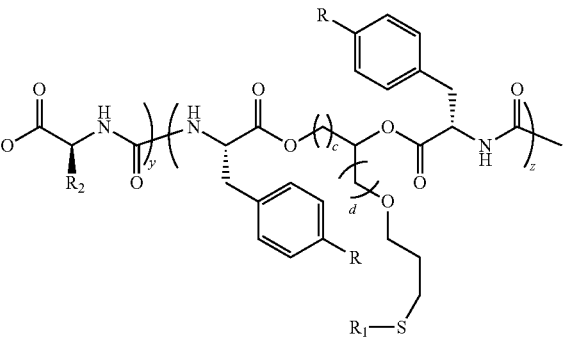

0.400. Here, as well as elsewhere in the specification and claims, individual range values can be combined to form additional non-disclosed ranges.

In one or more embodiments, the PEU-based adhesion barrier of the present invention will comprise a zwitterionic terpolymer having the formula:

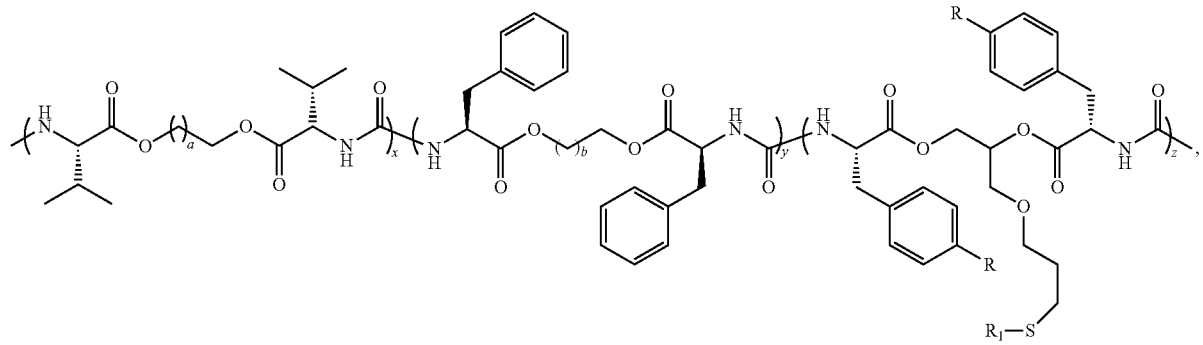

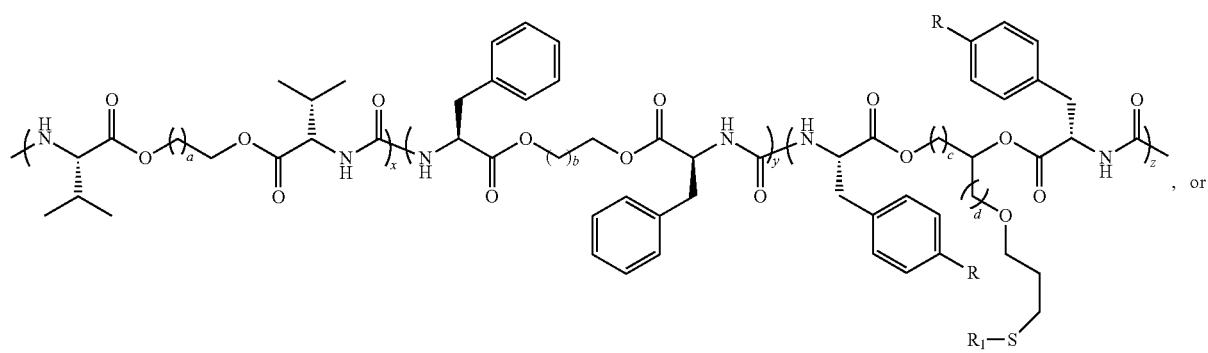

, or

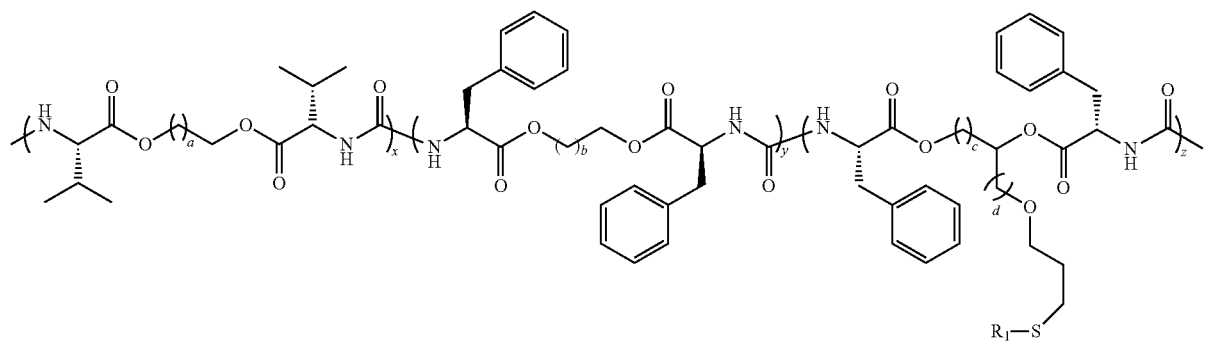

(60)

where R is OCH$_2$Ph, H, OCH$_2$C≡CH, OCH$_2$CH$_2$CH$_2$N$_3$, OCH$_2$CH$_2$CH$_2$CH=CH$_2$, OCH$_2$Ph, OCOCH$_2$CH$_2$COCH$_3$ or OH; R$_1$ is an alkyl or aryl group comprising a zwitterionic moiety; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500. In various embodiments, a, b, c, d, x, y, and z may each have any value or range of values set forth above for that variable.

In one or more embodiments, the PEU-based adhesion barrier of the present invention will comprise a zwitterionic terpolymer having the formula:

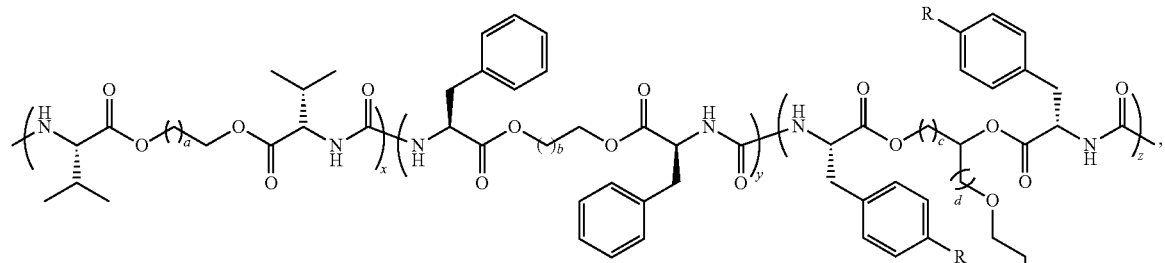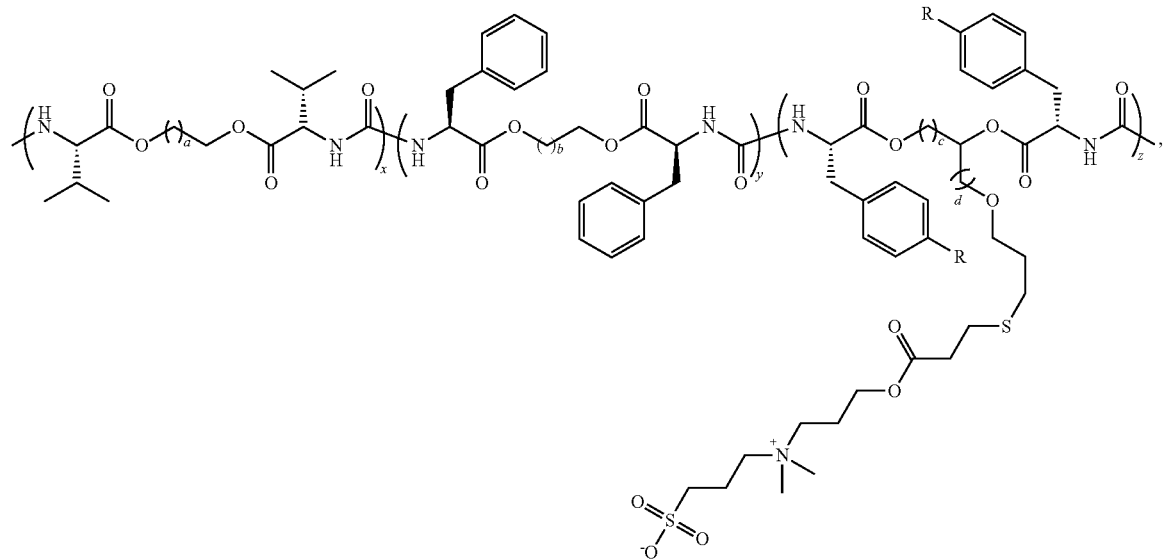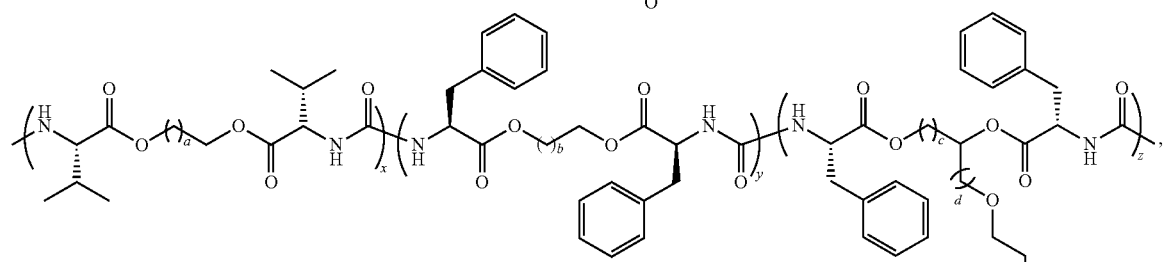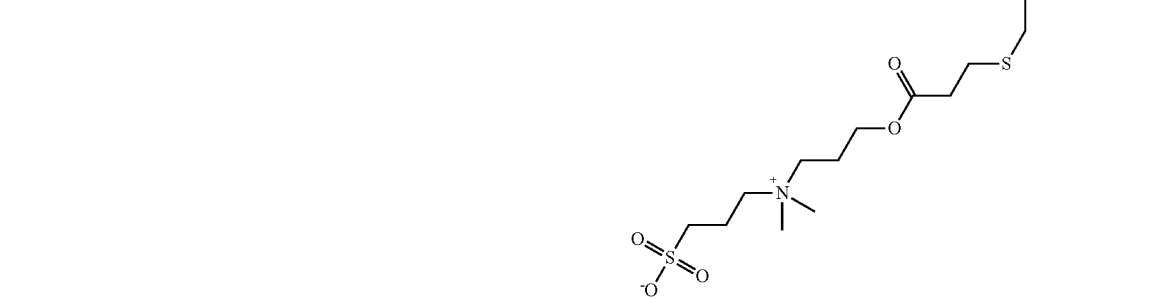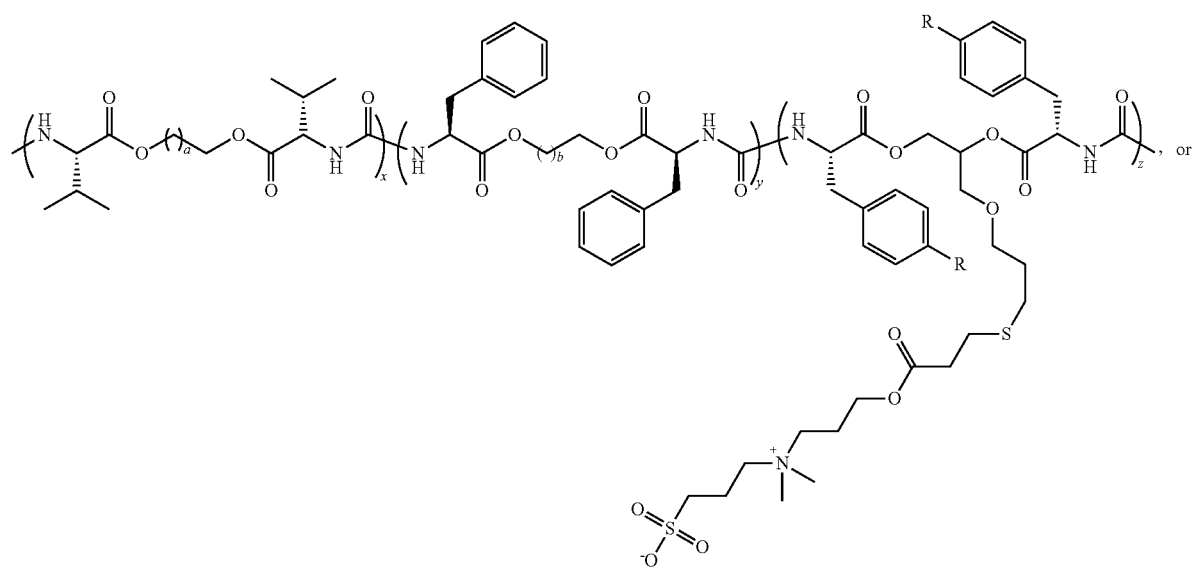

-continued

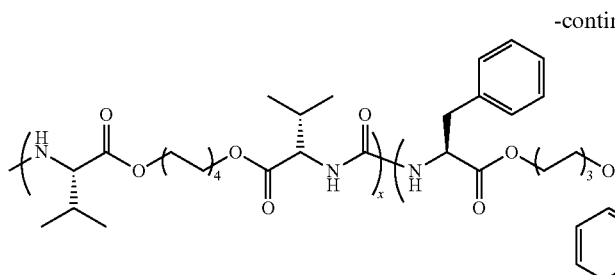
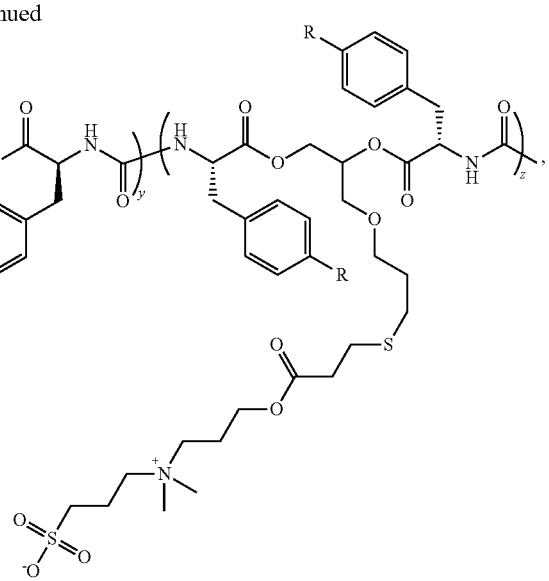

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500. In various embodiments, a, b, c, d, x, y, and z may each have any value or range of values set forth above for that variable.

In various embodiments, the poly(ester urea) (PEU)-based adhesion barrier of the present invention will have a relative stiffness of from about 20 N/cm to about 40 N/cm as measured by burst force testing. In some embodiments, the poly(ester urea) (PEU)-based adhesion barrier of the present invention will have a relative stiffness of from about 25 N/cm to about 40 N/cm, in other embodiments, from about 30 N/cm to about 40 N/cm, in other embodiments, from about 35 N/cm to about 40 N/cm, in other embodiments, from about 20 N/cm to about 35 N/cm, in other embodiments, from about 20 N/cm to about 30 N/cm, and in other embodiments, from about 20 N/cm to about 35 N/cm, as measured by burst force testing. In some embodiments, the poly(ester urea) (PEU)-based adhesion barrier of the present invention will have a relative stiffness of about 32 N/cm.

In another aspect, present invention is directed to a poly(ester urea) (PEU) polymer for use as an adhesion barrier comprising the reaction product of one or more amine protected amino acid-based diester monomers, one or more amine protected amino acid based-based allyloxy diester monomers, a urea bond forming compound and one or more thiol functionalized zwitterionic compounds, as described below. In one or more of these embodiments, the PEU polymer for use as an adhesion barrier comprises an amino acid based poly(ester urea) backbone, as described above, containing the residues of the one or more amino acid-based diester monomers, the residues of the one or more amino acid based allyloxy diester monomers, and the residues of the urea bond forming compound. In these embodiments, the PEU polymer for use as an adhesion barrier will further comprise one or more zwitterionic side chains comprising the residues of the thiol functionalized zwitterionic compounds, each connected to said amino acid based PEU backbone through a sulfide bond.

As used in connection with the amino acid-based diester and amino acid based-based allyloxy diester monomers described herein, the term "amine protected" refers to a configuration in which reaction at the amine groups of the amino acid-based diester and amino acid based-based allyloxy diester monomers is reversibly blocked to prevent or reduce unwanted transamidation reactions prior to polymerization. As will be apparent, the amino acid-based diester and amino acid based-based allyloxy diester monomers are used in their amine protected forms.

The mechanism for protecting amine groups on the amino acid-based diester and amino acid based-based allyloxy diester monomers is not particularly limited and any suitable method known in the art may be used. In one or more embodiments, the amine groups on the amino acid-based diester and amino acid based-based allyloxy diester monomers may be prevented by using one or more protecting groups that bond to the nitrogen atom in the amine groups to prevent transamidation reactions, but can be readily removed before or during polymerization. Suitable protecting groups may include, without limitation, tert-butyloxycarbonyl (Boc) groups, fluorenylmethyloxycarbonyl (Fmoc), carbobenzyloxy (Cbz) groups, or tosyl (Ts) groups. In some of these embodiments, Boc protecting groups are used to limit or prevent unwanted transamidation reactions. In one or more embodiments, the "amine protected" amino acid-based diester and amino acid based-based allyloxy diester monomers will be Boc protected amino acid-based diester monomers and Boc protected amino acid based-based allyloxy diester monomers. These protecting groups allow deprotection without reducing the ester bonds in the amino acid-based diester monomers.

In some other embodiments, these unwanted transamidation reactions may be prevented or limited by protecting the amine groups on the amino acid-based diester monomers being formed with one or more counter-ions. Accordingly, a suitable acid or other source of counter-ions may be added to the solution prior to or during formation of the diester monomer. One of ordinary skill in the art will be able to select a suitable counter-ion without undue experimentation.

Materials capable of producing suitable protecting counterions may include without limitation, p-toluene sulfonic acid monohydrate, chlorides, bromides, acetates. trifloroacetate, or combinations thereof. In some embodiments, the acid used may be p-toluene sulfonic acid monohydrate. In some embodiments, the acid used may be HCl. In some embodiments, the amino acid-based diester and amino acid based-based allyloxy diester monomers monomers are used as an acid salt.

In these embodiments, the amino-acid-based PEU polymer for use as an adhesion barrier will have a relative stiffness of from about 20 N/cm to about 40 N/cm as measured by burst force testing. In some embodiments, the amino-acid-based PEU polymer for use as an adhesion barrier will have a relative stiffness of from about 25 N/cm to about 40 N/cm, in other embodiments, from about 30 N/cm to about 40 N/cm, in other embodiments, from about 35 N/cm to about 40 N/cm, in other embodiments, from about 20 N/cm to about 35 N/cm, in other embodiments, from about 20 N/cm to about 30 N/cm, and in other embodiments, from about 20 N/cm to about 35 N/cm, as measured by burst force testing. In some embodiments, the amino-acid-based PEU polymer for use as an adhesion barrier will have a relative stiffness of about 32 N/cm.

In yet another aspect, present invention is directed to a PEU terpolymer for use as an adhesion barrier comprising the reaction product of amine protected analogues of two different types of amino acid-based diester monomers, as described above, one or more amine protected amino acid-based allyloxy diester monomer, a urea bond forming compound and one or more thiol functionalized zwitterionic compounds. As will be apparent, these PEU terpolymers will comprise an amino acid based PEU backbone made up of the residue of a first type of amino acid-based diester monomer, the residue of a second type of amino acid-based diester monomer, and the residue of the one or more amine protected amino acid-based allyloxy diester monomers, separated by residues of the urea bond forming compound. As will also be apparent, these PEU terpolymers in these embodiments will also comprise one or more zwitterionic side chains comprising the residues of the thiol functionalized zwitterionic compounds, which are connected to said amino acid based PEU backbone through a sulfide bond.

In one or more of these embodiments, the PEU terpolymer for use in the adhesion barrier of the present invention will have the formula:

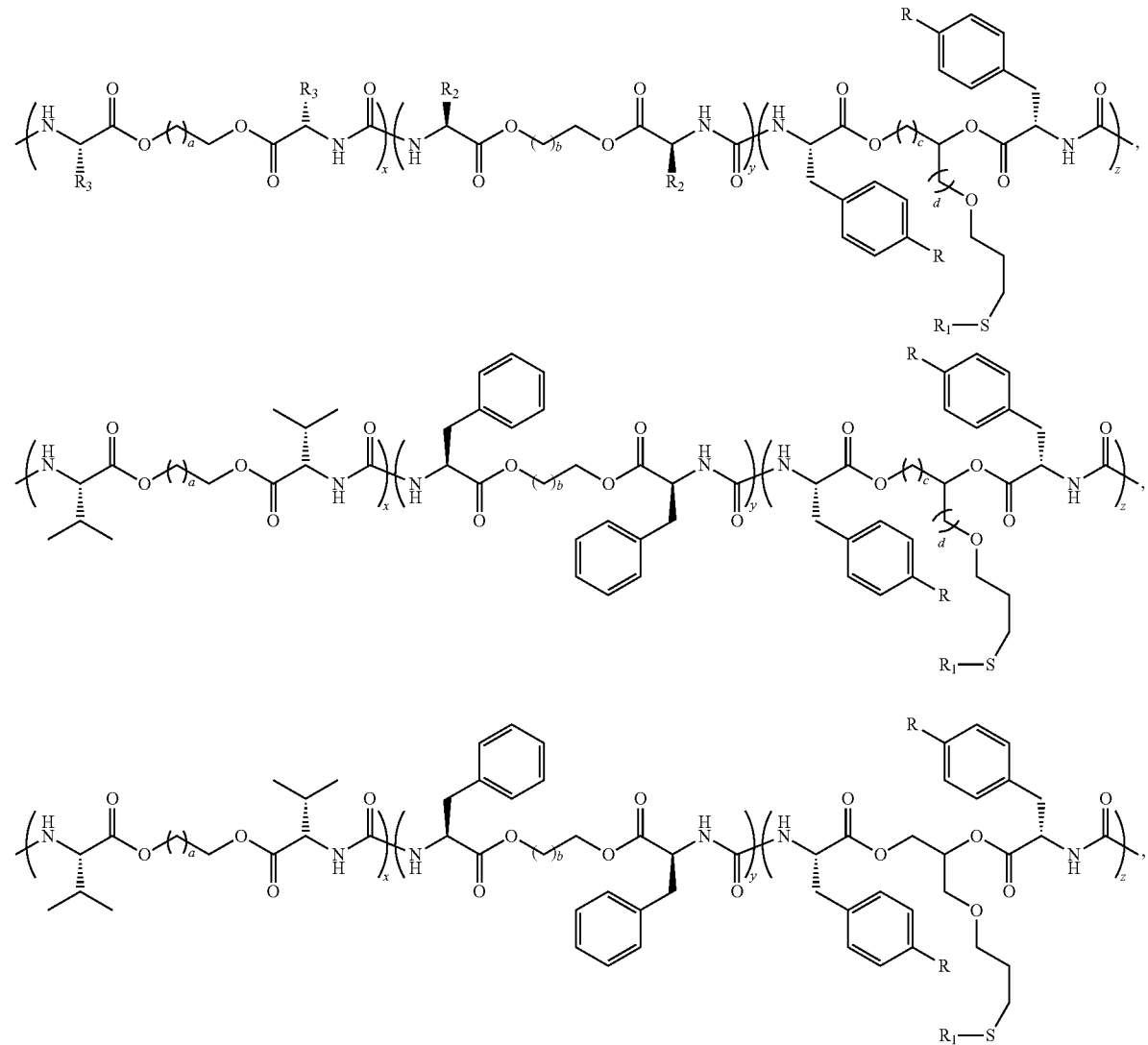

-continued
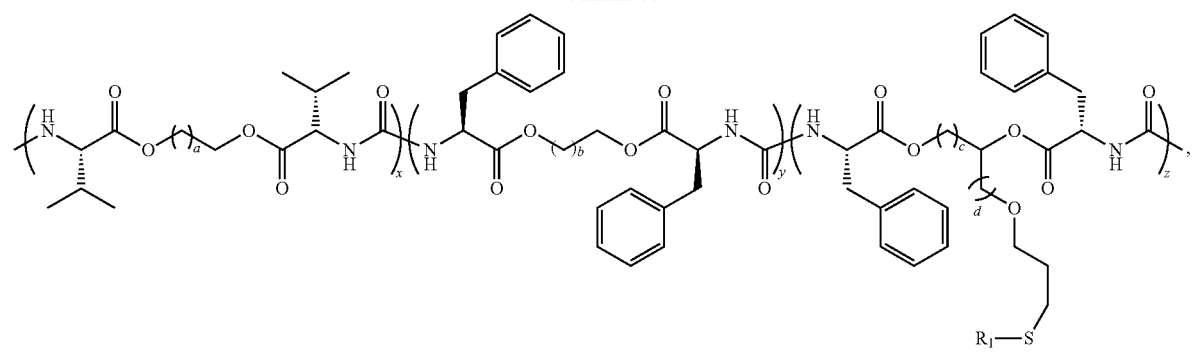
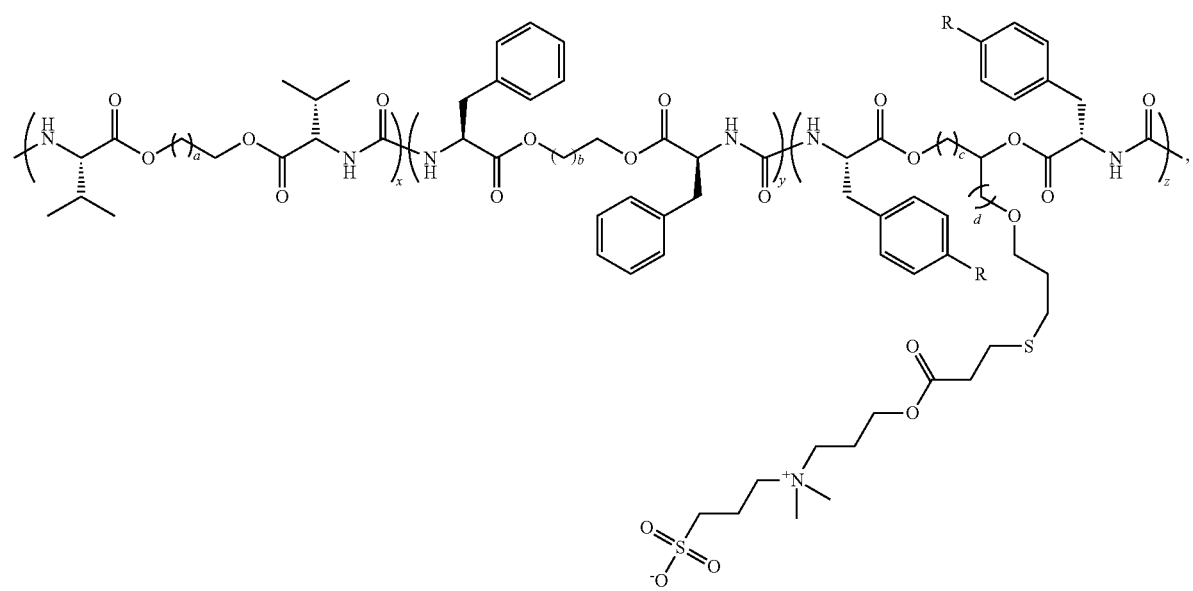
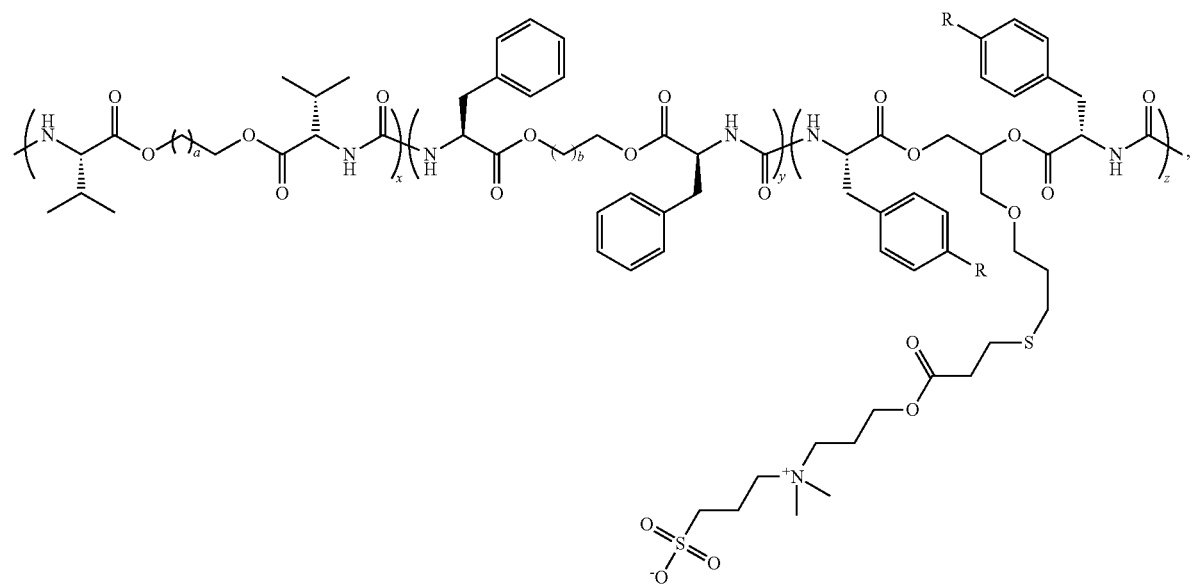

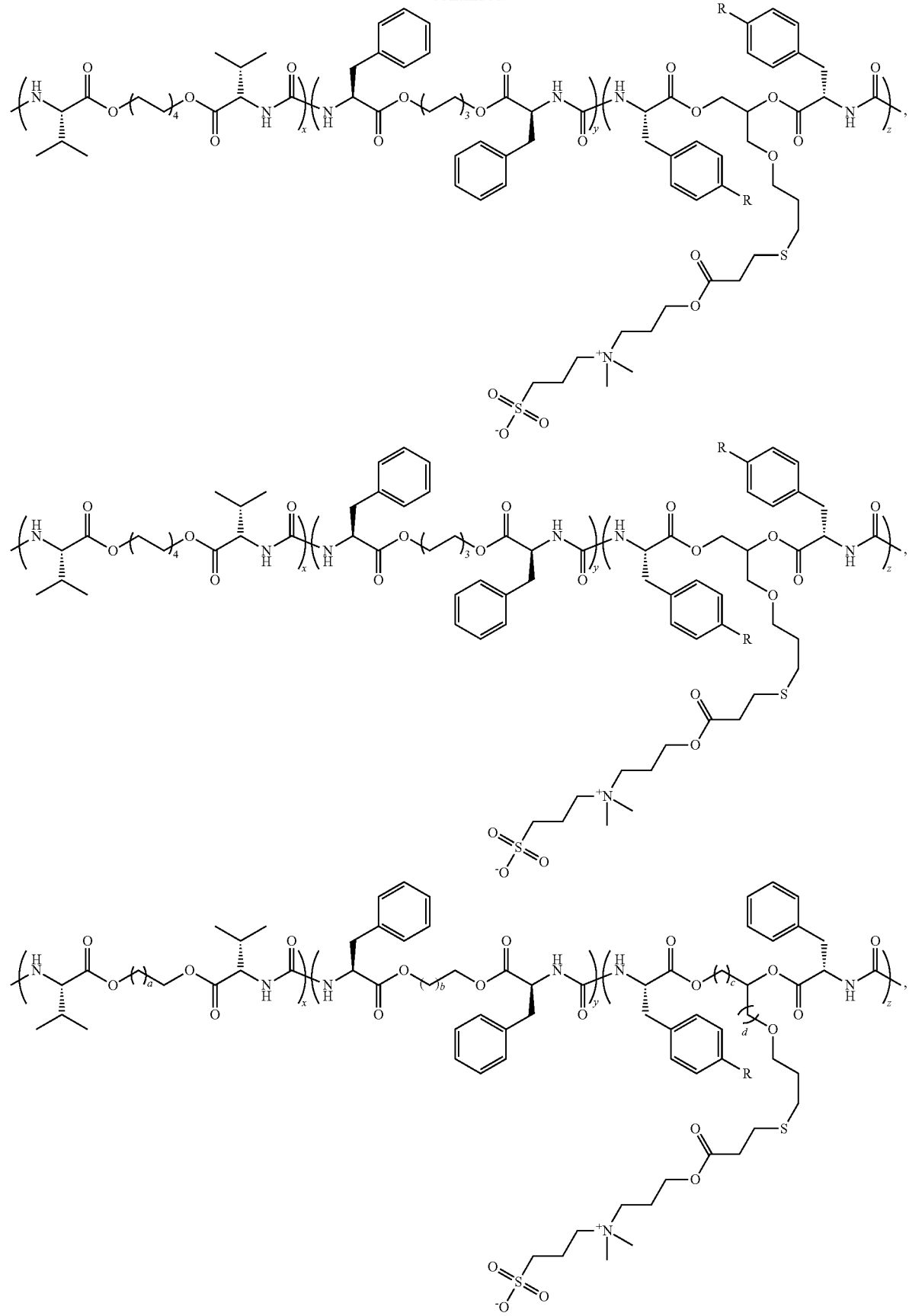

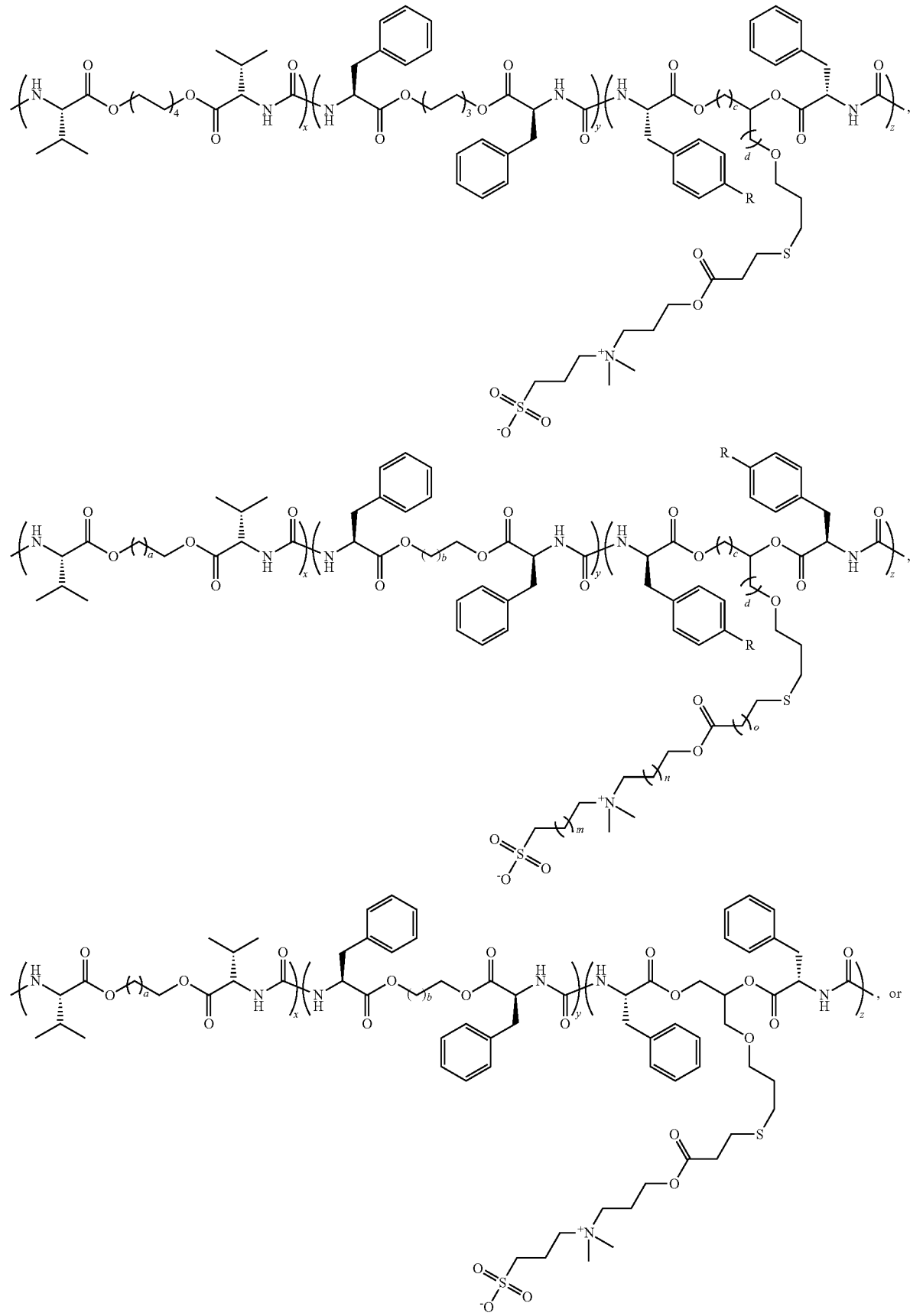

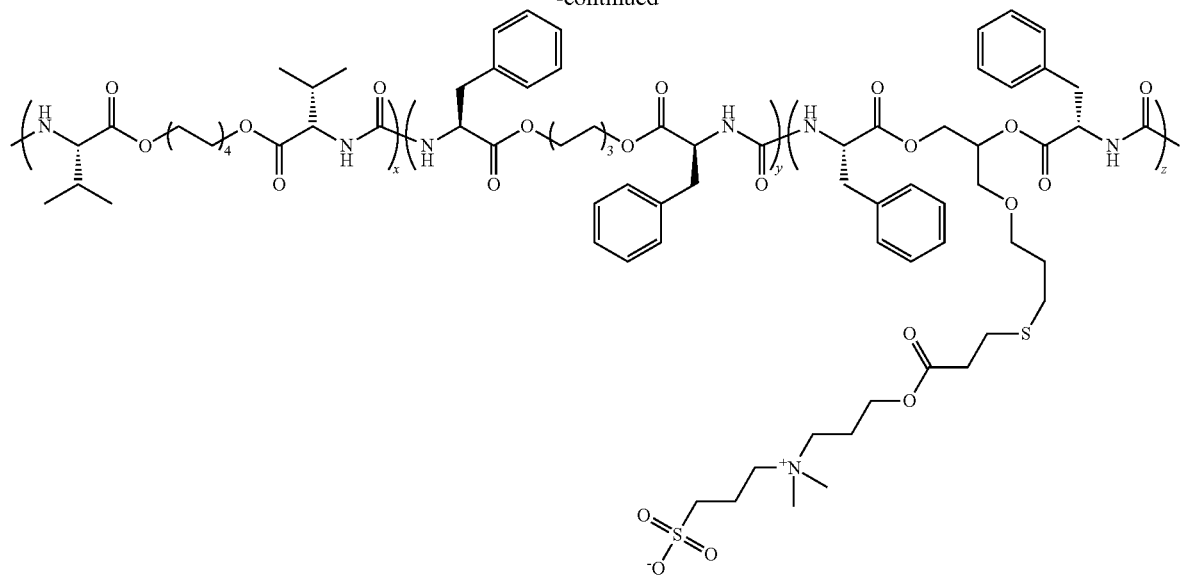

where R is OCH$_2$Ph, H, OCH$_2$C≡CH, OCH$_2$CH$_2$CH$_2$N$_3$, OCH$_2$CH$_2$CH=CH$_2$, OCH$_2$Ph, OCOCH$_2$CH$_2$COCH$_3$ or OH; R$_1$ is an alkyl or aryl group comprising a zwitterionic moiety; R$_2$ is a first amino acid side chain; R$_3$ is a second amino acid side chain; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500. In some embodiments, z is a mole fraction from about 0.05 to about 0.500, in other embodiments, from about 0.100 to about 0.500, in other embodiments, from about 0.200 to about 0.500, in other embodiments, from about 0.300 to about 0.500, in other embodiments, from about 0.005 to about 0.500, in other embodiments, from about 0.005 to about 0.400, in other embodiments, from about 0.005 to about 0.300, in other embodiments, from about 0.005 to about 0.200. In various embodiments, R$_2$ and R$_3$ may be any one or more of —CH$_3$, —(CH$_2$)$_3$NHC(NH$_2$)C=NH, —CH$_2$CONH$_2$, —CH$_2$COOH, —CH$_2$SH, —(CH$_2$)$_2$COOH, —(CH$_2$)$_2$CONH$_2$, —NH$_2$, —CH$_2$C=CH—N=CH—NH, —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH$_2$OH, —CH(OH)CH$_3$, —CH$_2$—C=CH—NH-Ph, —CH$_2$-Ph-OH, —CH(CH$_3$)$_2$. or —CH$_2$C$_6$H$_4$OCH$_2$C$_6$H$_5$, but are different from each other. In some embodiments, both R$_2$ side chains are the same, but this need not be the case. In some embodiments, both R$_3$ side chains are the same, but this need not be the case. In various embodiments, a, b, c, d, x, y, z, m, n, and o may each have any value or range of values set forth above for that variable.

In one or more of these embodiments, the PEU terpolymer for use as an adhesion barrier will have a relative stiffness of from about 20 N/cm to about 40 N/cm as measured by burst force testing. In some embodiments, PEU terpolymer for use as an adhesion barrier will have a relative stiffness of from about 25 N/cm to about 40 N/cm, in other embodiments, from about 30 N/cm to about 40 N/cm, in other embodiments, from about 35 N/cm to about 40 N/cm, in other embodiments, from about 20 N/cm to about 35 N/cm, in other embodiments, from about 20 N/cm to about 30 N/cm, and in other embodiments, from about 20 N/cm to about 35 N/cm, as measured by burst force testing. In some embodi- ments, PEU terpolymer for use as an adhesion barrier will have a relative stiffness of about 32 N/cm.

In still another aspect, the present invention is directed to a method for making the PEU-based adhesion barriers described above. In general outline, the method comprises: preparing an amino acid based PEU polymer having one or more pendent allyl functional groups; preparing a thiol functionalized zwitterionic compound; and then reacting the allyl functionalized PEU polymer with said thiol function- alized zwitterionic compound to form a PEU-based adhesion barrier comprising an amino acid based PEU backbone having zwitterionic side chains. As will be apparent from the description of the poly(ester urea) (PEU)-based adhesion barriers above, the step of forming the allyl-functionalized amino acid based PEU polymers involves the interfacial polymerization of one or more amino acid-based diester monomers as described above, one or more amino acid- based allyloxy diester monomers as described above, and a urea bond forming compound to form an allyl functionalized PEU intermediate. The thiol functionalized zwitterionic compound will have a zwitterionic moiety and a thiol functional group. The zwitterionic moiety is then added to the allyl functionalized PEU intermediate as a side chain by means of a thiol-ene type "click" reaction between pendent allyl group on the allyl functionalized PEU intermediate and the thiol functional group on the thiol functionalized zwit- terionic compound to form the poly(ester urea) (PEU)-based adhesion barriers of the present invention.

In various embodiments, the amino acid-based diester monomers will comprise the residues of two amino acids separated by from 1 to 20 carbon atoms and are most preferably used in their amine protected form, as described above. In these embodiments, the amino acid-based diester monomers may comprise the residues of valine, phenylala- nine, leucine, isoleucine, tyrosine, alanine, methionine, gly- cine, cysteine or any combinations or derivatives thereof. In some embodiments, the amino acid used to form the amino acid-based diester monomers may be a functionalized or protected α-amino acid. In some embodiments, the amino acid used to form the amino acid-based diester monomers may be a functionalized or protected non-canonical amino acid. In some embodiments, amino acid or acids used to form the amino acid-based diester monomers may comprise one or more benzyl protected tyrosine molecules or tert-butyloxycarbonyl (BOC) protected tyrosine molecules.

In various embodiments, the amino acid-based diester monomers may be formed by reacting two of the above described amino acids with a $C_1$ to $C_{20}$ linear diol, as shown below. Suitable linear diols, may include, without limitation, 1,6-hexanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol, 1,17-heptadecanediol, 1,18-octadecanediol, 1,19-nonadecanediol, 1,20-icosanediol, or a combinations thereof. In the embodiments, the polyol is 1,8-octanediol and is commercially available from Sigma Aldrich Company LLC (St. Louis, Mo.) or Alfa Aesar (Ward Hill, Mass.). In the embodiments, the polyol is 1,6-hexanediol and is commercially available from Sigma Aldrich Company LLC (St. Louis, Mo.) or Alfa Aesar (Ward Hill, Mass.).

The reaction of the polyol with the amino acid to create these amino acid-based polyester monomers can be achieved in any number of ways generally known to those of skill in the art. Generally, a condensation reaction at temperatures exceeding the boiling point of water involving a slight molar excess (~2.1 eq.) of the acid relative to the hydroxy groups is sufficient to enable the reaction to proceed. In some embodiments, the amino acid-based diester monomers are formed by first dissolving one or more selected amino acids and a selected polyol in a suitable solvent. One of ordinary skill in the art will also be able to select a suitable solvent for the selected amino acid or acids and the selected polyol the without undue experimentation. Suitable solvents include without limitation, toluene, dichloromethane, chloroform, dimethylformamide (DMF) or combinations thereof. In some embodiments, the solvent used may be toluene.

Further, as set forth above, steps should be taken to protect the amine groups on the monomer intermediates to limit or prevent transamidation. As such, all of the amino acid-based diester and amino acid based-based allyloxy diester monomers are used in their amine protected forms. In some embodiments, transamidation may be prevented or limited by protecting the amine groups on the amino acid-based diester monomers being formed with one or more counter-ions. Accordingly, a suitable acid or other source of counter-ions may be added to the solution prior to or during formation of the diester monomer. One of ordinary skill in the art will be able to select a suitable counter-ion without undue experimentation. As set forth above, materials capable of producing suitable amine protecting counter-ions may include without limitation, p-toluene sulfonic acid monohydrate, chlorides, bromides, acetates. trifloroacetate, or combinations thereof. In some embodiments, the acid used may be p-toluene sulfonic acid monohydrate. In some embodiments, the acid used may be HCl. As will be apparent, the amino acid-based diester monomers are used in their amine protected forms. In some embodiments, the amino acid-based diester monomers are used as an acid salt.

In some embodiments, one or more amino acid-based diester monomers has the formula:

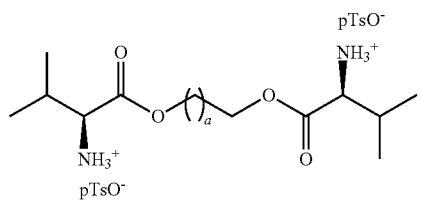

where a is an integer from about 1 to about 20. In various embodiments, a, may have any value or range of values for a set forth above. In some embodiments, one or more amino acid-based diester monomers has the formula:

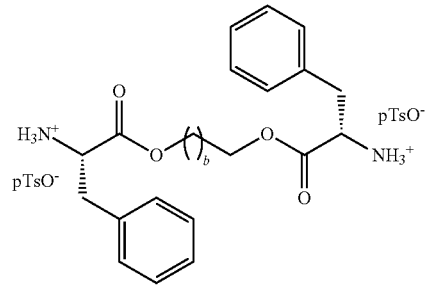

where b is an integer from about 1 to about 20. In various embodiments, a, may have any value or range of values for a set forth above.

In these embodiments, the solution is then heated to a temperature of from 110° C. to about 114° C. and refluxed for from about 20 hours to about 48 hours to form a amino acid-based diester monomer having two or more amino acid residues separated by from about 2 to about 20 carbon atoms, depending upon the polyol used. (See Scheme 1, below). In some embodiments, the solution is heated to a temperature of from about 110° C. to about 112° C. In some embodiments, the solution is heated to a temperature of about 110° C. In some of these embodiments, the solution may be refluxed for from about 20 hours to about 40 hours. In some of these embodiments, the solution may be refluxed for from about 20 hours to about 30 hours. In some of these embodiments, the solution may be refluxed for from about 20 hours to about 24 hours.

The crude product of the reactions may be purified using any means known in the art for that purpose, including, without limitation, filtration, crystallization, or column chromatography. One or ordinary skill in the art would know how to purify these products without undue experimentation. In some embodiments, the crude reaction product may be purified by first vacuum filtering to remove the residual solvent and then decolorized in activated carbon to remove any residual salts or unreacted monomers. In some embodiments, the crude reaction product may then be recrystallized from boiling water from 1 to 10 times to produce a purified product. In some embodiments, the crude product may be recrystallized from a 1:1 mixture of water and alcohol from 1 to 10 times to produce a purified product. In some embodiments, after cooling to ambient temperature, the crude product may be filtered, washed with diethyl ether and then recrystallized with water. In some embodiments, the crude product may be filtered, washed with diethyl ether, and collected by vacuum filtration. In some embodiments, the crude product was filtered, concentrated and dissolved in $CHCl_3$, washed with 5% HCl twice, brine once, dried over $Na_2SO_4$ and the solvent removed in vacuo to produce the purified product.

In some embodiments, the amino acid-based diester monomers may be synthesized as shown in Scheme 1, below.

Scheme 1

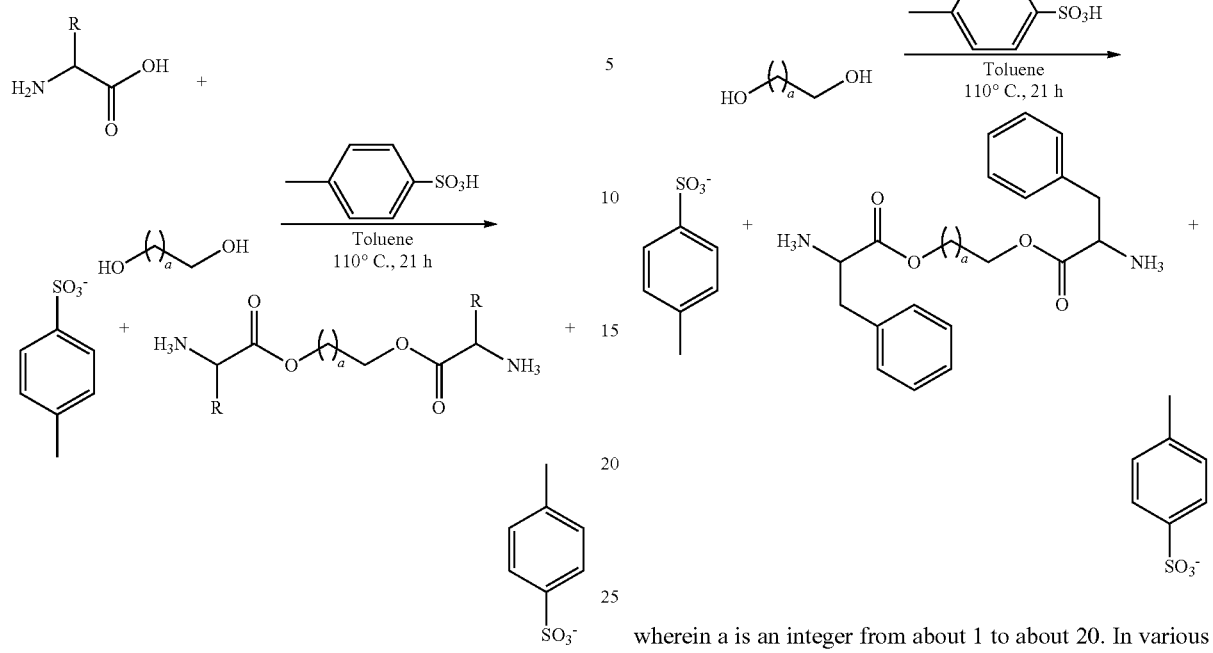

wherein R is an amino acid side chain and a is an integer from about 2 to about 20. In some embodiments, R may be any one or more of —CH$_3$, —(CH$_2$)$_3$NHC(NH$_2$)C=NH, —CH$_2$CONH$_2$, —CH$_2$COOH, —CH$_2$SH, —(CH$_2$)$_2$COOH, —(CH$_2$)$_2$CONH$_2$, —NH$_2$, —CH$_2$C=CH—N=CH—NH, —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH$_2$OH, —CH(OH)CH$_3$, —CH$_2$—C=CH—NH-Ph, —CH$_2$-Ph-OH, —CH(CH$_3$)$_2$. or —CH$_2$C$_6$H$_4$OCH$_2$C$_6$H$_5$. In some embodiments, may be a benzyl protected tyrosine, a tert-butyloxycarbonyl (BOC) protected tyrosine or another functionalized or protected α-amino acid. In various embodiments, a may have any value or range of values for a set forth above.

In the embodiments shown in Scheme 1 above, one or more amino acids, a linear diol having from 2 to 20 carbon atoms, and p-toluene sulfonic acid monohydrate are dissolved in toluene, heated to a temperature of about 110° C. and refluxed for about 21 hours to produce the di-p-toluene sulfonic acid salt of an amino acid-based diester monomer having two or more amino acid residues separated by from about 2 to about 20 carbon atoms, depending upon the polyol used. (See also, Examples 1-20). In some embodiments, the amino acid, polyol and acid may be dissolved in a suitable solvent such as toluene, DMF, and 1,4-paradioxane. One of ordinary skill in the art will be able to select a suitable solvent without undue experimentation.

In some other embodiments, a counter-ion protected amino acid-based diester monomer for making an amino acid-based PEU polymer or terpolymer according to one or more embodiments of the present invention may be synthesized as shown in Scheme 2, below.

Scheme 2

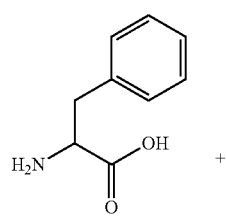

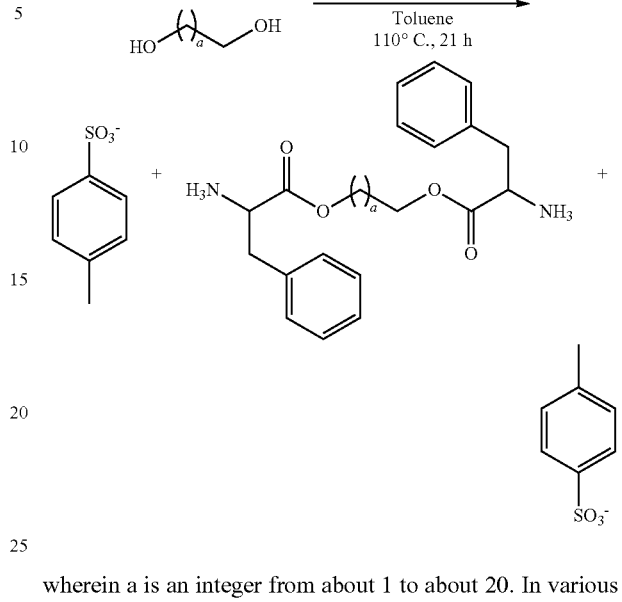

wherein a is an integer from about 1 to about 20. In various embodiments, a may have any value or range of values for a set forth above.

In the embodiments shown in Scheme 2 above, L-phenylalanine, a linear diol having from 2 to 20 carbon atoms, and p-toluene sulfonic acid monohydrate are dissolved in toluene, heated to a temperature of from about 110° C. and refluxed for about 21 hours produce the di-p-toluene sulfonic acid salt of a L-phenylalanine based diester monomer having two phenylalanine residues separated by from about 2 to about 20 carbon atoms, depending upon the diol used. (See Scheme 2, above). In some of these embodiments, the solution may be heated to a temperature of from about 110° C. to about 112° C. In some of these embodiments, the solution may be refluxed for from about 20 hours to about 48 hours. In some of these embodiments, the solution may be refluxed for from about 20 hours to about 40 hours. In some of these embodiments, the solution may be refluxed for from about 20 hours to about 30 hours. In some embodiments, the di-p-toluene sulfonic acid salt of an L-phenylalanine based diester monomer XXXI, having two L-phenylalanine residues separated by from about 2 to about 20 carbon atoms, may be synthesized as set forth in Examples 5-8, below.

In some embodiments, amino acid-based diester monomers according to one or more embodiments of the present invention may be synthesized from L-leucine, a linear diol from 2 to 20 carbon atoms in length, and p-toluene sulfonic acid monohydrate as shown in Scheme 3, below.

Scheme 3

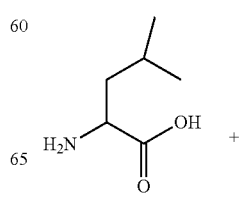

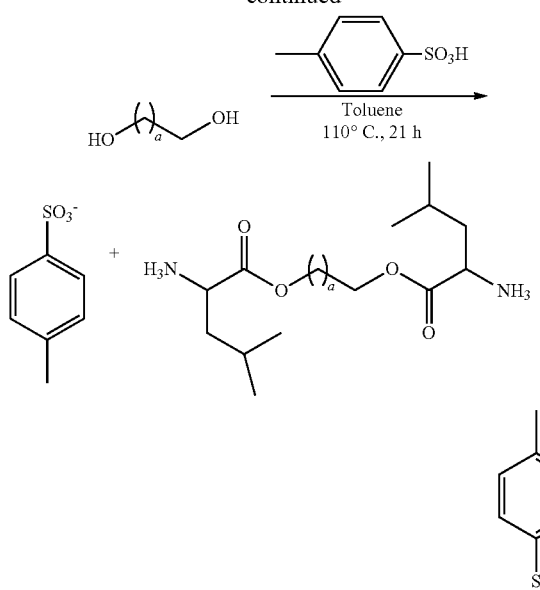

wherein a is an integer from about 1 to about 20. In some of these embodiments, a may be an integer from about 1 to about 15. In various embodiments, a may have any value or range of values for a set forth above.

In the embodiments shown in Scheme 3 above, L-leucine, linear diol of from 2 to 20 carbon atoms in length, and p-toluene sulfonic acid monohydrate are dissolved in toluene, heated to a temperature of from about 110° C. and refluxed for about 21 hours produce the di-p-toluene sulfonic acid salt of an L-leucine based diester monomer having two L-leucine residues separated by from about 2 to about 20 carbon atoms, depending upon the diol used. (See Scheme 3, above). One of ordinary skill in the art will be able to select a suitable solvent or solvents without undue experimentation. In some of these embodiments, the solution may be heated to a temperature of from about 110° C. to about 112° C. In some of these embodiments, the solution may be refluxed for from about 20 hours to about 48 hours. In some of these embodiments, the solution may be refluxed for from about 20 hours to about 40 hours. In some of these embodiments, the solution may be refluxed for from about 20 hours to about 30 hours. In some embodiments, the di-p-toluene sulfonic acid salt of an L-leucine based diester monomer, having two L-leucine residues separated by from about 2 to about 20 carbon atoms, may be synthesized as set forth in Example 11.

In some other embodiments, another type of counter-ion protected amino acid-based diester monomers according to the invention having one or more benzyl protected tyrosine residues may be synthesized as shown in Scheme 4, below.

Scheme 4

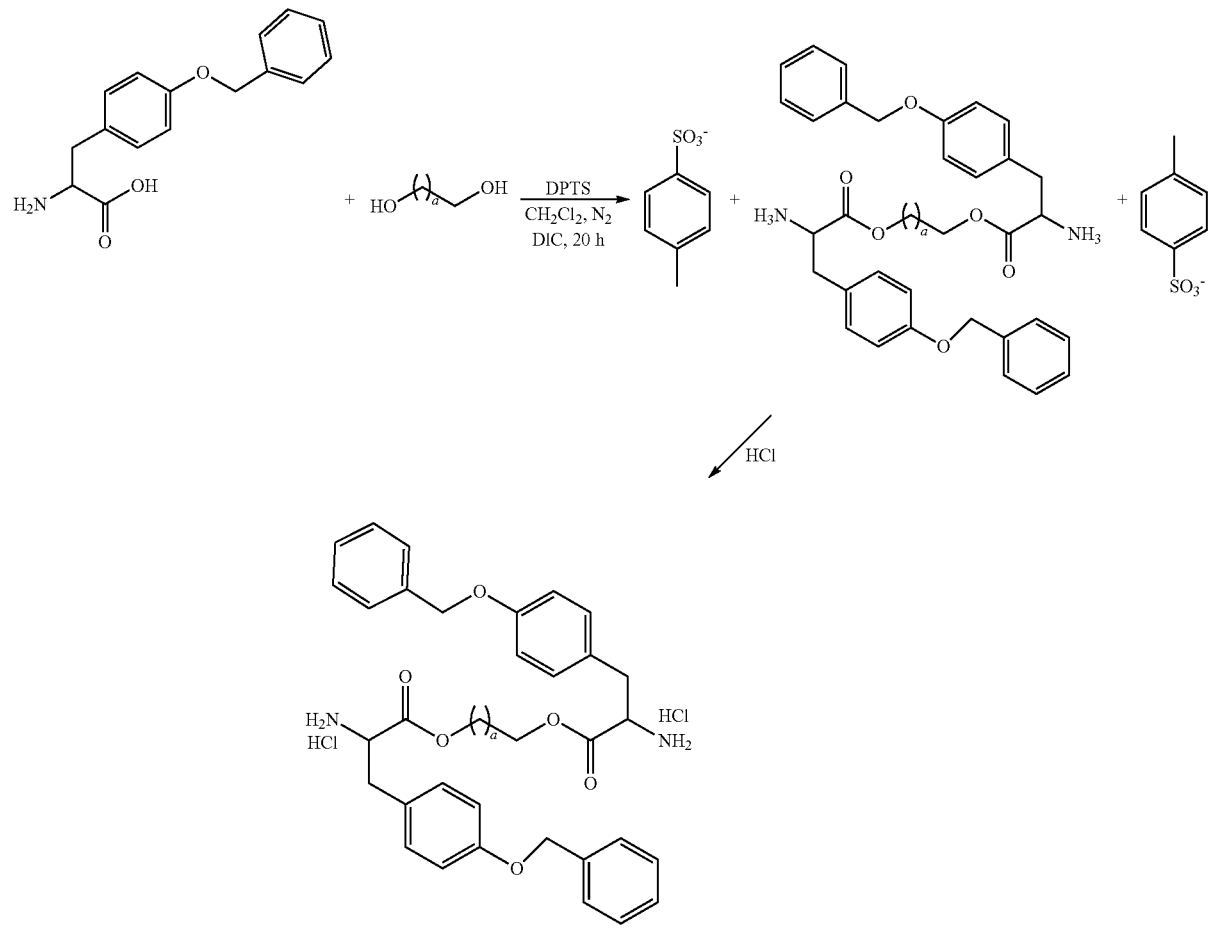

wherein a is an integer from about 1 to about 20. In various embodiments, a may have any value or range of values for a set forth above.

In these embodiments, a benzyl protected tyrosine is used as the amino acid for the formation of the amino acid based diester monomer. In these embodiments, the method used to produce the amino acid-based diester monomer described above may be modified slightly to produce the di-p-toluene sulfonic acid salt of the benzyl protected tyrosine based diester monomer, as shown in the first part of Scheme 4, above. In these embodiments, the benzyl protected L-tyrosine (N-Boc-O-benzyl-L-tyrosine), a linear diol of from about 2 to about 20 carbon atoms in length, and a suitable coupling agent such as 4-(dimethylamino)pyridinium 4-toluenesulfonate (DPTS) are first dissolved in a suitable solvent (such as anhydrous dichloromethane) under a nitrogen atmosphere. One of ordinary skill in the art will be able to select a suitable coupling agent without undue experimentation. Suitable coupling agents may include without limitation Suitable coupling agents may include, without limitation, 2-(1H-benzotriazol-1-yl)-1,1,3,3-tetramethyluronium hexafluorophosphate (HBTU), (benzotriazol-1-yloxy) tris(dimethylamino)phosphonium hexafluorophosphate (BOP), bis-(2-oxo-3-oxazolidinyl)phosphinic chloride (BOP-Cl), (1-cyano-2-ethoxy-2-oxoethylidenaminooxy)dimethylamino-morpholino-carbenium hexafluorophosphate (COMU™), dicyclohexylcarbodiimide (DCC), diisopropylcarbodiimide (DIC), 3-(diethoxyphosphoryloxy)-1,2,3-benzotriazin-4(3H)-one (DEPBT), N-(3-dimethylaminopropyl)-N'-ethylcarbodiimide hydrochloride (EDC), 2-(1H-7-azabenzotriazol-1-yl)-1,1,3,3-tetramethyl uronium hexafluorophosphate (HATU), O-benzotriazole-N,N,N',N'-tetramethyl-uronium-hexafluorophosphate (HBTU), 2-(6-Chloro-1H-benzotriazole-1-yl)-1,1,3,3-tetramethylaminium hexafluorophosphate (HCTU), (7-azabenzotriazol-1-yloxy) tripyrrolidinophosphonium hexafluorophosphate (PyAOP), (benzotriazol-1-yloxy)tripyrrolidinophosphonium hexafluorophosphate (PyBOP), bromotripyrrolidinophosphonium hexafluorophosphate (PyBrOP), O-(7-azabenzotriazole-1-yl)-N,N,N',N'-tetramethyluronium tetrafluoroborate (TATU), O-(benzotriazol-1-yl)-N,N,N',N'-tetramethyluronium tetrafluoroborate (TBTU), N,N,N',N'-tetramethyl-O-(3,4-dihydro-4-oxo-1,2,3-benzotriazin-3-yl)uranium tetrafluoroborate (TDBTU), 2-(5-norborene-2,3-dicarboximido)-1,1,3,3-tetramethyluronium tetrafluoroborate (TNTU), O-[(ethoxycarbonyl)cyanomethylenamino]-N,N,N',N'-tetra methyluronium tetrafluoroborate (TOTU), 2-(2-pyridon-1-yl)-1,1,3,3-tetramethyluronium tetrafluoroborate (TPTU), or N,N,N'N'-tetramethyl-O—(N-succinimidyl)uronium tetrafluoroborate (TSTU).

In some embodiments, the amino acid based polyester monomers described above may be synthesized as described in U.S. Pat. Nos. 9,745,414 and 9,988,492; U.S. Published Patent Application Nos. 2016/0250382, 2017/0081476, and 2017/0210852; and International Application No. WO 2017/189534, the disclosures of which are incorporated herein by reference in their entirety. In one or more embodiments, a counter-ion protected amino acid-based diester monomers according to the invention having one or more benzyl protected tyrosine residues may be synthesized as shown in Examples 9 and 10, below.

The allyl functionalized amino acid-based diester monomers used to form the PEU-based adhesion barriers described above are not particularly limited and will comprise the residues of two of the amino acids described above, which may be protected or functionalized, separated by a branched chain of from 2 to 20 carbon atoms and will be functionalized to include a pendent allyl group. In some embodiments, allyl functionalized amino acid-based polyester monomer will comprise a pendent allyloxy group, In some embodiments, the allyl functionalized amino acid-based diester monomer used to form the PEU-based adhesion barriers described above may be a benzyl-protected L-tyrosine-1,3-allyloxy-diester monomer. In some embodiments, the allyl functionalized amino acid-based diester monomer used to form the PEU-based adhesion barriers described above is bis-O-benzyl-L-tyrosine-1,3-alkoxy-diester monomer. Suitable benzyl-protected L-tyrosine and 1,3-allyloxy-diester monomers are commercially available (Alfa Aesar, (Tewksbury, Mass.) or Sigma Aldrich, (Milwaukee, Wis.)) and can be synthesized using any known methods.

In some embodiments, allyl functionalized amino acid-based diester monomers used to form the PEU-based adhesion barriers described above may be synthesized as shown in Scheme 5, below.

Scheme 5

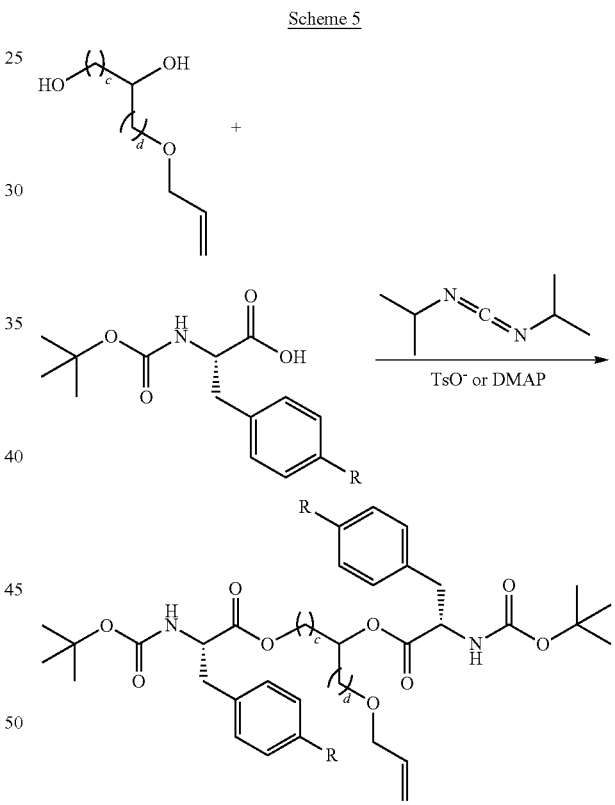

where c and d are each an integer from about 1 to about 20. In these embodiments, a diol having a pendent allyl group is reacted with an amine protected amino acid by diisopropylcarbodiimide (DIC) coupling in the presence of a proton source, such as p-toluenesulfonate (pTsO-) and 4-dimethylaminopyridine (DMAP) to facilitate ester formation, as shown in Scheme 5, above. In one or more embodiments, the allyl functionalized amino acid-based diester monomers used to form the PEU-based adhesion barriers described above may be synthesized as shown in Example 21, below. In various embodiments, c and d may have any value or range of values for a and b set forth above.

In some embodiments, the allyl functionalized amino acid-based diester monomer may have the formula:

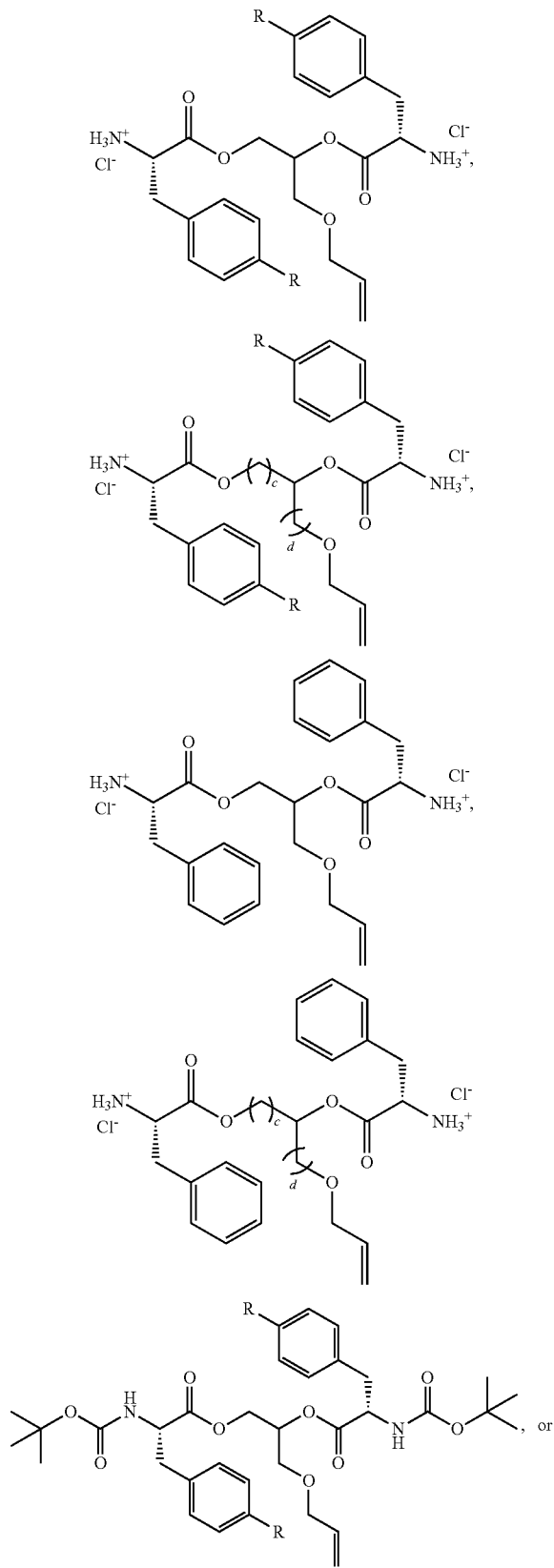

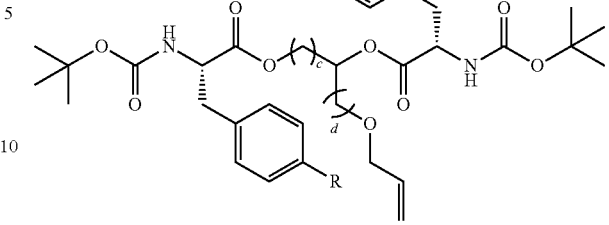

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; and c and d are each an integer from about 1 to about 20. In various embodiments, c and d may have any value or range of values for a and b set forth above.

As with the amino acid-based diester monomers, the allyl functionalized amino acid-based polyester monomers are used in their amine protected form. In some embodiments, the allyl functionalized amino acid-based polyester monomers are used as an acid salt. In some embodiments, the allyl functionalized amino acid-based polyester monomers are used in their Boc-protected form.

As set forth above, one or more type of the amino acid-based diester monomers as described above and at least one of the amino acid-based allyloxy polyester monomers as described above the monomers are polymerized using an interfacial polymerization method to form the an allyl functionalized PEU intermediate. As used herein interfacial polymerization refers to polymerization that takes place at or near the interfacial boundary of two immiscible fluids. In these embodiments, the amine protected monomers are first combined in a desired molar ratio with a first fraction of a suitable organic water soluble base such as sodium carbonate, potassium carbonate, sodium bicarbonate, or potassium bicarbonate and dissolved in water using mechanical stirring and a warm water bath (approximately 35° C.).

In one or more embodiments, the amine protected amino acid-based allyloxy diester monomers will comprise from about 0.5 to about 50 mole percent of the protected diester monomers in the reaction vessel. In some embodiments, the amine protected amino acid-based allyloxy diester monomers will comprise from about 1 mol % to about 50 mol %, in other embodiments, from about 5 mol % to about 50 mol %, in other embodiments, from about 10 mol % to about 50 mol %, in other embodiments, from about 15 mol % to about 50 mol %, in other embodiments, from about 20 mol % to about 50 mol %, in other embodiments, from about 30 mol % to about 50 mol %, in other embodiments, from about 0.5 mol % to about 40 mol %, in other embodiments, from about 0.5 mol % to about 30 mol %, in other embodiments, from about 0.5 mol % to about 20 mol % of the amine protected diester monomers added to the reaction vessel.

In one or more embodiments, the reaction is then cooled to a temperature of from about −10° C. to about 2° C. and an additional fraction of an organic water soluble base such as sodium carbonate, potassium carbonate, sodium bicarbonate, or potassium bicarbonate is dissolved in water and then added to the reaction mixture. A first fraction of PEU forming compound is then added to the reaction mixture. The reaction may be cooled by any means known in the art for that purpose, including, without limitation, ice baths, water baths, or recirculating coolers. A first fraction of a PEU forming compound such as triphosgene or phosgene is dissolved in a suitable solvent, such as distilled chloroform or dichloromethane, and is then added to the reaction mixture. After a period of from about 2 to about 60 minutes, a second fraction of the PEU forming compound (such as triphosgene or phosgene) is dissolved in a suitable solvent, such as distilled chloroform or dichloromethane, and added dropwise to the reaction mixture over a period of from about 0.5 to about 6 hours to produce a crude copolymer containing the allyl functionalized PEU intermediate. The allyl functionalized PEU intermediate may be further purified by any conventional means. In one or more embodiment, allyl functionalized PEU intermediate may be further purified by precipitation in a non-solvent and/or recrystallization.

In one or more embodiments, allyl functionalized PEU intermediate may be a copolymer having the formula:

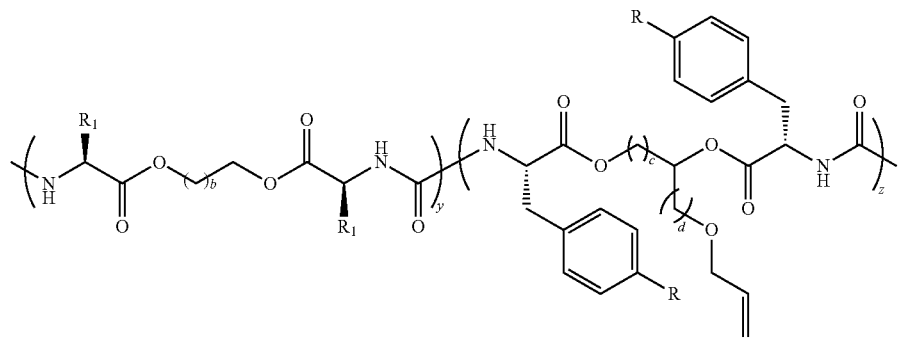

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$, or OH; $R_1$ is an amino acid side chain; b is an integer from 1 to 20; c and d are each an integer from about 1 to about 20; y is a mole fraction from about 0 to about 0.995; and z is a mole fraction from about 0.005 to about 0.500. In some embodiments, z is a mole fraction from about 0.05 to about 0.500, in other embodiments, from about 0.100 to about 0.500, in other embodiments, from about 0.200 to about 0.500, in other embodiments, from about 0.300 to about 0.500, in other embodiments, from about 0.005 to about 0.500, in other embodiments, from about 0.005 to about 0.400, in other embodiments, from about 0.005 to about 0.300, in other embodiments, from about 0.005 to about 0.200. In various embodiments, $R_1$ may be any one or more of —$CH_3$, —$(CH_2)_3NHC(NH_2)C=NH$, —$CH_2CONH_2$, —$CH_2COOH$, —$CH_2SH$, —$(CH_2)_2COOH$, —$(CH_2)_2CONH_2$, —$NH_2$, —$CH_2C=CH-N=CH-NH$, —$CH(CH_3)CH_2CH_3$, —$CH_2CH(CH_3)_2$, —$(CH_2)_4NH_2$, —$(CH_2)_2SCH_3$, —$CH_2Ph$, —$CH_2OH$, —$CH(OH)CH_3$, —$CH_2$—$C=CH-NH-Ph$, —$CH_2$-Ph-OH, —$CH(CH_3)_2$, or —$CH_2C_6H_4OCH_2C_6H_5$. In some embodiments, both $R_1$ side chains are the same, but this need not be the case. In various embodiments, the variables b, c, d, y, and z, may each have any value or range of values set forth above for that variable.

In one or more embodiments, allyl functionalized PEU intermediate may be a terpolymer having the formula:

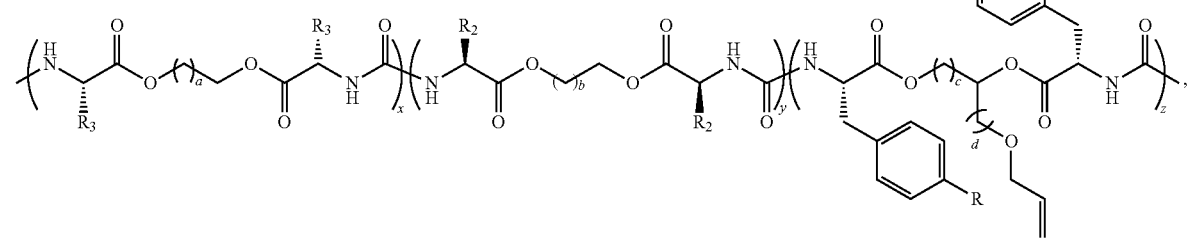

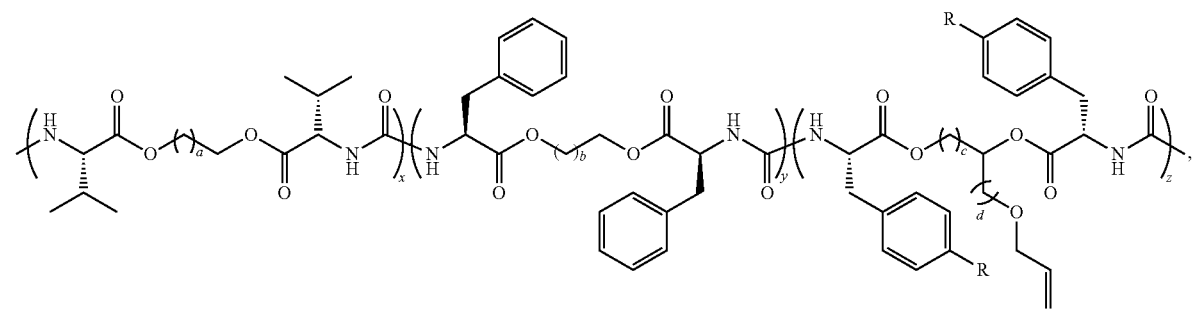

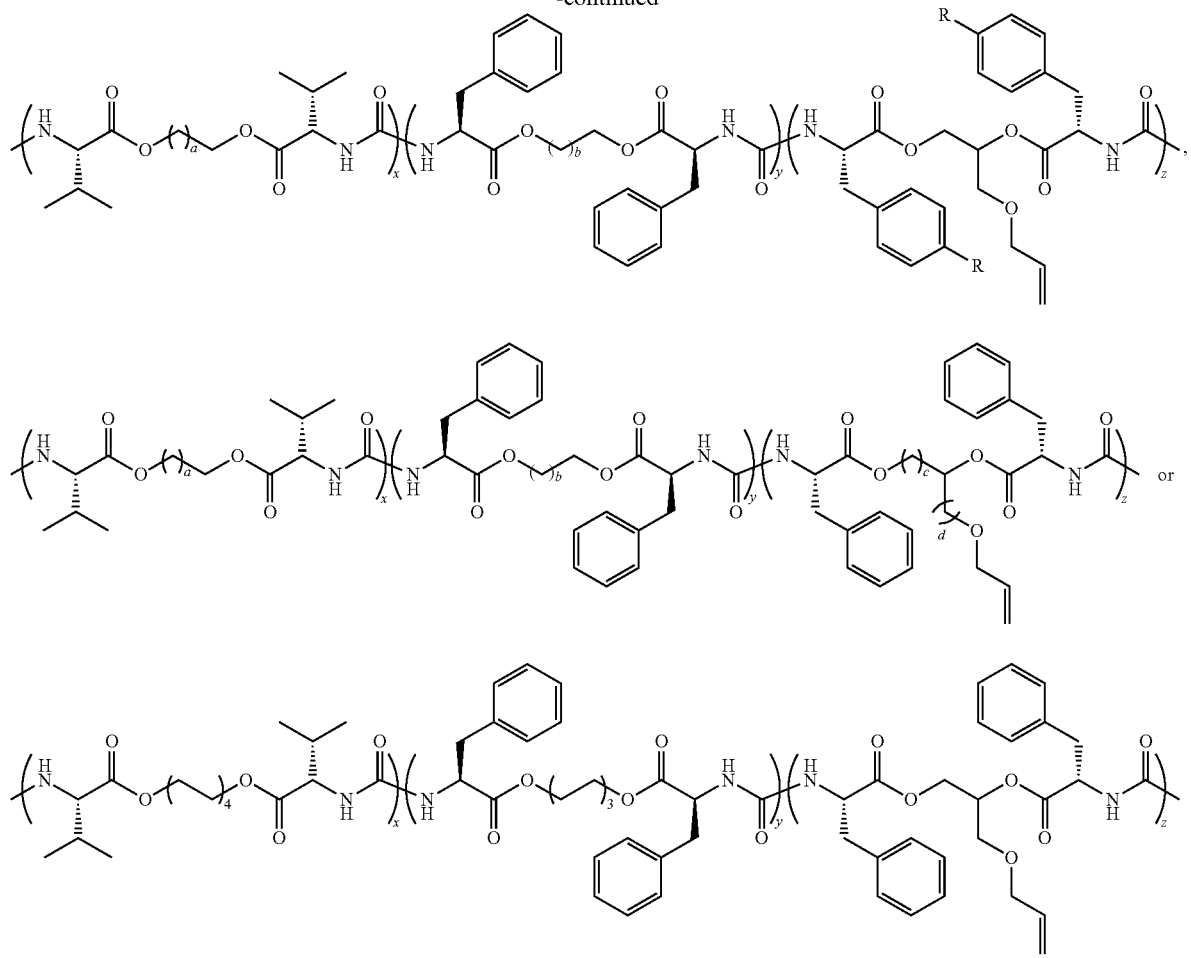

where R is OCH$_2$Ph, H, OCH$_2$C≡CH, OCH$_2$CH$_2$CH$_2$N$_3$, OCH$_2$CH$_2$CH$_2$CH=CH$_2$, OCH$_2$Ph, OCOCH$_2$CH$_2$COCH$_3$ or OH; R$_1$ is an alkyl or aryl group comprising a zwitterionic moiety; R$_2$ is a first amino acid side chain; R$_3$ is a second amino acid side chain; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500. In some embodiments, z is a mole fraction from about 0.05 to about 0.500, in other embodiments, from about 0.100 to about 0.500, in other embodiments, from about 0.200 to about 0.500, in other embodiments, from about 0.300 to about 0.500, in other embodiments, from about 0.005 to about 0.500, in other embodiments, from about 0.005 to about 0.400, in other embodiments, from about 0.005 to about 0.300, in other embodiments, from about 0.005 to about 0.200. In some embodiments, both R$_2$ side chains are the same, but this need not be the case. In some embodiments, both R$_3$ side chains are the same, but this need not be the case. In various embodiments, R$_2$ and R$_3$ may be any one or more of —CH$_3$, —(CH$_2$)$_3$NHC(NH$_2$)C=NH, —CH$_2$CONH$_2$, —CH$_2$COOH, —CH$_2$SH, —(CH$_2$)$_2$COOH, —(CH$_2$)$_2$CONH$_2$, —NH$_2$, —CH$_2$C=CH—N=CH—NH, —CH(CH$_3$)CH$_2$CH$_3$, —CH$_2$CH(CH$_3$)$_2$, —(CH$_2$)$_4$NH$_2$, —(CH$_2$)$_2$SCH$_3$, —CH$_2$Ph, —CH$_2$OH, —CH(OH)CH$_3$, —CH$_2$—C=CH—NH-Ph, —CH$_2$-Ph-OH, —CH(CH$_3$)$_2$. or —CH$_2$C$_6$H$_4$OCH$_2$C$_6$H$_5$. In various embodiments, the variables a, b, c, d, x, y, and z may each have any value or range of values set forth above for that variable.

Next, a suitable thiol functionalized zwitterionic compound is selected and/or synthesized. In one or more embodiment, the thiol functionalized zwitterionic compound will comprise a zwitterionic moiety, such as 3-((3-((3-mercaptopropanoyl) oxy) propyl) dimethylammonio) propane-1-sulfonate, and a thiol functional group. In one or more embodiments, the thiol functionalized zwitterionic compound will be a thiol functionalized ring-opened sultone. In some embodiments, the thiol functionalized zwitterionic compound will have the formula:

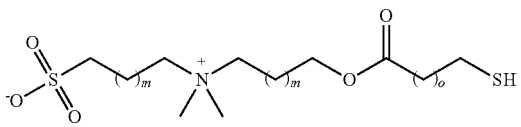

where m is an integer from about 1 to about 20; n is an integer from about 1 to about 20, and o is an integer from about 1, to about 20. In various embodiments, the variables m, n, and o may each have any value or range of values set forth above for that variable. In some embodiments, the thiol functionalized zwitterionic compound may have the formula:

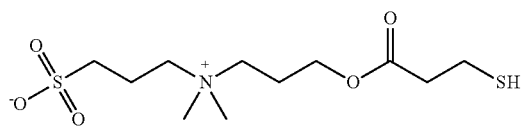

In some embodiments, the thiol functionalized zwitterionic compound may have the formula:

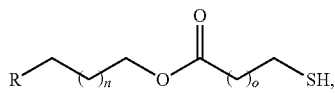

where R comprises a quaternary ammonium compound or a ring opened sultone; and n is an integer from 1 to 20; and o is an integer from 1 to 20. In various embodiments, the variables n, and o may each have any value or range of values set forth above for that variable.

In some embodiments, the thiol functionalized zwitterionic compound may synthesized by: reacting 3,3'-dithiodipropionic acid with thionyl chloride under an inert atmosphere to form a 3,3'-dithiodiproionyl chloride intermediate; dissolving 3-dimethyamino-1-propanol in anhydrous dichloromethane under an inert atmosphere and adding the 3,3'-dithiodipropionyl chloride intermediate of step a, wherein said 3-dimethyamino-1-propanol and said 3,3'-dithiodipropionyl chloride intermediate react to form a bis((3-dimethylamino)propyl) 3,3'-disulfanediyldipropionate intermediate; dissolving 1,3-propane sultone in a suitable solvent; dissolving said bis((3-dimethylamino)propyl) 3,3'-disulfanediyldipropionate intermediate in a suitable solvent, such as water, chloroform, and combinations thereof, and adding it to the solution to form a zwitterion disulfide intermediate; and then cleaving said zwitterion disulfide intermediate using 1,4-dithiothreitol (DTT) to produce two thiol functionalized zwitterionic compounds.

Finally, to form the PEU-based adhesion barriers of the present invention, the allyl functionalized PEU intermediate and said thiol functionalized zwitterionic compounds are combined and with a suitable photoinitiator and irradiated with ultraviolet light to produce a PEU-based adhesion barrier comprising an amino acid based PEU backbone having zwitterionic side chains.

In another aspect, the present invention is directed to a method of making a zwitterionic amino acid-based PEU terpolymer as described above comprising: preparing an acid salt of a first amino acid-based diester monomer having the formula:

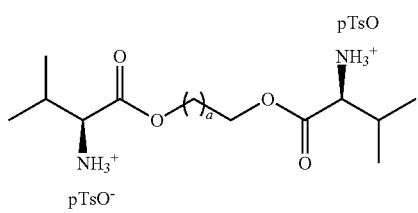

where a is an integer from about 1 to about 20; preparing an acid salt of a second amino acid-based diester monomer having the formula:

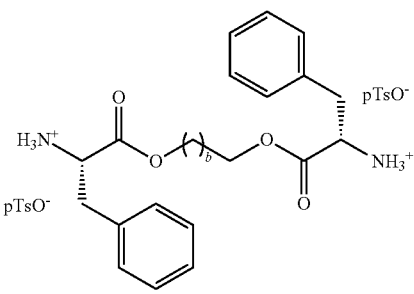

where b is an integer from about 1 to about 20; preparing an acid salt of an allyl functionalized amino acid-based diester monomer having a formula selected from:

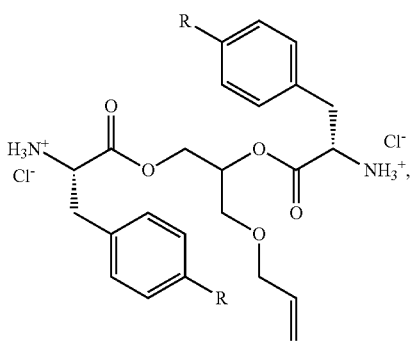

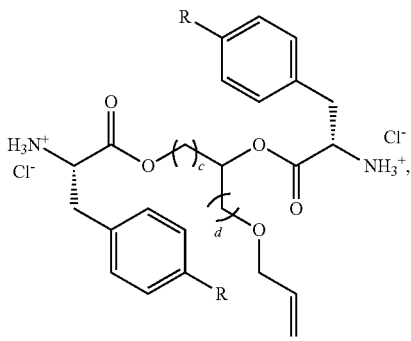

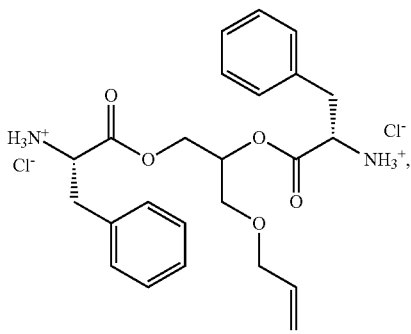

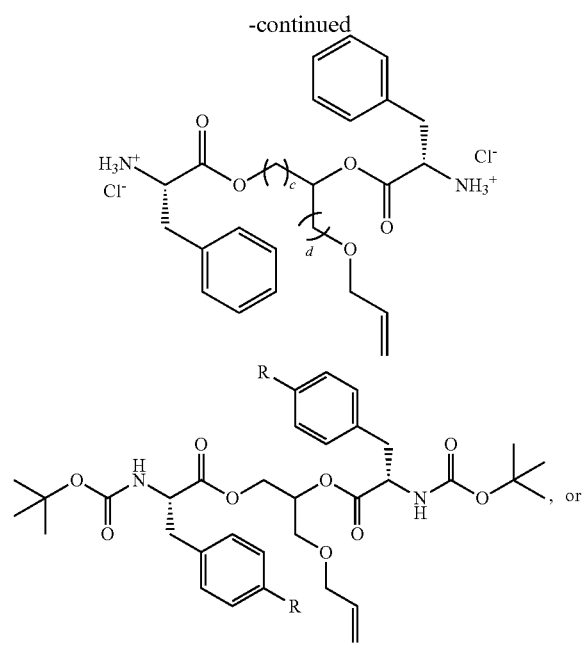

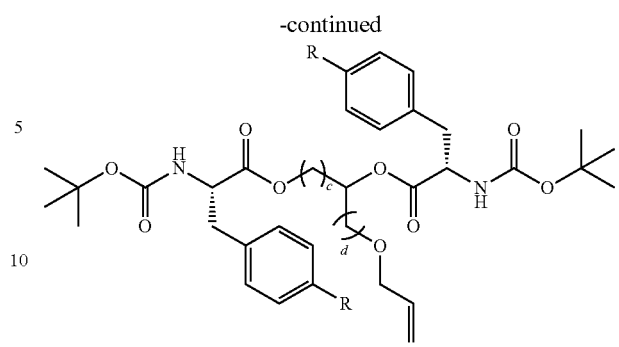

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; and c and d are each an integer from about 1 to about 20; dissolving said first amino acid-based diester monomer, said second amino acid-based diester monomer; and said allyl functionalized amino acid-based polyester monomer is a suitable solvent with a suitable water soluble organic base; adding a urea bond forming compound to the solution of step D to form an allyl functionalized amino acid based PEU terpolymer intermediate having a formula selected from:

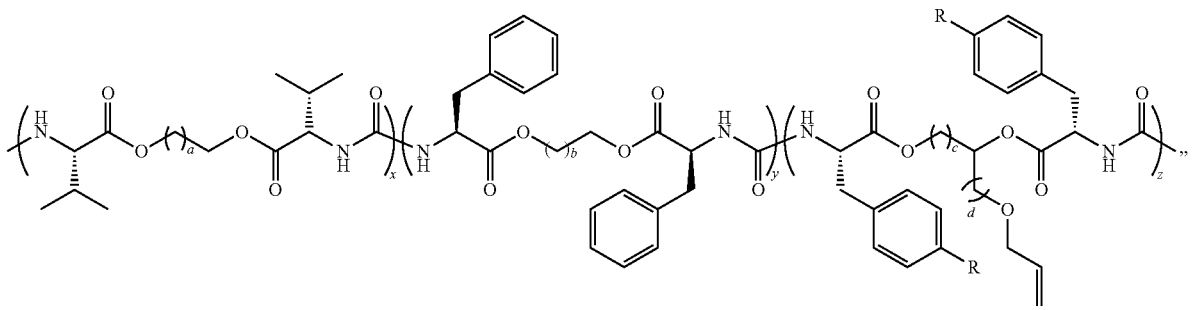

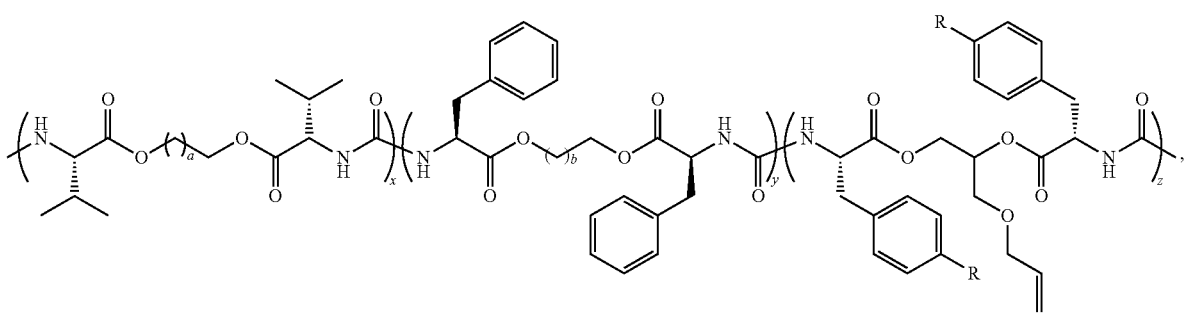

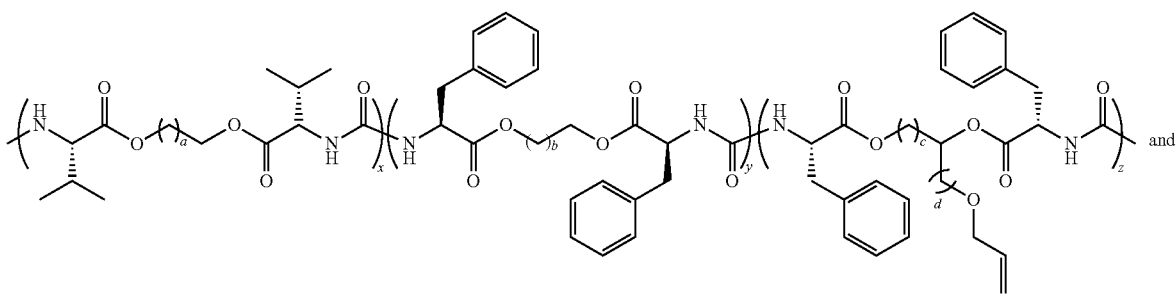

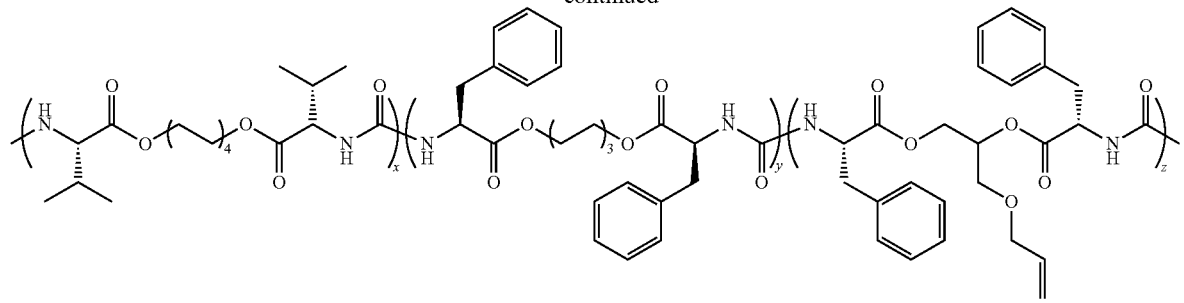

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500.; reacting 3,3'-dithiodipropionic acid with thionyl chloride under an inert atmosphere to form a 3,3'-dithiodiproionyl chloride intermediate; dissolving 3-dimethyamino-1-propanol in anhydrous dichloromethane under an inert atmosphere and adding the 3,3'-dithiodipropionyl chloride intermediate of step F, wherein said 3-dimethyamino-1-propanol and said 3,3'-dithiodipropionyl chloride intermediate react to form a bis((3-dimethylamino)propyl) 3,3'-disulfanediyldipropionate intermediate; dissolving 1,3-propane sultone in a suitable solvent; dissolving said bis((3-dimethylamino)propyl) 3,3'-disulfanediyldipropionate intermediate in a suitable solvent and adding it to the solution of step H to form a zwitterion disulfide intermediate having the formula:

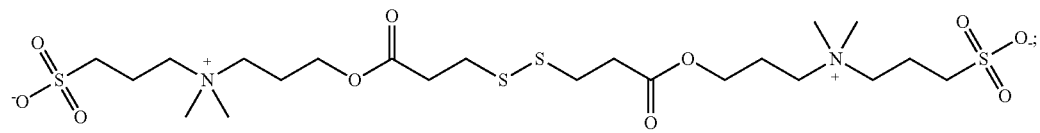

cleaving said zwitterion disulfide intermediate of step I using 1,4-dithiothreitol (DTT) to produce two thiol functionalized zwitterionic compounds each having the formula:

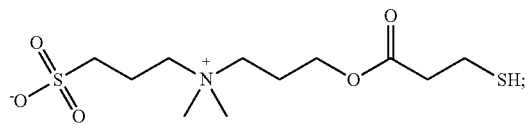

combining said allyl functionalized amino acid based PEU terpolymer intermediate and said thiol functionalized zwitterionic compounds and adding a suitable photoinitiator; and irradiating the combination to form the PEU-based adhesion barrier having a formula selected from:

73
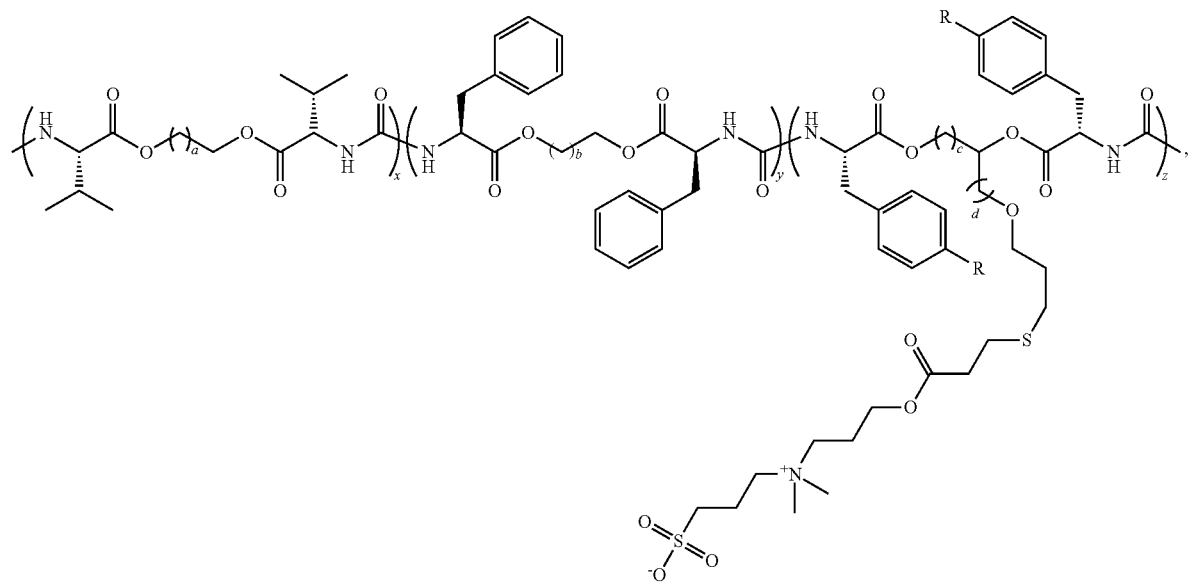
74
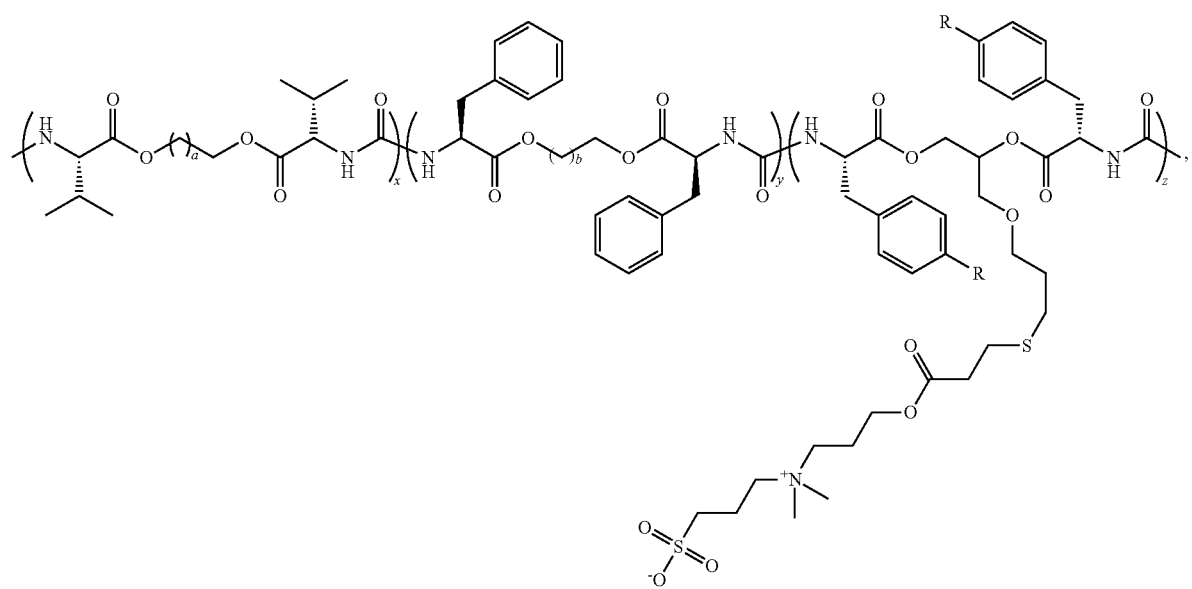

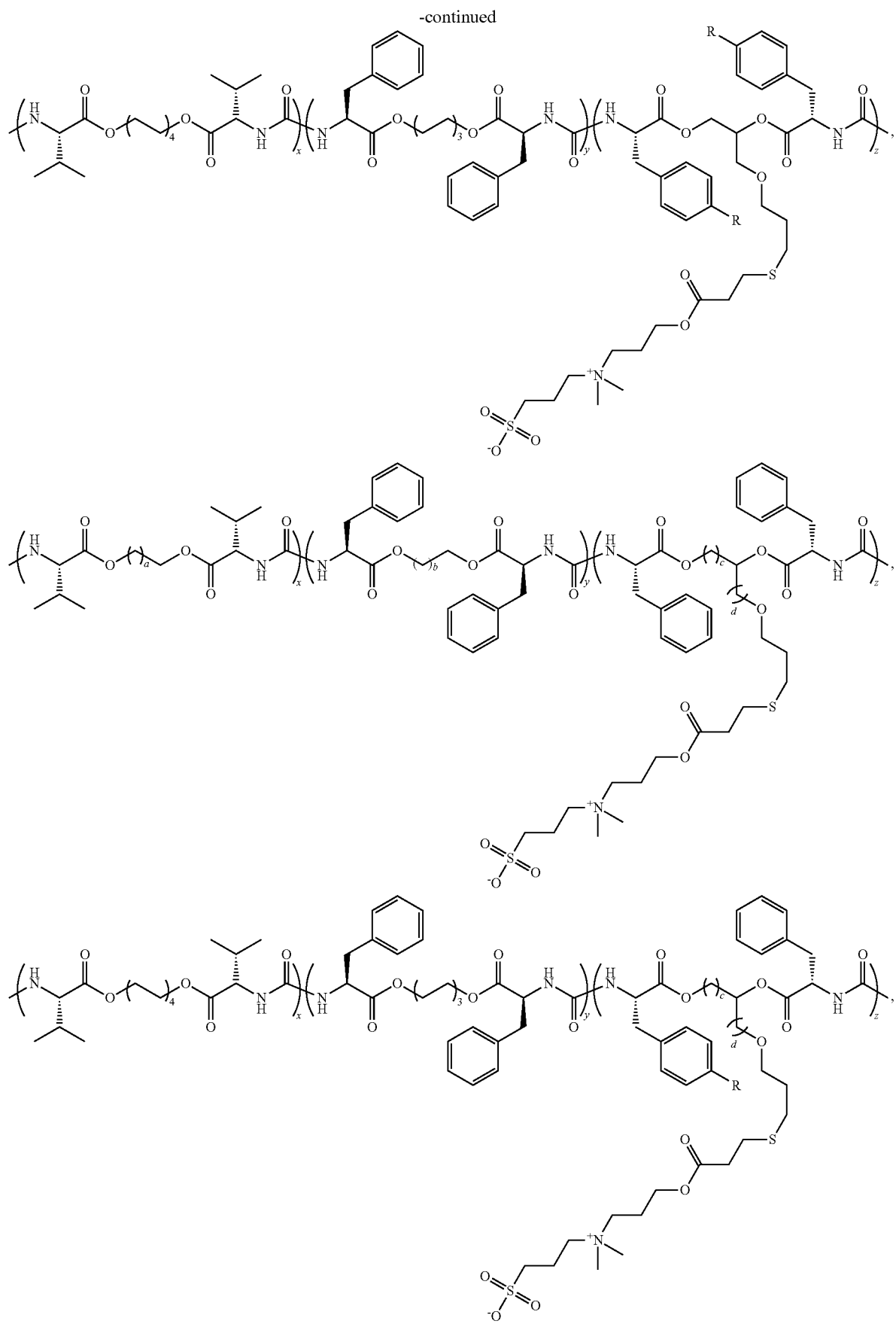

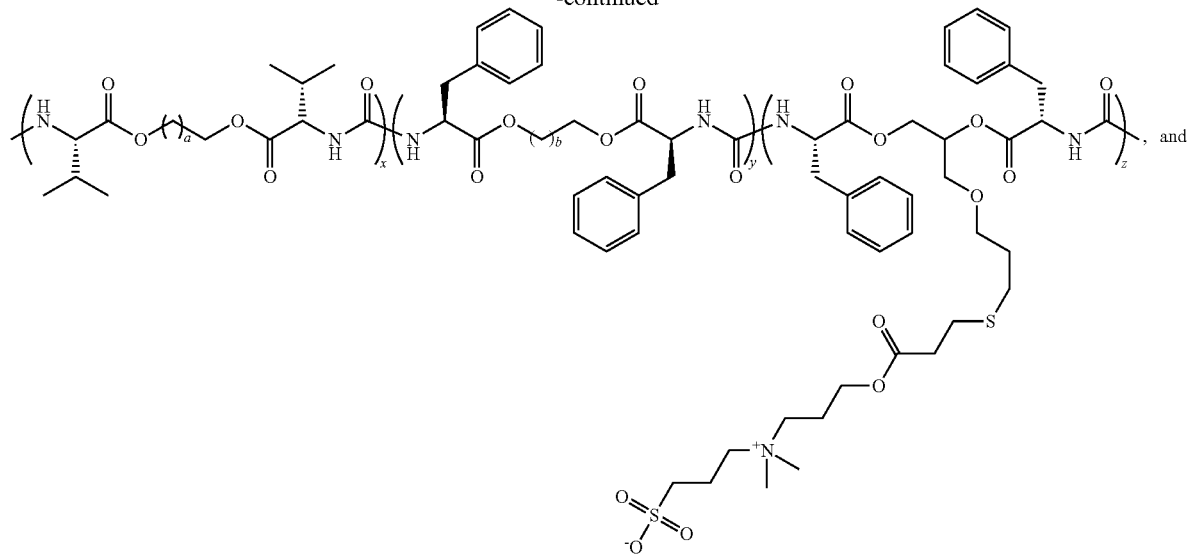

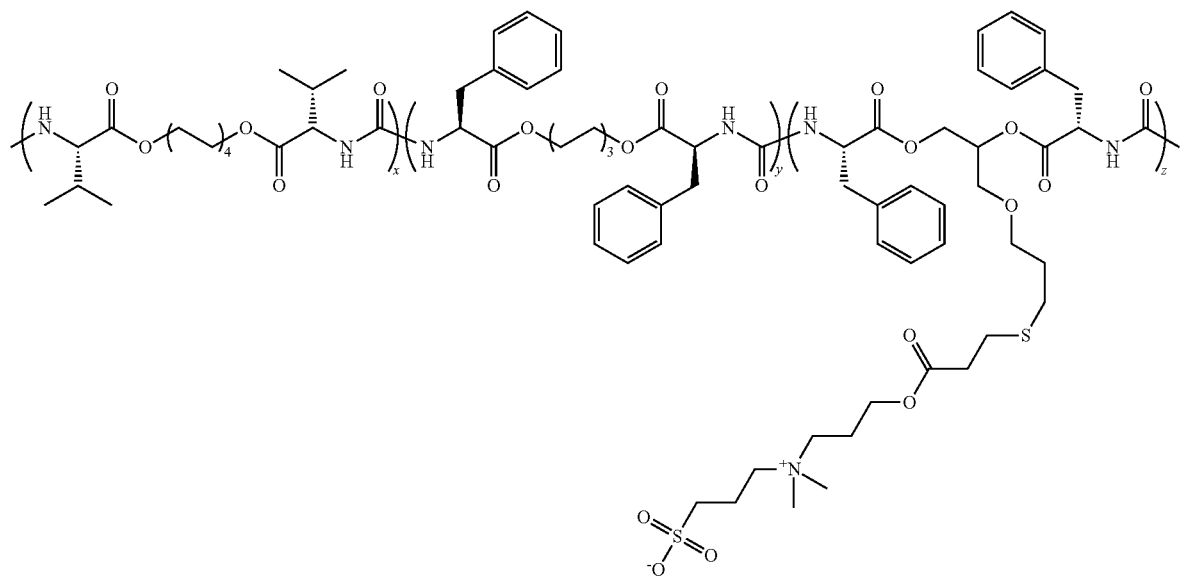

where R is $OCH_2Ph$, H, $OCH_2C{\equiv}CH$, $OCH_2CH_2CH_2N_3$, $OCH_2CH_2CH_2CH{=}CH_2$, $OCH_2Ph$, $OCOCH_2CH_2COCH_3$ or OH; a is an integer from 1 to 20; b is an integer from 1 to 20; c, d, m, n, and o are each an integer from about 1 to about 20; x is a mole fraction from about 0 to about 0.995; y is a mole fraction from about 0 to about 0.995; and z is a mole fraction from about 0.005 to about 0.500. In various embodiments, the variables a, b, c, d, x, y, and z may each have any value or range of values set forth above for that variable.

In various embodiments, the zwitterion disulfide intermediate may have the formula:

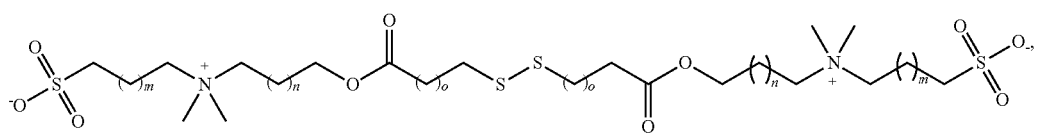

where m, n, and o are each an integer from about 1 to about 20. In various embodiments, the variables m, n, and o may each have any value or range of values set forth above for that variable. In these embodiments, the cleaving step described above will produce two thiol functionalized zwitterionic compounds each having the formula:

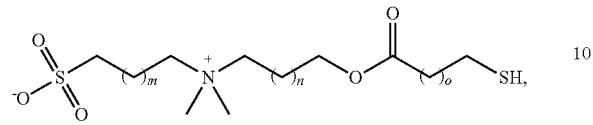

where m, n, and o are as above.

In one or more embodiments, the zwitterionic amino acid-based PEU terpolymer described above may be synthesized as shown in Scheme 6, below.

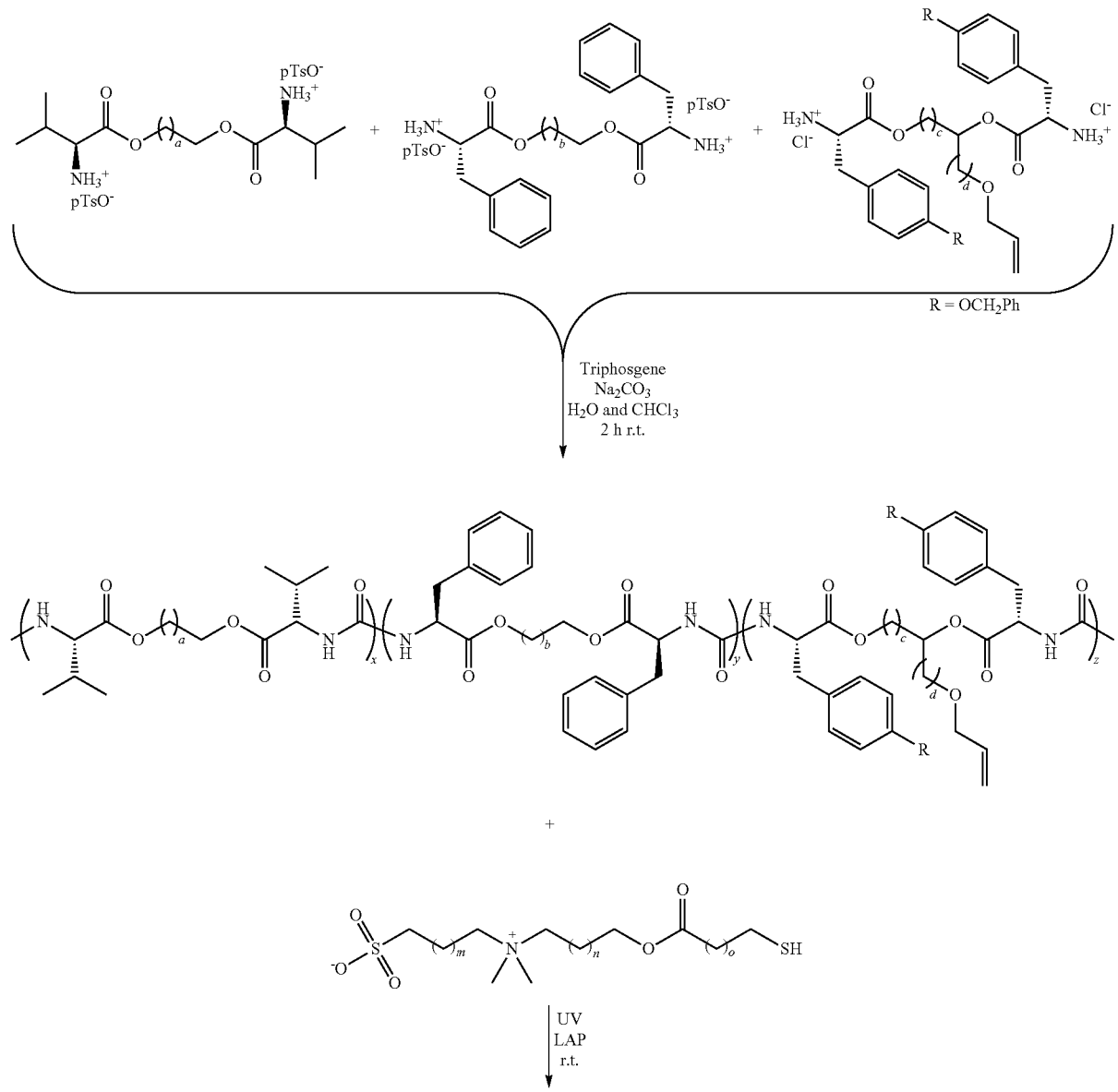

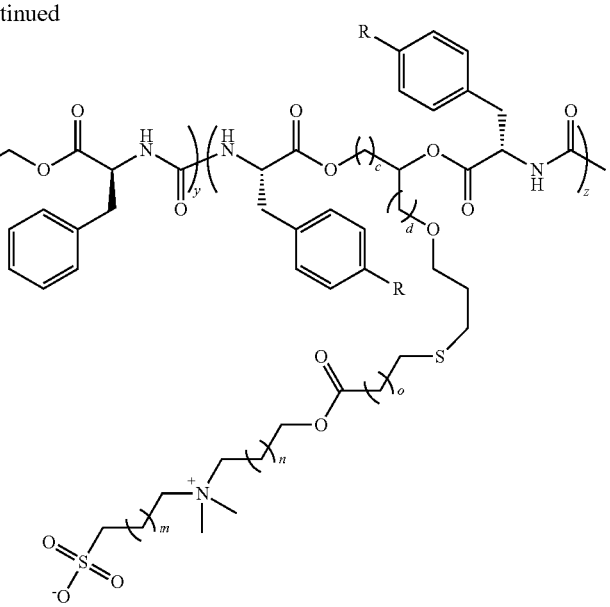

where R is OCH$_2$Ph, H, OCH$_2$C≡CH, OCH$_2$CH$_2$CH$_2$N$_3$, OCH$_2$CH$_2$CH$_2$CH=CH$_2$, OCH$_2$Ph, OCOCH$_2$CH$_2$COCH$_3$, or OH; each a, b, c, d, m, n, and o are each an integer from about 1 to about 20; x is a mole fraction from about 0 to about 0.995; y is a mole fraction from about 0 to about 0.995; and z is a mole fraction from about 0.005 to about 0.500. In various embodiments, the variables a, b, c, d, x, y, z, m, n, and o may each have any value or range of values set forth above for that variable.

EXPERIMENTAL

In order to evaluate and further reduce them to practice, the PEU-based adhesion barriers of the present invention were synthesized and characterized as follows. In a first set of experiments, PEU terpolymers according to embodiments of the present invention were synthesized by altering the molar feed ratio of 1-VAL-8, 1-PHE-6, and 1-TYR-2 alloc in an interfacial polymerization with triphosgene to afford 0% alloc, 5% alloc, and 10% alloc PEUs, which were functionalized, tested and characterized.

Synthesis of 0% alloc, 5% alloc, and 10% alloc PEUs: Amino acid-based monomers were synthesized and characterized using H-NMR (FIGS. 1A-B, 2 and 3). 1,6-hexanediol and 1,8-octanediol were coupled to the carboxylic acid of L-valine or L-phenylalanine through an esterification using p-toluenesulfonic acid to prevent amine moiety. The resulting monomers were named based on their diol chain length and amino acid; (1-VAL-8) formed from 1,8-octanediol and L-valine, (1-PHE-6) formed from 1,6-hexanediol and L-phenylalanine, and (1-PHE-8) formed from 1,8-octanediol and L-phenylalanine. 1-PHE-6 and 1-PHE-8 can be differentiated from the integration of the methylene peak at 1.06-1.14 ppm.

Figure 1A:
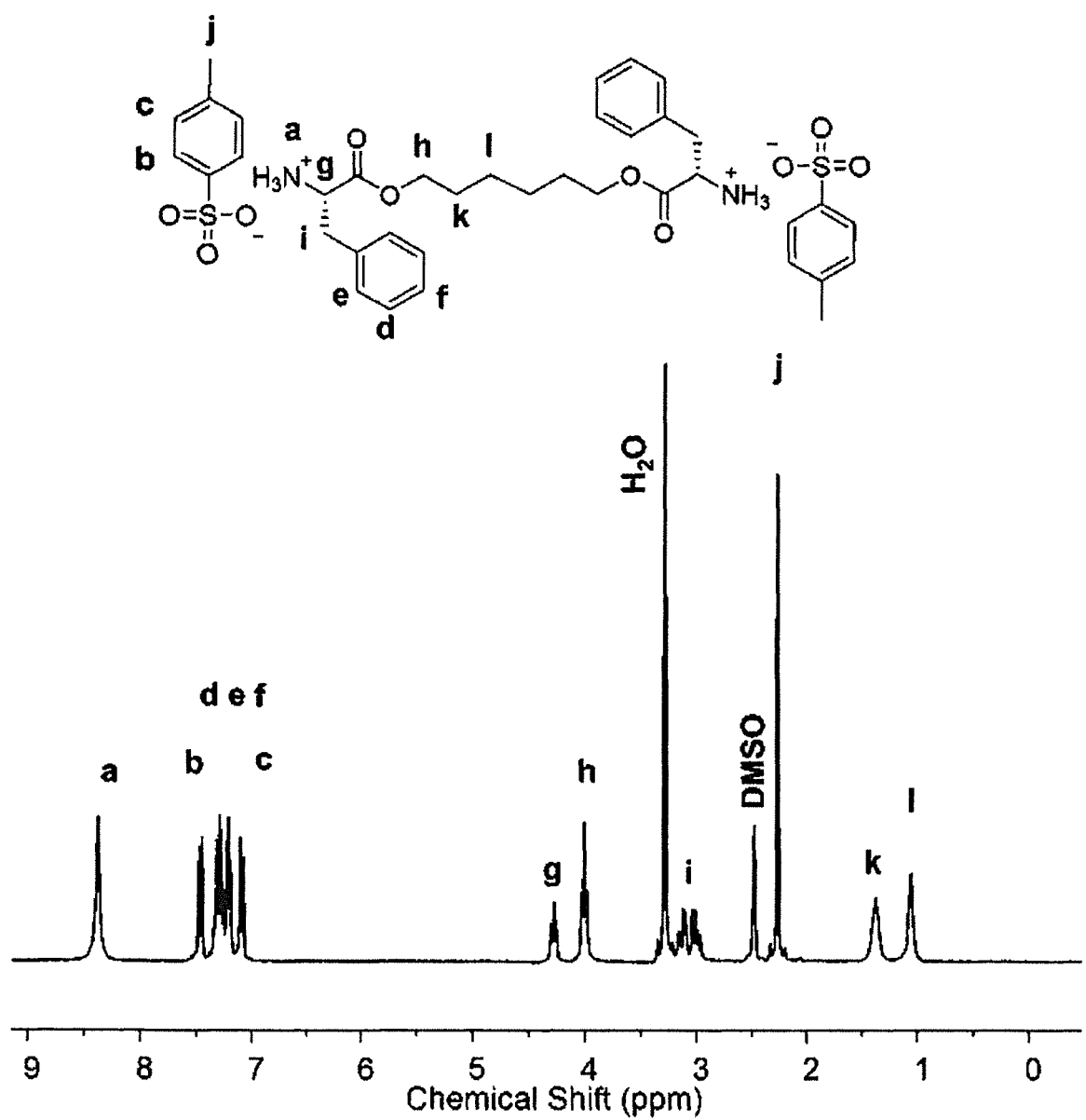
FIGS. 1A-B are a $^1$H-NMR overlay for the 1-PHE-6 (FIG. 1A) and 1-PHE-8 (FIG. 1B) monomers. The 1-PHE-8 monomer shows successful synthesis based on the characteristic L-phenylalanine aromatic peaks denoted 'd, e, f' and the p-toluenesulfonic acid aromatic peaks. Integration confirms that this monomer is a bifunctional monomer with two protonated amine moieties.
Figure 1B:
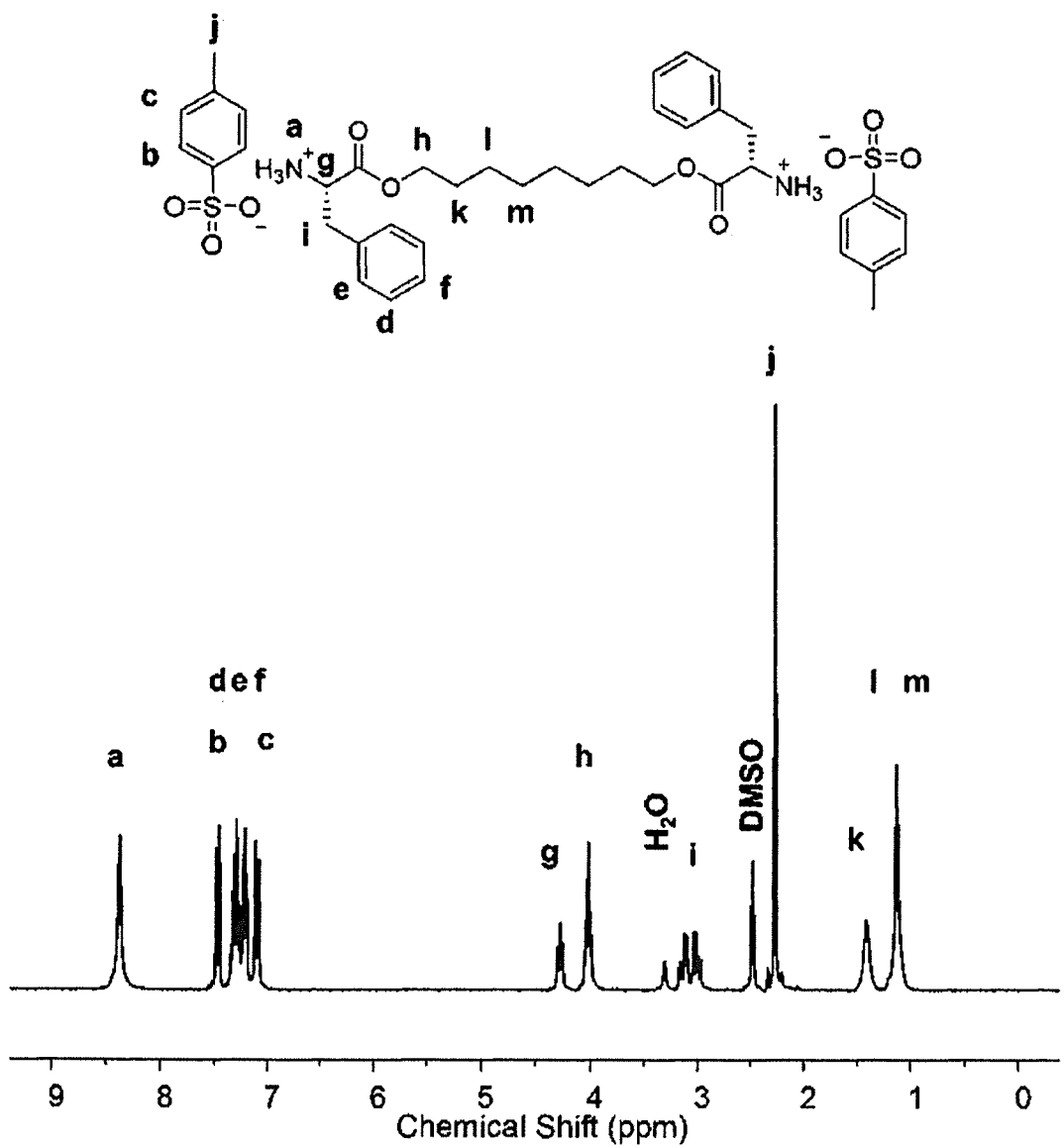
Figure 3:
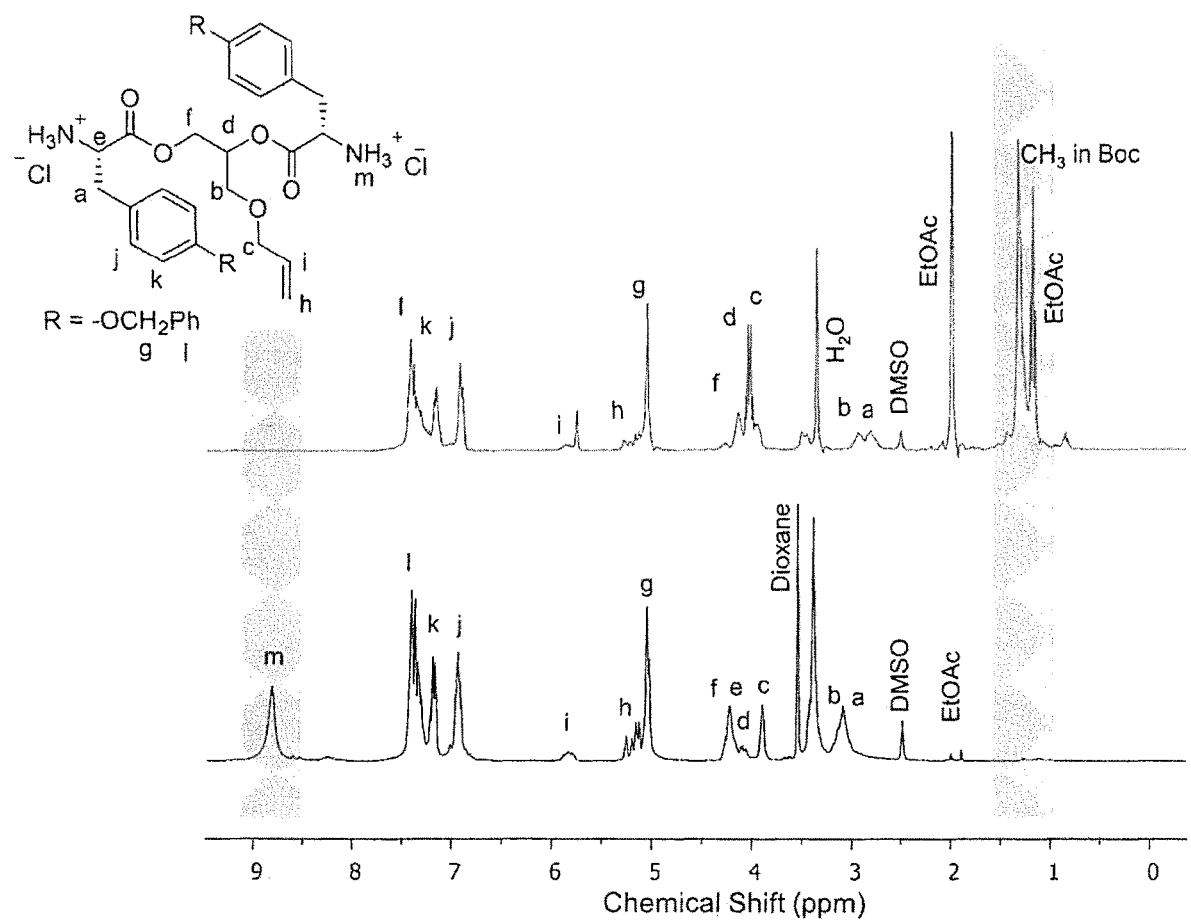
FIG. 3 is a $^1$H-NMR overlay of the 1-TYR-2 Alloc monomer before (upper) and after (lower) deprotection. The $^1$H-NMR overlay for the 1-TYR-2 Alloc monomer shows successful synthesis based on the successful deprotection noted by the disappearance of the boc peak and appearance of the broad amine.
Figure 4:
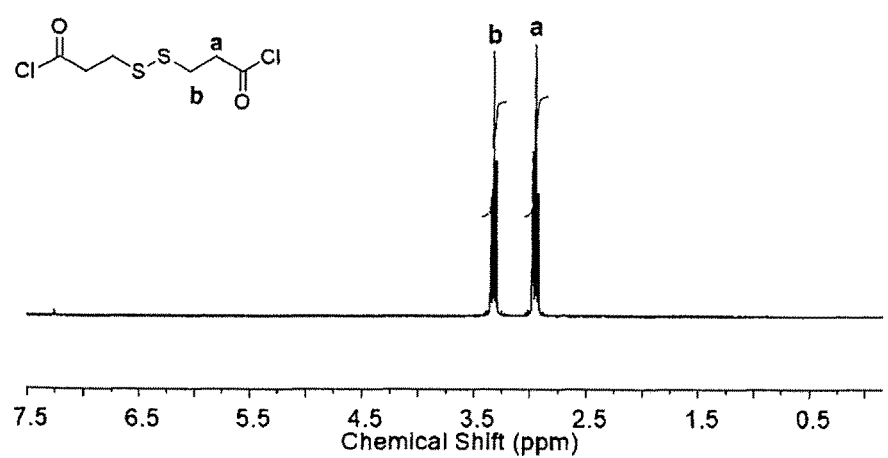
FIG. 4 is a $^1$H-NMR of 3,3'-dithiodipropionyl chloride.
Figure 5:
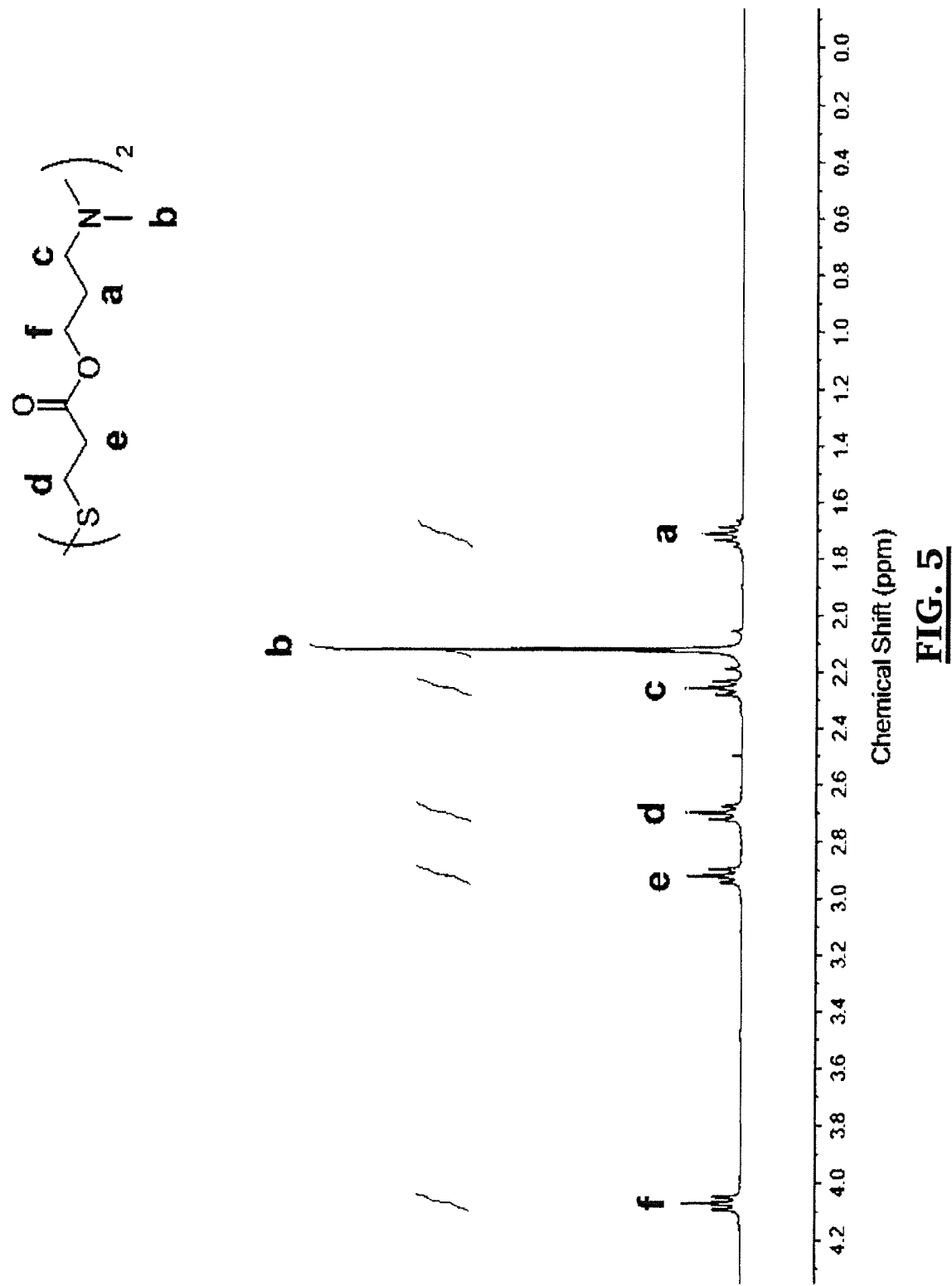
FIG. 5 is a $^1$H-NMR overlay of bis(3-(dimethylamino) propyl) 3,3'-disulfanediyldipropionate.
Figure 6:
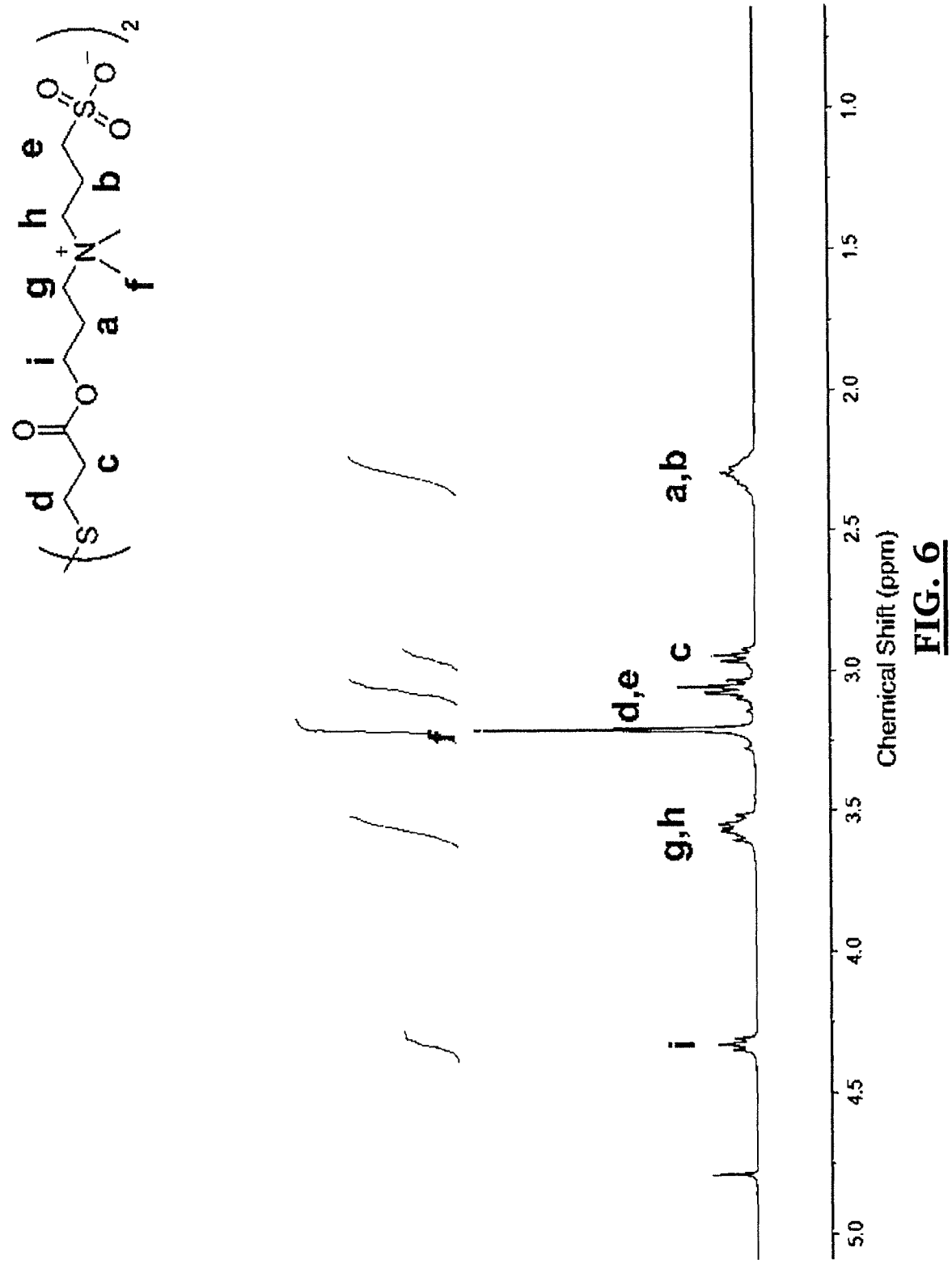
FIG. 6 is a $^1$H-NMR overlay of a zwitterion disulfide.
Figure 7:
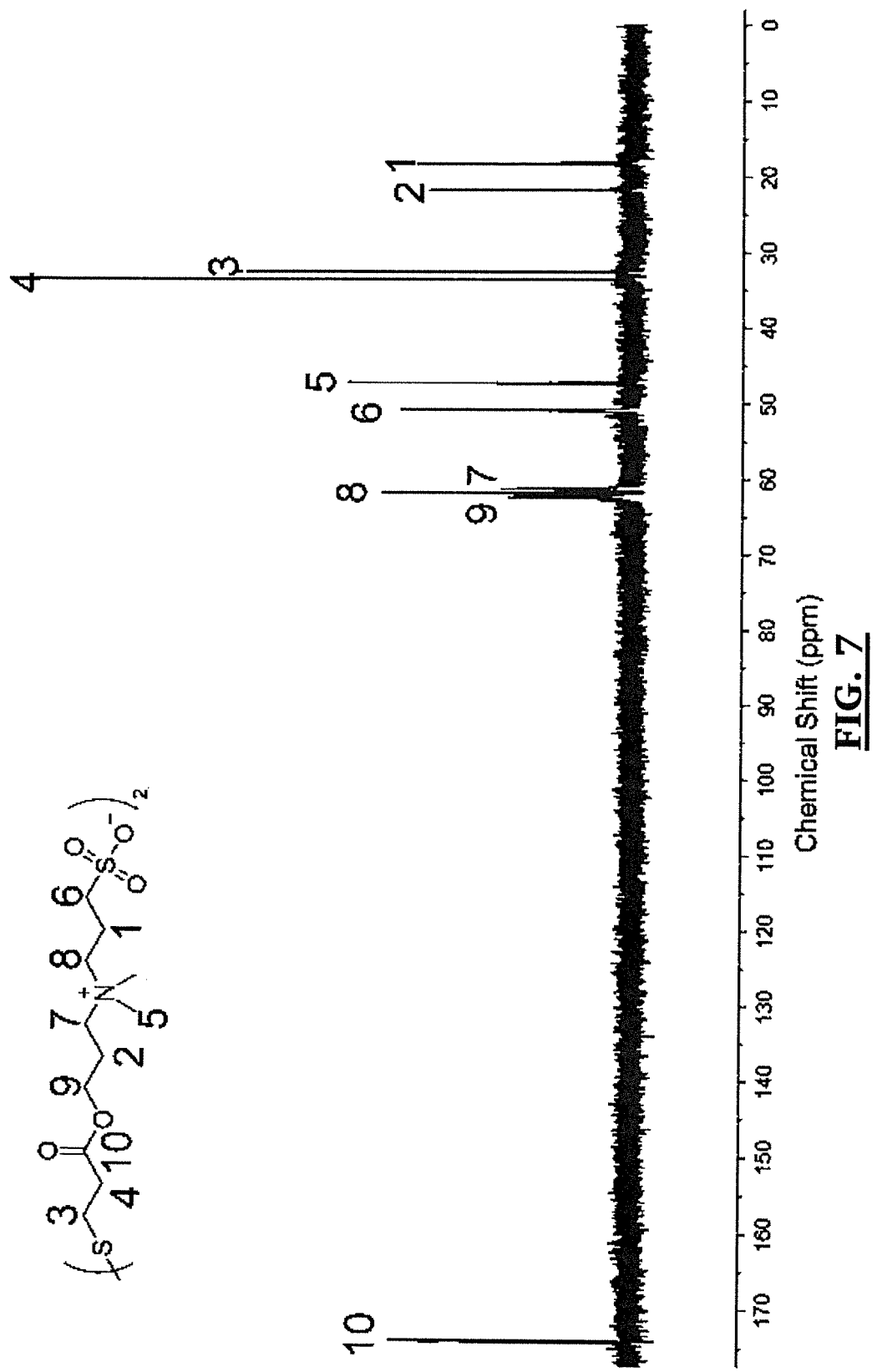
FIG. 7 is a $^{13}$C-NMR overlay of the zwitterion disulfide shown in FIG. 6.
Figure 8:
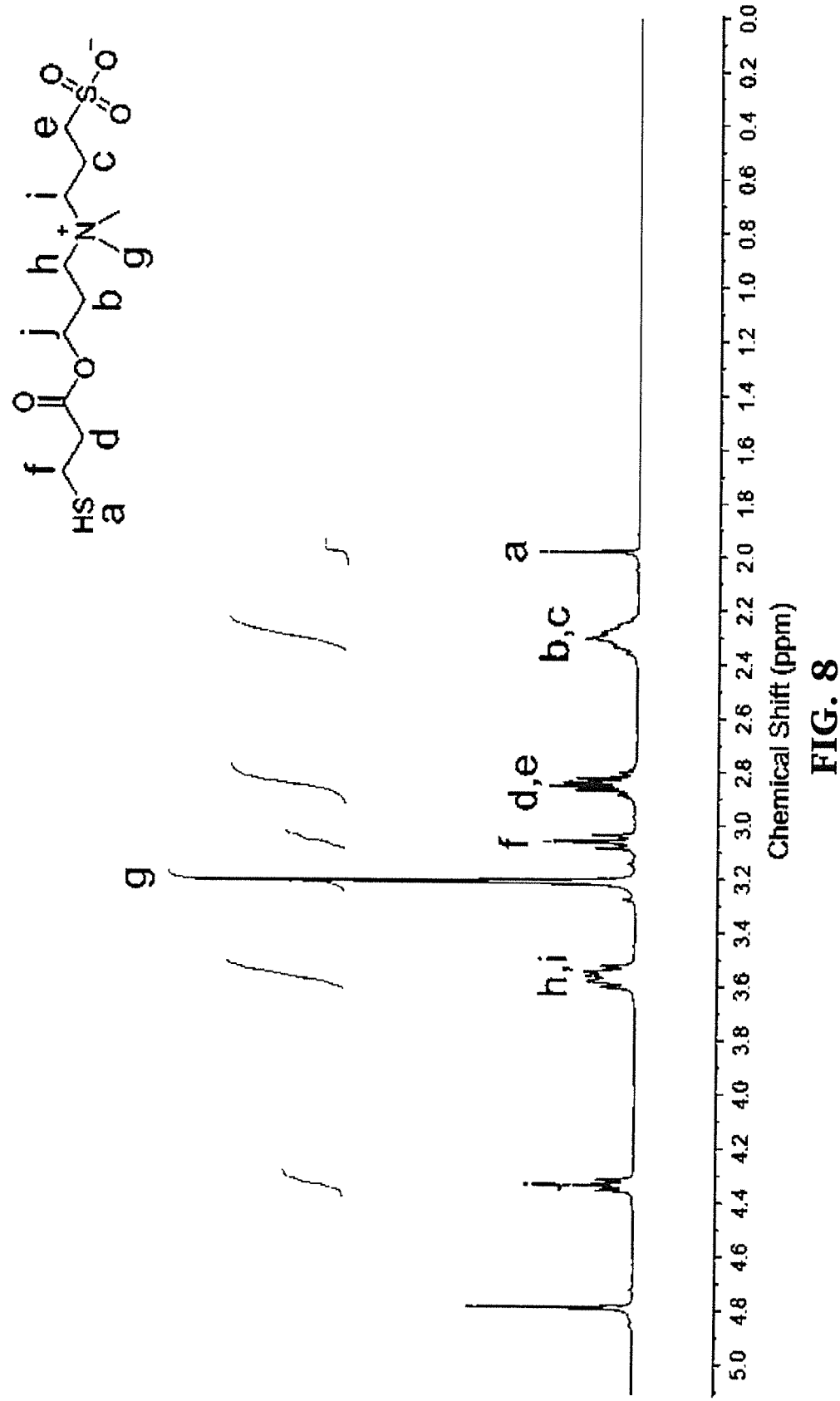
FIG. 8 is a $^1$H-NMR overlay of a zwitterion thiol.
Figure 9:
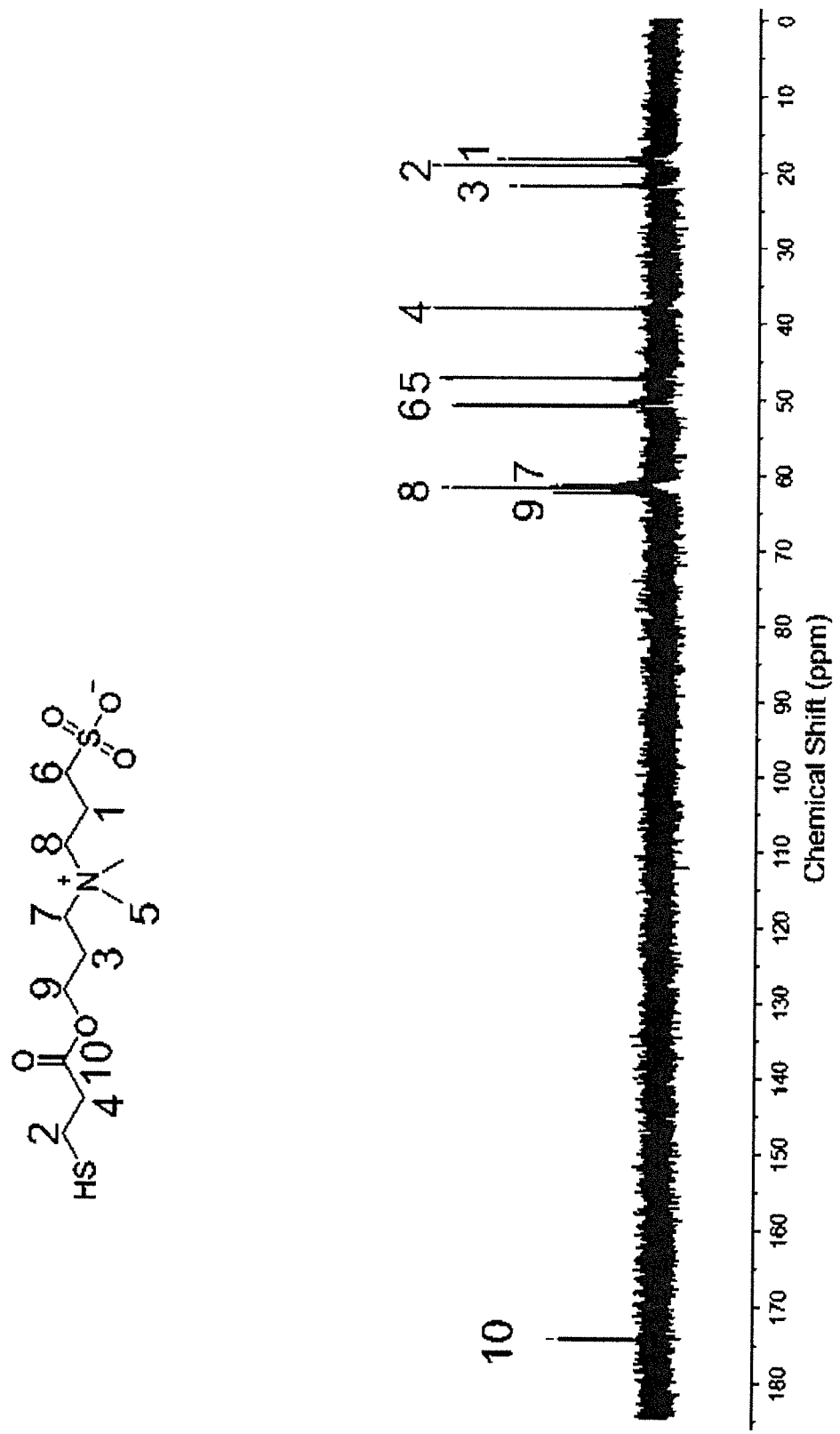
FIG. 9 is a $^{13}$C-NMR overlay of the zwitterion thiol shown in FIG. 8.
Figure 10:
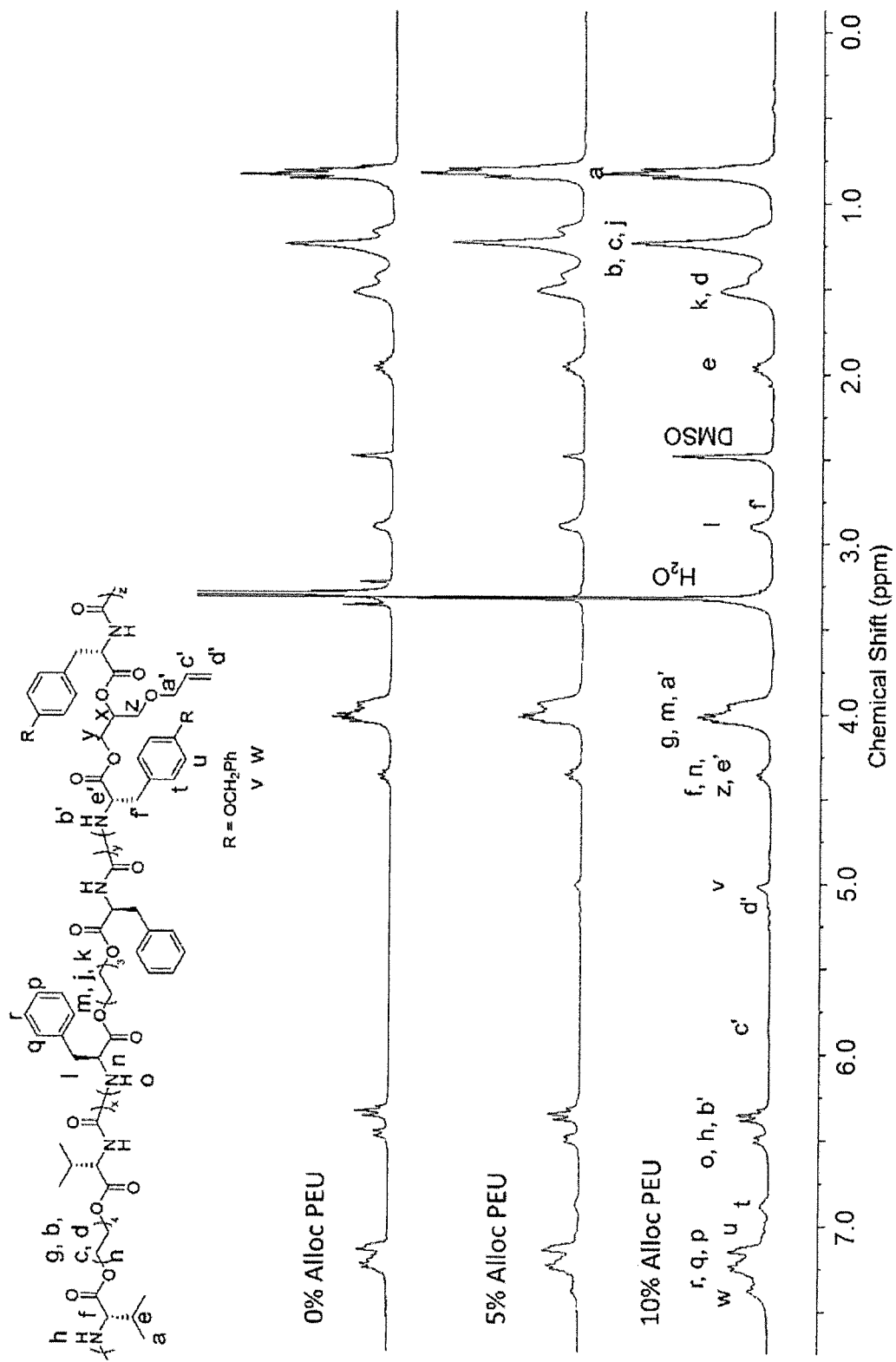
FIG. 10 is a polymer $^1$H-NMR spectrum overlay for an 0% Alloc PEU (upper), a 5% Alloc PEU (middle), and a 10% Alloc PEU (lower). The monomer molar composition in the afforded polymers were calculated from the characteristic 'a' resonances from L-valine, the methylene resonances from L-phenylalanine denoted 'l', and the methylene resonances from the benzyl protected L-tyrosine denoted 'v'.

(See FIGS. 1A-B) 1-VAL-8 synthesis was confirmed based on the characteristic L-valine methyl peak at 0.96 ppm. (See FIG. 2) Synthesis of 1-TYR-2 Alloc was carried out through a DIC coupling with Boc-O-benzyl-L-tyrosine and 1,3-allyoxyl-2-propanediol. The final product was collected and confirmed after HCl deprotection with the disappearance of the characteristic Boc protecting group at 1.31 ppm and the appearance of the broad amine peak at 8.82 ppm (FIG. 3). Synthesis of the zwitterion thiol occurred in several steps where a halogenation reaction was performed between 3,3'-dithiodipropionic acid and thionyl chloride to afford 3,3'-dithiodipropionyl chloride (FIG. 4). This product was then reacted in an S$_n$2 substitution with 3-dimethylamino-1-propanol to obtain the bis(3-dimethylamino)propyl) 3,3'-disulfanediyldipropionate (FIG. 5). This was further functionalized with 1,3-propane sultone to afford the zwitterion disulfide (FIGS. 6 and 7). Finally, the zwitterion-SH was obtained by cleavage of the zwitterion disulfide using 1,4-dithiothreitol (DTT) and the product was thus collected (FIGS. 8 and 9). Terpolymer PEU synthesis was carried out by altering the molar feed ratio of 1-VAL-8, 1-PHE-6, and 1-TYR-2 alloc in an interfacial polymerization with triphosgene to afford 0% alloc, 5% alloc, and 10% alloc PEUs (see, Scheme 7) (FIG. 10). Polymers were named according to the amount of 1-TYR-2 alloc in the monomer feed ratio. Successful polymer synthesis and monomer incorporation was confirmed using $^1$H NMR. The monomers were readily identified by the characteristic methyl L-valine peaks denoted 'a', methylene from L-phenylalanine denoted '1', and methylene of O-bzn-TYR denoted 'v'. Additionally, the alkene functionality from 1-TYR-2 alloc could be observed with peaks at 5.13 ppm (d') and 5.84 ppm (c').

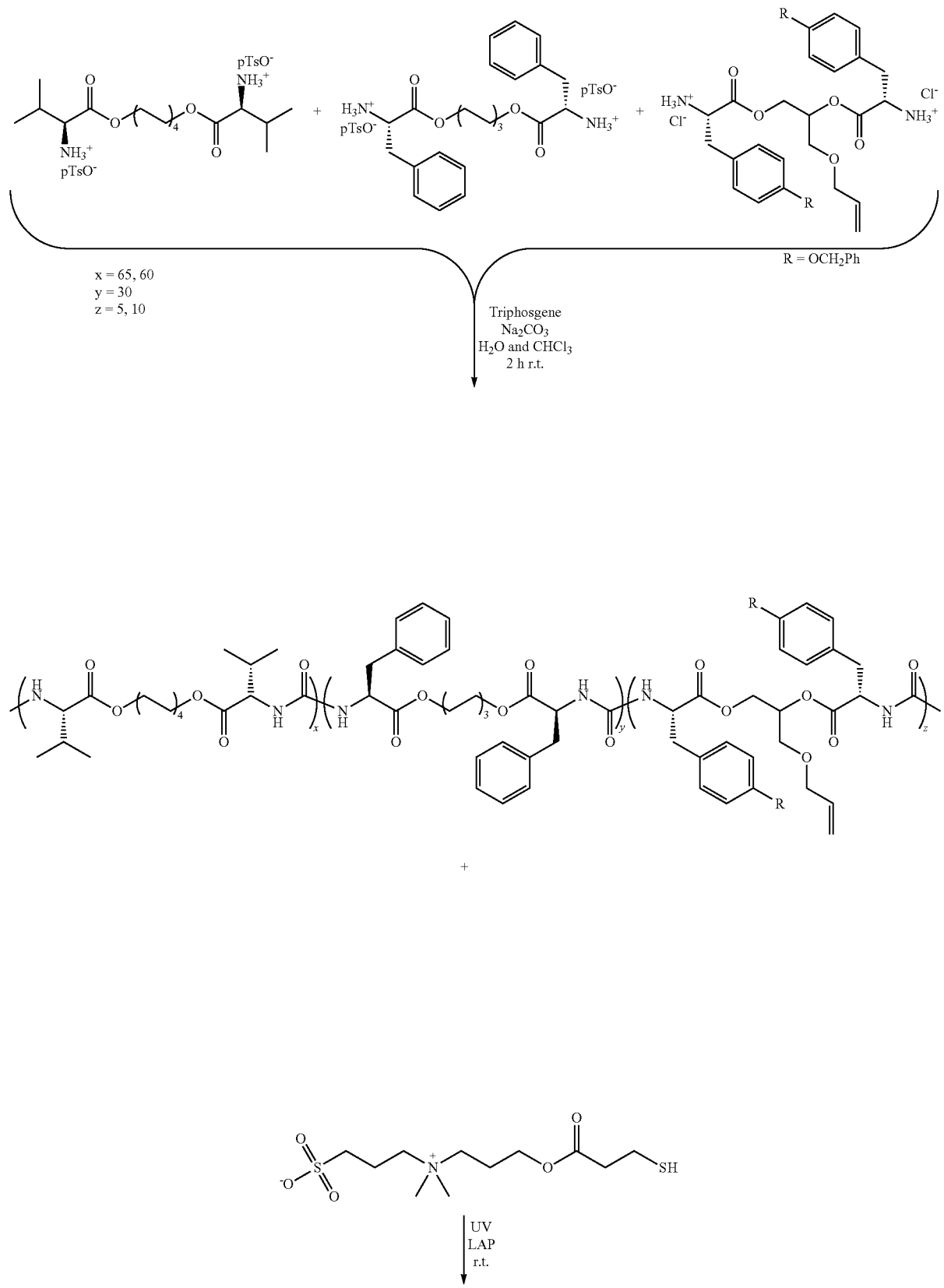
Scheme 7
Synthetic scheme for the 0% alloc, 5% alloc, and 10% alloc PEU terpolymer analogues

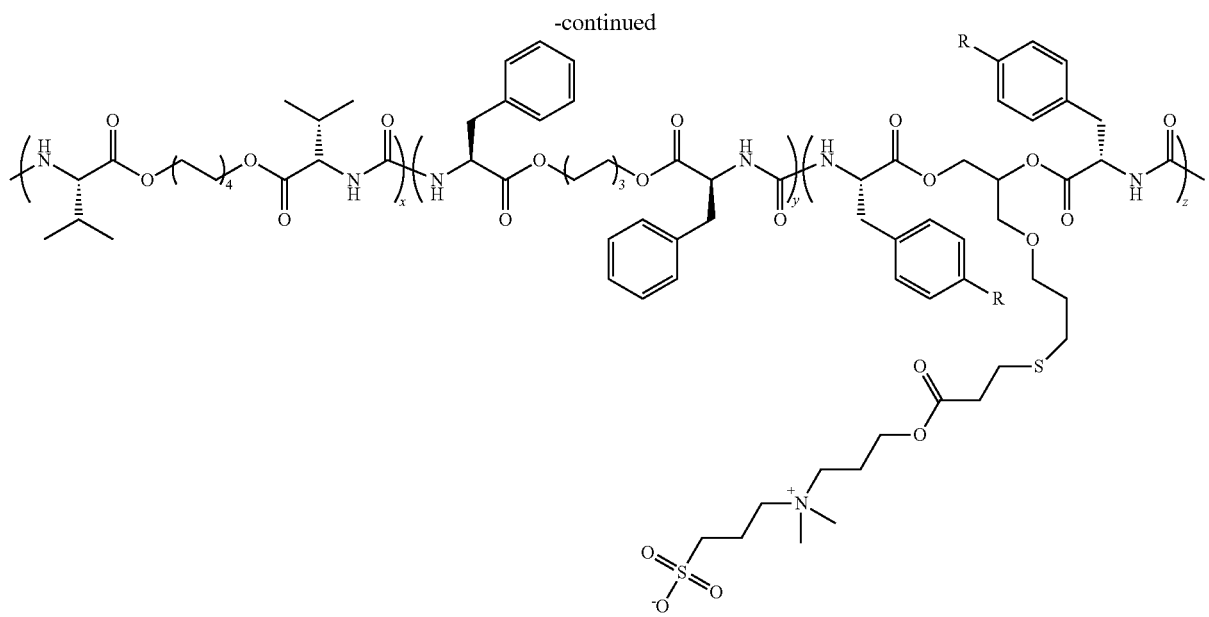

Scheme 7 shows the general synthetic scheme for forming these PEU terpolymer analogues. As set forth above, synthesis of the 1-VAL-8, 1-PHE-6, and 1-TYR-2 alloc monomers (not shown) may be carried out via a Fischer esterification or a DIC coupling between varying diol chain lengths and amino acids. In total two terpolymers were synthesized by combining 1-VAL-8 and 1-PHE-6 and 1-TYR-2 alloc in two stoichiometric amounts to form 5% alloc-PEU and 10% alloc-PEU. Both polymers were formed through interfacial polymerization with triphosgene to afford urea units. Polymers were further functionalized with a thiol-ene reaction between a zwitterion-SH and the alkene functionality. The 0% alloc PEU was formed without any alloc monomer.

Figure 11:
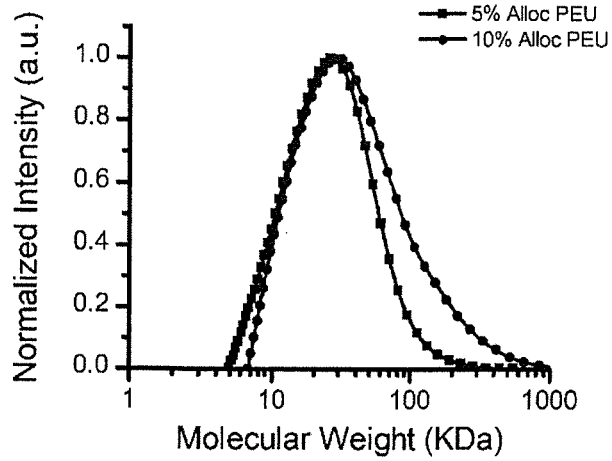
FIG. 11 is a graph showing size-exclusion chromatography (SEC) data for 5% and 10% alloc PEUs.
Figure 12:
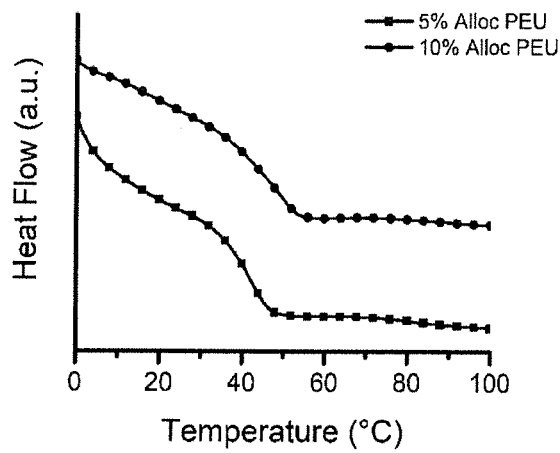
FIG. 12 is a graph showing the results of differential scanning calorimetry (DSC) results for 5 and 10% alloc PEUs.
Figure 13:
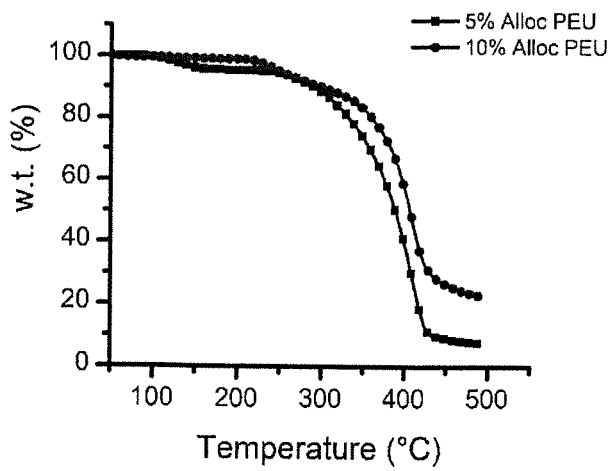
FIG. 13 is a graph showing the results of thermogravimetric analysis of 5 and 10% alloc PEUs.

Physical Properties:

Size-exclusion chromatography (SEC) reported molecular weights are post-precipitation in acetone (Table 1) (FIG. 11). The molar mass distributions ($Đ_m$) can be less than the theoretical value of 2 because the low molecular weight fractions are lost during precipitation. Molecular weights were sufficiently high to allow for mechanical testing and subsequent in vivo characterization. Differential scanning calorimetry (DSC) curves show the glass transition temperatures ($T_g$) are above body temperature indicating that the materials will be sufficiently stiff upon any implantation application (FIG. 12). All terpolymer PEUs had sufficiently high degradation temperatures ($T_d$) enabling them to be thermally processed with sufficient stability for processing and storage (Table 1) (FIG. 13).

TABLE 1

| Physical properties | | | | | |
|---|---|---|---|---|---|
| Polymer | $M_n$ (KDa) | $M_w$ (KDa) | $Đ_m$ | $T_g$ (° C.) | $T_d$ (° C.) |
| 0% Alloc PEU | 57 | 95 | 1.7 | 48 | 340 |
| 5% Alloc PEU | 24 | 35 | 1.5 | 40 | 289 |
| 10% Alloc PEU | 28 | 62 | 2.2 | 49 | 299 |

Figure 14A:
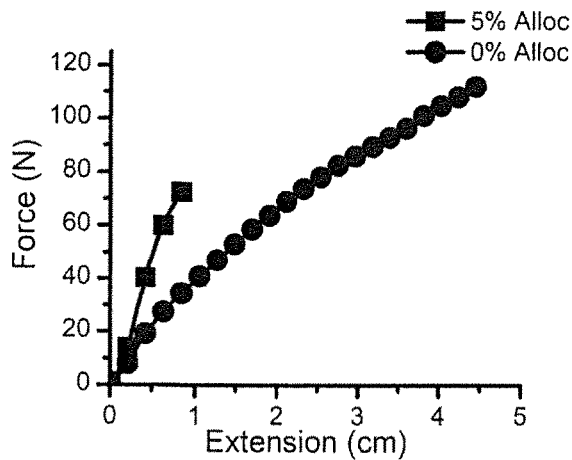
FIGS. 14A-D are graphs showing the results of ball-burst mechanical tests performed on 0% Alloc and 5% Alloc PEU terpolymers according to one or more embodiments of the present invention. The force versus extension curve (FIG. 14A) indicates that there is greater stiffness (FIG. 14B) for the 5% alloc PEU when compared to the 0% alloc analogue. The force at break (FIG. 14C) and extension at break (FIG. 14D) for the 5% alloc was diminished when compared to the 0% alloc. An * indicates a p value<0.05 (n=4 samples).
Figure 14B:
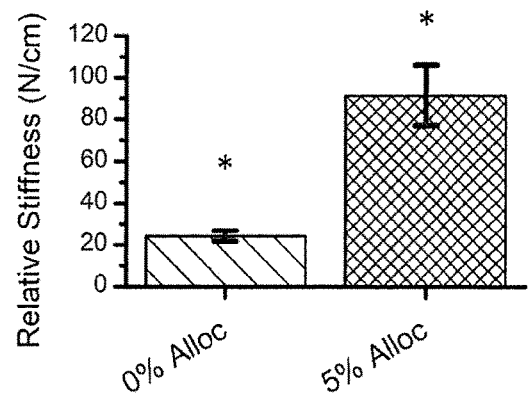
Figure 14C:
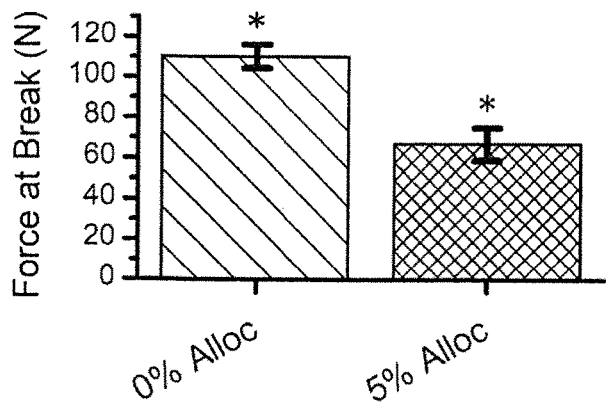
Figure 14D:
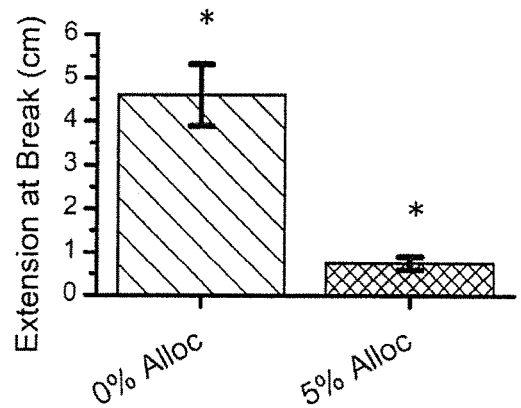

Mechanical Properties:

Burst-Test Mechanics Free-Standing Films. PEU terpolymers were blade coated on PET substrate and dried under reduced pressure before being cut in to squares (3"×3"). Films were hydrated in PBS for 5 minutes prior to being attached to the ASTM D 3787-07 burst test apparatus. Films were fixed and burst at a constant rate (25.4 mm/min) and the force versus extension curves were recorded (FIG. 14A). The force versus extension curves show that as alloc content is increased, the stiffness is significantly increased when compared to the 0% alloc PEU (FIG. 14B). Additionally, the force at break and extension at break are significantly less for the 5% alloc PEU (FIGS. 14C-D). These changes in mechanical properties were expected and are attributed to the bulky side chain in the 1-TYR-2 alloc monomer restricting interchain mobility.

Figure 15A:
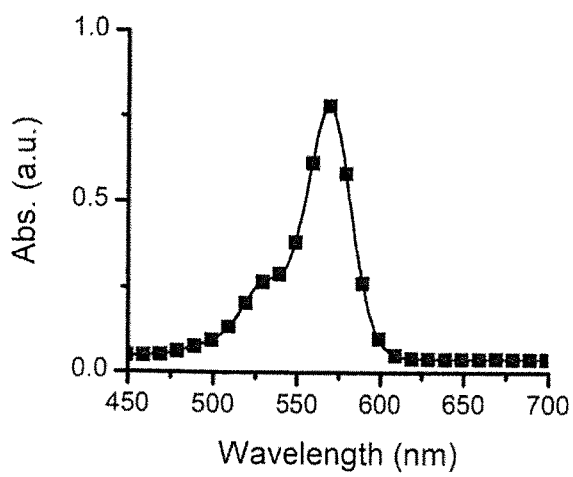
FIGS. 15A-D are graphs showing the results of rhodamine-SH characterization. The rhodamine-SH was tested to find the maximum absorbance (FIG. 15A) which was determined to be at 568 nm; emission spectra were run from 586-700 with a maximum at 592 (FIG. 15B); the purity of rhodamine-SH was confirmed using mass spec (FIG. 15C); and a calibration curve was created for the rhodamine-SH ranging from nanomolar to micromolar concentrations (FIG. 15D).
Figure 15B:
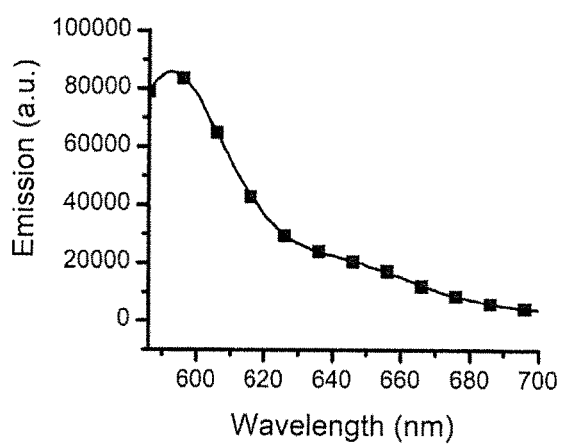
Figure 15C:
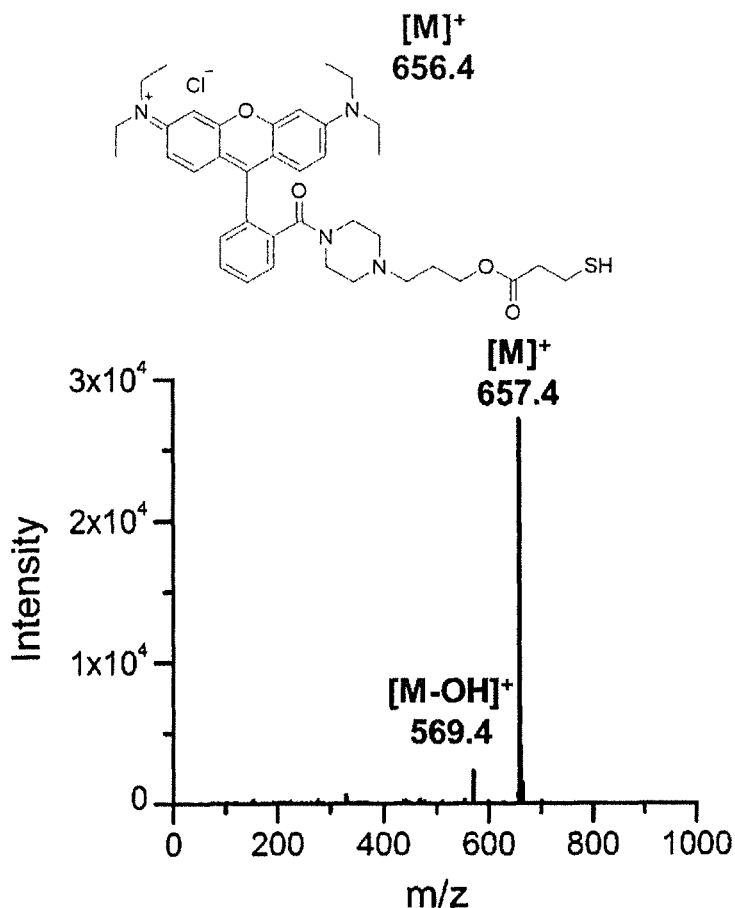
Figure 15D:
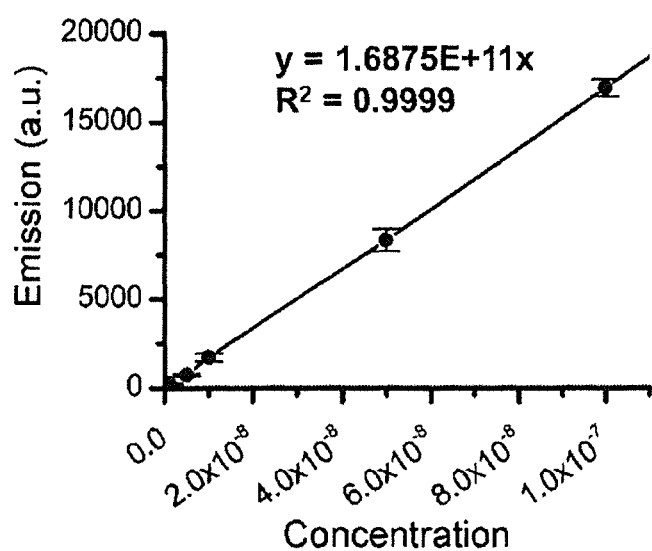
Figure 16:
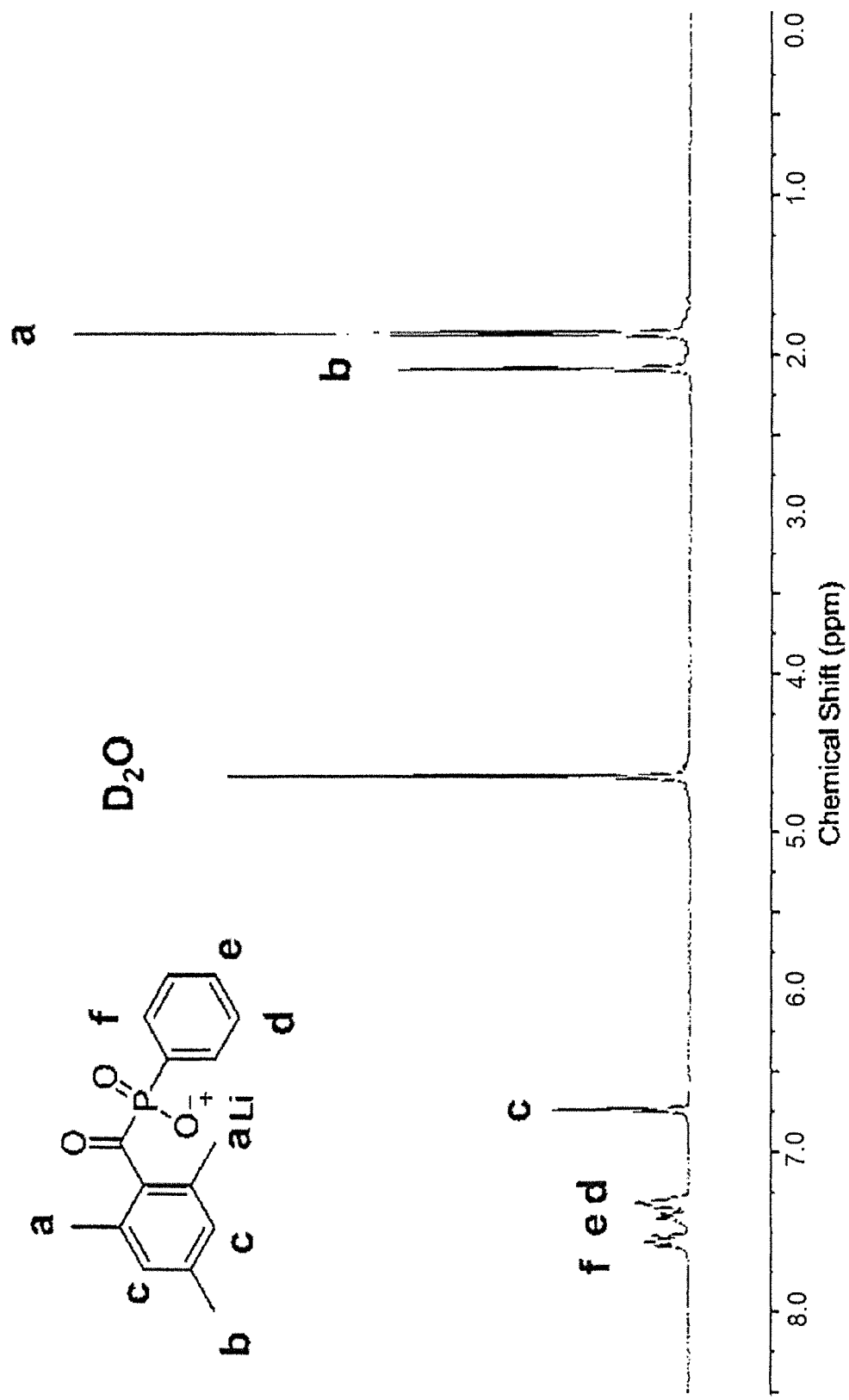
FIG. 16 is a $^1$H-NMR overlay for lithium phenyl-2,4,6-trimethylbenzoylphosphinate (LAP).

Surface Functionalization:

Rhodamine. To quantify how much functionality could be exploited at the surface by the alloc PEUs, samples were functionalized with a rhodamine-SH dye which has the same core as the zwitterion-SH. Prior to functionalization, rhodamine-SH was tested for maximum absorbance and maximum emission (FIGS. 15A-C). Additionally, compound purity was established using mass spec where the mass of the charged rhodamine-SH ion was observed (FIG. 15C). A calibration curve was created with values ranging from nanomolar to micromolar concentrations (FIG. 15D). Blade coated 5% alloc PEUs were punched in to 8 mm disks and then functionalized through the alkene moiety with previously synthesized photoinitiator LAP and rhodamine-SH (FIG. 16). (See, Makromol. Chem., 192 (10) (1991), pp. 2307-2315, the disclosure of which is incorporated herein by reference in its entirety).

Figure 17A:
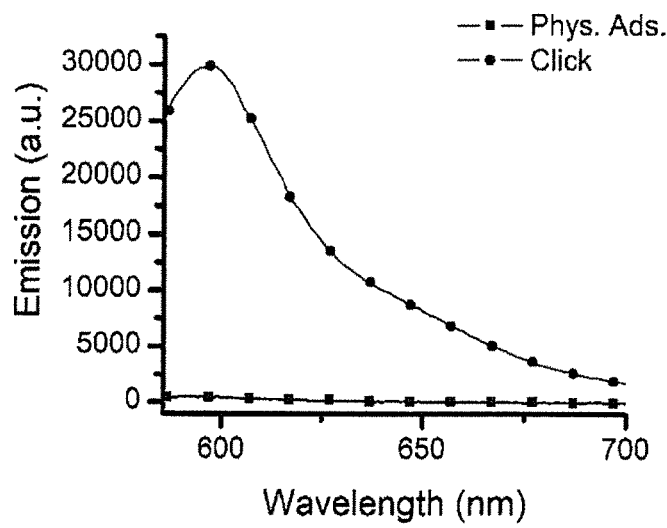
FIGS. 17A-B is a are graphs showing the results of fluorescence dye attachment experiments for surface functionalization of 5% alloc PEU comparing physical adsorption (FIG. 17A) and functionalization (FIG. 17B) via a thiol-ene "click" reaction.
Figure 17B:
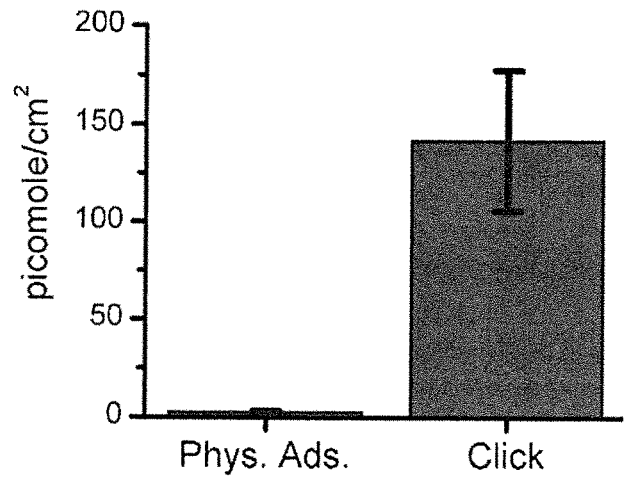

Samples were divided in to three groups labeled click, physically adsorbed, and blank where the click samples were treated with LAP, rhodamine-SH, and UV light, physically adsorbed only had LAP and rhodamine-SH, and blank were only exposed to UV light. All samples were dissolved in DMSO and fluorescence measurements were taken (FIG. 17A-B). The blank polymer was subtracted out from both click and physically adsorbed samples. The emission curves indicate that the amount of rhodamine-SH present on the click samples is greater than that of the physically adsorbed samples. This indicates that there must be some covalent attachment and that any intensity observed is not attributed to physical adsorption. This is ideal as it shows control over chemically attached functionality. Additionally, the amount of attachment per area was quantified and again indicated that the thiol-ene reaction was successful (FIG. 17A-B).

Figure 18A:
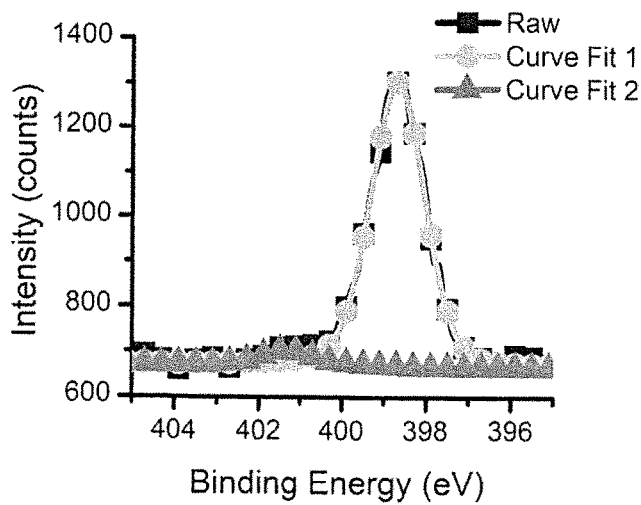
FIGS. 18A-D are a polymer X-ray Photoelectric Spectroscopy (XPS) graphs (FIGS. 18B-C) and graph overlays (FIGS. 18A, D) of click (FIG. 18A), physically adsorbed (FIG. 18B), control (FIG. 18C) of a 5% alloc PEU at binding energies from about 398 eV to about 406 eV and a 5% alloc click sample at binding energies from about 158 eV to about 172 eV (FIG. 18D). The 5% alloc click sample (FIG. 18A) showed two nitrogen peaks, one corresponding to the urea nitrogens (398 eV) and the other corresponding to the quaternary ammonium peak (402 eV) ($X^2$=0.99; Area=5: 55). Neither the physical adsorbed ($X^2$=1.07) (FIG. 18B) nor the control ($X^2$=1.15) (FIG. 18C) showed a quaternary ammonium peak. Additionally, the 5% alloc click sample showed two distinct sulfur peaks with the thioether peak from the zwitterion-SH (162 eV) and the ring opened sultone (168 eV) (FIG. 18D).
Figure 18B:
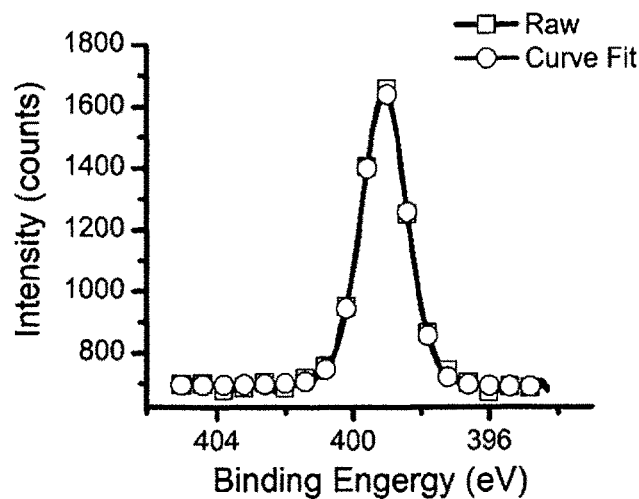
Figure 18C:
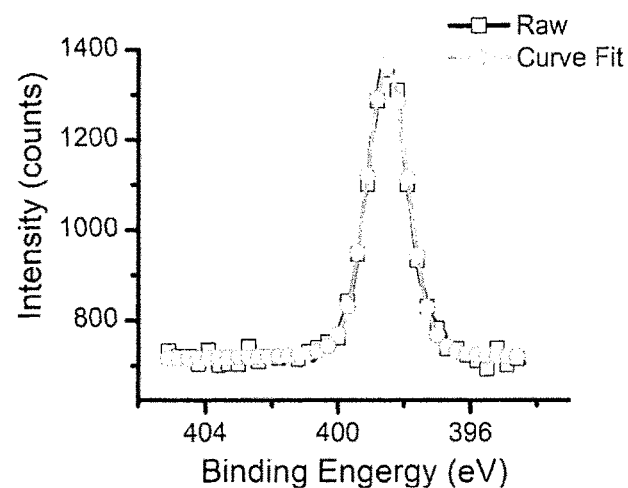
Figure 18D:
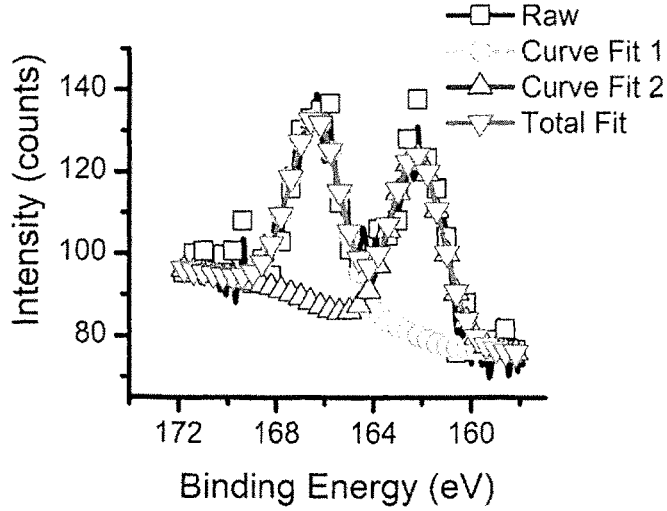

X-ray Photoelectric Spectroscopy (XPS). After the model reaction with rhodamine-SH, quantification of the zwitterion-SH on the surface of 5% alloc PEU was performed using x-ray photoelectric spectroscopy (XPS). Samples were divided in to three different groups labeled click, physically adsorbed, and blank where the click samples were treated with LAP, zwitterion-SH, and UV light, physically adsorbed only had LAP and zwitterion-SH, and blank were only exposed to UV light. Following XPS analysis, it was shown that the 5% alloc click sample had two distinct nitrogen peaks (FIG. 18A). One of the peaks belongs to the nitrogen in the urea groups while the other correlates to the quaternary ammonium in the zwitterion with the integration ratio of those peaks being 95:5 respectively. The quaternary ammonium peak is shifted to higher energy because it is more stable and requires more energy to displace an electron from its N1S shell. Both the 5% alloc physically adsorbed and control samples showed the urea nitrogen peak (FIGS. 18B-C), however no quaternary ammonium peak was observed. This correlated well with what was observed in the rhodamine-SH model reaction where the only detectable zwitterion-SH is from the samples treated with UV light. Additionally, two distinct sulfur peaks are observed for the 5% alloc click sample where the zwitterion-SH sulfur is seen at lower energy than the ring opened sultone sulfur. (FIG. 18D) This again was expected as the stability of the ring opened sultone outer shell of electrons is greater, requiring greater energy to displace the S2p electrons. These results indicate that the thiol-ene attachment of the zwitterion-SH to the alloc PEUs is feasible with a reasonable amount of control.

Figure 19A:
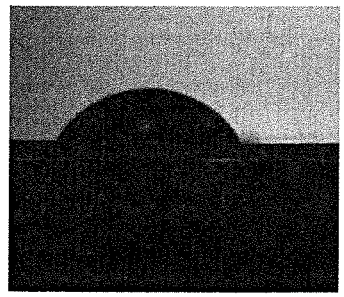
FIGS. 19A-C are images (FIGS. 19A-B) and a graph (FIG. 19C) showing contact angle measurements for blank and clicked 5% Alloc PEU at 10 min.
Figure 19B:
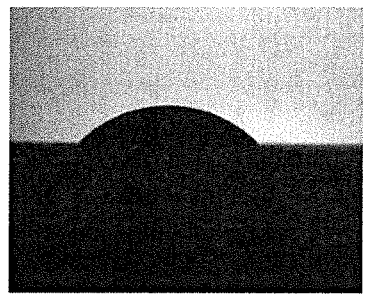
Figure 19C:
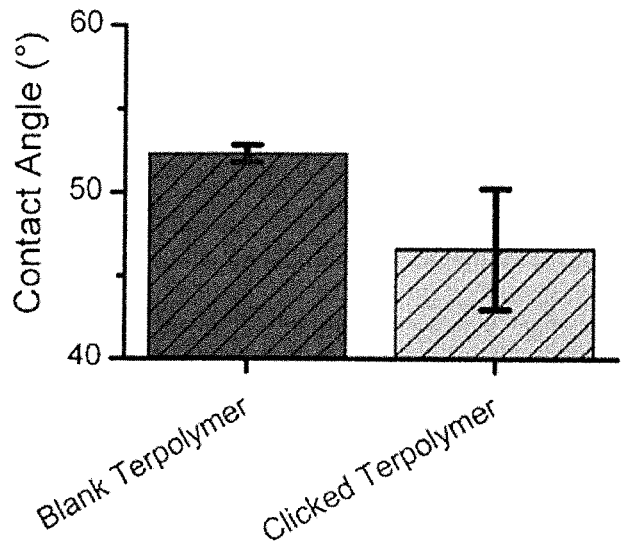

Water Contact Angle. To observe if there was a change in the macroscopic properties for the alloc PEUs post functionalization with the zwitterion-thiol, water contact angle measurements were taken before and after functionalization (FIG. 19A-C). After ten minutes, the contact angle diminishes from 52.3±0.5 to 46.6±3.6 after zwitterion-SH is attached to the 5% alloc PEU. The decrease in water contact angle is indicative of the zwitterion-SH forming a tighter hydration layer with the water and thus improving the hydrophobicity of the material. This is ideal as the formation of a tight hydration layer can prevent the adhesion of proteins, cells, and other molecules.

In a second set of experiments, two anti-adhesion poly(ester urea)s (PEUs) according to the present invention with varied amount of an allyl ether side chain with terminal alkene functionality for surface modification (5% alloc-PEU or 10% alloc-PEU) were prepared and tested. These alloc-PEUs were processed through roll-to-roll fabrication methods to afford films which were further surface functionalized with a zwitterion-thiol (3-((3-((3-mercaptopropanoyl)oxy)propyl)dimethylammonio)propane-1-sulfonate) used to prevent adhesion. Control and extent of functional groups available on the surface were confirmed through attachment of a FITC-PEG-SH dye. Zwitterion-thiol click attachment to the alloc-PEU surfaces was confirmed through water contact angle, x-ray photoelectron spectroscopy (XPS), and quartz crystal microbalance (QCM). Anti-adhesion PEUs reduce fibrinogen attachment when compared to unfunctionalized controls while displaying nominal cytotoxicity in vitro behaving equivalent to negative controls. 10% alloc-PEU materials were implanted in a rat intrabdominal cecal abrasion adhesion model and assessed for the extent and tenacity of adhesion. The 10% alloc-PEU zwitterion functionalized material was found to reduce the average extent and tenacity of adhesions when compared to adhesion controls and the 10% alloc-PEU blank material. Functionalized anti-adhesion PEUs demonstrated their ability to be translatable materials to prevent adhesion in ventral hernia repair.

Synthesis: The amino acid-based monomers were synthesized and characterized using $^1$H-NMR (FIGS. 1A-B, 2). 1,6-hexanediol and 1,8-octanediol were coupled to the carboxylic acid of L-valine or L-phenylalanine through an esterification using p-toluenesulfonic acid to prevent reactions at the amine moiety. The resulting monomers were named based on their diol chain length and amino acid; (1-VAL-8) formed from 1,8-octanediol and L-valine, (1-PHE-6) formed from 1,6-hexanediol and L-phenylalanine, and (1-PHE-8) formed from 1,8-octanediol and L-phenylalanine. 1-PHE-6 and 1-PHE-8 can be differentiated from the integration of the methylene peak at 1.06-1.14 ppm. 1-VAL-8 synthesis was confirmed based on the characteristic L-valine methyl peak at 0.96 ppm. Synthesis of 1-TYR-2 Alloc was carried out through a DIC coupling with Boc-O-benzyl-L-tyrosine and 1,3-allyoxyl-2-propanediol. The final product was collected and confirmed after HCl deprotection with the disappearance of the characteristic Boc protecting group at 1.31 ppm and the appearance of the broad amine peak at 8.82 ppm (FIG. 3). Synthesis of the zwitterion thiol occurred in several steps where a halogenation reaction was performed between 3,3'-dithiodipropionic acid and thionyl chloride to afford 3,3'-dithiodipropionyl chloride (FIG. 4). This product was then reacted in an $S_n2$ substitution with 3-dimethylamino-1-propanol to obtain the bis(3-dimethylamino)propyl) 3,3'-disulfanediyldipropionate (FIG. 5). This was further functionalized with 1,3-propane sultone to afford the zwitterion disulfide (FIGS. 6-7). Finally, the zwitterion-SH was obtained by cleavage of the zwitterion disulfide using 1,4-dithiothreitol (DTT) and the product was thus collected (FIGS. 8-9). Terpolymer PEU synthesis was carried out by altering the molar feed ratio of 1-VAL-8, 1-PHE-6, and 1-TYR-2 alloc in an interfacial polymerization with triphosgene to afford the 5% alloc-PEU and 10% alloc-PEU (See, Scheme 7, above) (FIG. 10). Polymers were named according to the amount of 1-TYR-2 alloc in the monomer feed ratio. Successful polymer synthesis and monomer incorporation was confirmed using $^1$H NMR. The monomers were readily identified by the characteristic methyl L-valine peaks denoted 'a', methylene from L-phenylalanine denoted '1', and methylene of O-bzn-TYR denoted 'v'. Additionally, the alkene functionality from 1-TYR-2 alloc could be observed with peaks at 5.13 ppm (d') and 5.84 ppm (c').

Physical Properties: Size-exclusion chromatography (SEC) reported molecular weights are post-precipitation in acetone (Table 2) (FIG. 11). The molar mass distributions ($Ð_m$) can be less than the theoretical value of 2 because the low molecular weight fractions are lost during precipitation. Molecular weights were sufficiently high to allow for mechanical testing and subsequent in vivo characterization. Differential scanning calorimetry (DSC) curves show the glass transition temperatures ($T_g$) are above body temperature indicating that the materials will be sufficiently stiff upon any implantation application (FIG. 12). An increase in the $T_g$ is observed as the amount of 1-TYR-2 alloc monomer is elevated from 5% to 10%. This is expected as the rigid side chain unit from the benzyl protected tyrosine inhibits chain mobility. Ideally, all terpolymer PEUs had sufficiently high degradation temperatures ($T_d$) enabling them to be thermally processed with sufficient stability for processing and storage in future applications (Table 2) (FIG. 13).

TABLE 2

Physical properties of PEU Terpolymers

| Polymer | $M_n$ (KDa) | $M_w$ (KDa) | $Đ_m$ | $T_g$ (° C.) | $T_d$ (° C.) |
|---|---|---|---|---|---|
| 5% Alloc PEU | 24 | 35 | 1.5 | 40 | 289 |
| 10% Alloc PEU | 28 | 62 | 2.2 | 49 | 299 |

Figure 20A:
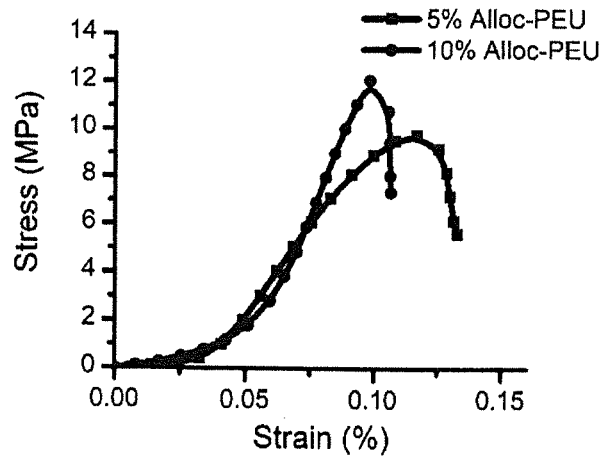
FIGS. 20A-D are graphs showing the results of tensile testing of the mechanical properties of the 5% and 10% alloc PEU terpolymers. The stress versus strain curves (FIG. 20A) indicate that there is greater stiffness (FIG. 20B) for the 10% alloc-PEU when compared to the 5% alloc analogue. There is also an increase in yield strain for the 5% alloc-PEUs when compared to the 10% alloc-PEUs (FIG. 20C). No statistical difference for yield stress was observed for between the PEU derivatives (FIG. 20D). An * indicates a p value<0.05 (n=3 samples).
Figure 20B:
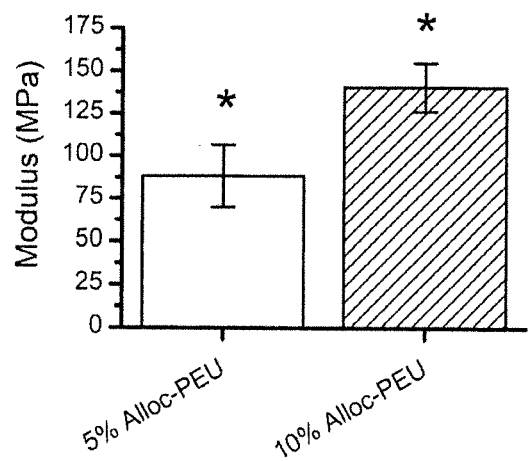
Figure 20C:
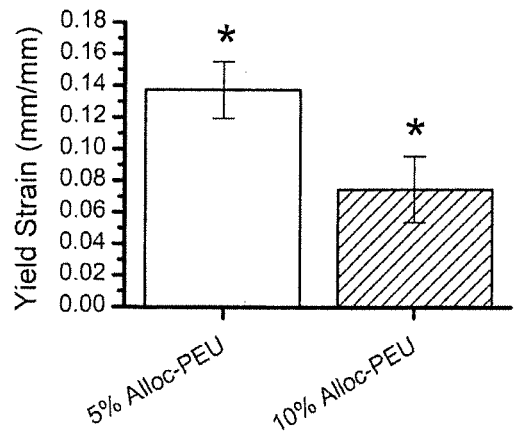
Figure 20D:
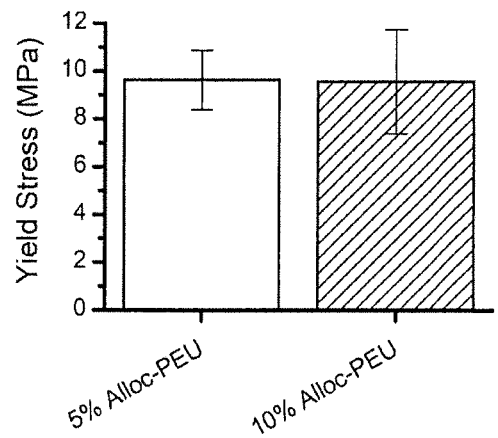

Mechanical Properties:

Tensile-Test Mechanics on Free-Standing Films. PEU free-standing films were prepared by blade coating, sterilized with ethylene oxide, and cut in to tensile bars for mechanical assessment. Tensile bars were pulled with a constant rate of extension (25.4 mm/min) and the stress versus strain curves were recorded (FIG. 20A). A significant elevation in the modulus and suppression of the yield strain was observed for 10% alloc-PEU samples when compared to 5% alloc-PEU samples (FIGS. 20B-C). These changes in mechanical properties were expected and are attributed to the bulky side chain in the 1-TYR-2 alloc monomer restricting interchain mobility. It is common for a stiffer material to concomitantly possess a lower yield strain. No statistical difference was observed for the yield stress between samples (FIG. 20D).

Figure 21:
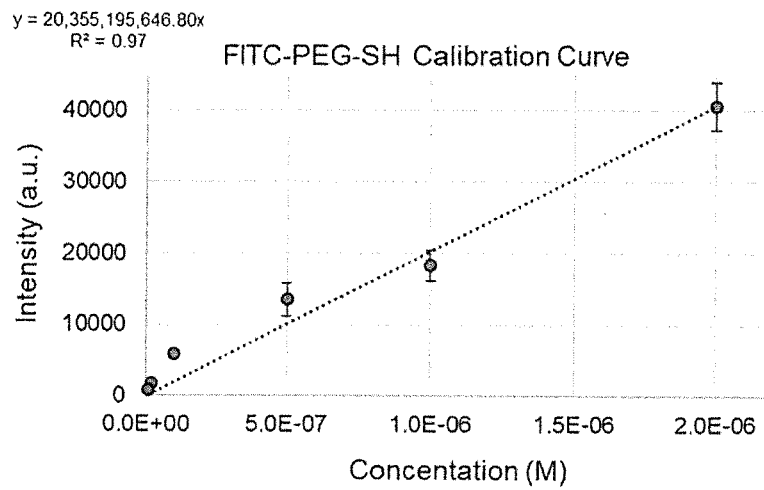
FIG. 21 is a calibration curve for 1000 MW FITC-PEG-SH with concentration values reported in triplicate and mean intensity of emission at 550 nm recorded.
Figure 22:
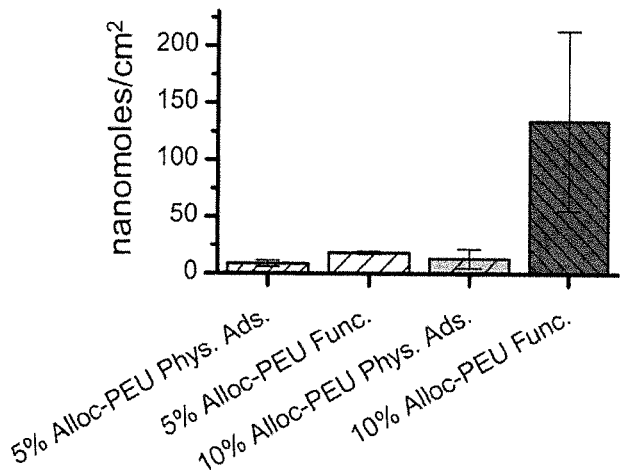
FIG. 22 is a graph showing FITC-PEG-SH fluorescence dye attachment for surface functionalized and physically adsorbed mechanisms for 5% and 10% alloc-PEU analogues at 550 nm endpoint emission. An increase in dye concentration is observed for the 10% alloc-PEU functionalized polymer when compared to 10% alloc-PEU physically adsorbed. The same trend is observed for the 5% alloc-PEU analogues.

Surface Functionalization:

1000 MW FITC-PEG-SH. Alloc-PEUs samples were functionalized with a FITC-PEG-SH dye to quantify how much functionality could be exploited at the surface. (See Example 29). A calibration curve was created with values ranging from nanomolar to micromolar concentrations (FIG. 21). Blade coated 5% alloc-PEUs and 10% alloc-PEUs were punched in to 8 mm disks and then functionalized through the alkene moiety with previously synthesized photoinitiator LAP and FITC-PEG-SH (FIG. 16). Samples were divided into three groups labeled functionalized, physically adsorbed, and blank where the functionalized samples were treated with LAP, FITC-PEG-SH, and UV light, physically adsorbed only were treated with LAP and FITC-PEG-SH, and blank samples were left untreated. All samples were dissolved in DMSO and fluorescence measurements were taken to observe the emission at 550 nm (FIG. 22) (Table 3). The blank polymer was subtracted out from both functionalized and physically adsorbed samples. The emission intensity at 550 nm indicates that the amount of FITC-PEG-SH present on the functionalized samples is greater than that of the physically adsorbed samples for both the 5% alloc-PEU and 10% alloc-PEU analogues. Additionally, the 10% alloc-PEU shows greater dye attachment for the functionalized material when compared to the 5% alloc-PEU functionalized analogue. This was expected as more 1-TYR-2 alloc monomer incorporated into the polymer should correspond with an increase in the amount of available alkene functionality on the surface. The increase in observable dye on the functionalized alloc-PEUs also supports that there is covalent attachment occurring under the thiol-ene reaction conditions. This is desirable as controlled attachment will be important when modulating surface properties for an anti-adhesion implantable device (FIG. 22).

TABLE 3

FITC-PEG-SH Dye Attachment

| Polymer | Dye Attachment (nanomole/cm$^2$) |
|---|---|
| 5% Alloc-PEU Phys. Ads. | 8.8 ± 2.6 |
| 5% Alloc-PEU Func. | 18.1 ± 1.3 |
| 10% Alloc-PEU Phys. Ads | 13.3 ± 8.2 |
| 10% Alloc-PEU Func. | 134.2 ± 78.9 |

XPS. After the model reaction with FITC-PEG-SH, quantification of the zwitterion-SH on the surface of the 5% alloc-PEU and 10% alloc-PEU analogues was performed using x-ray photoelectron spectroscopy (XPS). Samples were divided in to three groups labeled functionalized, physically adsorbed, and blank. The functionalized samples were treated with LAP, zwitterion-SH, and UV light, physically adsorbed samples were treated with LAP and zwitterion-SH without UV light exposure, and blank samples were kept separate from LAP and the zwitterion-SH. Following XPS analysis, it was shown that the 5% alloc-PEU functionalized material has an observable broadening and two distinct nitrogen peaks when compared to one major peak observed for the physically adsorbed and blank material (FIG. 23A). The major peak (~399.9) corresponds to the nitrogen in the urea groups while the other peak (~401.5) correlates to the quaternary ammonium in the zwitterion. The integration ratios for the urea and quaternary ammonium peaks are 95.2:4.8 respectively (FIG. 23B). The quaternary ammonium peak is shifted to higher energy as it is more stable and requires more energy to displace an electron from its N1s orbital. Additionally, two distinct sulfur peaks are observed for the 5% alloc-PEU functionalized samples where the zwitterion-S—C sulfur is seen at lower energy than the ring opened sultone sulfur (48:52 respectively) (FIG. 23C). This again was expected as the stability of the ring opened sultone outer shell of electrons is greater, requiring greater energy to displace the S2p electrons. Similar trends were observed for the 10% PEU-alloc samples. A noticeable broadening is again observed for the raw XPS curves of the 10% alloc-PEU functionalized material when compared to the physical adsorbed and blank materials (FIG. 23D). Only the 10% alloc-PEU functionalized material has the secondary peak correlating to the quaternary ammonium peak attributed to the zwitterion-SH (integration urea:quaternary ammonium is 65.5:35.5) (FIG. 23E). The amount of detectable quaternary ammonium was greater for the 10% alloc-PEU functionalized material than it was for the 5% alloc-PEU functionalized material. This was expected as more functional monomer incorporation into the polymer allows for greater surface attachment of zwitterion-SH. Finally, two distinct sulfur peaks are observed for the 10% alloc-PEU functionalized material (integration ratio zwitterion-S—C sulfur:ring opened sultone sulfur is 55:45) (FIG. 23F). These results correlate well with what was observed in the FITC-PEG-SH model reaction where the most detectable zwitterion-SH is from the samples functionalized with UV light. These results provide further evidence that the thiol-ene attachment of the zwitterion-SH to alloc-PEUs is feasible with reasonable control based on molar feed ratio of 1-TYR-2 alloc monomer.

Water Contact Angle. To observe if there was a change in the macroscopic properties for the alloc-PEUs post functionalization with the zwitterion-thiol, water contact angle measurements were taken before and after functionalization (FIGS. 24A-D Samples were allowed to equilibrate for ten minutes prior to imaging and measurement. After ten minutes, the contact angle of the 5% alloc-PEU blank material (52.3±0.5) is greater than the 5% alloc-PEU functionalized material (46.6±3.6) (FIG. 24E). The same contact angle suppression was observed for the 10% alloc-PEU analogues were the blank material (61.8±3.1) contact angle was greater than that of the functionalized material (56.3±7.6) (FIG. 24E). The decrease in water contact angle is indicative of the zwitterion-SH forming a hydration layer with the water and thus improving the hydrophilicity of the material. This is ideal as the formation of a tight hydration layer has been shown to prevent the adhesion of proteins, cells, and other molecules.

Protein Adsorption:

Quartz Crystal Microbalance. Fibrinogen adsorption profiles for 5% alloc-PEU blank, 5% alloc-PEU functionalized, 10% alloc-PEU blank, and 10% alloc-PEU functionalized materials were obtained using QCM (FIGS. 25A-B). A drop-in frequency can be observed on all curves which is indicative of the adsorption of fibrinogen to the material surface. After equilibration and the 1×PBS rinse, an amount of reversibly adsorbed material is washed from the surface indicated by an increase in the frequency. The amount of fibrinogen initially attached is an important feature for an antiadhesion material as fibrinogen is likely to be one of the first substances to interact with the polymer implant. The calculated amount of attached fibrinogen for 5% alloc-PEU blank sample was statistically greater than all of the other materials under study (FIG. 25C). This was ideal as functionalization of the 5% alloc-PEU is able to inhibit adhesion to the surface when compared to the blank counterpart (953±97 ng/cm$^2$ and 5070±339 ng/cm$^2$ respectively). While there were no significant differences between the 10% alloc-PEU blank (1271±692 ng/cm$^2$) and 10% alloc-PEU functionalized (686±51 ng/cm$^2$) materials, an average adhesion suppression is still observed for the functionalized material. Additionally, the material with the lowest average adhesion is the 10% alloc-PEU functionalized material. These data lend further evidence to successful surface functionalization and the promise for these materials as antiadhesion barriers. In addition to initial fibrinogen attached to the material surface, irreversibly adsorbed fibrinogen was calculated after the 1×PBS rinse (FIG. 25D). As was observed with the initial fibrinogen attachment, the 5% alloc-PEU blank (4720±841 ng/cm$^2$) material has significantly more adsorbed fibrinogen when compared to the other alloc-PEU materials under these conditions. No statistical difference is observed between the 5% alloc-PEU functionalized (701±344 ng/cm$^2$), 10% alloc-PEU blank (307±318 ng/cm$^2$), and 10% alloc-PEU functionalized (468±51 ng/cm$^2$) materials (FIG. 25D). It is expected that the tight hydration layer formed from the functionalization of the zwitterion-SH to the alloc-PEU surfaces helps to prevent adhesion of competing molecules like fibrinogen. The differences observed in fibrinogen adhesion based on polymer composition and surface functionalization are promising results for modulating the adhesion properties of an implantable material.

Cytotoxicity Assessment: To assess the cell compatibility of 5% and 10% alloc-PEU analogues, a cytotoxicity assay was performed. Solvent cast films (5×5 cm) were submerged in 20 mL centrifuge tubes and covered in extraction media (DMEM with penicillin-streptomycin, no Bovine Calf Serum (BCS)) (8.3 mL). Three controls were used as comparisons for cytotoxicity. Extraction media negative and positive control samples had 10 mL of extraction media added to a 15 mL centrifuge tube. Latex finger cots were used as an additional positive control and placed in a 15 mL centrifuge tube with 6 mL of extraction media. All were shaken gently at 37° C. for 24 h. NIH 3T3 cells were plated and allowed to reach confluency. Cells were subsequently harvested with trypsin and combined with complete DMEM media and BCS. An aliquot of the cell solution (1 mL) and complete media (1 mL) (2 mL total) were added to each plate. The plates were placed in a cell culture incubator (37° C., 5% $CO_2$) for 24 h. Following incubation, the extracts were removed from the shaker and added to a syringe. The volume in the syringe was noted and BCS was added to the total volume extract (except for no serum negative control) (BCS accounts to 10% of extraction volume). Extraction solutions were filtered with a nylon, 0.2 m filter. Each well of cells had the media removed and 2 mL of the extract or control was pipetted into appropriate wells. The controls were cells in DMEM media plus FBS (filtered the same way as the sample extractions), cells in media without serum (NS), and cells in the filtered latex extract plus FBS. The plates were returned to a cell culture incubator (37° C., 5% $CO_2$) for 48 hours. After 48 hours, one picture was taken of each well with the 10× objective on an inverted microscope. The wells were analyzed and subsequently ranked based on cell viability.

Alloc-PEU Films. Any material will be exposed to a wide array of bodily fluids that will interact with the surface upon implantation. Even the most inert implantable devices are not precluded from some level of swelling which can lead to small molecule impurities and physically adsorbed or trapped compounds migrating in to the dynamic physiological system. With a solvent cast surface functionalized material like the alloc-PEU analogues, it is important to ensure that the processing methods and functionalizing conditions do not lead to unwanted cytotoxicity side effects upon prolonged exposure. A solution-based cytotoxicity assay was performed to assess cell viability for the alloc-PEU materials. Briefly, alloc-PEU films were submerged in extraction media for 24 hours. This extraction media was then used to culture NIH-3T3 cells for 48 hours and cell culture plates were used to assess cell viability and were subsequently ranked (FIGS. 26A-G). Scoring was based on a scale from 0-4 where the extreme scores of 0 indicates very little cell distress and no observable empty spaces in the culture plate in contrast to a score of 4 which indicates >75% of observable cell death or distress with large empty areas on the culture plate (FIG. 26). Cells exposed to the alloc-PEU sample extracts were similar to the negative control cells and had very few empty spaces. All sample extracts and the negative controls passed (Score=0) (FIGS. 26A-D, F). Both of the positive controls did not pass as expected (Score=4) (FIG. 26 E, G). Additionally, the alloc-PEU samples did not change the pH of the extraction media and the extracts filtered well. During the 24-hour incubation in extraction media, the polymers went from clear to cloudy which is attributed to a small amount of water uptake leading to a change in opacity. All alloc-PEU analogues eliciting a cytotoxic response equivalent to the negative control was ideal as it shows the compatibility of these PEU materials under the processing conditions. These results lend further evidence that alloc-PEUs would not be considered cytotoxic for an implantable adhesion barrier in a dynamic fluid environment.

In Vivo Characterization:

Adhesion Animal Model. Despite in vitro analysis, no benchtop assessment or computer model to date can successfully encompass adhesiogenesis and the complex interplay factors involved. For this reason, an intrabdominal rat adhesion model was used to assess adhesiogenesis of the alloc-PEUs understudy. 10% alloc-PEU blank and 10% alloc-PEU functionalized derivatives were selected for implantation because of successful adhesion prevention observed in QCM.

All procedures and animal handling were in accordance with The University of Minnesota Institutional Animal Care and Use Committee (IACUC Protocol Number 1805-35945A) where female Sprague-Dawley rats (32) were divided in to four groups (sham, adhesion control, 10% alloc-PEU blank, and 10% alloc-PEU functionalized) (n=8 per group). All animals underwent a paramedian laparotomy followed by exposure and abrasion of the cecum (FIG. 27 (left image)). Cecum abrasion was not performed for the sham group and consequently no adhesion was expected. Following abrasion, the 10% alloc-PEUs were applied, secured in place around the cecum with sutures, and the incision was subsequently closed (FIG. 27 (middle and right images)). Following implantation (21 d) all groups were examined for extent and tenacity of adhesions present. Extent of adhesion was scored based on the relative percentage of adhesion to the abraded cecum (Table 4) and the tenacity of adhesions present was scored based on the resistance for separation (Table 5). The goal of an antiadhesion material in a ventral hernia application is to keep inner organs from interacting with the abdominal wall. Additionally, it would be preferable for limited adhesion between tissue and the device itself. The overall extent of adhesion (includes adhesions between tissue and abraded cecum and adhesion of abraded cecum to the device) was scored with the 10% alloc-PEU functionalized material (2.0±1.1) obtaining the lowest average although no significant difference was noted between the abraded cecum adhesion control (2.3±1.4) and the 10% alloc-PEU blank materials (2.4±1.0) (See, FIGS. 28A-B; 29A-D; 30A-D; 31A-H; 32A-D). No extent of adhesions was observed for the sham animals which was anticipated (FIGS. 29A; 30A; 31A, E.

Tenacity of adhesions to the device and underlying tissue were scored with the 10% alloc-PEU functionalized material (2.3±0.7) again eliciting the lowest score (FIG. 29B;30B; 31E-H). The observed drop in adhesion tenacity was not statistically significant from the abraded cecum control and 10% alloc-PEU blank material. While the reduction in extent and tenacity of adhesions present is ideal for the functionalized material, a larger study may show statistical differences between the materials under study. The extent of adhesions exclusively attached to the implanted device and abraded cecum were also scored and reported (FIG. 32A-D). Promisingly, there were minimally observed adhesions between the 10% alloc-PEU functionalized material (0.3±0.5) and 10% alloc-PEU blank material (0.9±0.7) to the abraded cecum (FIG. 32C).

Figure 32D:
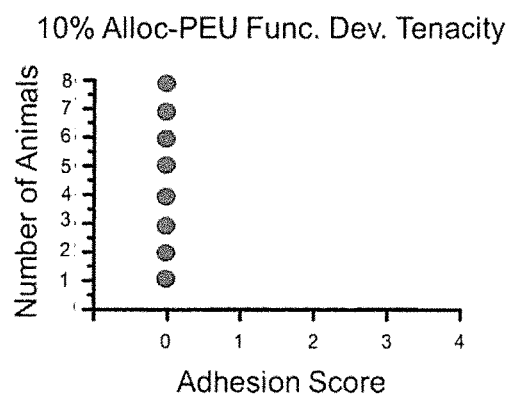

The tenacity between the materials and tissue were also recorded with no tenacity of adhesion being observed for the 10% alloc-PEU functionalized material (0.0±0.0) and only minimal tenacity shown for the 10% alloc-PEU blank material (1.1±0.9) (FIG. 32D). Similar to when device, tissue, and abraded cecum were used to assess extent and tenacity of adhesions, there was no significant difference observed between groups for extent however there was statistically significant difference in tenacity between the 10% alloc-PEU blank material and the 10% alloc-PEU functionalized material (p<0.004). The functionalized material has a lower average extent and tenacity in all cases which could be an indication that the surface treatment is having a desired effect. An increase in sample size could help differentiate between the groups under study to find more statistical significance.

TABLE 4

Extent of adhesions to abraded cecum scoring scale

| Score | Extent |
|---|---|
| 4 | >75% adhesions on abraded cecum |
| 3 | <75% adhesions on abraded cecum |
| 2 | <50% adhesions on abraded cecum |
| 1 | <25% adhesions on abraded cecum |
| 0 | No adhesions |

TABLE 5

Tenacity of adhesions scoring scale

| Score | Tenacity |
|---|---|
| 4 | Sharp dissection for separation |
| 3 | Marked resistance for separation |
| 2 | Moderate resistance for separation |
| 1 | Mild resistance for separation |
| 0 | No resistance for separation |

Adhesion Histological Assessment. Tissue samples were collected post-mortem and subjected to histological staining to identify cell type and inflammation present at the location of observed adhesions. The degree of collagen deposition, necrosis, and inflammation were all qualitatively compared between treatment groups. The sham control did not demonstrate histological evidence of adhesion formation. Primarily, the cecum was normal with no notable hyperplastic lymphoid tissue and limited fibroblasts (FIGS. 33A-B). This was expected as no adhesion method was employed to these samples. All other groups demonstrated adhesion tissue characterized by infiltration of fibroblasts, macrophages, and occasional giant cells. The adhesion in these areas was moderate to heavy and cecal hyperplastic lymphoid tissue was observed. This is indicative of an inflammatory response attributed the tissue adhesions (FIGS. 33C-D). Additionally, collagen deposition was observed with bluestained collagen bundles surrounded by multiple fibroblasts and identifiable giant cells (FIGS. 33E-F). These cell types are indicative of an inflammatory response that could be expected from the observed adhesions. No implant material was observed, likely due to dissolution during alcohol processing as part of the histological preparation.

Polymer Degradation. Polymer implanted samples were further characterized to assess the extent of degradation in vivo. Scanning electron microscopy (SEM) was used to observe the surface morphology of films after sterilization and after implantation (FIGS. 34A-C). Both 10% alloc-PEU blank and 10% alloc-PEU functionalized films are predominantly smooth after sterilization (FIG. 34A). This was ideal as it indicates that the sterilization technique does not damage the implant surface topology which would alter adhesion properties. After implantation, surface roughness is noticeable for both the blank and functionalized derivatives (FIGS. 34B-C). While there is some change, the degradation does not appear extreme, as would be expected if the material had significantly eroded.

In addition to surface morphology, polymer molecular mass was determined using SEC-GPC to assess the extent of polymer chain scission in vivo. Differential distribution curves for the SEC-GPC traces were collected and molecular mass values were reported (FIG. 35) (Table 6). Minimal changes in molecular mass are observed with the implanted materials when compared to their initial starting values. The sustained molecular mass through implantation is ideal for this study as the extent and tenacity of adhesion can be more easily quantified. However, the observed molecular mass fidelity is an indication that a thinner and lighter-weight film could prove useful as an adhesion barrier for hernia applications.

TABLE 6

Molecular mass* degradation values of 10% alloc-PEU derivatives

| Polymer | $M_n$ (KDa) | $M_w$ (KDa) | $Đ_m$ |
|---|---|---|---|
| 10% Alloc-PEU Initial | 14.0 | 29.5 | 2.10 |
| 10% Alloc-PEU Blank 21 d | 15.0 | 29.9 | 1.99 |
| 10% Alloc-PEU Func. 21 d | 13.7 | 29.6 | 2.17 |

*Size-exclusion chromatography-gel permeation chromatography (SEC-GPC) molecular mass and dispersity values are calculated from a polystyrene standard in THF.

The experiments show that surface modification of hernia repair materials according to embodiments of the present invention may be utilized to prevent adhesion in vitro and in vivo. Two anti-adhesion poly(ester urea)s (PEUs) with varied amount of an allyl ether side chain with terminal alkene functionality for surface modification (5% alloc-PEU or 10% alloc-PEU) with a zwitterion thiol were studied. Control and extent of functional groups available on the surface were confirmed through attachment of a FITC-PEG-SH dye with both functionalized materials displaying increased dye attachment. As the molar concentration of alkene functional side chain increased from 5-10% for the alloc-PEUs, an increase in dye attachment was also observed. A zwitterion-thiol was attached through a click thiol-ene reaction to the alloc-PEU surface. Attachment was confirmed through water contact angle, XPS, and QCM. Anti-adhesion PEUs reduce fibrinogen attachment when compared to unfunctionalized controls demonstrating reasonable control over surface modification. Furthermore, these materials display limited cytotoxicity in vitro towards NIH-3T3 cells with all alloc-PEU analogues behaving similar to negative controls. 10% alloc-PEU materials were implanted in a rat intrabdominal adhesion model with the 10% alloc-PEU zwitterion functionalized material being found to reduce the average extent and tenacity of adhesions when compared to adhesion controls and the 10% alloc-PEU blank material. A statistical difference was observed between the tenacity of adhesion between the 10% alloc-PEU blank material and 10% alloc-PEU functionalized materials.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials 1,8-octanediol, 1,6-hexanediol, sodium carbonate, p-toluenesulfonic acid monohydrate, 3-allyloxy-1,2-propanediol, 1,3-diisopropyl carbodiimide, and triphosgene were all purchased from Sigma Aldrich (Milwaukee, Wis.). Toluene, ethyl acetate, hexane, chloroform, acetone, and N,N-dimethylformamide were purchased from Fischer Scientific (Pittsburgh, Pa.). L-valine, Boc-O-benzyl-L-tyrosine, and L-phenylalanine were purchased from Acros (Pittsburgh, Pa.) and Alfa Aesar (Tewksbury, Mass.). SIS-ECM was provided by Cook Medical and used as provided. All solvents were reagent grade and all chemicals were used without further purification unless otherwise stated.

Instrumental Methods

Proton (H) NMR spectra were conducted using a 300 MHz and 500 MHz Varian NMR spectrophotometer respectively. Chemical shifts are reported in ppm (δ) and referenced to residual solvent resonances ($^1$H NMR DMSO-$d_6$ 2.50 ppm). Multiplicities were explained using the following abbreviations: s=singlet, d=doublet, t=triplet, br=broad singlet, and m=multiplet. Size exclusion chromatography (SEC) was performed using an EcoSEC HLC-8320GPC (Tosoh Bioscience, LLC) equipped with a TSKgel SuperH-RC 6.0 mmI.D.×15 cm mixed bed column and refractive index (RI) detector. The number average molecular mass ($M_n$), weight average molecular mass ($M_w$), and molecular mass distribution ($Đ_M$) for each sample was calculated using a calibration curve determined from poly(styrene) standards (PStQuick MP-M standards, Tosoh Bioscience LLC) with DMF (with 0.01 M LiBr) or THF as eluent flowing at 1.0 mL/min at 50° C. Differential scanning calorimetry (DSC) was performed using TA Q200 DSC with heating and cooling cycles of 20° C./min and 10° C. respectively with temperature sweeps from 0-100° C. The glass transition temperature ($T_g$) was determined from the midpoint of the second heating cycle curve. Thermogravimetric analysis (TGA) was performed using a TA Q50 with heating ramps of 20° C./min in the temperature range from 0-500° C./min. The degradation temperature ($T_d$) was determined from 10% mass loss. A Rame-Hart Contact Angle Goniometer was used to determine contact angle for 5 µL of deionized water on a sample surface. Statistical analyses were performed using a post-hoc Tukey ANOVA test unless otherwise stated.

Example 1

Synthesis of Di-p-toluenesulfonic Acid Salts of Bis (L-valine)-Octane 1,8-Diester Monomer (1-VAL-8)

Synthesis of di-p-toluenesulfonic acid salts of bis(L-valine)-octane 1,8-diester (1-VAL-8) was carried out following previously published procedures. Briefly, in a 1 L 1-neck round bottom flask, 1,8-octanediol (43.8 g, 0.3 mol, 1 eq.), L-valine (73.8 g, 0.63 mol, 2.3 eq.), p-toluenesulfonic acid monohydrate (131.3 g, 0.69 mol, 2.4 eq.), and toluene (1300 mL) were added and equipped with a stir bar. A Dean-Stark trap was fastened to the round bottom flask and the reaction was heated to 110° C. and allowed to reflux for 24 h. The reaction was cooled to room temperature, and the resulting white precipitate was isolated by vacuum filtration using a Buchner funnel. The product was dissolved in boiling water (1 L), hot vacuum filtered, and cooled to room temperature to further purify the white solid precipitate. The precipitate was collected via filtration and the recrystallization process was performed three times for purity (82% yield). The resulting product was characterized by Proton Nuclear Magnetic Resonance Imagery ($^1$H NMR) ((300 MHz, 303 K, DMSO-d$_6$): δ=0.94 (m, 12H), 1.28 (s, 8H), 1.59 (m, 4H), 2.07-2.18 (m, 2H), 2.27 (s, 6H), 2.50 (m, DMSO), 3.33-3.38 (s, H$_2$O), 3.89 (d, $^3J_{H-H}$=3.0 Hz, 2H), 4.07-4.23 (m, 4H), 7.07-7.23 (d, $^3J_{H-H}$=8.2 Hz, 4H, aromatic H), 7.45-7.48 (d, $^3J_{H-H}$=8.1 Hz, 4H, aromatic H), 8.25 (br, 6H) ppm).

Example 2

Synthesis of Di-p-toluenesulfonic Acid Salts of Bis (L-valine)-Octane 1,8-Diester Monomer (1-VAL-8)

Synthesis of di-p-toluenesulfonic acid salts of bis(L-valine)-octane 1,8-diester (1-VAL-8) was carried out following previously published procedures. See, Yu, J.; Lin, F.; Lin, P.; Gao, Y.; Becker, M. L. "Phenylalanine-based poly(ester urea): Synthesis, characterization, and in vitro degradation." Macromolecules 2014 DOI: 10.1021/ma401752b, the disclosure of which is incorporated herein by reference. 1,8-octanediol (43.8 g, 0.3 mol, 1 eq.), L-valine (73.8 g, 0.63 mol, 2.3 eq.), p-toluenesulfonic acid monohydrate (131.3 g, 0.69 mol, 2.4 eq.), and toluene (1300 mL) were added to a 3 L 3-neck round bottom flask and mixed with overhead mechanical stirring. A Dean-Stark Trap was attached to the round bottom flask and the reaction was heated to reflux for 24 h. The reaction was cooled to ambient temperature, and the resulting white precipitate was isolated by vacuum filtration using a Buchner funnel. The product was recrystallized by dissolving in boiling water (2 L), vacuum filtering hot, and cooling to room temperature to afford a white solid precipitate. The precipitate was collected via filtration and the recrystallization process was performed three times for purity (166 g, 79% yield). The resulting product was characterized by $^1$H NMR (300 MHz, DMSO-d$_6$): δ=0.95-0.99 (m, 12H, —CH(CH$_3$)$_2$), 1.24-1.35 (s, 8H, —COOCH$_2$CH$_2$(CH$_2$)$_4$—), 1.55-1.65 (m, 4H, —COOCH$_2$CH$_2$(CH$_2$)$_4$CH$_2$—), 2.06-2.22 (m, 2H, (CH$_3$)$_2$CH—), 2.26-2.31 (s, 6H, —CH$_3$Ar—), 2.50 (m, DMSO), 3.33-3.38 (s, H$_2$O), 3.88-3.90 (d, J=4.3 Hz, 2H, $^+$NH$_3$CHCOO—), 4.08-4.24 (m, 4H, —COOCH$_2$CH$_2$(CH$_2$)$_4$—), 7.10-7.14 (d, J=8.2 Hz, 4H, aromatic H), 7.48-7.50 (d, J=8.1 Hz, 4H, aromatic H), 8.25-8.33 (br, 6H, —NH$_3$$^+$).

Example 3

Synthesis of Di-p-toluenesulfonic Acid Salts of Bis (L-valine)-Decane 1,10-Diester Monomer. (1-VAL-10)

Synthesis of di-p-toluenesulfonic acid salts of bis(L-valine)-decane 1,10-diester (1-VAL-10) was carried out using the method shown in Example 2, above with 1,10 decanediol as the diol (154 g, 71% yield). The resulting product was characterized by H NMR ((300 MHz, DMSO-d$_6$): δ=0.93-1.00 (m, 12H, —CH(CH$_3$)$_2$—), 1.22-1.33 (s, 12H, —COOCH$_2$CH$_2$(CH$_2$)$_6$—), 1.55-1.64 (m, 4H, —COOCH$_2$CH$_2$(CH$_2$)$_4$CH$_2$—), 2.09-2.21 (m, 2H, (CH$_3$)$_2$CH—), 2.28-2.31 (s, 6H, —CH$_3$Ar—), 2.50 (m, DMSO), 3.30-3.35 (s, H$_2$O), 3.87-3.91 (d, J=4.5 Hz, 2H, $^+$NH$_3$CHCOO—), 4.08-4.24 (m, 4H, —COOCH$_2$CH$_2$(CH$_2$)$_6$—), 7.10-7.13 (d, J=7.8 Hz, 4H, aromatic H), 7.47-7.51 (d, J=7.8 Hz, 4H, aromatic H), 8.27-8.31 (br, 6H, —NH$_3$$^+$)).

Example 4

Synthesis of Di-p-toluenesulfonic Acid Salts of Bis-(L-valine)-Dodecane 1,12-Diester Monomer. (1-VAL-12)

Synthesis of di-p-toluenesulfonic acid salts of bis(L-valine)-dodecane 1,12-diester (1-VAL-12) was carried out using the method shown in Example 2, above with 1,12 dodecanediol as the diol (106 g, 82% yield). The resulting product was characterized by $^1$H NMR (300 MHz, DMSO-d$_6$): δ=0.90-0.98 (m, 12H, —CH(CH$_3$)$_2$), 1.22-1.27 (s, 16H, —COOCH$_2$CH$_2$(CH$_2$)$_8$—), 1.53-1.63 (m, 4H, —COOCH$_2$CH$_2$(CH$_2$)$_8$CH$_2$—), 2.07-2.18 (m, 2H, (CH$_3$)$_2$CH$^+$—), 2.27-2.29 (s, 6H, —CH$_3$Ar—), 2.50 (m, DMSO), 3.29-3.33 (s, H$_2$O), 3.87-3.90 (d, J=4.3 Hz, 2H, $^+$NH$_3$CHCOO—), 4.06-4.22 (m, 4H, —COOCH$_2$CH$_2$(CH$_2$)$_8$—), 7.08-7.11 (d, J=7.9 Hz, 4H, aromatic H), 7.45-7.49 (d, J=8.1 Hz, 4H, aromatic H), 8.25-8.28 (br, 6H, —NH$_3$$^+$)).

Example 5

Synthesis of Di-p-toluene Sulfonic Acid Salts of Bis-L-phenylalanine-hexane-1,6-diester Monomer. (1-PHE-6)

Di-p-toluene sulfonic acid salts of bis-L-phenylalanine-diol-diester monomers were prepared using previously published procedures, (See, Yu, J.; Lin, F.; Lin, P.; Gao, Y.; Becker, M. L. Macromolecules 2014, 47, 121; Lin, F.; Yu, J.; Tang, W.; Zheng, J.; Xie, S.; Becker, M. L. Macromolecules 2013, 46, 9515; and Pang, X.; Chu, C.-C. Biomaterials 2010, 31, 3745, the disclosure of which are incorporated herein by reference.), and as shown in Scheme 8, below.

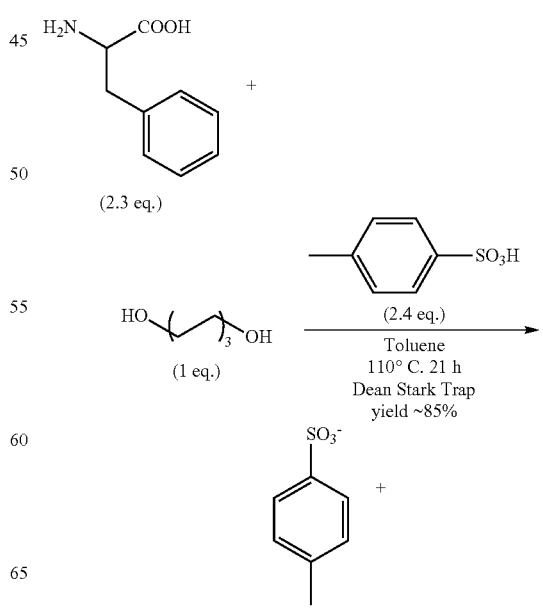

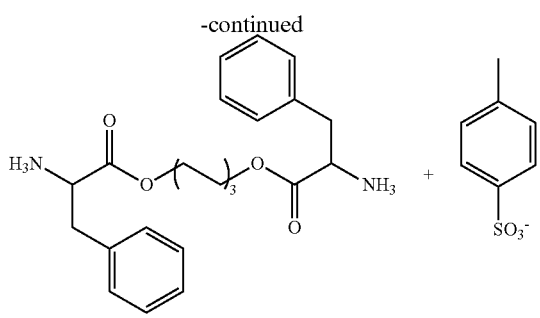

In brief, 1,6-hexanediol (10.0 g, 90 mmol, 1.0 equiv.), L-phenylalanine (32.2 g, 200 mmol, 2.3 equiv.), p-toluene sulfonic acid monohydrate (TsOH) (38.7 g, 200 mmol, 2.4 equiv.), and toluene (200 mL) were mixed in a 500 mL 2-neck round bottom flask equipped with Dean-Stark trap and a magnetic stir bar. The TsOH acidifies the solution conditions preventing the amidation of the carboxylic acids. The Dean Stark trap was used to collect the water biproducts, increasing the yield of the reaction. The system was heated to reflux (110° ° C.) and purged with nitrogen for 20 h. After 20 h, the reaction mixture was cooled to ambient temperature and the product was filtered with diethyl ether. The solid product was dissolved in 3 L of hot water and decolored using activated carbon black (2.0 g) for 2-3 minutes and the decolorized hot liquid obtained by vacuum filtration. When the decolorized hot liquid was cooled to room temperature, the white solid product formed was collected by vacuum filtration. The white solid product was recrystallized 3 times using 3 L of water to yield 57.0 g (yield 85%) of the di-p-toluene sulfonic acid salt of bis-L-phenylalanine-1, 6-hexanediol-diester as a white powder. The compound produced was characterized by $^1$H NMR ((300 MHz, DMSO-d$_6$): 1.04-1.13 (m, 4H, —COOCH$_2$CH$_2$CH$_2$—) 1.38-1.44 (m, 4H, —COOCH$_2$CH$_2$CH$_2$—) 2.27 (s, 6H, CH$_3$Ar—) 2.50 (DMSO) 2.98-3.19 (m, 4H, —CHCH$_2$—Ar—) 3.89-4.03 (m, 4H, —COOCH$_2$CH$_2$—) 4.25-4.32 (m, 2H, $^+$NH$_3$CHCOO—) 7.09-7.13 (d, 4H, aromatic H) 7.21-7.34 (m, 10H, aromatic H) 7.47-7.50 (d, 4H, aromatic H) 8.36 (s, 6H, $^+$NH$_3$—)) and by $^{13}$C-NMR ((75 MHz, DMSO-d$_6$): 20.75, 24.66, 27.62, 35.97, 38.80-40.28 (DMSO-d$_6$), 53.07, 65.46, 125.39, 127.14, 127.95, 128.49, 129.30, 134.69, 137.78, 145.33, 169.03).

Example 6

Synthesis of Di-p-toluenesulfonic Acid Salts of Bis (L-phenylalanine)-Hexane 1,6-Diester Monomer. (1-PHE-6)

Synthesis of di-p-toluene sulfonic acid of bis(L-phenylalanine)-hexane 1,6-diester (1-PHE-6) was carried out following previously published procedures. Briefly, in a 3 L 3-neck round bottom flask, 1,6-hexanediol (1 eq.), L-phenylalanine (2.3 eq.), p-toluenesulfonic acid monohydrate (2.4 eq.), and toluene (1300 mL) were added to a 1 neck flask and equipped with a stir bar. A Dean-Stark trap was fastened to the round bottom flask and the reaction was heated to 110° C. and allowed to reflux for 24 h. The reaction was cooled to room temperature, and the resulting white precipitate was isolated by vacuum filtration using a Buchner funnel. The product was dissolved in boiling water (2 L), hot vacuum filtered, and cooled to room temperature to further purify the white solid precipitate. The precipitate was collected via filtration and the recrystallization process was performed three times for purity. (81% yield). The compound produced was characterized by $^1$H NMR ((300 MHz, 303 K, DMSO-d$_6$): δ=1.06 (s, 4H), 1.38 (m, 4H), 2.27 (s, 6H), 2.50 (m, DMSO), 2.96-3.17 (m, 4H), 4.01 (t, $^3J_{H-H}$=9.0 Hz, 4H), 4.28 (t, $^3J_{H-H}$=6.0 Hz, 2H), 7.08-7.11 (d, 4H), 7.20-7.35 (m, 10H), 7.45-7.48 (d, 4H), 8.37 (s, 6H) ppm).

Example 7

Synthesis of Di-p-toluenesulfonic Acid Salts of Bis (L-phenylalanine)-Octane 1,8-Diester Monomer. (1-PHE-8)

Synthesis of di-p-toluene sulfonic acid of bis(L-phenylalanine)-octane 1,8-diester (1-PHE-8) was carried out using the method described in Example 6, above with 1,8 octanediol as the diol (157 g, 75% yield). The compound produced was characterized by H NMR ((300 MHz, 303 K, DMSO-d$_6$): δ=1.14 (s, 8H) 1.41 (m, 4H), 2.27 (s, 6H), 2.50 (m, DMSO), 2.96-3.17 (m, 4H), 4.02 (t, $^3J_{H-H}$=6.0 Hz, 4H), 4.28 (t, $^3J_{H-H}$=6.0 Hz, 2H) 7.08-7.11 (d, 4H) 7.20-7.35 (m, 10H) 7.48-7.49 (d, 4H) 8.36 (s, 6H) ppm).

Example 8

Synthesis of Di-p-toluenesulfonic Acid Salt of Bis-L-phenylalanine-octane-1,8-diester (1-PHE-8)

1,8-octanediol (10.00 g, 0.068 mol), L-phenylalanine (25.79 g, 0.156 mol), p-toluenesulfonic acid monohydrate (31.07 g, 0.163 mol) and toluene (200 mL) were mixed in a 500 mL round-bottom flask equipped with Dean-Stark trap and a magnetic stir bar. The system was heated to reflux for 20 h. After the reaction mixture was cooled to ambient temperature, the product was filtered and washed with diethyl ether. The solid product was dissolved in 3 L of hot water and decolored using activated carbon black (2.00 g) for 2-3 min. After hot filtration and cooling to room temperature, a white solid product was obtained by vacuum filtration. The product was then recrystallized with water for three times to yield 45.9 g (yield 86%) white powders as product. The compound produced was characterized by $^1$H NMR ((500 MHz, DMSO-d$_6$): 1.08-1.22 (m, 8H), 1.37-1.49 (m, 4H), 2.29 (s, 6H), 3.02 (dd, J=14.06, 7.95 Hz, 2H), 3.14 (dd, J=13.94, 5.87 Hz, 2H), 3.98-4.08 (m, 4H), 4.28 (dd, J=7.83, 6.11 Hz, 2H), 7.11 (dd, J=8.44, 0.61 Hz, 4H), 7.20-7.36 (m, 10H), 7.48 (d, J=7.83 Hz, 4H), 8.36 (br. s., 6H)) and 13C NMR ((125 MHz, DMSO-d$_6$): 21.25, 25.49, 28.20, 28.86, 36.65, 53.83, 65.96, 125.99, 127.65, 128.65, 128.97, 129.76, 135.18, 138.56, 145.46, 169.47).

Example 9

Synthesis of Di-Hydrochloric Acid Salt of Bis-O-benzyl-L-tyrosine-hexane-1,6-diester Monomer The di-hydrochloric acid salt of the bis-O-benzyl-L-tyrosine-hexane-1,6-diester monomer was synthesized through the general esterification between Boc-O-benzyl-L-tyrosine and 1,6-hexanediol, as shown below in Scheme 9, below.

Scheme 9 The synthetic route of protected tyrosine monomer.

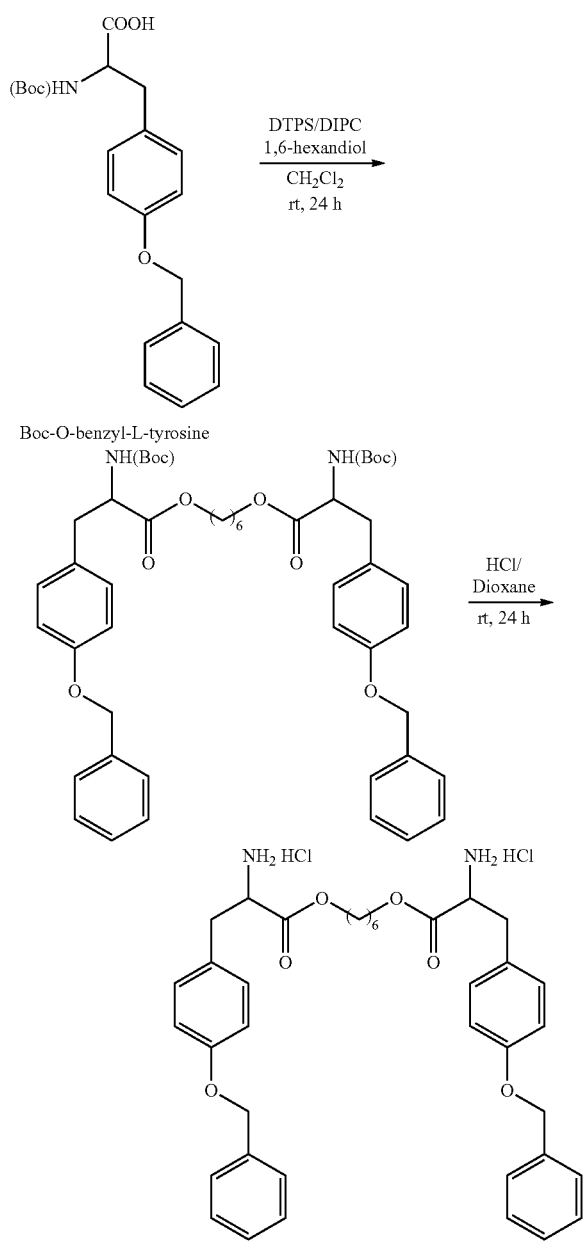

The bis-N-boc-O-benzyl-L-tyrosine-hexane-1,6-diester intermediate compound was prepared as shown in Scheme 9, above. The boc-O-benzyl-L-tyrosine reagent was condensed onto both ends of the 1,6-hexanediol reagent using base (DPTS) and carbodiimide coupling reagents (DIC) in methylene chloride. The reaction was stirred under an inert atmosphere at ambient temperature for 24 hours to yield the bis-N-boc-O-benzyl-L-tyrosine-hexane-1,6-diester intermediate compound. This compound was characterized by $^1$H NMR ((300 MHz, CDCl$_3$): S-7.25-7.50 (m, 10H), 7.00-7.10 (m, 4H), 6.85-6.95 (m, 4H), 4.85-5.15 (m, 6H), 4.4-0-4.60 (m, 2H), 3.95-4.20 (m, 4H), 2.85-3.15 (m, 4H), 1.15-1.70 (m, 26H)).

The di-hydrochloric acid salt of the bis-O-benzyl-L-tyrosine-hexane-1,6-diester monomer was then prepared from the bis-N-boc-O-benzyl-L-tyrosine-hexane-1,6-diester intermediate compound as shown in Scheme 9 above. Removal of the Boc protecting group was accomplished by stirring intermediate compound in a solution of HCl in dioxane at ambient temperature for 24 h under and inert gas atmosphere to produce the di-hydrochloric acid salt of the bis-O-benzyl-L-tyrosine-hexane-1,6-diester monomer. The benzyl protected tyrosine monomer was characterized by $^1$H NMR ((300 MHz, DMSO-d$_6$): S=8.71 (br, 6H, NH$_3$—), 7.25-7.50 (m, 10H, benzyl unit aromatic), 7.10-7.20 (m, 4H, tyrosine unit aromatic), 6.85-7.00 (m, 4H, tyrosine unit aromatic), 5.06 (s, 4H, —Ar—OCH$_2$—Ar), 4.07-4.20 (m, 2H, $^+$NH$_3$CHCOO—), 4.01 (t, 4H, —COOCH$_2$CH$_2$—), 2.90-3.25 (m, 4H, —CHCH$_2$—Ar), 1.30-1.55 (m, 4H, —COOCH$_2$CH$_2$CH$_2$—), 1.10-1.25 (m, 4H, —COOCH$_2$CH$_2$CH$_2$—)) and by $^{13}$C NMR ((75 MHz, DMSO-d$_6$): S=169.6, 158.0, 137.5, 131.0, 128.9, 128.0, 127.2, 115.2, 69.6, 66.8, 53.8, 35.6, 29.0, 28.3, 25.6).

Example 10

Synthesis of Bis-N-Boc-O-benzyl-L-tyrosine-octane-1,8-diester 1,8-octanediol (1.64 g, 11.2 mmol), N-Boc-O-benzyl-L-tyrosine (10.00 g, 26.9 mmol) and DPTS (0.66 g, 2.24 mmol) were dissolved in 60 mL anhydrous dichloromethane under N$_2$. The temperature was lowered to 0° C. with an ice bath after all the solids were dissolved. DIC (4.9 mL, 31.36 mol) was added via syringe in one portion. The reaction was stirred overnight while the temperature gradually increased to room temperature. The mixture was filtered, concentrated and dissolved in CHCl$_3$. The solution was washed with 5% HCl twice, brine once, dried over Na$_2$SO$_4$ and solvent was removed in vacuo. A light yellow solid (9.31 g, 97%) was obtained with column chromatography on silica gel in MeOH/CHCl$_3$ (5/95, v/v). The compound produced was characterized by $^1$H NMR ((500 MHz, DMSO-d$_6$): 1.31 (s, 8H), 1.43 (s, 18H), 1.55-1.65 (m, 4H), 2.96-3.10 (m, 4H), 4.03-4.15 (m, 4H), 4.53 (d, J=6.85 Hz, 2H), 4.97 (d, J=7.58 Hz, 2H), 5.04 (s, 4H), 6.87-6.94 (m, 4H), 7.02-7.09 (m, 4H), 7.30-7.46 (m, 10H)) and by $^{13}$C NMR ((125 MHz, DMSO-d$_6$): 25.78, 28.32, 28.48, 29.07, 37.57, 54.57, 65.36, 70.02, 114.90, 127.40, 127.93, 128.55, 130.34, 137.03, 157.90).

Example 11

Synthesis of Di-p-toluenesulfonic Acid Salt of Bis-L-leucine-octane-1,8-diester (1-LEU-8)

1,8-octanediol (10.00 g, 0.068 mol), L-leucine (20.46 g, 0.156 mol), p-toluenesulfonic acid monohydrate (31.07 g, 0.163 mol) and toluene (200 mL) were mixed in a 500 mL round-bottom flask equipped with Dean-Stark trap and a magnetic stir bar. The system was heated to reflux for 20 h. After the reaction mixture was cooled to ambient temperature, the product was filtered and washed with diethyl ether. The solid product was recrystallized with water for three times to yield 42.9 g (yield 88%) white powder as the product. The compound produced was characterized by $^1$H NMR ((300 MHz, DMSO-d$_6$): 0.89 (d, J=5.86 Hz, 12H), 1.28 (br. s., 8H), 1.51-1.65 (m, 8H), 1.66-1.78 (m, 2H), 2.29 (s, 6H), 3.98 (t, J=7.03 Hz, 2H), 4.07-4.23 (m, 4H), 7.12 (dd, J=8.49, 0.59 Hz, 4H), 7.42-7.54 (m, 4H), 8.30 (br. s., 6H)) and by $^{13}$C NMR ((125 MHz, DMSO-d$_6$): 21.22, 22.37, 22.58, 24.26, 25.58, 28.32, 28.89, 51.09, 66.06, 125.93, 128.51, 138.18, 145.94, 170.38).

Example 12

General Procedure for Synthesis of Di-p-toluenesulfonic Acid Salts of Bis-L-alanine-diester Monomers Either 1,6-hexanediol, 1,8-octanediol, 1,10-decanediol, or 1,12-dodecandiol (1.0 mol equiv), L-alanine (2.3 mol equiv), p-toluenesulfonic acid monohydrate (TsOH) (2.4 mol equiv), and toluene (1 mL per gram of TsOH) were added to round-bottom flask equipped with Dean-Stark trap and condenser. The solution was heated to reflux (ca. 110° C.) while stirring with a magnetic stir bar. After ca. 20 h, the reaction mixture was cooled to ambient temperature. The resulting precipitate was collected by vacuum filtration. The solid product was dissolved in minimal hot water and decolored using a small amount of activated carbon black for 2-3 min. This solution was filtered to remove the carbon black and was left to cool to room temperature. The precipitate was then recrystallized three times using hot water to give the purified monomer.

Example 13

Synthesis of Di-p-toluenesulfonic Acid Salt of Bis-L-alanine-hexane-1,6-diester. (1-ALA-6)

The di-p-toluenesulfonic acid salt of bis-L-alanine-hexane-1,6-diester monomer (1-ALA-6) was prepared by following the general procedure described in Example 12, above, with the exception of the recrystallization procedure. The monomer was recrystallized four times from a 1:1 mixture (by volume) of ethanol and isopropanol. The monomer was prepared on a 145 mmol scale (based on the diol) and obtained with a 79% yield. The compound produced was characterized by $^1$H NMR ((500 MHz, DMSO-d6, δ): 8.27 (s, 6H; $NH_3$), 7.49 (d, J=8.0 Hz, 4H; Ar—H), 7.12 (d, J=7.8 Hz, 4H; Ar—H), 4.16 (m, 4H; $CH_2$), 4.10 (q, J=7.2 Hz, 2H; CH), 2.29 (s, 6H; $CH_3$), 1.61 (m, 4H; $CH_2$), 1.39 (d, J=7.2 Hz, 6H; $CH_3$), 1.35 (m, 4H; $CH_2$)) and by $^{13}$C NMR ((126 MHz, DMSO-d6, δ): 169.92, 145.21, 137.89, 128.10, 125.46, 65.49, 47.93, 27.76, 24.71, 20.75, 15.70. IR ($cm^{-1}$): 1743 (—C—(CO)—O—)).

Example 14

Synthesis of Di-p-toluenesulfonic Acid Salt of Bis-L-alanine-octane-1,8-diester. (1-ALA-8)

The di-p-toluenesulfonic acid salt of bis-L-alanine-octane-1,8-diester monomer (1-ALA-8) was prepared by following the general procedure described in Example 12, above, with the exception of the recrystallization procedure. The monomer was recrystallized four times from a 1:1 mixture (by volume) of ethanol and isopropanol. The monomer was prepared on a 147 mmol scale (based on the diol) and obtained with a 79% yield. The compound produced was characterized by $^1$H NMR ((500 MHz, DMSO-d6, δ): 8.27 (s, 6H; $NH_3$), 7.49 (d, J=8.0 Hz, 4H; Ar—H), 7.12 (d, J=7.8 Hz, 4H; Ar—H), 4.13 (m, 6H; $CH_2$ and CH), 2.29 (s, 6H; $CH_3$), 1.59 (m, 4H; $CH_2$), 1.39 (d, J=7.2 Hz, 6H; $CH_3$), 1.32 (m, 8H; $CH_2$)O and by $^{13}$C NMR ((126 MHz, DMSO-d6, δ): 169.92, 145.27, 137.83, 128.10, 125.45, 65.56, 47.92, 28.43, 27.87, 25.05, 20.71, 15.69. IR ($cm^{-1}$): 1749 (—C—(CO)—O—)).

Example 15

General Procedure for Synthesis of L-2-aminobutyric acid (ABA)-based Polyester Monomers Either 1,6-hexanediol, 1,8-octanediol, 1,10-decanediol, or 1,12-dodecandiol (1.0 mol equiv), the unnatural amino acid L-2-aminobutyric acid (ABA) (2.3 mol equiv), p-toluenesulfonic acid monohydrate (TsOH) (2.4 mol equiv), and toluene (1 mL per gram of TsOH) were added to round-bottom flask equipped with Dean-Stark trap and condenser. The solution was heated to reflux (ca. 110° C.) while stirring with a magnetic stir bar. After ca. 20 h, the reaction mixture was cooled to ambient temperature. The resulting precipitate was collected by vacuum filtration. The solid product was dissolved in minimal hot water and decolored using a small amount of activated carbon black for 2-3 min. This solution was filtered to remove the carbon black and was left to cool to room temperature. The precipitate was then recrystallized three times using hot water to give the purified monomer.

Example 16

Synthesis of Di-p-toluenesulfonic Acid Salt of Bis-L-2-aminobutyric acid-hexane-1,6-diester. (1-ABA-6)

The di-p-toluenesulfonic acid salt of bis-L-2-aminobutyric acid-hexane-1,6-diester. (1-ABA-6) was prepared by following the general procedure described in Example 15, above, with the exception of the recrystallization procedure. The monomer was recrystallized three times from a 3:4 (by volume) of ethanol and ethyl acetate. The monomer was prepared on a 46 mmol scale (based on the diol) and obtained with a 73% yield. The compound produced was characterized by $^1$H NMR ((300 MHz, DMSO-d6, δ): 8.33 (s, 6H, $NH_3$), 7.49 (d, J=8.0 Hz, 4H; Ar—H), 7.13 (d, J=7.8 Hz, 2H; Ar—H), 4.15 (m, 4H; $CH_2$), 4.01 (m, 2H; CH), 2.29 (s, 6H; $CH_3$), 1.81 (m, 4H; $CH_2$), 1.60 (m, 4H; $CH_2$), 1.34 (m, 4H; $CH_2$), 0.91 (t, J=7.4 Hz, 6H; $CH_3$)) and by $^{13}$C NMR ((75 MHz, DMSO-d6, δ): 169.46, 145.08, 138.07, 128.21, 125.53, 65.51, 53.11, 27.84, 24.80, 23.46, 20.83, 9.06. IR ($cm^{-1}$): 1745 (—C—(CO)—O—)).

Example 17

Synthesis of Di-p-toluenesulfonic Acid Salt of Bis-L-2-aminobutyric acid-octane-1,8-diester. (1-ABA-8)

The di-p-toluenesulfonic acid salt of bis-L-2-aminobutyric acid-octane-1,8-diester (1-ABA-8) monomer was prepared by following the general procedure described in Example 15, above, with the exception of the recrystallization procedure. The monomer was recrystallized three times from a 3:4 (by volume) of ethanol and ethyl acetate. The monomer was prepared on a 46 mmol scale (based on the diol) and obtained with an 81% yield. The compound produced was characterized by $^1$H NMR ((300 MHz, DMSO-d6, δ): 8.31 (s, 6H, $NH_3$), 7.49 (d, J=8.0 Hz, 4H; Ar—H), 7.12 (d, J=7.9 Hz, 2H; Ar—H), 4.16 (m, 4H; $CH_2$), 4.00 (m, 2H; CH), 2.29 (s, 6H; $CH_3$), 1.81 (m, 4H; $CH_2$), 1.59 (m, 4H; $CH_2$), 1.29 (m, 8H; $CH_2$), 0.92 (t, J=7.5 Hz, 6H; $CH_3$)) and by $^{13}$C NMR (975 MHz, DMSO-d6, δ): 169.47, 144.92, 138.23, 128.27, 125.58, 65.61, 53.18, 28.54, 27.99, 25.21, 23.49, 20.87, 9.09. IR (cm$^{-1}$): 1745 (—C—(CO)—O—)O.

Example 18

General Procedure for Synthesis of Isoleucine-Based Polyester Monomers

Either 1,6-hexanediol, 1,8-octanediol, 1,10-decanediol, or 1,12-dodecandiol (1.0 mol equiv), a L-isoleucine (2.3 mol equiv), p-toluenesulfonic acid monohydrate (TsOH) (2.4 mol equiv), and toluene (1 mL per gram of TsOH) were added to round-bottom flask equipped with Dean-Stark trap and condenser. The solution was heated to reflux (ca. 110° C.) while stirring with a magnetic stir bar. After ca. 20 h, the reaction mixture was cooled to ambient temperature. The resulting precipitate was collected by vacuum filtration. The solid product was dissolved in minimal hot water and decolored using a small amount of activated carbon black for 2-3 min. This solution was filtered to remove the carbon black and was left to cool to room temperature. The precipitate was then recrystallized three times using hot water to give the purified monomer.

Example 19

Synthesis of Di-p-toluenesulfonic Acid Salt of Bis-L-isoleucine-hexane-1,6-diester. (1-ILE-6)

The di-p-toluenesulfonic acid salt of bis-L-isoleucine-hexane-1,6-diester (1-ILE-6) monomer was synthesized as described in the general procedures set forth in Example 18, above. The monomer was prepared on an 80 mmol scale (based on the diol) and obtained with an 85% yield. The compound produced was characterized by $^1$H NMR ((500 MHz, DMSO-d6, δ): 8.30 (s, 6H; NH$_3$), 7.49 (d, J=8.0 Hz, 4H; Ar—H), 7.12 (d, J=8.1 Hz, 4H; Ar—H), 4.16 (m, 4H; CH$_2$), 3.96 (s, 2H; CH), 2.29 (s, 6H; CH$_3$), 1.87 (m, 2H; CH), 1.60 (m, 4H; CH$_2$), 1.36 (m, 8H; CH$_2$), 0.89 (m, 12H; CH$_3$)) and by $^{13}$C NMR (126 MHz, DMSO-d6, δ): 168.69, 145.44, 137.69, 128.01, 125.43, 65.40, 56.06, 35.91, 27.75, 25.23, 24.74, 20.71, 14.18, 11.41. IR (cm$^{-1}$): 1736 (—C—(CO)—O—)).

Example 20

Synthesis of Di-p-toluenesulfonic Acid Salt of Bis-L-isoleucine-octane-1,8-diester. (1-ILE-8)

The di-p-toluenesulfonic acid salt of bis-L-isoleucine-octane-1,8-diester (1-ILE-8) monomer was synthesized as described in the general procedures set forth in Example 18, above. The monomer was prepared on a 70 mmol scale (based on the diol) and obtained with a 92% yield. The compound produced was characterized by $^1$H NMR ((500 MHz, DMSO-d6, δ): 8.29 (s, 6H, NH$_3$), 7.49 (d, J=8.0 Hz, 4H; Ar—H), 7.12 (d, J=8.2 Hz, 4H; Ar—H), 4.15 (m, 4H; CH$_2$), 3.96 (d, J=3.9 Hz, 2H; CH), 2.29 (s, 6H; CH$_3$), 1.88 (m, 2H; CH), 1.59 (m, 4H; CH$_2$), 1.44 (m, 2H; CH$_2$) 1.28 (m, 10H; CH$_2$), 0.88 (m, 12H; CH$_3$)) and by $^{13}$C NMR ((126 MHz, DMSO-d6, δ): 168.71, 145.42, 137.70, 128.01, 125.43, 65.49, 56.07, 35.92, 28.35, 27.85, 25.23, 25.14, 20.72, 14.17, 11.41. IR (cm$^{-1}$): 1747 (—C—(CO)—O—)).

Example 21

Synthesis of Di-Hydrochloric Acid Salts of Bis-O-benzyl-L-tyrosine-1,3-Allyloxy-Diester Monomer. (1-TYR-2 Alloc)

Synthesis of di-hydrochloric acid salts of bis-O-benzyl-L-tyrosine-1,3-allyloxy-diester monomer (1-TYR-2 Alloc) was carried out following previously published procedures. (See, Yu, J.; Lin, F.; Becker, M. L. Branched amino acid based poly(ester urea)s with tunable thermal and water uptake properties. *Macromolecules* 2015, 48, 2916-2924 DOI: 10.1021/acs.macromol.5b00376, the disclosure of which is incorporated herein by reference in its entirety.) 1-TYR-2 Alloc was prepared using Boc-O-benzyl-L-tyrosine and 1,3-allyoxyl-2-propanediol in anhydrous DMF. Once dissolved, the reaction was placed in an ice bath for 10 minutes followed by syringe addition of 1,3-diisopropyl carbodiimide (DIC, 5 eq.). The reaction gradually came to ambient temperature while stirring for 24 h, as a yellow precipitate formed. DMF was removed under reduced pressure and the product was purified using column chromatography (4:1 hexanes: ethyl acetate) with all fractions collected for rotary evaporation. The resulting Boc-protected Bis-O-benzyl-L-tyrosine-1,3-allyloxy-diester monomer intermediate was characterized by proton Nuclear Magnetic Imagery ($^1$H NMR) ((300 MHz, DMSO-d$_6$): δ=1.31 (s, 18H), 2.50 (s, DMSO), 2.77 (m, 4H), 2.93 (m, 2H), 3.35 (s, H2O), 4.01 (m, 2H), 4.06 (s, 1H), 4.14 (s, 2H), 4.26 (s, 2H), 5.04 (s, 4H), 5.21 (m, 2H), 5.85 (m, 1H), 6.89-7.38 (m, 18H, aromatic H)). The Boc protecting groups were removed with 4 M HCl/dioxane under nitrogen. The yellow product was dried under reduced pressure to yield the 1-TYR-2 Alloc monomer. (71%). The resulting chloride acid salt of Bis-O-benzyl-L-tyrosine-1,3-allyloxy-diester monomer was characterized by $^1$H NMR ((300 MHz, DMSO-d$_6$): δ=2.50 (s, DMSO), 3.09 (m, 6H), 3.38 (s, H2O), 3.90 (s, 2H), 4.07 (m, 1H), 4.22 (m, 2H), 4.26 (m, 2H), 5.05 (s, 4H), 5.19 (m, 2H), 5.83 (m, 1H), 6.93-7.43 (m, 18H, aromatic H), 8.82 (br, 6H)).

Example 22

Lithium Phenyl-2,4,6-trimethylbenzoylphosphinate (LAP) Photoinitiator Synthesis LAP was synthesized according to previously published work. (See Makromol. Chem., 192 (10) (1991), pp. 2307-2315) the disclosure of which is incorporated herein by reference in its entirety). Briefly, dimethyl phenylphosphonite (1.00 eq) was added to an oven dried flask under Ar at 23° C. While stirring, 2,4,6-trimethylbenzoyl chloride (1.00 eq) was added dropwise to the solution and allowed to stir for 24 hours. A four-fold excess of LiBr (6.1 g) in ca. 100 mL of 2-butanone was added to the reaction mixture and heated to 50° C. for one hour until a white precipitate formed. The solution was cooled to room temperature, then suction filtered, and finally rinsed 3× with 2-butanone to remove excess LiBr. The solid white precipitate (82% yield) was dried under vacuum and analyzed by $^1$H-NMR. H-NMR (300 MHz, 303K, D$_2$O): δ=2.01 (s, 6H), 2.23 (s, 3H), 6.88 (s, 2H), 7.41-7.51 (m, 2H), 7.51-7.61 (m, 1H), 7.70 (m, 2H) ppm.

Example 23

Synthesis of Zwitterion-SH

The synthesis of the 3-((3-((3-mercaptopropanoyl)oxy) propyl) dimethylammonio)propane-1-sulfonate (zwitterion- SH) was carried out in several steps. First, the synthesis of 3,3'-dithiodipropionyl chloride was synthesized in a 250 mL 2 neck round bottom flask. The flask was attached with a jacketed condenser and an addition funnel. 3,3'-dithiodipropionic acid (1.0 eq.) was added and purged with nitrogen at room temperature followed by dropwise addition of thionyl chloride (6.0 eq.). The reaction was heated (90° C.) for 24 hours and a color change to yellow was noted. Excess thionyl chloride was removed using a vacuum transfer and the residual product was dried under reduced pressure. The product was stored under anhydrous conditions without further purification. $^1$H-NMR (300 MHz, 303 K, CDCl3): δ=2.95 (t, $^3J_{H-H}$=7.0 Hz, 4H), 3.32 (t, $^3J_{H-H}$=7.0 Hz, 4H) ppm.

Synthesis of bis(3-dimethylamino)propyl) 3,3'-disulfanediyldipropionate was carried out in an anhydrous 100 mL 2 neck round bottom flask. 3-dimethylamino-1-propanol (2.0 eq.) was added through a rubber septum and subsequently dissolved in 25 mL of anhydrous dichloromethane under nitrogen. 3,3'-dithiodipropionyl chloride was then added (1.0 eq.) slowly to the flask and allowed to stir. Following addition, a jacketed condenser was attached to the flask with positive pressure from nitrogen occupying the other neck. The reaction was refluxed and stirred for 16 hours. The solution was then cooled, and dichloromethane was removed under reduced pressure. The product was dissolved in a saturated sodium bicarbonate solution for 15 minutes. The sodium bicarbonate solution was transferred to a separatory funnel with dichloromethane where the organic layer was collected (4×). The organic layer was then extracted in saturated sodium bicarbonate aqueous solution (2×) and finally distilled water (1×) with the final organic layer stirred over magnesium sulfate for 15 minutes. The product was then filtered and residual solvent was removed under reduced pressure to obtain the tan oil (77% yield). $^1$H-NMR (300 MHz, 303 K, DMSO-d6) δ=4.08 (q, $^3J_{H-H}$=6.7 Hz, 4H), 2.92 (t, $^3J_{H-H}$=6.9 Hz, 4H), 2.70 (t, $^3J_{H-H}$=6.9 Hz, 4H), 2.26 (t, $^3J_{H-H}$=7.0 Hz, 1H), 2.12 (s, 12H), 1.71 (hept, $^3J_{H-H}$=6.3 Hz, 1H). $^{13}$C-NMR (75 MHz, 303 K, DMSO-d6) δ=170.89 (s, 2C), 62.50 (s, 2C), 55.43 (s, 2C), 44.97 (s, 2C), 33.39 (s, 2C), 32.76 (s, 2C), 26.24 (s, 2C).

Zwitterion disulfide synthesis was carried out in a 100 mL round bottom flask where 1,3-propane sultone (4.0 eq.) was dissolved and stirred in 5 mL of acetone at 0° C. Separately, bis(3-dimethylamino)propyl) 3,3'-disulfanediyldipropionate (1.0 eq.) was dissolved in 15 mL of acetone and subsequently added slowly to the 100 mL round bottom flask. The reaction was allowed to stir and warm up to room temperature for 4 hours where the white product was collected in the flask. Following the reaction, the product was collected in centrifuge tubes, washed with acetone, centrifuged (5×), and finally the white product was placed under reduced pressure (87% yield). $^1$H-NMR (300 MHz, d$_2$o) δ 4.33 (t, $^3J_{H-H}$=5.8 Hz, 4H), 3.64-3.49 (m, 8H), 3.21 (s, 12H), 3.07 (dt, $^3J_{H-H}$=12.7, 6.2 Hz, 8H), 2.94 (t, $^3J_{H-H}$=6.4 Hz, 4H), 2.39-2.19 (m, 8H). $^{13}$C-NMR (75 MHz, d$_2$o) δ 174.16 (s, 1C), 62.36 (s, 1C), 61.85 (s, 1C), 61.27 (s, 1C), 50.81 (s, 1C), 47.25 (s, 2C), 33.55 (s, 1C), 32.53 (s, 1C), 21.67 (s, 1C), 18.20 (s, 1C).

Finally, the zwitterion-SH was obtained by cleavage of the zwitterion disulfide using 1,4-dithiothreitol (DTT). Zwitterion disulfide (1 eq.) and DTT (4 eq.) were added to a sodium bicarbonate solution (10 mM, pH=7.4) with nitrogen bubbling through. The mixture was allowed to react for 4 hours. The reaction was quenched by addition of acetic acid to reduce the pH to 6.5. Water was removed under reduced pressure followed by a washing step with acetone to remove DTT, and centrifugation to afford the white product. $^1$H-NMR (300 MHz, d$_2$o) δ 4.33 (t, $^3J_{H-H}$=5.8 Hz, 4H), 3.63-3.51 (m, 8H), 3.21 (s, $^3J_{H-H}$=19.8 Hz, 12H), 3.07 (q, $^3J_{H-H}$=6.9 Hz, 8H), 2.94 (t, $^3J_{H-H}$=6.4 Hz, 4H), 2.29 (tt, $^3J_{H-H}$=15.5, 7.9 Hz, 8H). $^{13}$C-NMR (75 MHz, d$_2$) δ 174.29 (s, 1C), 62.31 (s, 1C), 61.70 (s, 1C), 61.33 (s, 1C), 50.76 (s, 1C), 47.23 (s, 2C), 37.91 (s, 1C), 21.69 (s, 1C), 19.02 (s, 1C), 18.18 (s, 1C).

Example 24

Synthesis of Poly(ester urea) Terpolymers

The synthesis was adapted form previously published work. (See *ACS Biomater. Sci. Eng.*, 2018, 4 (4), pp 1346-1356, the disclosure of which is incorporated herein by reference in its entirety). Interfacial polymerization of p-toluenesulfonic acid salts of bis(L-valine), p-toluenesulfonic acid salts of bis(L-phenylalanine), hydrochloric acid salts of bis-O-benzyl-L-tyrosine-1,3-allyloxy-diester monomers ((1-VAL-8), (1-PHE-6), and (1-TYR-2 Alloc), respectively) was performed by dissolving the monomers in various molar feed ratios (1 eq. total) with sodium carbonate (3.4 eq.) in distilled water (0.1 M, 35° C.) in a 2 L 2-neck round bottom flask. The solution was attached with an overhead mechanical stir rod and allowed to stir until the solution turned clear. Triphosgene (0.35 eq.) was dissolved in chloroform and subsequently added to the reaction vessel through an addition funnel. The clear solution turned white upon addition and continued to stir for 4 hours. The reaction was transferred to a separatory funnel where the organic phase was precipitated in to boiling water to remove chloroform and starting material impurities. Off white polymer was collected, frozen in liquid nitrogen, and dried under reduced pressure (90-95% yield).

Poly[(1-VAL-8)$_{0.65}$-co-(1-PHE-6)$_{0.30}$-co-(1-TYR-2 Alloc)$_{0.05}$]. (5% Alloc PEU). $^1$H NMR (300 MHz, 303 K, DMSO-d$_6$): δ=0.83 (m, 12H, —CH(CH$_3$)$_2$), 1.95 (m, 2H, —NHCH(CH(CH$_3$)$_2$)C(O)O—), 2.82-2.97 (m, 4H, —NHCH(CH$_2$Ph)C(O)O—), 4.38 (m, 2H, —NHCH(CH$_2$Ph) C(O)O—), 5.02 (s, 4H, —OCH$_2$Ph), 5.13 (m, 2H, —CHCH$_2$), 5.84 (m, 1H, —CHCH$_2$), 6.36 (d, $^3J_{H-H}$=9 Hz, 2H, —NHCH(CH(CH$_3$)$_2$)C(O)O—), 6.48 (d, $^3J_{H-H}$=9 Hz, 2H, —C(O)NHC(CH$_2$Ph)HC(O)—), 7.13-7.28 (m, 10H, —C$_6$H5), 1.18, 1.24, 1.44, 1.51, 3.95-4.05, 6.88, 7.38 (all remaining protons) ppm. (M$_w$=35 kDa, M$_n$=24 kDa, Đ$_m$=1.5, T$_g$=40.2° C., T$_d$=289° C.)

Poly[(1-VAL-8)$_{0.60}$-co-(1-PHE-6)$_{0.30}$-co-(1-TYR-2 Alloc)$_{0.10}$]. (10% Alloc PEU). $^1$H NMR (300 MHz, 303 K, DMSO-d$_6$): δ=0.83 (m, 12H, —CH(CH$_3$)$_2$), 1.95 (m, 2H, —NHCH(CH(CH$_3$)$_2$)C(O)O—), 2.82-2.97 (m, 4H, —NHCH(CH$_2$Ph)C(O)O—), 4.38 (m, 2H, —NHCH(CH$_2$Ph) C(O)O—), 5.02 (s, 4H, —OCH$_2$Ph), 5.13 (m, 2H, —CHCH$_2$), 5.84 (m, 1H, —CHCH$_2$), 6.36 (d, $^3J_{H-H}$=9 Hz, 2H, —NHCH(CH(CH$_3$)$_2$)C(O)O—), 6.48 (d, $^3J_{H-H}$=9 Hz, 2H, —C(O)NHC(CH$_2$Ph)HC(O)—), 7.13-7.28 (m, 10H, —C$_6$H5), 1.18, 1.24, 1.44, 1.51, 3.95-4.05, 6.87, 7.40 (all remaining protons) ppm. (M, =62 kDa, M$_n$=28 kDa, Đ$_m$=2.2, T$_g$=49.4° C., T$_d$=299° C.)

Poly[(1-VAL-8)$_{0.70}$-co-(1-PHE-6)$_{0.30}$-co-(1-TYR-2 Alloc)$_{0.00}$]. (0% Alloc PEU). $^1$H NMR (300 MHz, 303 K, DMSO-d$_6$): δ=0.83 (m, 12H, —CH(CH$_3$)$_2$), 1.95 (m, 2H, —NHCH(CH(CH$_3$)$_2$)C(O)O—), 2.82-2.97 (m, 4H, —NHCH(CH$_2$Ph)C(O)O—), 4.38 (m, 2H, —NHCH(CH$_2$Ph) C(O)O—), 6.36 (d, $^3J_{H-H}$=9 Hz, 2H, —NHCH(CH(CH$_3$)$_2$)C(O)O—), 6.48 (d, $^3J_{H-H}$=9 Hz, 2H, —C(O)NHC(CH$_2$Ph)HC(O)—), 7.13-7.28 (m, 10H, —C$_6$H5), 1.18, 1.24, 1.44, 1.51, 3.95-4.05 (all remaining protons) ppm. ($M_w$=95 kDa, $M_n$=57 kDa, $Đ_m$=1.7, $T_g$=29° C., $T_d$=340° C.)

Example 25

Synthesis of 5% Alloc-PEU and 10% Alloc-PEU Terpolymers

The synthesis was adapted form previously published work. (See, Dreger, N. Z.; Wandel, M. B.; Robinson, L. L.; Luong, D.; Sondergaard, C. S.; Hiles, M.; Premanadan, C.; Becker, M. L. Preclinical in vitro and in vivo Assessment of Linear and Branched L-Valine Based Poly(ester urea)s for Soft-tissue Applications. ACS Biomater. Sci. Eng. 2017, 4 (4) 1346-1356, the disclosure of which is incorporated herein by reference in its entirety.) Interfacial polymerization of p-toluenesulfonic acid salts of bis(L-valine), p-toluenesulfonic acid salts of bis(L-phenylalanine), hydrochloric acid salts of bis-O-benzyl-L-tyrosine-1,3-allyloxy-diester monomers ((1-VAL-8), (1-PHE-6), and (1-TYR-2 Alloc) respectively) were performed by dissolving the monomers in various molar feed ratios (1 eq. total) with sodium carbonate (3.4 eq.) in distilled water (0.1 M, 35° C.) in a 2 L 2-neck round bottom flask. The solution was attached with an overhead mechanical stir rod and allowed to stir until the solution turned clear. Triphosgene (0.35 eq.) was dissolved in chloroform and subsequently added to the reaction vessel through an addition funnel. The clear solution turned white upon addition and continued to stir for 4 hours. The reaction was transferred to a separatory funnel where the organic phase was precipitated in to boiling water to remove chloroform and starting material impurities. Off white polymer was collected, frozen in liquid nitrogen, and dried under reduced pressure (90-95% yield).

Poly[(1-VAL-8)$_{0.65}$-co-(1-PHE-6)$_{0.30}$-co-(1-TYR-2 Alloc)$_{0.05}$]. (5% Alloc-PEU). $^1$H NMR (300 MHz, 303 K, DMSO-d$_6$): δ=0.83 (m, 12H, —CH(CH$_3$)$_2$), 1.95 (m, 2H, —NHCH(CH$_3$)$_2$)C(O)O—), 2.82-2.97 (m, 4H, —NHCH(CH$_2$Ph)C(O)O—), 4.38 (m, 2H, —NHCH(CH$_2$Ph) C(O)O—), 5.02 (s, 4H, —OCH$_2$Ph), 5.13 (m, 2H, —CHCH$_2$), 5.84 (m, 1H, —CHCH$_2$), 6.36 (d, $^3J_{H-H}$=9 Hz, 2H, —NHCH(CH(CH$_3$)$_2$)C(O)O—), 6.48 (d, $^3J_{H-H}$=9 Hz, 2H, —C(O)NHC(CH$_2$Ph)HC(O)—), 7.13-7.28 (m, 10H, —C$_6$H$_5$), 1.18, 1.24, 1.44, 1.51, 3.95-4.05, 6.88, 7.38 (all remaining protons) ppm. ($M_w$=35 kDa, $M_n$=24 kDa, $Đ_m$=1.5, $T_g$=40° C., $T_d$=289° C.)

Poly[(1-VAL-8)$_{0.60}$-co-(1-PHE-6)$_{0.30}$-co-(1-TYR-2 Alloc)$_{0.10}$]. (10% Alloc-PEU). $^1$H NMR (300 MHz, 303 K, DMSO-d$_6$): δ=0.83 (m, 12H, —CH(CH$_3$)$_2$), 1.95 (m, 2H, —NHCH(CH$_3$)$_2$)C(O)O—), 2.82-2.97 (m, 4H, —NHCH(CH$_2$Ph)C(O)O—), 4.38 (m, 2H, —NHCH(CH$_2$Ph) C(O)O—), 5.02 (s, 4H, —OCH$_2$Ph), 5.13 (m, 2H, —CHCH$_2$), 5.84 (m, 1H, —CHCH$_2$), 6.36 (d, $^3J_{H-H}$=9 Hz, 2H, —NHCH(CH(CH$_3$)$_2$)C(O)O—), 6.48 (d, $^3J_{H-H}$=9 Hz, 2H, —C(O)NHC(CH$_2$Ph)HC(O)—), 7.13-7.28 (m, 10H, —C$_6$H$_5$), 1.18, 1.24, 1.44, 1.51, 3.95-4.05, 6.87, 7.40 (all remaining protons) ppm. ($M_w$=62 kDa, $M_n$=28 kDa, $Đ_m$=2.2, $T_g$=49° C., $T_d$=299° C.)

Example 26

Terpolymer PEU Free-Standing Films

PEU free-standing films of the alloc PEU analogue of Example 24 were prepared by blade coating with slight adaptations from the procedure described above. In short, PEU analogues were dissolved in acetone at 35% or 20% weight. Polymer solutions were then blade coated (8 cm blade width, 1000 μm or 700 μm gap height) on PET and allowed to air dry for 24 hours. Alloc PEU analogue films were named according to their alloc content and gap height during blade coating (i.e. 5% alloc PEU terpolymer blade coated at 1000 μm is named 5% Alloc PEU-1000). The PEU films were then further dried under reduced pressure to remove residual solvent. Films were then cut into 5×5 cm sheets and submerged in 1×PBS (pH=7.4) for five minutes. They were subsequently fastened in an ASTM D 3787-07 standard ball-burst apparatus and burst with a constant rate of traverse (25.4 mm/min). Force at break, extension at break, and relative stiffness were recorded until film failure along with the location of the failure. Statistical analyses were done using a one-way ANOVA with Tukey post hoc analysis. A value of p<0.05 was considered significant. Sections of 5% Alloc PEU-1000, 5% Alloc PEU-600, 10% Alloc PEU-1000, and Alloc PEU-600 (5 cm×5 cm) were cut and divided in to two groups (click and control, n=4 per group). Click samples were functionalized with zwitterion-SH as described above with control samples remaining bare films. All films were sterilized using ethylene oxide for further in vivo characterization. The results are shown in FIGS. 14A-D.

Example 27

Terpolymer PEU Free-Standing Films

PEU free-standing films of the alloc PEU analogue of Example 25 were prepared by blade coating with slight adaptations from previously reported procedures. (See, e.g., Dreger, N. Z.; Fan, Z.; Zander, Z. K.; Tantisuwanno, C.; Haines, M. C.; Waggoner, M.; Parsell, T.; Sondergaard, C. S.; Hiles, M.; Premanandan, C.; et al. Amino acid-based Poly (ester urea) copolymer films for hernia-repair applications. Biomaterials 2018, 182 (June), 44-57 DOI: 10.1016/j.biomaterials.2018.08.003, the disclosure of which is encorporated herein by reference in its entirety). In short, PEU analogues were dissolved in acetone at 35% weight. Polymer solutions were then blade coated (8 cm blade width, 1000 μm gap height) on poly(ethylene terephthalate) (PET) and allowed to air dry for 24 hours. The PEU films were then further dried under reduced pressure to remove residual solvent (film thickness=200 μm). Films were then cut into 2×8 cm sheets and all films were sterilized using ethylene oxide for further in vivo characterization. Following sterilization, films were cut in to tensile bars using a custom dye cutter (ASTM D-638-V). Bars were pulled with a constant rate of extension (25.4 mm/min). The modulus, yield strain, and yield stress for each tensile bar were calculated from the linear elastic region. Statistical analyses were done using a one-way ANOVA with Tukey post hoc analysis. A value of p<0.05 was considered significant. The results are reported in FIGS. 20A-D.

Example 28

Rhodamine Surface Functionalization of Terpolymer PEUs

Blade coated alloc PEUs of Example 26 were punched in to 8 mm disks using a dye punch set. Disks were placed in a 24-well plate and submerged in deionized water (2 mL) to presoak for 30 minutes. Disks were divided in to three groups. Click treated samples had the aqueous solution removed and replaced with an Argon purged aqueous solution containing rhodamine-SH (2 eq.) and LAP (1.0 eq.). Disks were soaked in the aqueous solution for 30 minutes. Click disks were treated with UV light ($\lambda$=365 nm, I=1.2 mW/cm$^2$) for 30 minutes. Physically adsorbed disks had the aqueous solution removed and replaced with an Argon purged aqueous solution containing rhodamine-SH (2 eq.) and LAP (1.0 eq.). Physically adsorbed disks were kept in the dark and not exposed to UV light for 30 minutes. Finally, control disks were kept in deionized water and exposed to UV light for 30 minutes to serve as a baseline control for the alloc PEUs. After treatment, samples were rinsed with deionized water (3×) and then submerged in 2 mL of deionized water for 30 minutes. Disks were removed, dried with nitrogen, and finally dissolved in DMSO for fluorescence measurements. For surface quantification, fluorescence studies were carried out using a BioTek Synergy™ Mx Microplate Reader (BioTek, Vermont) with Gen 5™ reader control and data analysis software ($\lambda_{ex}$=568 nm, emission range 586-700 nm). A Rhodamine-SH standard curve was constructed with serial dilutions in DMSO ($\lambda_{em\ max}$=592 nm). To quantify the dye present on click, physically adsorbed, and control alloc PEUs, disks were dissolved in DMSO (2 mL). 300 µL of DMSO from each group was added to a 96 quartz well plate and subjected to the plate reader (n=3). Dye concentration was extrapolated from the calibration curve. The results are shown in FIGS. 15A-D and FIGS. 17A-B.

Example 29

FITC-PEG-Thiol Surface Functionalization of Terpolymer PEUs

Blade coated Alloc PEUs of Example 27 were punched in to 8 mm disks using a dye punch set. Disks were placed in a 24-well plate and divided in to three groups. Functionalized treated samples had the aqueous solution (100 µL) containing FITC-PEG-SH (2 eq.) and LAP (1.0 eq.) added to the surface. Disks were soaked in the aqueous solution for 30 minutes. Functionalized disks were treated with UV light ($\lambda$=365 nm, I=0.4 mW/cm$^2$) for 30 minutes. Physically adsorbed disks had the aqueous solution containing FITC-PEG-SH (1000 MW) (2 eq.) and LAP (1.0 eq.) placed on the surface and were kept in the dark for 30 minutes. Finally, blank samples had DI water placed on the surface for 30 minutes. After treatment, all samples were rinsed with deionized water (3×) and then submerged in 2 mL of deionized water (2×) for 30 minutes. Disks were removed, dried with nitrogen, and finally dissolved in DMSO (0.5 mL) for fluorescence measurements. For surface quantification, fluorescence studies were carried out using a BioTek Synergy™ Mx Microplate Reader (BioTek, Vermont) with Gen 5™ reader control and data analysis software ($\lambda_{ex}$=495 nm, emission range 530-550 nm). A FITC-PEG-SH (1000 MW) standard curve was constructed with serial dilutions in DMSO ($\lambda_{em\ max}$=550 nm). Once dissolved, 300 µL of DMSO from each group was added to a 96 quartz well plate and subjected to the plate reader (n=3). Dye concentration was extrapolated from the calibration curve. Statistical analyses were done using a one-way ANOVA with Tukey post hoc analysis. A value of p<0.05 was considered significant. The results are reported in Table 3, above and in FIGS. 21 and 22.

Example 30

Zwitterion Surface Functionalization of Terpolymer PEUs

Functionalizing alloc PEU disks with zwitterion-SH were performed as described in Example 28 above for rhodamine-SH. Disks were placed in a 24-well plate and submerged in deionized water (2 mL) to presoak for 30 minutes. Disks were divided in to three groups. Click treated samples had the aqueous solution removed and replaced with an Argon purged aqueous solution containing zwitterion-SH (2 eq.) and LAP (1.0 eq.). Disks were soaked in the aqueous solution for 30 minutes. Click disks were treated with UV light ($\lambda$=365 nm, I=1.2 mW/cm$^2$) for 30 minutes. Physically adsorbed disks had the aqueous solution removed and replaced with an Argon purged aqueous solution containing zwitterion-SH (2 eq.) and LAP (1.0 eq.). Physically adsorbed disks were kept in the dark and not exposed to UV light for 30 minutes. Finally, control disks were kept in deionized water and exposed to UV light for 30 minutes to serve as a baseline control for the alloc PEUs. After treatment, samples were rinsed with deionized water (3×) and then submerged in 2 mL of deionized water for 30 minutes. Disks were removed, dried with nitrogen, and finally subjected to x-ray photoelectron spectroscopy (XPS). The XPS spectra were obtained using a VersaProbe II Scanning XPS Microprobe from Physical Electronics (PHI), under ultrahigh vacuum conditions with a pressure of 2.0 µPa. Automated dual beam charge neutralization was used during the analysis of the samples to provide accurate data. The analyzer pass energy was 117.4 eV for the survey spectra and 23.5 eV for the high-resolution scans in the N1s and S2p regions. The survey scans in the range 0-700 eV were used to evaluate the percentage of different atoms present on the surface of the samples. Atomic concentrations were calculated with PHI MultiPak software. The XPS high resolution spectra of Nis were decomposed into two components by using the curve fitting routine in MultiPak. A goodness of fit ($\chi^2$) better than 1.5 was achieved for each fit. Each spectrum was collected using a monochromatic (Al K$_\alpha$) x-ray beam (E=1486.6 eV) over a 100 m×1400 m probing area with a beam power of 100 W. The results are reported in FIG. 18.

Example 31

Zwitterion Surface Functionalization of Terpolymer PEUs

Functionalizing alloc PEU disks with zwitterion-SH were performed as described in Example 29 above for FITC-PEG-SH. Disks were placed in a 24-well plate and submerged in deionized water (2 mL) to presoak for 30 minutes. Disks were divided in to three groups. Functionalized samples had the aqueous solution removed and replaced with an Argon purged aqueous solution containing zwitterion-SH (2 eq.) and LAP (1.0 eq.). Disks were soaked in the aqueous solution for 30 minutes. Functionalized disks were treated with UV light ($\lambda$=365 nm, I=1.2 mW/cm$^2$) for 30 minutes. Physically adsorbed disks had the aqueous solution removed and replaced with an Argon purged aqueous solution containing zwitterion-SH (2 eq.) and LAP (1.0 eq.). Physically adsorbed disks were kept in the dark and not exposed to UV light for 30 minutes. Finally, control disks were kept in deionized water for 30 minutes to serve as a baseline control for the alloc-PEUs. After treatment, samples were rinsed with deionized water (3×) and then submerged in 2 mL of deionized water for 30 minutes. Disks were removed, dried with nitrogen, and finally subjected to x-ray photoelectron spectroscopy (XPS). The XPS spectra were obtained using a VersaProbe II Scanning XPS Microprobe from Physical Electronics (PHI), under ultrahigh vacuum conditions with a pressure of 2.0 µPa. Automated dual beam charge neutralization was used during the analysis of the samples to provide accurate data. The analyzer pass energy was 117.4 eV for the survey spectra and 23.5 eV for the high-resolution scans in the N1s and S2p regions with binding energy referenced to the high resolution N1s peak (~398.9 eV). The survey scans in the range 0-700 eV were used to evaluate the percentage of different atoms present on the surface of the samples. Atomic concentrations were calculated with PHI MultiPak software. The XPS high resolution spectra of N1s were decomposed into two components using the curve fitting routine in MultiPak along with assessment of the full width at half max (FWHM) to further confirm elemental distribution. Each spectrum was collected using a monochromatic (Al $K_\alpha$) x-ray beam (E=1486.6 eV) over a 100 µm×1400 µm probing area with a beam power of 100 W. The results are reported in FIGS. 23A-F.

Example 32

Protein Adsorption

Protein adsorption profiles on the click, physically adsorbed, and control alloc PEUs of Example 30 were obtained using a quartz crystal microbalance with dissipation (QCM-D) (Qsense E4, Biolin Scientific AB). Terpolymer PEUs were spin coated onto $SiO_2$ QCM chips (Qsense, 335 $SiO_2$) using a 2% (wt/wt) solution of polymer in N,N-dimethylformamide (DMF) at 2000 rpm for 1 min. Film thickness was confirmed using an ellipsometer (J. A Woolham, M-2000) over a spectral range of 250 nm to 17000 nm, between angles 50°-70°, and taken every 5°. Spin coated terpolymer PEU films were thus reported. (See FIG. 36A-B)

Example 33

Protein Adsorption

Protein adsorption profiles on functionalized, physically adsorbed, and control alloc-PEUs of Example 31 were obtained using a quartz crystal microbalance with dissipation (QCM-D) (Qsense E4, Biolin Scientific AB). Terpolymer PEUs were spin coated onto QCM chips (Qsense, 335 $SiO_2$) using a 1% (wt/wt) solution of polymer in acetone at 8000 rpm for 1 min. Chips were further annealed for 24 hours prior to being subjected to measurements. A solution of human derived fibrinogen in 1×PBS was prepared (1.5 mg/mL). Samples were loaded in to their respective QCM chambers and a separate solution of 1×PBS was run (0.150 mL/min at 37° C.) to establish a baseline. Once a baseline was achieved (~30 minutes), the fibrinogen solution was added and flushed through at the same constant rate (0.150 mL/min). The solution flow was stopped when a frequency drop was observed and fibrinogen coverage equilibrium was allowed to occur (~30 minutes). Once a baseline equilibrium was established, the solution of 1×PBS was again flushed over the QCM chips and any frequency change was observed and noted. Samples were flushed until a similar equilibrium baseline was achieved. Fibrinogen adsorption to the surface was calculated from the $5^{th}$ overtone using the Sauerbrey equation. See, Childers, E. P.; Peterson, G. I.; Ellenberger, A. B.; Domino, K.; Seifert, G. V; Becker, M. L. Adhesion of Blood Plasma Proteins and Platelet-rich Plasma on L-Valine-Based Poly(ester urea). *Biomacromolecules* 2016, No. 17, 3396-3403 DOI. 10.1021/acs.biomac.6b01195, the disclosure of which is incorporated herein by reference in its entirety. The equilibrium mass of adsorption after fibrinogen addition and mass removed after 1×PBS wash were thus reported. Statistical analyses were done using a one-way ANOVA with Tukey post hoc analysis. A value of p<0.05 was considered significant. The results are reported in FIGS. 25A-D.

Example 34

Film Surface Topology

Surface topology images of blade coated films formed in Example 33, above were obtained using scanning electron microscopy (SEM). Using a JEOL USA SEM, samples were scanned at 2.0 kV excitation at 50× magnification. 10% alloc-PEU functionalized and 10% alloc-PEU blank films were imaged after ethylene oxide sterilization and after implantation for 21 days to observe surface morphology changes. The results are shown in FIGS. 34A-C.

Example 35

PEU Terpolymer Implantation

PEU free-standing films were prepared by blade coating as described in Example 26, above. In short, PEU analogues were dissolved in acetone at 35% or 20% weight. Polymer solutions were then blade coated (8 cm blade width, 1000 µm or 600 µm gap height) on PET and allowed to air dry for 24 hours. The PEU films were then further dried under reduced pressure to remove residual solvent. Sections of 5% Alloc PEU-1000, 5% Alloc PEU-600, 10% Alloc PEU-1000, and Alloc PEU-600 (5 cm×5 cm) were cut and divided in to two groups (click and control, n=4 per group). Click samples were functionalized with zwitterion-SH as described above with control samples remaining bare films. All films were sterilized using ethylene oxide for further in vivo characterization.

Example 36

PEU Terpolymer Implantation

PEU free-standing films were prepared by blade coating as described in Example 27 above. In short, 10% PEU analogues were dissolved in acetone at 35% weight. Polymer solutions were then blade coated (8 cm blade width, 1000 µm gap height) on PET and allowed to air dry for 24 hours (~150-200 µm thick). The PEU films were then further dried under reduced pressure to remove residual solvent. Sections of 10% alloc-PEUs were cut (2 cm×6 cm) and divided into two groups (functionalized with zwitterion thiol or blank unfunctionalized control, n=8 per group). All films were sterilized using ethylene oxide for further in vivo characterization. A hernia adhesion rat model was adapted from previously reported studies. (See, e.g., (Hodde, J. P.; Suckow, M. D.; Johnson, C.; Rodenberg, E.; Ritchie, R. D. Histological and adhesiogenic characterization of the Zenapro Hybrid Hernia Repair Device. *Int. J. Surg. Open* 2016, 5, 27-32 DOI: 10.1016/j.ijso.2016.09.005 and Suckow, M. A.; Hodd, J. P.; Wolter, W. R.; Wood, K. V.; Hiles, M. C.; Janis, A. D. Addition of nimesulide to small intestinal submucosa biomaterial inhibits postsurgical adhesiogenesis in rats. *J Biomed Mat Res Pt B Appl Biomater* 2010, 93B, 18-23, the disclosure of which is incorporated herein by reference in its entirety).

All procedures and animal handling were in accordance with The University of Minnesota Institutional Animal Care and Use Committee (IACUC Protocol Number 1805-

35945A). Female Sprague-Dawley rats (32) were used to test adhesion between four groups (sham, adhesion control, 10% alloc-PEU functionalized, and 10% alloc-PEU-blank) (n=8 per group). Buprenorphine SR was subcutaneously injected two to four hours prior to surgery and used for analgesic effect. Each animal was anesthetized with 1-4% isoflurane administered through a nose cone. Animals underwent a paramedian laparotomy followed by exposure and abrasion of the cecum (abrasion not performed for sham). (See, FIG. 27) Each implant was applied, secured in place around the cecum with sutures, followed by closure of the laparotomy. (See, FIG. 27) Samples were left implanted for 21 days. Animals were humanely euthanized using carbon dioxide and polymer implants were examined for extent and tenacity of adhesions present. Samples were scored accordingly and reported. Statistical analyses were done using a Kruskall-Wallis test with exact option and a post-hoc Mann-Whitney U test with a Bonferroni adjusted alpha of 0.0083. Extent and tenacity to device were compared using a Mann-Whitney U test with exact option to determine significant difference between the two groups. The results are reported in FIGS. 29A-D.

Example 37

Cytotoxicity Assessment

To assess compatibility of 5% and 10% alloc-PEU analogues prepared as set forth in Example 36, above, a cytotoxicity assay was performed. Solvent cast films (5×5 cm) were submerged in 20 mL centrifuge tubes and covered in extraction media (DMEM with penicillin-streptomycin, no Bovine Calf Serum (BCS)) (8.3 mL). Three controls were used as comparisons for cytotoxicity. Extraction media negative and positive control samples had 10 mL of extraction media added to a 15 mL centrifuge tube. Latex finger cots were used as an additional positive control and placed in a 15 mL centrifuge tube with 6 mL of extraction media. All were shaken gently at 37° C. for 24 hr. NIH 3T3 cells were plated and allowed to reach confluency. Cells were subsequently harvested with trypsin and combined with complete DMEM media and BCS. An aliquot of the cell solution (1 mL) and complete media (1 mL) (2 mL total) were added to each plate. The plates were placed in a cell culture incubator (37° C., 5% $CO_2$) for 24 hours. Following incubation, the extracts were removed from the shaker and added to a syringe. The volume in the syringe was noted and BCS was added to the total volume extract (except for no serum negative control) (BCS accounts to 10% of extraction volume). Extraction solutions were filtered with a nylon, 0.2 m filter. Each well of cells had the media removed and 2 mL of the extract or control was pipetted into appropriate wells. The controls were cells in DMEM media plus FBS (filtered the same way as the sample extractions), cells in media without serum (NS), and cells in the filtered latex extract plus FBS. The plates were returned to a cell culture incubator (37° C., 5% $CO_2$) for 48 hours. After 48 hours, one picture was taken of each well with the 10× objective on an inverted microscope. The wells were analyzed and subsequently ranked based on cell viability. The results are shown in FIGS. 26A-G.

Example 38

Adhesion Histological Assessment

Tissue samples from the adhesions on Example 37 were placed in 10% neutral buffered formalin for fixation prior to sectioning and staining with Masson's trichrome and with hematoxylin and eosin for microscopic evaluation. The fixed samples were to be evaluated for degree of collagen deposition, necrosis, and inflammation. After staining, samples were collected and characterization by a board-certified veterinary pathologist. (See, FIGS. 33A-F)

In light of the foregoing, it should be appreciated that the present invention significantly advances the art by providing a PEU-based surgical adhesion barrier that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A poly(ester urea) (PEU) terpolymer for use as an adhesion barrier comprising the reaction product of one or more first amine protected amino acid-based diester monomers, one or more second amine protected amino acid-based diester monomers, one or more amine protected L-tyrosine-based allyloxy diester monomers, a urea bond forming compound and one or more thiol functionalized zwitterionic compounds.

2. The PEU terpolymer of claim 1 comprising:
an amino acid based poly(ester urea) backbone, wherein said amino acid based poly(ester urea) backbone comprises: the residue of said one or more first amine protected amino acid-based diester monomer, the residue of said one or more second amine protected amino acid-based diester monomer, the residue of said one or more amine protected L-tyrosine-based allyloxy diester monomer, and the residue of said urea bond forming compound; and
one or more zwitterionic side chains, wherein said one or more zwitterionic side chains comprises the residues of said thiol functionalized zwitterionic compounds and is connected to said amino acid based poly(ester urea) backbone through a sulfide bond.

3. A poly(ester urea) (PEU)-based adhesion barrier comprising an amino acid based poly(ester urea) backbone and one or more zwitterionic side chains connected to said amino acid based poly(ester urea) backbone through a sulfide bond.

4. The poly(ester urea) (PEU)-based adhesion barrier of claim 3 wherein the amino acid based poly(ester urea) backbone comprises one or more amino acid-based diester monomer residues and one or more amino acid-based allyloxy diester monomer residues.

5. The poly(ester urea) (PEU)-based adhesion barrier of claim 4 wherein each one of said one or more amino acid-based diester monomer residues comprises two valine, phenylalanine, leucine, isoleucine, tyrosine, alanine, methionine, glycine, or cysteine with residues separated by from 2 to 20 carbon atoms.

6. The poly(ester urea) (PEU)-based adhesion barrier of claim 4 wherein said one or more amino acid-based allyloxy diester monomer residues are residues of an amine protected L-tyrosine-1,3-allyloxy-diester monomer.

7. The poly(ester urea) (PEU)-based adhesion barrier of claim 4 wherein said amino acid-based allyloxy diester monomer is an amine protected L-tyrosine-1,3-allyloxy-diester monomer.

8. The poly(ester urea) (PEU)-based adhesion barrier of claim 4 wherein said amino acid-based allyloxy diester monomer residue is the residue of a monomer having a formula selected from:

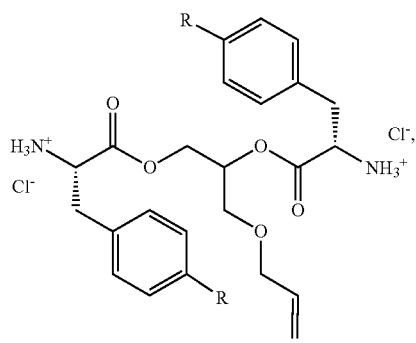

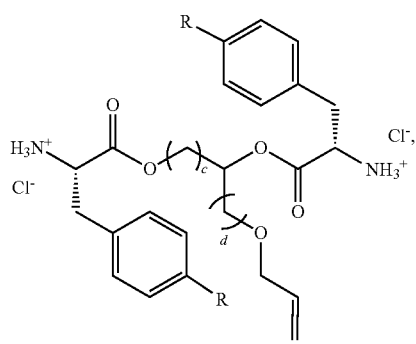

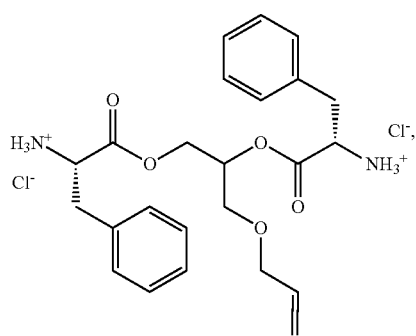

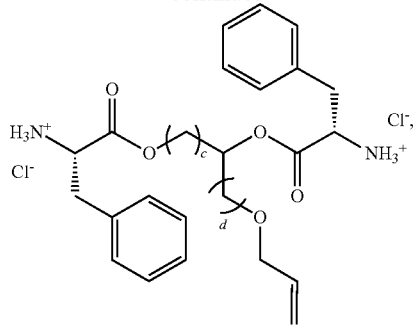

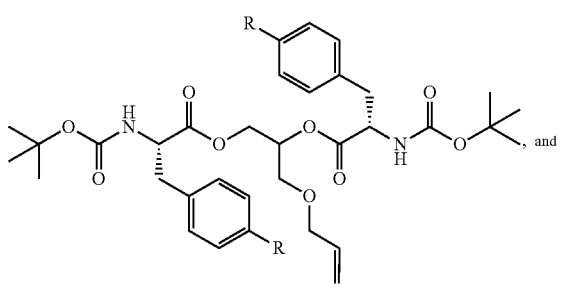

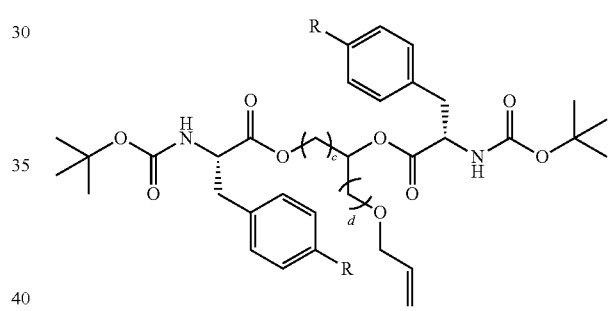

where R is $OCH_2Ph$, H, $OCH_2C{\equiv}CH$, $OCH_2CH_2CH_2N_3$, $OCH_2CH_2CH_2CH{=}CH_2$, $OCH_2Ph$, $OCOCH_2CH_2COCH_3$ or OH; and c and d are each an integer from about 1 to about 20.

9. The poly(ester urea) (PEU)-based adhesion barrier of claim 4 comprising from about 0.5 to about 50 mole percent L-tyrosine-based allyloxy diester monomer residues.

10. The poly(ester urea) (PEU)-based adhesion barrier of claim 4 comprising a zwitterionic terpolymer having a formula selected from:

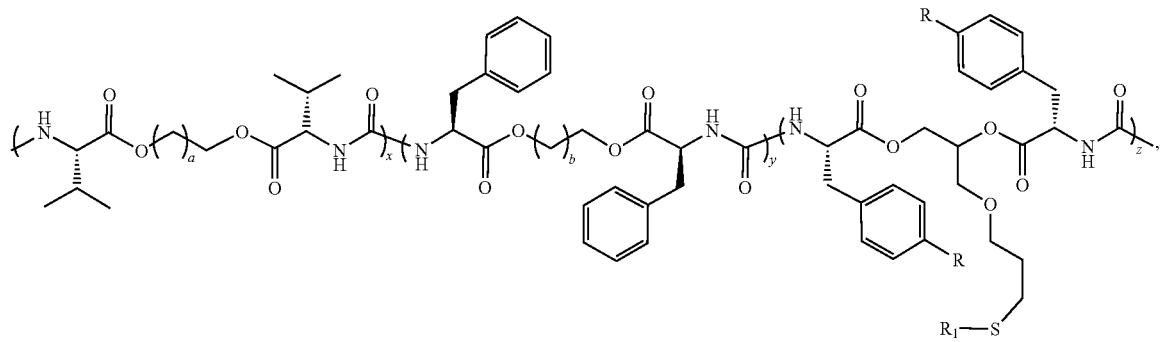

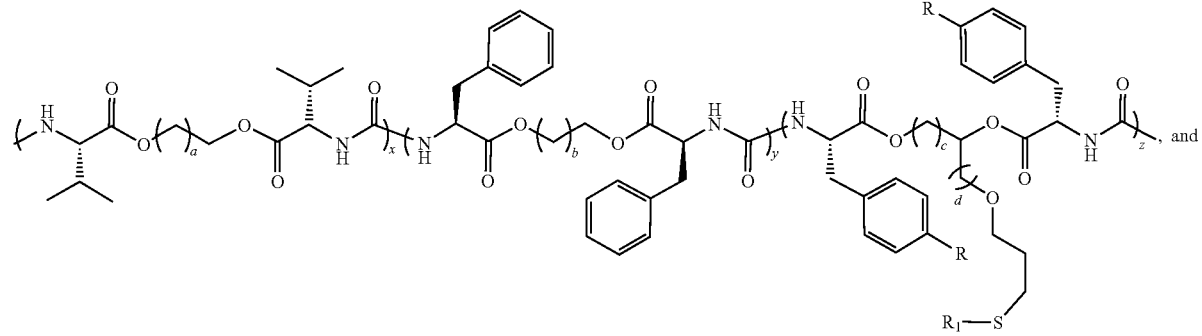

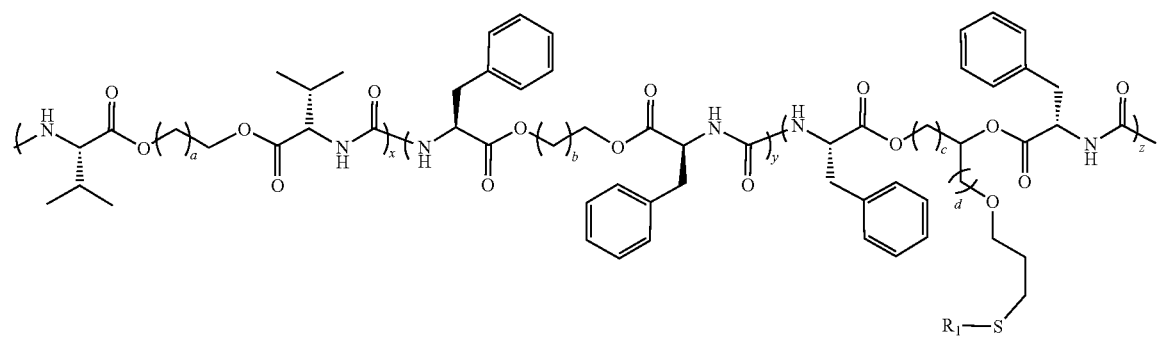

where R is OCH$_2$Ph, H, OCH$_2$C≡CH, OCH$_2$CH$_2$CH$_2$N$_3$, OCH$_2$CH$_2$CH$_2$CH=CH$_2$, OCH$_2$Ph, OCOCH$_2$CH$_2$COCH$_3$ or OH; R$_1$ is an alkyl or aryl group comprising a zwitterionic moiety; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500.

11. The poly(ester urea) (PEU)-based adhesion barrier of claim 4 comprising a zwitterionic terpolymer having a formula selected from:

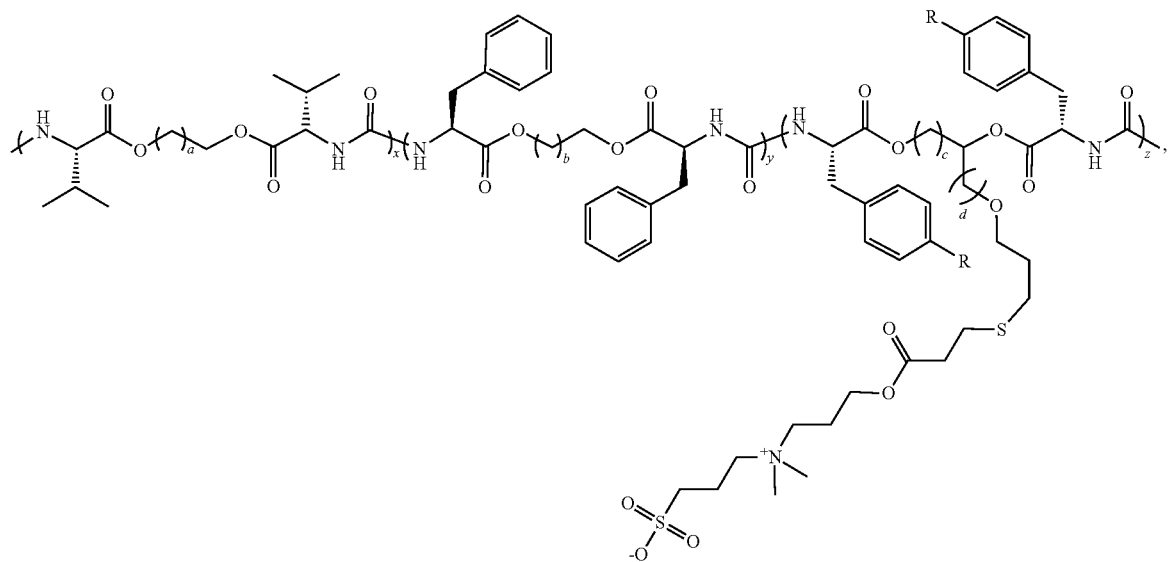

-continued
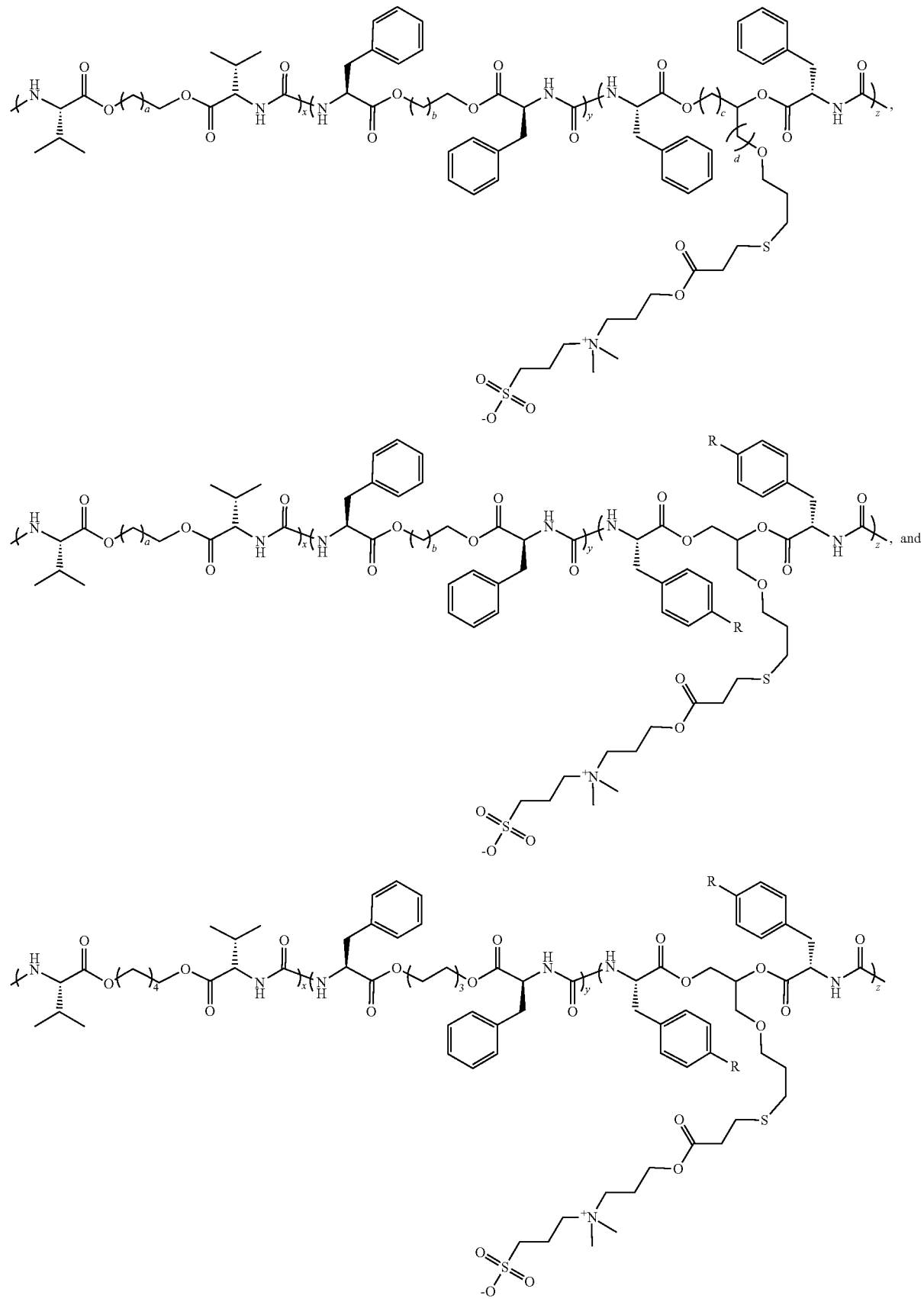

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; a is an integer from 1 to 20; b is an integer from 1 to 20; c and d are each an integer from about 1 to about 20; x is a mole fraction from about 0 to about 0.995; y is a mole fraction from about 0 to about 0.995; and z is a mole fraction from about 0.005 to about 0.500.

12. The poly(ester urea) (PEU)-based adhesion barrier of claim 3 wherein the amino acid based poly(ester urea) backbone comprises the residues of one or more first amino acid-based diester monomer, one or more second amino acid-based diester monomer, and one or more amino acid-based allyloxy diester monomer; and one or more said zwitterionic side chains are attached to said amino acid based poly(ester urea) backbone through said one or more amino acid-based allyloxy diester monomer residues.

13. The poly(ester urea) (PEU)-based adhesion barrier of claim 12 wherein said one or more first amino acid-based diester monomer comprises two valine, phenylalanine, leucine, isoleucine, tyrosine, alanine, methionine, glycine, or cysteine with residues separated by from 2 to 20 carbon atoms.

14. The poly(ester urea) (PEU)-based adhesion barrier of claim 12 wherein said one or more first amino acid-based diester monomers comprise two lysine residues separated by from 2 to 20 carbon atoms.

15. The poly(ester urea) (PEU)-based adhesion barrier of claim 12 wherein said one or more second amino acid-based diester monomer comprises two lysine, phenylalanine, or valine, phenylalanine, leucine, isoleucine, tyrosine, alanine, methionine, glycine, or cystine with residues separated by from 2 to 20 carbon atoms.

16. The poly(ester urea) (PEU)-based adhesion barrier of claim 12 wherein said one or more second amino acid-based diester monomers comprise two phenylalanine residues separated by from 2 to 20 carbon atoms.

17. The poly(ester urea) (PEU)-based adhesion barrier of claim 3 wherein said one or more zwitterionic side chains comprise the residue of a zwitterionic thiol.

18. The poly(ester urea) (PEU)-based adhesion barrier of claim 17 wherein said zwitterionic thiol has the formula:

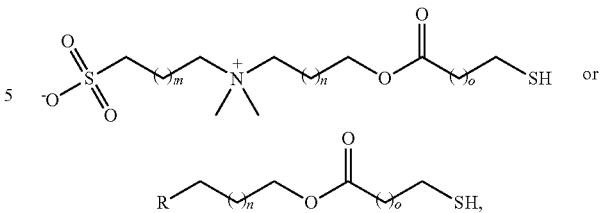

where R comprises a quaternary ammonium compound and a ring opened sultone; and m, n, and o are each an integer from 1 to 20.

19. The poly(ester urea) (PEU)-based adhesion barrier of claim 17 wherein said zwitterionic thiol has the formula:

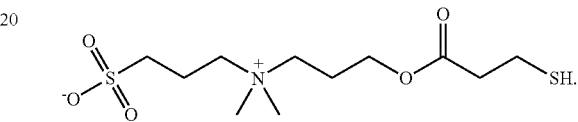

20. The poly(ester urea) (PEU)-based adhesion barrier of claim 3 wherein said one or more zwitterionic side chains comprise a zwitterionic moiety selected from the group consisting of a quaternary ammonium compound, a ring opened sultone, and a combination thereof.

21. The poly(ester urea) (PEU)-based adhesion barrier of claim 3 having a relative stiffness of from about 20 N/cm to about 40 N/cm as measured by burst force testing.

22. The poly(ester urea) (PEU)-based adhesion barrier of claim 3 comprising a zwitterionic copolymer having the formula:

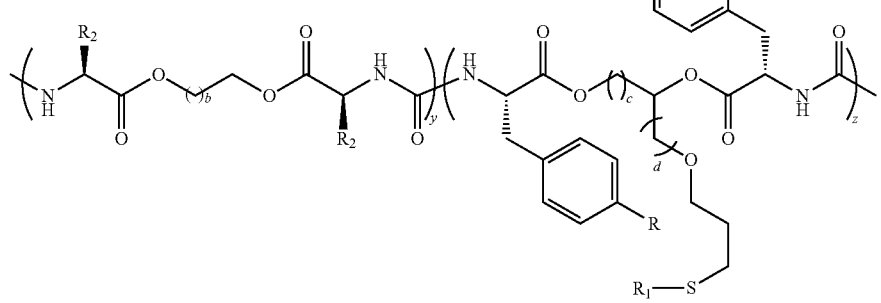

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; $R_1$ is an alkyl or aryl group comprising a zwitterionic moiety; $R_2$ is an amino acid side chain; b is an integer from 1 to 20; c and d are each an integer from about 1 to about 20; y is a mole fraction from about 0.500 to about 0.995; and z is a mole fraction from about 0.005 to about 0.500.

23. The poly(ester urea) (PEU)-based adhesion barrier of claim 3 comprising a zwitterionic terpolymer having the formula:

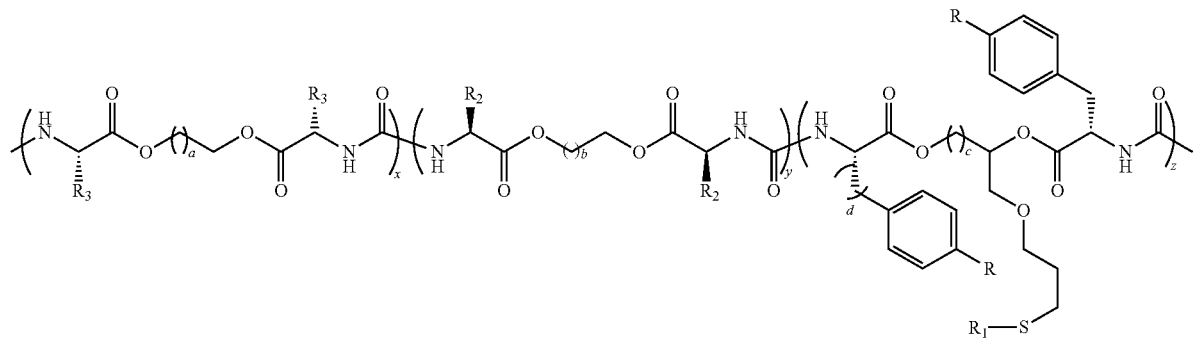

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; $R_1$ is an alkyl or aryl group comprising a zwitterionic moiety; $R_2$ is a first amino acid side chain; $R_3$ is a second amino acid side chain; a is an integer from 1 to 20; b is an integer from 1 to 20; each c and d are each an integer from about 1 to about 20; x is a mole fraction from about 0 to about 0.995; y is a mole fraction from about 0 to about 0.995; and z is a mole fraction from about 0.005 to about 0.500.

24. A method of making the poly(ester urea) (PEU)-based adhesion barrier of claim 3 comprising:

A) preparing an amino acid based PEU polymer having one or more allyl functional groups;

B) preparing a thiol functionalized zwitterionic compound;

C) reacting said allyl functionalized PEU terpolymer with said thiol functionalized zwitterionic compound to form a PEU-based adhesion barrier comprising an amino acid based PEU backbone having zwitterionic side chains.

25. The method of claim 24 wherein the step of preparing an amino acid based PEU polymer having an allyl functional group (step A) comprises:

a) preparing one or more amine protected amino acid-based diester monomers;

b) preparing an amine protected allyl functionalized amino acid-based polyester monomer; and c) dissolving said one or more amine protected amino acid-based diester monomers and said amine protected allyl functionalized amino acid-based polyester monomer is a suitable solvent with a suitable water soluble organic base;

d) adding a urea bond forming compound to the solution of step c to form an amino acid based PEU polymer having one or more allyl functional groups.

26. The method of claim 25 wherein said amine protected allyl functionalized amino acid-based polyester monomer has a formula selected from:

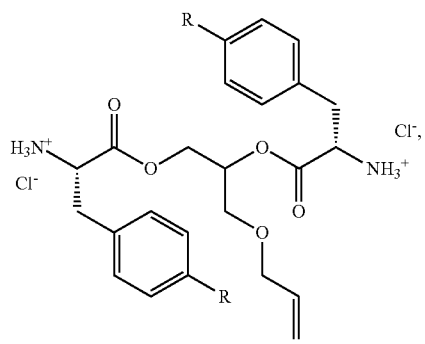

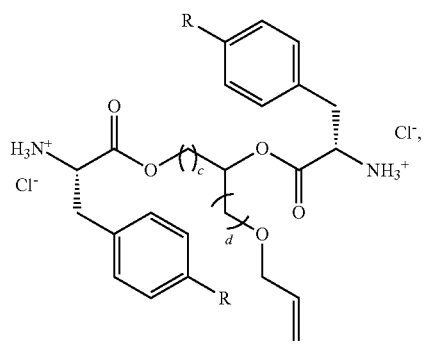

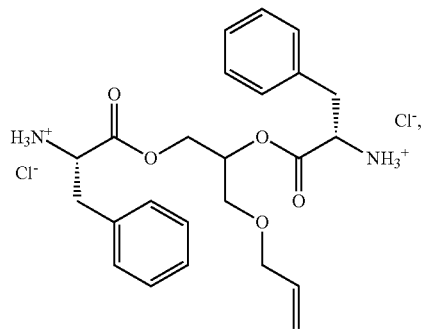

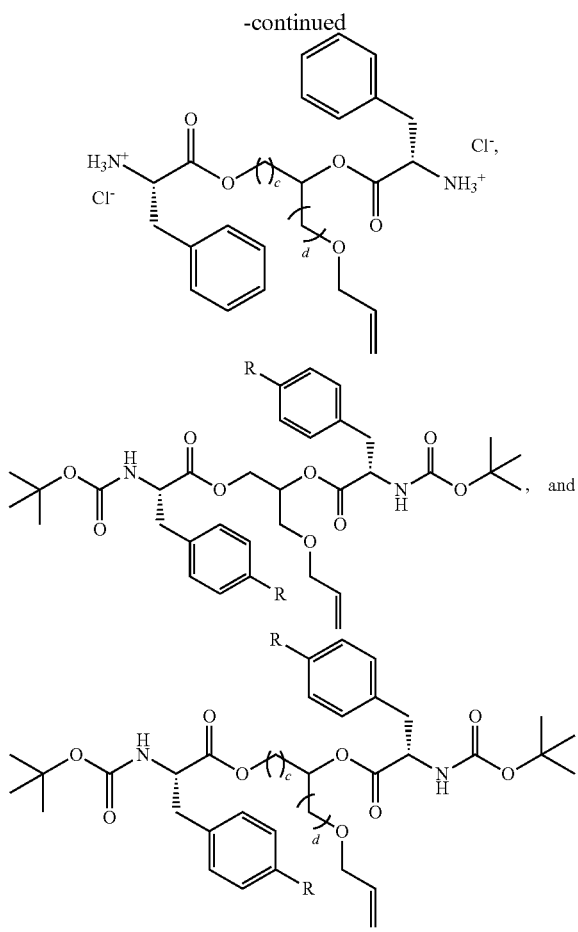

where R is $OCH_2Ph$, H, $OCH_2C\equiv CH$, $OCH_2CH_2CH_2N_3$, $OCH_2CH_2CH_2CH=CH_2$, $OCH_2Ph$, $OCOCH_2CH_2COCH_3$ or OH; and c and d are each an integer from about 1 to about 20.

27. The method of claim 25 wherein said suitable water soluble organic base is selected from the group consisting of sodium carbonate, potassium carbonate, sodium bicarbonate, potassium bicarbonate, and combinations thereof.

28. The method of claim 24 wherein the step of preparing an amino acid based PEU polymer having an allyl functional group (step A) comprises:
   i) preparing a first amine protected amino acid-based diester monomer;
   ii) preparing a second amine protected amino acid-based diester monomer;
   iii) preparing an amine protected allyl functionalized amino acid-based diester monomer; and
   iv) dissolving said first amine protected amino acid-based diester monomer, said second amine protected amino acid-based diester monomer; and said amine protected allyl functionalized amino acid-based diester monomer is a suitable solvent with a suitable water soluble organic base;
   v) adding a urea bond forming compound to the solution of step (iv) to form an amino acid based PEU terpolymer having one or more allyl functional groups.

29. The method of claim 28 wherein said first amine protected amino acid-based diester monomers comprises two lysine, phenylalanine, or valine, phenylalanine, lysine, phenylalanine, leucine, isoleucine, tyrosine, alanine, methionine, glycine, or cysteine residues separated by from 2 to 20 carbon atoms.

30. The method of claim 28 wherein said first amine protected amino acid-based diester monomers comprises two lysine residues separated by from 2 to about 20 carbon atoms.

31. The method of claim 28 wherein said second amine protected amino acid-based diester monomers comprise two phenylalanine residues separated by from 2 to about 20 carbon atoms.

32. The method of claim 24 wherein the step of preparing a thiol functionalized zwitterionic compound (step B) comprises:
   1. Reacting 3,3'-dithiodipropionic acid with thionyl chloride under an inert atmosphere to form a 3,3'-dithiodiproionyl chloride intermediate;
   2. Dissolving 3-dimethyamino-1-propanol in anhydrous dichloromethane under an inert atmosphere and adding the 3,3'-dithiodipropionyl chloride intermediate of step a, wherein said 3-dimethyamino-1-propanol and said 3,3'-dithiodipropionyl chloride intermediate react to form a bis((3-dimethylamino)propyl) 3,3'-disulfanediyldipropionate intermediate;
   3. Dissolving 1,3-propane sultone in a suitable solvent;
   4. Dissolving said bis((3-dimethylamino)propyl) 3,3'-disulfanediyldipropionate intermediate in a suitable solvent and adding it to the solution of step (c) to form a zwitterion disulfide intermediate;
   5. Cleaving said zwitterion disulfide intermediate using 1,4-dithiothreitol (DTT) to produce two thiol functionalized zwitterionic compounds.

33. The method of claim 24 wherein the step of reacting (step C) comprises reacting said allyl functionalized PEU terpolymer with said thiol functionalized zwitterionic compounds to form the PEU-based adhesion barrier comprising an amino acid based PEU backbone having zwitterionic side chains.

34. The method of claim 24 wherein the step of reacting (step C) comprises:
   I) combining said allyl functionalized PEU terpolymer and said thiol functionalized zwitterionic compounds and adding a suitable photoinitiator; and
   II) irradiating the combination of step (I) to form the PEU-based adhesion barrier comprising an amino acid based PEU backbone having zwitterionic side chains.

* * * * *